United States Patent
Feng et al.

(10) Patent No.: US 12,384,833 B2
(45) Date of Patent: Aug. 12, 2025

(54) **YEAST-BASED IMMUNOTHERAPY AGAINST *CLOSTRIDIUM DIFFICILE* INFECTION**

(71) Applicants: Hanping Feng, Ellicott City, MD (US); James Eugene Galen, Eldersburg, MD (US); Kevin Chen, Baltimore, MD (US); Yixuan Zhu, Ellicott City, MD (US)

(72) Inventors: Hanping Feng, Ellicott City, MD (US); James Eugene Galen, Eldersburg, MD (US); Kevin Chen, Baltimore, MD (US); Yixuan Zhu, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 132 days.

(21) Appl. No.: 17/955,537

(22) Filed: Sep. 29, 2022

(65) Prior Publication Data
US 2023/0340087 A1    Oct. 26, 2023

Related U.S. Application Data

(62) Division of application No. 15/768,331, filed as application No. PCT/US2016/056875 on Oct. 13, 2016, now Pat. No. 11,466,075.

(60) Provisional application No. 62/240,810, filed on Oct. 13, 2015.

(51) Int. Cl.
| | |
|---|---|
| *C07K 16/12* | (2006.01) |
| *A61K 9/00* | (2006.01) |
| *A61K 36/064* | (2006.01) |
| *A61K 39/00* | (2006.01) |
| *A61K 45/06* | (2006.01) |
| *A61P 31/04* | (2006.01) |
| *C12N 1/18* | (2006.01) |
| *G01N 33/569* | (2006.01) |

(52) U.S. Cl.
CPC ........ *C07K 16/1282* (2013.01); *A61K 9/0031* (2013.01); *A61K 9/0043* (2013.01); *A61K 9/0053* (2013.01); *A61K 36/064* (2013.01); *A61K 45/06* (2013.01); *A61P 31/04* (2018.01); *C12N 1/18* (2013.01); *G01N 33/56961* (2013.01); *A61K 2039/505* (2013.01); *C07K 2317/14* (2013.01); *C07K 2317/21* (2013.01); *C07K 2317/22* (2013.01); *C07K 2317/31* (2013.01); *C07K 2317/35* (2013.01); *C07K 2317/52* (2013.01); *C07K 2317/569* (2013.01); *C07K 2317/64* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | |
|---|---|---|
| 2002/0018749 A1 | 2/2002 | Hudson et al. |
| 2003/0228665 A1* | 12/2003 | Gautvik ............... C12N 15/70 435/254.2 |
| 2010/0272698 A1 | 10/2010 | Stateva et al. |
| 2012/0237496 A1 | 9/2012 | Birkenfeld et al. |
| 2013/0058962 A1 | 3/2013 | Shoemaker et al. |
| 2014/0294826 A1* | 10/2014 | Shoemaker ........ C07K 16/1278 424/134.1 |

FOREIGN PATENT DOCUMENTS

| | | |
|---|---|---|
| WO | WO-2015/100409 A2 | 7/2015 |
| WO | WO-2016/127104 A2 | 8/2016 |

OTHER PUBLICATIONS

Yang et al. (JID vol. 210, pp. 964-972, Sep. 2014) (Year: 2014).*
Qamar et al., Infection and Immunity vol. 69, n.4, pp. 2762-2765, 2001. (Year: 2001).*
Feng, Hanping, "Multispecific single domain antibody for treatment of Clostridium difficile infection," BIT's 5th international Congress of Antibodies, 2013, Hangzhou, China, 186.
Hamedi et al., "Generation of a Uracil Auxotroph Strain of the Probiotic Yeast *Saccharomyces boulardii* as a Host for the Recombinant Protein Production," Avicenna J. Med. Biotech., 2013. 5(1):29-34.
Hudson et al., "Functional Heterologous Protein Expression by Genetically Engineered probiotic Yeast *Saccharomyces boulardii*," PLoS ONE, Nov. 12, 2014, 9(11):e112660, 1-12.
Kagaku to Seibutsu (Chemistry and Biology), 2012, vol. 50, No. 3, pp. 163-174.
Liu et al., "Expression of cellulase genes in *Saccharomyces cerevisiae* via d-integration subject to auxotrophic markers," Biotechnol Lett, 35:1303-1307 (2013).
Liu et al., "Single domain antibody-alkaline phosphatase fusion proteins for antigen detection—Analysis of affinity and thermal stability of single domain antibody," Journal of Immunological Methods, 2013, 393:1-7.
Palma et al., "Probiotic Saccharomyces cerevisiae strains as biotherapeutic tools: is there room for improvement?", Appl. Microbiol. Biotechnol., 2015, 99:6563-6570.

(Continued)

*Primary Examiner* — Jana A Hines
*Assistant Examiner* — Khatol S Shahnan Shah
(74) *Attorney, Agent, or Firm* — Foley & Lardner LLP

(57) ABSTRACT

Antibody-based binding agents derived from human and camelid immunoglobulins are described, as well as strains of yeast engineered to secrete the binding agents, and methods of treating and preventing *Clostridium difficile* infections using the engineered strains of yeast. These binding agents recognize and bind with specificity to *Clostridium difficile* toxin A and/or toxin B and in some cases exhibit toxin neutralizing activity. The binding agents include camelid $V_HH$ peptide monomers, linked groups of $V_HH$ peptide monomers, $V_HH$ peptide monomers joined to antibody Fc domains, and $V_HH$ peptide monomers joined to IgG antibodies.

12 Claims, 21 Drawing Sheets

Specification includes a Sequence Listing.

(56) References Cited

OTHER PUBLICATIONS

Schmidt et al., "A Tetraspecific VHH-Based Neutralizing Antibody Modifies Disease Outcome in Three Animal Models of Clostridium difficile Infection," Clin. Vaccine Immunol., Sep. 2016, 23(9):774-784.

Shi et al.,. "Engineering of Chromosomal Wax Ester Synthase Integrated *Saccharomyces cerevisiae* Mutants for Improved Biosynthesis of Fatty Acid Ethyl Esters," Biotechnol. Bioeng., 2014, 111(9):1740-1747.

Spiess et al., "Alternative molecular formats and therapeutic applications for bispecific antibodies," Molecular Immunology, 2015, 67:95-106.

Vickers et al., "Dual gene expression cassette vectors with antibiotic selection markers for engineering in *Saccharomyces cerevisiae*," Microbial Cell Factories, 2013, 12(96):1-10.

Von Heijne et al., "Species-specific variation in signal peptide design, Implications for protein secretion in foreign hosts," FEBS Letters, Feb. 1989, 244(2):439-446.

Yang et al., "The protective effect of recombinant Lactococcus lactis oral vaccine on a Clostridium difficile-infected animal model," BMC Gastroenterology, 2013, 13:117, 13 pages.

* cited by examiner

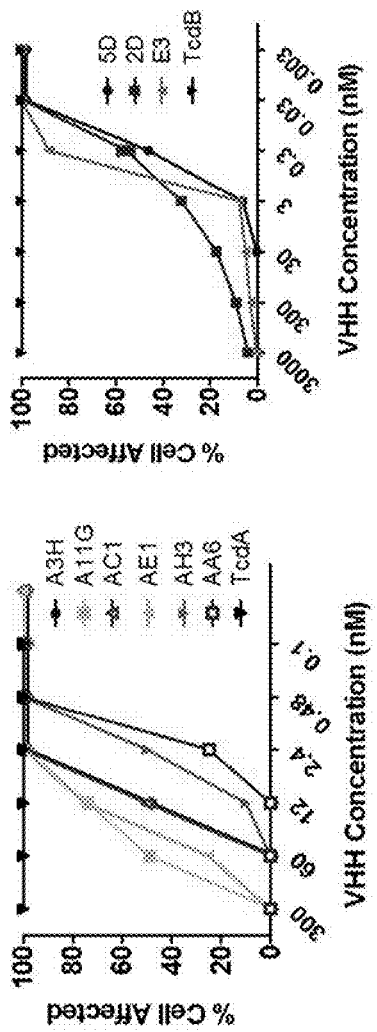
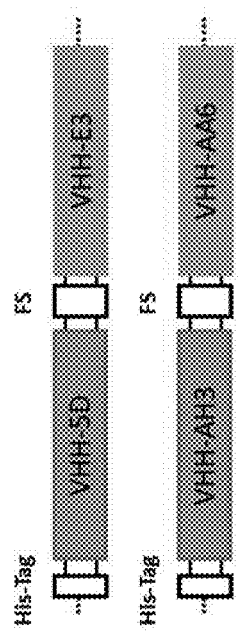
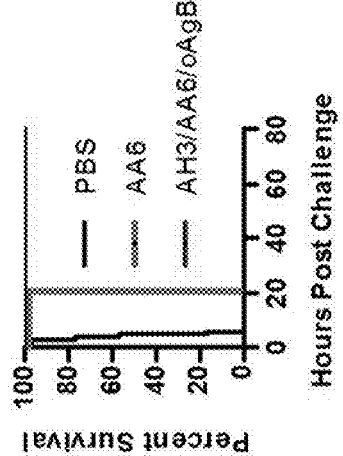
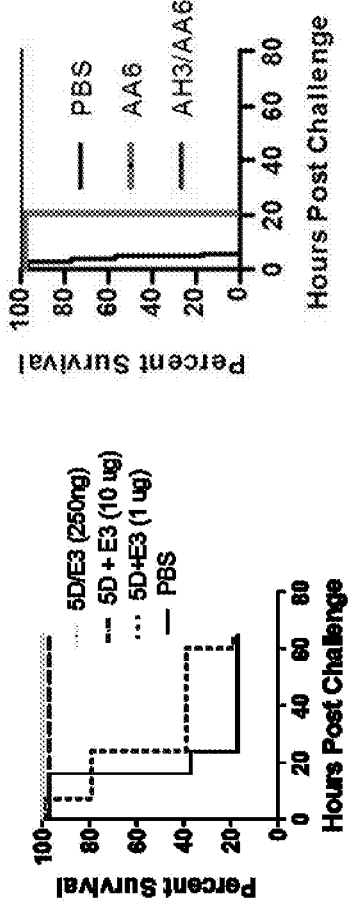
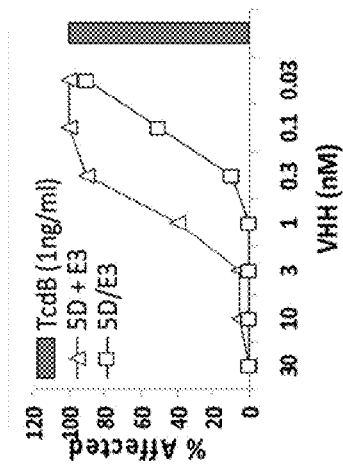

Coat TcdA to detect TcdB

FIG. 9A

Coat TcdB to detect TcdA

FIG. 9B

SEQUENCE LISTING

```
Sequence total quantity: 117
SEQ ID NO: 1                    moltype = AA   length = 127
FEATURE                         Location/Qualifiers
REGION                          1..127
                                note = Codon-optimized VHH peptide monomer 5D
source                          1..127
                                mol_type = protein
                                organism = synthetic construct
SEQUENCE: 1
QVQLVESGGG LVQPGGSLRL SCEASGFTLD YYGIGWFRQP PGKEREAVSY ISASARTILY    60
ADSVKGRFTI SRDNAKNAVY LQMNSLKRED TAVYYCARRR FSASSVNRWL ADDYDVWGRG   120
TQVAVSS                                                             127

SEQ ID NO: 2                    moltype = DNA   length = 381
FEATURE                         Location/Qualifiers
misc_feature                    1..381
                                note = Codon-optimized VHH peptide monomer 5D
source                          1..381
                                mol_type = other DNA
                                organism = synthetic construct
SEQUENCE: 2
caggtgcaac tggttgaatc tggggggaggc ttggtacaac tgggggggatc cctgagactc   60
tcttgcgagg cctccggatt caccttggac tactatggca tcggctggtt ccgccagccc  120
ccaggggaagg agcgggaggc cgtttcatac attagtgcca gtgcccggac catactgtac  180
gcagactctg tgaagggacg ctttaccatc tctagggaca tgccaaaaa tgctgtgtac  240
ctgcaaatga acagcctcaa gcgggaggat accgcagtgt actactgcgc gagacggcgc  300
ttctccgctt ctagcgtgaa tagatggctg gccgacgact acgacgtgtg gggacggggc  360
acacaggtgg ctgtctcgag c                                            381

SEQ ID NO: 3                    moltype = AA   length = 111
FEATURE                         Location/Qualifiers
REGION                          1..111
                                note = Codon-optimized VHH peptide monomer E3
source                          1..111
                                mol_type = protein
                                organism = synthetic construct
SEQUENCE: 3
QVQLVESGGG LVQTGGSLRL SCASSGSIAG FETVTWSRQA PGKSLQWVAS MTKTNNEIYS    60
DSVKGRFIIS RDNAKNTVYL QMNSLKPEDT GVYFCKGPEL RGQGIQVTVS S            111

SEQ ID NO: 4                    moltype = DNA   length = 333
FEATURE                         Location/Qualifiers
misc_feature                    1..333
                                note = Codon-optimized VHH peptide monomer E3
source                          1..333
                                mol_type = other DNA
                                organism = synthetic construct
SEQUENCE: 4
caagttcagc tggtcgaatc cggggggcgga ctggtccaga cagggggctc cctgaggctc   60
tcctgtgcat cttccggaag catcgccggc ttcgagaccg tgacctggtc tcgccaggct  120
cccgggaagt ctctgcagtg ggtcgcttcc atgactaaga ctaacaacga gatctactct  180
gactcagtga aggccgcttt catcatttct agagataacg ctaaaaacac agtgtatctg  240
cagatgaata gtctcaaacc tgaagacaca ggcgtgtatt tctgtaaggg tcctgagctg  300
aggggccagg gcatccaggt aacagtctcg agt                               333

SEQ ID NO: 5                    moltype = AA   length = 121
FEATURE                         Location/Qualifiers
REGION                          1..121
                                note = Codon-optimized VHH peptide monomer AA6
source                          1..121
                                mol_type = protein
                                organism = synthetic construct
SEQUENCE: 5
QLQLVETGGG LVQPGGSLRL SCAASGFTFS DYVMTWVRQA PGKGPEWIAT INTDGSTMRD    60
DSTKGRFTIS RDNAKNTLYL QMTSLKPEDT ALYYCARGRV ISASAIRGAV RGPGTQVTVS   120
S                                                                   121

SEQ ID NO: 6                    moltype = DNA   length = 363
FEATURE                         Location/Qualifiers
misc_feature                    1..363
                                note = Codon-optimized VHH peptide monomer AA6
source                          1..363
                                mol_type = other DNA
                                organism = synthetic construct
SEQUENCE: 6
caactgcagc tggtagagac aggggggcggc ttagttcagc ctggagggtc tctcagactg   60
tcatgcgctc cctctggctt taccttcagt gactacgtga tgacatgggt ccgccaagct  120
ccaggggaagg ggcctgagtg gatcgctact attaatacag atggcagcac aatgcgggac  180
```

```
gactccacaa agggycggtt caccatttcc agagacaacg ccaagaaatac tctgtaccct    240
cagatgacca gtctgaaacc cgaggacact gctctgtact attgtgcaag aggccgggtg    300
atctctgctt ccgctatcag aggcgcagta aggggccctg aacacaagt aactgtctcg    360
agc                                                                  363
```

| SEQ ID NO: 7 | moltype = AA  length = 126 |
|---|---|
| FEATURE | Location/Qualifiers |
| REGION | 1..126 |
|  | note = Codon-optimized VHH peptide monomer AH3 |
| source | 1..126 |
|  | mol_type = protein |
|  | organism = synthetic construct |

SEQUENCE: 7
```
QVQLVETGGL VQPGGSLRLS CAASGFTLDY SSIGWFRQAP GKEREGVSCI SSSGDSTKYA    60
DSVKGRFTTS RDNAKNTVYL QMNSLKPDDT AVYYCAAFRA TMCGVFPLSP YGKDDWGKGT   120
LVTVSS                                                              126
```

| SEQ ID NO: 8 | moltype = DNA  length = 378 |
|---|---|
| FEATURE | Location/Qualifiers |
| misc_feature | 1..378 |
|  | note = Codon-optimized VHH peptide monomer AH3 |
| source | 1..378 |
|  | mol_type = other DNA |
|  | organism = synthetic construct |

SEQUENCE: 8
```
caggtacagc tggtggagac ggggggggctg gtacaaccag gcgggtcact gaggctttcc    60
tgtgccgcat ctgggttcac actgattat tcgtccatag ggtggtttcg gcaggctcct   120
ggcaaagagc gtgaggggt ctcatgtatt agtagtagtg gtgatagcac aaagtacgcc   180
gattccgtaa agggccggtt tacaacctcc agggataatg ctaagaacac cgtatatctc   240
cagatgaact ctctgaagcc cgacgatacg gccgtatatt actgtgcggc tttcagggcg   300
actatgtgcg gcgtgttccc tctgagccct tacggcaagg acgactgggg caaggggacc   360
ctggtgaccg tctcgagt                                                 378
```

| SEQ ID NO: 9 | moltype = AA  length = 15 |
|---|---|
| FEATURE | Location/Qualifiers |
| REGION | 1..15 |
|  | note = Codon-optimized flexible linker 1 |
| source | 1..15 |
|  | mol_type = protein |
|  | organism = synthetic construct |

SEQUENCE: 9
```
GGGGSGGGGS GGGGS                                                     15
```

| SEQ ID NO: 10 | moltype = DNA  length = 45 |
|---|---|
| FEATURE | Location/Qualifiers |
| misc_feature | 1..45 |
|  | note = Codon-optimized flexible linker 1 |
| source | 1..45 |
|  | mol_type = other DNA |
|  | organism = synthetic construct |

SEQUENCE: 10
```
ggcggtggag ggtctggtgg gggaggctca ggggtggag gcagc                     45
```

| SEQ ID NO: 11 | moltype = AA  length = 16 |
|---|---|
| FEATURE | Location/Qualifiers |
| REGION | 1..16 |
|  | note = Codon-optimized flexible linker 2 |
| source | 1..16 |
|  | mol_type = protein |
|  | organism = synthetic construct |

SEQUENCE: 11
```
GGGSGGGSGG GSGGGS                                                    16
```

| SEQ ID NO: 12 | moltype = DNA  length = 48 |
|---|---|
| FEATURE | Location/Qualifiers |
| misc_feature | 1..48 |
|  | note = Codon-optimized flexible linker 2 |
| source | 1..48 |
|  | mol_type = other DNA |
|  | organism = synthetic construct |

SEQUENCE: 12
```
ggtggcggaa gcggaggggg cagcggggt gggagcggtg ggggcagc                  48
```

| SEQ ID NO: 13 | moltype = AA  length = 15 |
|---|---|
| FEATURE | Location/Qualifiers |
| REGION | 1..15 |
|  | note = Codon-optimized flexible linker 3 |
| source | 1..15 |
|  | mol_type = protein |

```
                            organism = synthetic construct
SEQUENCE: 13
GGGGSGGGGS GGGGS                                                        15

SEQ ID NO: 14           moltype = DNA  length = 45
FEATURE                 Location/Qualifiers
misc_feature            1..45
                        note = Codon-optimized flexible linker 3
source                  1..45
                        mol_type = other DNA
                        organism = synthetic construct
SEQUENCE: 14
ggggaggcg gttcaggcgg tgggggatct ggcggggtg gatcc                        45

SEQ ID NO: 15           moltype = AA  length = 269
FEATURE                 Location/Qualifiers
REGION                  1..269
                        note = AH3-5D heterodimer
source                  1..269
                        mol_type = protein
                        organism = synthetic construct
SEQUENCE: 15
QVQLVETGGG LVQPGGSLRL SCAASGFTLD YSSIGWFRQA PGKEREGVSC ISSSGDSTKY        60
ADSVKGRFTT SRDNAKNTVY LQMNSLKPDD TAVYYCAAFR ATMCGVFPLS PYGKDDWGKG       120
TLVTVSSGGG GSGGGGSGGG GSQVQLVESG GGLVQPGGSL RLSCEASGFT LDYYGIGWFR       180
QPPGKEREAV SYISASARTI LYADSVKGRF TISRDNAKNA VYLQMNSLKR EDTAVYYCAR       240
RRFSASSVNR WLADDYDVWG RGTQVAVSS                                        269

SEQ ID NO: 16           moltype = DNA  length = 807
FEATURE                 Location/Qualifiers
misc_feature            1..807
                        note = AH3-5D heterodimer
source                  1..807
                        mol_type = other DNA
                        organism = synthetic construct
SEQUENCE: 16
caggtacagc tggtgagac ggggggaggg ctggtacaac caggcgggtc actgaggctt         60
tcctgtgccg catctgggtt cacactggat tattcgtcca tagggtggtt tcggcaggct       120
cctggcaaag agcgtgaggg ggtctcatgt attagtagta gtggtgatag cacaaagtac       180
gccgattccg taaagggccg gtttacaacc tccaggata atgctaagaa caccgtatat        240
ctccagatga actctctgaa gcccgacgat acggccgtat attactgtgc ggctttcagg       300
gcgactatgt gcgcgtgtt ccctctgagc ccttacggca aggacgactg gggcaagggg        360
accctggtga ccgtatcctc aggcggtgga gggtctggtg gaggaggctt aggggggtgga      420
ggcagccagg tgcaactggt tgaatctggg ggaggcttgg tacaacctgg ggatccctg        480
agactctctt gcgaggcctc cggattcacc ttgactact atggcatcgg ctggttccgc        540
cagccccag gaaggagcg ggaggccgtt tcatacatta tgccagtgc ccggaccata         600
ctgtacgcag actctgtgaa gggacgcttt accatctcga caaatgc caaaaaatgct        660
gtgtacctgc aaatgaacag cctcaagcgg aggataccg cagtgtacta ctgcgcgaga       720
cggcgcttct ccgcttctag cgtgaataga tggctggccg acgactacga cgtgtgggga      780
cggggcacac aggtggctgt ctcgagc                                          807

SEQ ID NO: 17           moltype = AA  length = 247
FEATURE                 Location/Qualifiers
REGION                  1..247
                        note = AA6-E3 heterodimer
source                  1..247
                        mol_type = protein
                        organism = synthetic construct
SEQUENCE: 17
QLQLVETGGG LVQPGGSLRL SCAASGFTFS DYVMTWVRQA PGKGPEWIAT INTDGSTMRD        60
DSTKGRFTIS RDNAKNTLYL QMTSLKPEDT ALYYCARGRV ISASAIRGAV RGPGTQVTVS       120
SGGGGSGGGG SGGGGSQVQL VESGGGLVQT GGSLRLSCAS SGSIAGFETV TWSRQAPGKS       180
LQWVASMTKT NNEIYSDSVK GRFIISRDNA KNTVYLQMNS LKPEDTGVYF CKGPELRGQG       240
IQVTVSS                                                                247

SEQ ID NO: 18           moltype = DNA  length = 741
FEATURE                 Location/Qualifiers
misc_feature            1..741
                        note = AA6-E3 heterodimer
source                  1..741
                        mol_type = other DNA
                        organism = synthetic construct
SEQUENCE: 18
caactgcagc tggtagagac aggggggcggc ttagttcagc ctggagggtc tctcagactg       60
tcatgcgctg cctctggctt taccttcagt gactacgtga tgacatgggt ccgccaagct      120
ccagggaagg ggcctgagtg gatcgctact attaatacag atggcagcac aatgcgggac      180
gactccacaa aggggcggtt caccatttcc agagacaacg ccaagaatac tctgtacctt      240
cagatgacca gtctgaaacc cgaggacact gctctgtact attgtgcaag aggccgggtg      300
atctctgctt ccgctatcag aggcgcagta aggggccctg gaacacaggt aaccgtttca      360
```

```
tccgggggag gcggttcagg cggtggggga tctggcgggg gtggatccca agttcagctg    420
gtcgaatccg ggggcggact ggtccagaca gggggctccc tgaggctctc ctgtgcatct    480
tccggaagca tcgccggctt cgagaccgtg acctggtctc gccaggctcc cgggaagtct    540
ctgcagtggg tcgcttccat gactaagact aacaacgaga tctactctga ctcagtgaaa    600
ggccgcttca tcatttctag agataacgct aaaaacacag tgtatctgca gatgaatagt    660
ctcaaacctg aagacacagg cgtgtatttc tgtaagggtc ctgagctgag gggccagggc    720
atccaggtaa cagtctcgag t                                              741
```

```
SEQ ID NO: 19         moltype = AA  length = 532
FEATURE               Location/Qualifiers
REGION                1..532
                      note = ABAB binding agent
source                1..532
                      mol_type = protein
                      organism = synthetic construct
SEQUENCE: 19
QVQLVETGGG LVQPGGSLRL SCAASGFTLD YSSIGWFRQA PGKEREGVSC ISSSGDSTKY     60
ADSVKGRFTT SRDNAKNTVY LQMNSLKPDD TAVYYCAAFR ATMCGVFPLS PYGKDDWGKG    120
TLVTVSSGGG GSGGGGSGGG GSQVQLVESG GGLVQPGGSL RLSCEASGFT LDYYGIGWFR    180
QPPGKEREAV SYISASARTI LYADSVKGRF TISRDNAKNA VYLQMNSLKR EDTAVYYCAR    240
RRFSASSVNR WLADDYDVWG RGTQVAVSSG GGSGGGSGGG SGGGSQLQLV ETGGGLVQPG    300
GSLRLSCAAS GFTFSDYVMT WVRQAPGKGP EWIATINTDG STMRDDSTKG RFTISRDNAK    360
NTLYLQMTSL KPEDTALYYC ARGRVISASA IRGAVRGPGT QVTVSSGGGG SGGGGSGGGG    420
SQVQLVESGG GLVQTGGSLR LSCASSGSIA GFETVTWSRQ APGKSLQVVA SMTKTNNEIY    480
SDSVKGRFII SRDNAKNTVY LQMNSLKPED TGVYFCKGPE LRGQGIQVTV SS            532
```

```
SEQ ID NO: 20         moltype = DNA  length = 1596
FEATURE               Location/Qualifiers
misc_feature          1..1596
                      note = ABAB binding agent
source                1..1596
                      mol_type = other DNA
                      organism = synthetic construct
SEQUENCE: 20
caggtacagc tggtggagac ggggggaggg ctggtacaac caggcgggtc actgaggctt     60
tcctgtgccg catctgggtt cacactggat tattcgtcca tagggtggtt tcggcaggct    120
cctggcaaaa agcgtgaggg ggtctcatgt attagtagta gtggtgatag cacaaagtac    180
gccgattccg taaagggccg gtttacaacc tccaggata atgctaagaa caccgtatat     240
ctccagatga actctctgaa gcccgacgat acggccgtat attactgtgc ggcttttcagg    300
gcgactatgt gcggcgtgtt ccctctgagc ccttacggca aggacgactg gggcaagggg    360
accctggtga ccgtatcctc aggcggtgga gggtctggtg ggagggctc aggggggtgga    420
ggcagccagg tgcaactggt tgaatctggg ggaggcttgg tacaacctgg gggatccctg    480
agactctctt gcgaggcctc cggattcacc ttggactact atggcatcgg ttggttccgc    540
cagcccccag ggaaggagcg ggaggccgtt tcatacatta gtgccagtgc ccggaccata    600
ctgtacgcag actctgtgaa gggacgcttt accatctcta gggacaatgc caaaaatgct    660
gtgtacctgc aaatgaacag cctcaagcgg gaggataccg cagtgtacta ctgcgcgaga    720
cggcgcttct ccgcttctag cgtgaataga tggctgaccg acgactacga cgtgtgggga    780
cggggcacac aggtggctgt gtcttccggt ggcggaagcg gagggggcag cggggggtggg    840
agcggtgggg gcagccaact gcagctggta gagacagggg gcggcttagt tcagcctgga    900
gggtctctca gactgtcatg cgctgcctct ggctttacct tcagtgacta cgtgatgaca    960
tgggtccgcc aagctccagg gaaggggcct gagtggatcg ctactattaa tacagatggt   1020
agcacaatgc gggacgactc cacaaagggg cggttcacca tttccagaga caacgccaag   1080
aatactctgt accttcagat gaccagtctg aaacccgagg acactgctct gtactattgt   1140
gcaagaggcc gggtgatctc tgcttccgct atcagaggcg cagtaagggg ccctggaaca   1200
caggtaaccg tttcatccgg ggaggcggt tcaggcggtg ggggatctgg cgggggtgga   1260
tcccaagttc agctggtcga atccggggc ggactggtcc agacagggg ctccctgagg   1320
ctctcctgtg catcttccgg aagcatcgcc ggcttcgaga ccgtgacctg gtctcgccag   1380
gctcccggga agtctctgca gtgggtcgct tccatgacta gactaacaa cgagatctac   1440
tctgactcag tgaaaggccg cttcatcatt tctagagata cgctaaaaa cacagtgtat   1500
ctgcagatga atagtctcaa acctgaagac acaggcgtgt atttctgtaa gggtcctgag   1560
ctgaggggcc agggcatcca ggtaacagtc tcgagt                             1596
```

```
SEQ ID NO: 21         moltype = AA  length = 12
FEATURE               Location/Qualifiers
REGION                1..12
                      note = Albumin-binding peptide
source                1..12
                      mol_type = protein
                      organism = synthetic construct
SEQUENCE: 21
DICLPRWGCL WD                                                         12
```

```
SEQ ID NO: 22         moltype = AA  length = 761
FEATURE               Location/Qualifiers
REGION                1..761
                      note = ABAB-Fc binding agent
source                1..761
                      mol_type = protein
                      organism = synthetic construct
```

```
SEQUENCE: 22
QVQLVETGGG LVQPGGSLRL SCAASGFTLD YSSIGWFRQA PGKEREGVSC ISSSGDSTKY   60
ADSVKGRFTT SRDNAKNTVY LQMNSLKPDD TAVYYCAAFR ATMCGVFPLS PYGKDDWGKG  120
TLVTVSSGGG GSGGGGSGGG GSQVQLVESG GGLVQPGGSL RLSCEASGFT LDYYGIGWFR  180
QPPGKEREAV SYISASARTI LYADSVKGRF TISRDNAKNA VYLQMNSLKR EDTAVYYCAR  240
RRFSASSVNR WLADDYDVWG RGTQVAVSSG GGSGGGSGGG SGGGSQLQLV ETGGGLVQPG  300
GSLRLSCAAS GFTFSDYVMT WVRQAPGKGP EWIATINTDG STMRDDSTKG RFTISRDNAK  360
NTLYLQMTSL KPEDTALYYC ARGRVISASA IRGAVRGPGT QVTVSSGGGG SGGGGSGGGG  420
SQVQLVESGG GLVQTGGSLR LSCASSGSIA GFETVTWSRQ APGKSLQWVA SMTKTNNEIY  480
SDSVKGRFII SRDNAKNTVY LQMNSLKPED TGVYFCKGPE LRGQGIQVTV SSGGDKTHTC  540
PPCPAPELLG GPSVFLFPPK PKDTLMISRT PEVTCVVVDV SHEDPEVKFN WYVDGVEVHN  600
AKTKPREEQY NSTYRVVSVL TVLHQDWLNG KEYKCKVSNK ALPAPIEKTI SKAKGQPREP  660
QVYTLPPSRE EMTKNQVSLT CLVKGFYPSD IAVEWESNGQ PENNYKTTPP VLDSDGSFFL  720
YSKLTVDKSR WQQGNVFSCS VMHEALHNHY TQKSLSLSPG K                     761

SEQ ID NO: 23           moltype = DNA  length = 2286
FEATURE                 Location/Qualifiers
misc_feature            1..2286
                        note = ABAB-Fc binding agent
source                  1..2286
                        mol_type = other DNA
                        organism = synthetic construct
SEQUENCE: 23
caggtacagc tggtggagac ggggggaggg ctggtacaac caggcgggtc actgaggctt   60
tcctgtgccg catctgggtt cacactggat tattcgtcca tagggtggtt tcggcaggct  120
cctgcaaag agcgtgaggg ggtctcatgt attagtagta gtggtgatag cacaaagtac  180
gccgattccg taaagggccg gtttacaacc tccaggagata tgctaagaa caccgtatat  240
ctccagatga actctctgaa gcccgacgat acggccgtat attactgtgc ggcttttcagg  300
gcgactatgt gcgcgtgtt ccctctgagc ccttacggca aggacgactg gggcaagggg  360
accctggtga ccgtatcctc aggcggtgga ggtctgggg gggaggctc agggggtgga  420
ggcagccagg tgcaactggt tgaatctggg ggaggcttgg tacaacctgg gggatccctg  480
agactctctt gcgaggcctc cggattcacc ttggactact atggcatcgg ctggttccgc  540
cagcccccag ggaaggagcg ggaggccgtt tcatacatta gtgccagtgc ccggaccata  600
ctgtacgcag actctgtgaa gggacgcttt accatctcga gggacaatgc caaaaatgct  660
gtgtacctgc aaatgaacag cctcaagcgt gaggataccg cagtgtacta ctgcgcgaga  720
cggcgcttct ccgcttctag cgtgaataga tggctggccg acgactacga cgtgcgggga  780
cggggcacac aggtggctgt gtcttccggt ggcggaagcg gagggggcag cggggtggg  840
agcggtgggg cagccaact gcagctggta gagacagggg gcggcttagt tcagcctgga  900
gggtctctca gactgtcatg cgctgcctct gcctttacct tcagtgacta cgtgatgaca  960
tgggtccgcc aagctccagg gaaggggcct gagtggatcg ctactattaa tacagatggc  1020
agcacaatgc gggacgactc cacaaagggg cggttcacca tttccagaga caacgccaag  1080
aatactctgt accttcagat gaccagtctg aaacccgagg acactgctct gtactattgt  1140
gcaagaggcc gggtgatctc tgcttccgct atcagaggcg cagtaagggg ccctggaaca  1200
caggtaaccg tttcatccgg gggaggcggt tcaggcggtg gggatctgg cgggggtgga  1260
tcccaagttc agctggtcga atccggggg ggactggtcc agacaggggg ctccctgagg  1320
ctctcctgtg catcttccgg aagcatcgcc ggcttcgaga ccgtgacctg gtctcgccag  1380
gctcccggga agtctctgca gtgggtcgct tccatgacta agactaacaa cgagatctac  1440
tctgactcag tgaaaggccg cttcatcatt tctagagata cgctaaaaa cacagtgtat  1500
ctgcagatga atagtctcaa acctgaagac acaggcgtgt atttctgtaa gggtcctgag  1560
ctgaggggc agggcatcca ggtaacagtc tcgagcggat ccgacaaaac tcacacatgc  1620
ccaccgtgcc cagcacctga actcctgggg ggaccgtcag tcttcctctt ccccccaaa  1680
cccaaggaca ccctcatgat ctcccggacc cctgaggtca catgcgtggt ggtggacgtg  1740
agccacgaag accctgaggt caagttcaac tggtacgtgg acggcgtgga ggtgcataat  1800
gccaagacaa agccgcggga ggagcagtac aacagcacgt accgtgtggt cagcgtcctc  1860
accgtcctgc accaggactg gctgaatggc aaggagtaca agtgcaaggt ctccaacaaa  1920
gccctcccag cccccatcga gaaaaccatc tccaaagcca aagggcagcc ccgagaacca  1980
caggtgtaca cctgcccccc atccgggag gagatgacca gaaccaggt cagcctgacc  2040
tgcctggtca aaggcttcta tccagcgac atcgccgtgg agtgggagag caatgggcag  2100
ccggagaaca actacaagac cacgcctccc gtgctggact ccgacggctc cttcttcctc  2160
tatagcaagc tcaccctgga caagagcagg tggcagcagg gaacgtctt ctcatgctcc  2220
gtgatgcatg aggctctgca caaccactac acgcagaaga gcctctccct gtctccgggt  2280
aaatga                                                            2286

SEQ ID NO: 24           moltype = AA  length = 356
FEATURE                 Location/Qualifiers
REGION                  1..356
                        note = 5D-Fc binding agent
source                  1..356
                        mol_type = protein
                        organism = synthetic construct
SEQUENCE: 24
QVQLVESGGG LVQPGGSLRL SCEASGFTLD YYGIGWFRQP PGKEREAVSY ISASARTILY   60
ADSVKGRFTI SRDNAKNAVY LQMNSLKRED TAVYYCARRR FSASSVNRWL ADDYDVWGRG  120
TQVAVSSGSD KTHTCPPCPA PELLGGPSVF LFPPKPKDTL MISRTPEVTC VVVDVSHEDP  180
EVKFNWYVDG VEVHNAKTKP REEQYNSTYR VVSVLTVLHQ DWLNGKEYKC KVSNKALPAP  240
IEKTISKAKG QPREPQVYTL PPSREEMTKN QVSLTCLVKG FYPSDIAVEW ESNGQPENNY  300
KTTPPVLDSD GSFFLYSKLT VDKSRWQQGN VFSCSVMHEA LHNHYTQKSL SLSPGK      356

SEQ ID NO: 25           moltype = DNA  length = 1071
```

```
FEATURE                 Location/Qualifiers
misc_feature            1..1071
                        note = 5D-Fc binding agent
source                  1..1071
                        mol_type = other DNA
                        organism = synthetic construct
SEQUENCE: 25
caggtgcaac tggttgaatc tggggggaggc ttggtacaac ctgggggatc cctgagactc    60
tcttgcgagg cctccggatt caccttggac tactatggca tcggctggtt ccgccagccc   120
ccaggggaagg agcgggaggc cgtttcatac attagtgcca gtgcccggac catactgtac   180
gcagactctg tgaagggacg ctttaccatc tctagggaca tgccaaaaa tgctgtgtac    240
ctgcaaatga acagcctcaa gcgggaggat accgcagtgt actactgcg gagacggcgc   300
ttctccgctt ctagcgtgaa tagatggctg ccgacgact acgacgtgtg gggacggggc   360
acacaggtgg ctgtctcgag cggatccgac aaaactcaca catgcccacc gtgcccagca   420
cctgaactcc tggggggacc gtcagtcttc ctcttccccc caaaacccaa ggacaccctc   480
atgatctccc ggacccctga ggtcacatgc gtggtggtgg acgtgagcca cgaagaccct   540
gaggtcaagt tcaactggta cgtggacggc gtggaggtgc ataatgccaa gacaaagccg   600
cggagaggg agtacaacag cacgtaccgt gtggtcagcg tcctcaccgt cctgcaccag   660
gactggctga atggcaagga gtacaagtgc aaggtctcca acaaagccct cccagccccc   720
atcgagaaaa ccatctccaa agccaaaggg cagccccgag aaccacaggt gtacaccctg   780
cccccatccc gggaggagat gaccaagaac caggtcagcc tgacctgcct ggtcaaaggc   840
ttctatccca gcgacatcgc cgtggagtgg gagagcaatg ggcagccgga gaacaactac   900
aagaccacgc ctcccgtgct ggactccgac ggctccttct tcctctatag caagctcacc   960
gtggacaaga gcaggtggca gcaggggaac gtcttctcat gctccgtgat gcatgaggct  1020
ctgcacaacc actacacgca gaagagcctc tccctgtctc cgggtaaatg a           1071

SEQ ID NO: 26           moltype = AA  length = 340
FEATURE                 Location/Qualifiers
REGION                  1..340
                        note = E3-Fc binding agent
source                  1..340
                        mol_type = protein
                        organism = synthetic construct
SEQUENCE: 26
QVQLVESGGG LVQTGGSLRL SCASSGSIAG FETVTWSRQA PGKSLQWVAS MTKTNNEIYS    60
DSVKGRFIIS RDNAKNTVYL QMNSLKPEDT GVYFCKGPEL RGQGIQVTVS SGSDKTHTCP   120
PCPAPELLGG PSVFLFPPKP KDTLMISRTP EVTCVVVDVS HEDPEVKFNW YVDGVEVHNA   180
KTKPREEQYN STYRVVSVLT VLHQDWLNGK EYKCKVSNKA LPAPIEKTIS KAKGQPREPQ   240
VYTLPPSREE MTKNQVSLTC LVKGFYPSDI AVEWESNGQP ENNYKTTPPV LDSDGSFFLY   300
SKLTVDKSRW QQGNVFSCSV MHEALHNHYT QKSLSLSPGK                         340

SEQ ID NO: 27           moltype = DNA  length = 1023
FEATURE                 Location/Qualifiers
misc_feature            1..1023
                        note = E3-Fc binding agent
source                  1..1023
                        mol_type = other DNA
                        organism = synthetic construct
SEQUENCE: 27
caagttcagc tggtcgaatc cggggggcgga ctggtccaga cagggggctc cctgaggctc    60
tcctgtgcat cttccggaag catcgccggc ttcgagaccg tgacctggtc tcgccaggct   120
cccgggaagt ctctgcagtg ggtcgcttcc atgactaaga ctaacaacga gatctactct   180
gactcagtga aggccgcttt catcatttct agagataacg ctaaaaacac agtgtatctg   240
cagatgaata gtctcaaacc tgaagacaca ggcgtgtatt tctgtaaggg tcctgagctg   300
aggggccagg gcatccaggt aacagtctcg agcggatccg acaaaactca cacatgccca   360
ccgtgcccag cacctgaact cctgggggga ccgtcagtct tcctcttccc cccaaaaccc   420
aaggacaccc tcatgatctc ccggacccct gaggtcacat gcgtggtggt ggacgtgagc   480
cacgaagacc ctgaggtcaa gttcaactgg tacgtggacg gcgtggaggt gcataatgcc   540
aagacaaagc cgcggggagga gcagtacaac agcacgtacc gtgtggtcag cgtcctcacc   600
gtcctgcacc aggactggct gaatggcaag gagtacaagt gcaaggtctc caacaaagcc   660
ctcccagccc ccatcgagaa aaccatctcc aaagccaaag gcagccccg agaaccacag   720
gtgtacaccc tgcccccatc ccgggaggag atgaccaaga accaggtcag cctgacctgc   780
ctggtcaaag gcttctatcc cagcgacatc gccgtggagt gggagagcaa tgggcagccg   840
gagaacaact acaagaccac gcctcccgtg ctggactccg acggctcctt cttcctctat   900
agcaagctca ccgtggacaa gagcaggtgg cagcagggga acgtcttctc atgctccgtg   960
atgcatgagg ctctgcacaa ccactacacg cagaagagcc tctccctgtc tccgggtaaa  1020
tga                                                                1023

SEQ ID NO: 28           moltype = AA  length = 350
FEATURE                 Location/Qualifiers
REGION                  1..350
                        note = AA6-Fc binding agent
source                  1..350
                        mol_type = protein
                        organism = synthetic construct
SEQUENCE: 28
QLQLVETGGG LVQPGGSLRL SCAASGFTFS DYVMTWVRQA PGKGPEWIAT INTDGSTMRD    60
DSTKGRFTIS RDNAKNTLYL QMTSLKPEDT ALYYCARGRV ISASAIRGAV RGPGTQVTVS   120
SGSDKTHTCP PCPAPELLGG PSVFLFPPKP KDTLMISRTP EVTCVVVDVS HEDPEVKFNW   180
```

```
YVDGVEVHNA KTKPREEQYN STYRVVSVLT VLHQDWLNGK EYKCKVSNKA LPAPIEKTIS   240
KAKGQPREPQ VYTLPPSREE MTKNQVSLTC LVKGFYPSDI AVEWESNGQP ENNYKTTPPV   300
LDSDGSFFLY SKLTVDKSRW QQGNVFSCSV MHEALHNHYT QKSLSLSPGK              350

SEQ ID NO: 29           moltype = DNA   length = 1053
FEATURE                 Location/Qualifiers
misc_feature            1..1053
                        note = AA6-Fc binding agent
source                  1..1053
                        mol_type = other DNA
                        organism = synthetic construct
SEQUENCE: 29
caactgcagc tggtagagac aggggggcggc ttagttcagc ctggagggtc tctcagactg    60
tcatgcgctg cctctggctt taccttcagt gactacgtga tgcatgtggg ccgcagaagct  120
ccagggaagg ggcctgagtg gatcgctact attaatacag atggcagcac aatgcgggac   180
gactccacaa aggggcggtt caccatttcc agagacaacg ccaagaatac tctgtacctt   240
cagatgacca gtctgaaacc cgaggacact gctctgtact attgtgcaag aggcggggtg   300
atctctgctt ccgctatcag aggcgcagta aggggccctg gaacaaagt aactgtctcg   360
agcggatccg acaaaactca cacatgccca ccgtgcccag cacctgaact cctgggggga   420
ccgtcagtct tcctcttccc cccaaaaccc aaggacaccc tcatgatctc ccggaccct   480
gaggtcacat gcgtggtggt ggacgtgagc cacgaagacc ctgaggtcaa gttcaactgg   540
tacgtggacg gcgtggaggt gcataatgcc aagacaaagc cgcgggagga gcagtacaac   600
agcacgtacc gtgtggtcag cgtcctcacc gtcctgcacc aggactggct gaatggcaag   660
gagtacaagt gcaaggtctc caacaaagcc ctcccagccc catcgagaa aaccatctcc   720
aaagccaaag ggcagccccg agaaccacag gtgtacaccc tgcccccatc ccgggaggag   780
atgaccaaga accaggtcag cctgacctgc ctggtcaaag gcttctatcc cagcgacatc   840
gccgtggagt gggagagcaa tgggcagccg gagaacaact acaagaccac gcctcccgtg   900
ctggactccg acggctcctt cttcctctat agcaagctca ccgtggacaa gagcaggtgg   960
cagcagggga acgtcttctc atgctccgtg atgcatgagg ctctgcacaa ccactacacg  1020
cagaagagcc tctccctgtc tccgggtaaa tga                               1053

SEQ ID NO: 30           moltype = AA   length = 356
FEATURE                 Location/Qualifiers
REGION                  1..356
                        note = AH3-Fc binding agent
source                  1..356
                        mol_type = protein
                        organism = synthetic construct
SEQUENCE: 30
QVQLVETGGG LVQPGGSLRL SCAASGFTLD YSSIGWFRQA PGKEREGVSC ISSSGDSTKY    60
ADSVKGRFTT SRDNAKNTVY LQMNSLKPDD TAVYYCAAFR ATMCGVFPLS PYGKDDWGKG   120
TLVTVSSGSD KTHTCPPCPA PELLGGPSVF LFPPKPKDTL MISRTPEVTC VVVDVSHEDP   180
EVKFNWYVDG VEVHNAKTKP REEQYNSTYR VVSVLTVLHQ DWLNGKEYKC KVSNKALPAP   240
IEKTISKAKG QPREPQVYTL PPSREEMTKN QVSLTCLVKG FYPSDIAVEW ESNGQPENNY   300
KTTPPVLDSD GSFFLYSKLT VDKSRWQQGN VFSCSVMHEA LHNHYTQKSL SLSPGK       356

SEQ ID NO: 31           moltype = DNA   length = 1071
FEATURE                 Location/Qualifiers
misc_feature            1..1071
                        note = AH3-Fc binding agent
source                  1..1071
                        mol_type = other DNA
                        organism = synthetic construct
SEQUENCE: 31
caggtacagc tggtggagac gggggggaggg ctggtacaac caggcgggtc actgaggctt    60
tcctgtgccg catctgggtt cacactggat tattcgtcca tagggtggtt tcggcaggct   120
cctggcaaag agcgtgaggg ggtctcatgt attagtagta gtggtgatag cacaaagtac   180
gccgattccg taaagggccg gtttacaacc tccagggata tgctaagaa caccgtatat   240
ctccagatga actctctgaa gcccgacgat acggccgtat attactgtgc ggcttttcagg   300
gcgactatgt gcggcgtgtt ccctctgagc ccttacggca aggacgactg ggggcaaggg   360
accctggtga ccgtctcgag cggatccgac aaaactcaca catgcccacc gtgcccagca   420
cctgaactcc tggggggacc gtcagtcttc ctcttccccc caaaacccaa ggacaccctc   480
atgatctccc ggacccctga ggtcacatgc gtggtggtgg acgtgagcca cgaagaccct   540
gaggtcaagt tcaactggta cgtggacggc gtggaggtgc ataatgccaa gacaaagccg   600
cgggaggagc agtacaacag cacgtaccgt gtggtcagcg tcctcaccgt cctgcaccag   660
gactggctga atggcaagga gtacaagtgc aaggtctcca acaaagccct cccagccccc   720
atcgagaaaa ccatctccaa agccaaaggg cagccccgag aaccacaggt gtacaccctg   780
cccccatccc gggaggagat gaccaagaac caggtcagcc tgacctgcct ggtcaaaggc   840
ttctatccca gcgacatcgc cgtggagtgg gagagcaatg ggcagccgga gaacaactac   900
aagaccacgc ctcccgtgct ggactccgac ggctccttct tcctctatag caagctcacc   960
gtggacaaga gcaggtggca gcaggggaac gtcttctcat gctccgtgat gcatgaggct  1020
ctgcacaacc actacacgca gaagagcctc tccctgtctc cgggtaaatg a           1071

SEQ ID NO: 32           moltype = AA   length = 498
FEATURE                 Location/Qualifiers
REGION                  1..498
                        note = AH3-5D-Fc binding agent
source                  1..498
                        mol_type = protein
```

-continued

```
                        organism = synthetic construct
SEQUENCE: 32
QVQLVETGGG LVQPGGSLRL SCAASGFTLD YSSIGWFRQA PGKEREGVSC ISSSGDSTKY    60
ADSVKGRFTT SRDNAKNTVY LQMNSLKPDD TAVYYCAAFR ATMCGVFPLS PYGKDDWGKG   120
TLVTVSSGGG GSGGGGSGGG GSQVQLVESG GGLVQPGGSL RLSCEASGFT LDYYGIGWFR   180
QPPGKEREAV SYISASARTI LYADSVKGRF TISRDNAKNA VYLQMNSLKR EDTAVYYCAR   240
RRFSASSVNR WLADDYDVWG RGTQVAVSSG SDKTHTCPPC PAPELLGGPS VFLFPPKPKD   300
TLMISRTPEV TCVVVDVSHE DPEVKFNWYV DGVEVHNAKT KPREEQYNST YRVVSVLTVL   360
HQDWLNGKEY KCKVSNKALP APIEKTISKA KGQPREPQVY TLPPSREEMT KNQVSLTCLV   420
KGFYPSDIAV EWESNGQPEN NYKTTPPVLD SDGSFFLYSK LTVDKSRWQQ GNVFSCSVMH   480
EALHNHYTQK SLSLSPGK                                                498

SEQ ID NO: 33           moltype = DNA  length = 1497
FEATURE                 Location/Qualifiers
misc_feature            1..1497
                        note = AH3-5D-Fc binding agent
source                  1..1497
                        mol_type = other DNA
                        organism = synthetic construct
SEQUENCE: 33
caggtacagc tggtggagac gggggaggg ctggtacaac caggcgggtc actgaggctt     60
tcctgtgccg catctgggtt cacactggat tattcgtcca tgggtggtt tcggcaggct   120
cctggcaaag agcgtgaggg ggtctcatgt attagtagta gtggtgatag cacaaagtac   180
gccgattccg taaagggccg gtttacaacc tccagggata atgctaagaa caccgtatat   240
ctccagatga actctctgaa gcccgacgat acggccgtat attactgtgc ggctttcagg   300
gcgactatgt gcggcgtgtt ccctctgagc ccttacggca aggacgactg gggcaaggtg   360
accctggtga ccgtatcctc aggcggtgga gggtctggtg ggggaggctc aggggggtgga   420
ggcagccagg tgcaactggt tgaatctggg ggaggcttgg tacaacctgg gggatccctg   480
agactctctt gcgaggcctc cggattcacc ttggactact atggcatcgg ctggttccgc   540
cagcccccag gaaaggagcg ggaggccgtt tcatacatta gccagtgc cggaccata     600
ctgtacgcag actctgtgaa gggacgcttt accatctcta gtgacaatgc caaaaatgct   660
gtgtacctgc aaatgaacag cctcaagcgg gaggataccg cagtgtacta ctgcgcgaga   720
cggcgcttct ccgcttctag cgtgaataga tggctggccg acgactacga cgtgtgggga   780
cggggcacac aggtggctgt ctcgagcgga tccgacaaaa ctcacacatg cccaccgtgc   840
ccagcacctg aactcctggg gggaccgtca gtcttcctct tccccccaaa acccaaggac   900
accctcatga tctcccggac ccctgaggtc acatgcgtgg tggtggacgt gagccacgaa   960
gaccctgagg tcaagttcaa ctggtacgtg gacggcgtgg aggtgcataa tgccaagaca  1020
aagccgcggg aggagcagta caacagcacg taccgtgtgg tcagcgtcct caccgtcctg  1080
caccaggact ggctgaatgg caaggagtac aagtgcaagg tctccaacaa agccctccca  1140
gcccccatcg agaaaaccat ctccaaagcc aaagggcagc cccgagaacc acaggtgtac  1200
accctgcccc catcccggga ggagatgacc aagaaccagg tcagcctgac ctgcctggtc  1260
aaaggcttct atcccagcga catcgccgtg gagtgggaga gcaatgggca gccggagaac  1320
aactacaaga ccacgcctcc cgtgctggac tccgacggct ccttcttcct ctatagcaag  1380
ctcaccgtgg acaagagcag gtggcagcag gggaacgtct tctcatgctc cgtgatgcat  1440
gaggctctgc acaaccacta cacgcagaag agcctctccc tgtctccggg taaatga     1497

SEQ ID NO: 34           moltype = AA  length = 476
FEATURE                 Location/Qualifiers
REGION                  1..476
                        note = AA6-E3-Fc binding agent
source                  1..476
                        mol_type = protein
                        organism = synthetic construct
SEQUENCE: 34
QLQLVETGGG LVQPGGSLRL SCAASGFTFS DYVMTWVRQA PGKGPEWIAT INTDGSTMRD    60
DSTKGRFTIS RDNAKNTLYL QMTSLKPEDT ALYYCARGRV ISASAIRGAV RGPGTQVTVS   120
SGGGGSGGGG SGGGGSQVQL VESGGGLVQT GGSLRLSCAS SGSIAGFETV TWSRQAPGKS   180
LQWVASMTKT NNEIYSDSVK GRFIISRDNA KNTVYLQMNS LKPEDTGVYF CKGPELRGQG   240
IQVTVSSGSD KTHTCPPCPA PELLGGPSVF LFPPKPKDTL MISRTPEVTC VVVDVSHEDP   300
EVKFNWYVDG VEVHNAKTKP REEQYNSTYR VVSVLTVLHQ DWLNGKEYKC KVSNKALPAP   360
IEKTISKAKG QPREPQVYTL PPSREEMTKN QVSLTCLVKG FYPSDIAVEW ESNGQPENNY   420
KTTPPVLDSD GSFFLYSKLT VDKSRWQQGN VFSCSVMHEA LHNHYTQKSL SLSPGK       476

SEQ ID NO: 35           moltype = DNA  length = 1431
FEATURE                 Location/Qualifiers
misc_feature            1..1431
                        note = AA6-E3-Fc binding agent
source                  1..1431
                        mol_type = other DNA
                        organism = synthetic construct
SEQUENCE: 35
caactgcagc tggtagagac aggggcggc ttagttcagc ctggagggtc tctcagactg      60
tcatgcgctc cctctggctt taccttcagt gactacgtga tgacatgggt ccgccaagct   120
ccaggaaagg gcccgagtg gatcgctact attaataccg atggcagcac aatgcgggac   180
gactccacaa aggggcggtt caccattcc agagacaacg ccaagaatac tctgtacctt   240
cagatgacca gtctgaaacc cgaggacact gctctgtact attgtgcaag aggccgggtg   300
atctctgctt ccgctatcag aggcgcagta aggggccctg gaacacaggt aaccgtttca   360
tccggggag gcggttcagg cggtgggga tctggcgggg gtggatccca agttcagctg   420
gtcgaatccg ggggcggact ggtccagaca gggggctccc tgaggctctc ctgtgcatct   480
```

-continued

```
tccggaagca tcgccggctt cgagaccgtg acctggtctc gccaggctcc cgggaagtct    540
ctgcagtggg tcgcttccat gactaagact aacaacgaga tctactctga ctcagtgaaa    600
ggccgcttca tcatttctag agataacgct aaaaacacag tgtatctgca gatgaatagt    660
ctcaaacctg aagacacagg cgtgtatttc tgtaagggtc ctgagctgag gggccagggc    720
atccaggtaa cagtctcgag cggatccgac aaaactcaca catgcccacc gtgcccagca    780
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggaggagat gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct tcctctatag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaatg a            1431

SEQ ID NO: 36          moltype = AA   length = 457
FEATURE                Location/Qualifiers
REGION                 1..457
                       note = AH3-IgG1-heavy chain
source                 1..457
                       mol_type = protein
                       organism = synthetic construct
SEQUENCE: 36
QVQLVETGGG LVQPGGSLRL SCAASGFTLD YSSIGWFRQA PGKEREGVSC ISSSGDSTKY    60
ADSVKGRFTT SRDNAKNTVY LQMNSLKPDD TAVYYCAAFR ATMCGVFPLS PYGKDDWGKG   120
TLVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APELLGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFFLYSKL   420
TVDKSRWQQG NVFSCSVMHE ALHNHYTQKS LSLSPGK                            457

SEQ ID NO: 37          moltype = DNA   length = 1374
FEATURE                Location/Qualifiers
misc_feature           1..1374
                       note = AH3-IgG1-heavy chain
source                 1..1374
                       mol_type = other DNA
                       organism = synthetic construct
SEQUENCE: 37
caggtacagc tggtggagac ggggggaggg ctggtacaac caggcgggtc actgaggctt    60
tcctgtgccg catctggglt cacactggat tattcgtcca tagggtggtt tcggcaggct   120
cctggcaaag agcgtgaggg ggtctcatgt attagtagta gtggtgatag cacaaagtac   180
gccgattccg taaagggccg gtttacaacc tccaggata atgctaagaa caccgtatat   240
ctcagaatga actctctgaa gcccgacgat acggccgtat attactgtgc ggcttttcagg   300
gcgactatgt gcggcgtgtt ccctctgagc ccttacggca aggacgactg ggggcaaggg   360
accctggtga ccgtctcgag tgcgtcgacc aagggcccat cggtcttccc gctagcaccc   420
tcctccaaga gcacctctgg gggcacagcg gccctgggct gcctggtcaa ggactacttc   480
cccgaacctg tgacggtgtc tgtggaactca ggcgccctga ccagcggcgt gcacaccttc   540
ccggctgtcc tacagtcctc aggactctac tccctcagca gcgtggtgac cgtgccctcc   600
agcagcttgg gcacccagac ctacatctgc aacgtgaatc acaagcccag caacaccaag   660
gtggacaaga gagttgagcc caaatcttgt gacaaaactc acacatgccc accgtgccca   720
gcacctgaac tcctgggggg accgtcagtc ttcctcttcc ccccaaaaccc caaggacacc   780
ctcatgatct cccggacccc tgaggtcaca tgcgtggtgg tggacgtgag ccacgaagac   840
cctgaggtca agttcaactg gtacgtggac ggcgtggagg tgcataatgc caagacaaag   900
ccgcggggagg agcagtacaa cagcacgtac cgtgtggtca gcgtcctcac cgtcctgcac   960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga tgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta tagcaagctc   1260
accgtggaca agagcaggtg gcagcagggg aacgtcttct catgctccgt gatgcatgag   1320
gctctgcaca accactacac gcagaagagc ctctccctgt ccccgggtaa atga         1374

SEQ ID NO: 38          moltype = AA   length = 457
FEATURE                Location/Qualifiers
REGION                 1..457
                       note = 5D-IgG1-heavy chain
source                 1..457
                       mol_type = protein
                       organism = synthetic construct
SEQUENCE: 38
QVQLVESGGG LVQPGGSLRL SCEASGFTLD YYGIGWFRQP PGKEREAVSY ISASARTILY    60
ADSVKGRFTI SRDNAKNAVY LQMNSLKRED TAVYYCARRR FSASSVNRWL ADDYDVWGRG   120
TQVAVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKRVEPKSC DKTHTCPPCP   240
APELLGGPSV FLFPPKPKDT LMISRTPEVT CVVVDVSHED PEVKFNWYVD GVEVHNAKTK   300
```

PREEQYNSTY RVVSVLTVLH QDWLNGKEYK CKVSNKALPA PIEKTISKAK GQPREPQVYT    360
LPPSREEMTK NQVSLTCLVK GFYPSDIAVE WESNGQPENN YKTTPPVLDS DGSFFLYSKL    420
TVDKSRWQQG NVFSCSVMHE ALHNHYTQKS LSLSPGK                             457

SEQ ID NO: 39           moltype = DNA  length = 1374
FEATURE                 Location/Qualifiers
misc_feature            1..1374
                        note = 5D-IgG1-heavy chain
source                  1..1374
                        mol_type = other DNA
                        organism = synthetic construct
SEQUENCE: 39
caggtgcaac tggttgaatc tgggggaggc ttggtacaac ctggggggatc cctgagactc     60
tcttgcgagg cctccggatt caccttggac tactatgcga tcggctggtt ccgccagccc    120
ccagggaagg agcgggaggc cgtttcatac attagtgcca gtgcccggac catactgtac    180
gcagactctg tgaagggacg ctttaccatc tctaggaca atgccaaaaa tgctgtgtac     240
ctgcaaatga acagcctcaa gcgggaggat accgcagtgt actactgcgc gagacggcgc    300
ttctccgctt ctagcgtgaa tagatggctg gccgacgact acgacgtgtg gggacgggc     360
acacaggtgg ctgtctcgag cgccgtcgacc aagggcccat cggtcttccc gctagcaccc    420
tcctccaaga gcacctctgg gggcacagcg gccctgggct gcctggtcaa ggactacttc    480
cccgaacctg tgacggtctc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga gagttgagcc caaatcttgt gacaaaactc acacatgccc accgtgccca    720
gcacctgaac tcctgggggg accgtcagtc ttcctcttcc cccaaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga tgatgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta tagcaagctc   1260
accgtggaca agagcaggtg gcagcagggg aacgtcttct catgctccgt gatgcatgag   1320
gctctgcaca accactacac gcagaagagc ctctccctgt ccccgggtaa atga          1374

SEQ ID NO: 40           moltype = AA  length = 228
FEATURE                 Location/Qualifiers
REGION                  1..228
                        note = AA6-IgG1-kappa chain
source                  1..228
                        mol_type = protein
                        organism = synthetic construct
SEQUENCE: 40
QLQLVETGGG LVQPGGSLRL SCAASGFTFS DYVMTWVRQA PGKGPEWIAT INTDGSTMRD     60
DSTKGRFTIS RDNAKNTLYL QMTSLKPEDT ALYYCARGRV ISASAIRGAV RGPGTQVTVS    120
SRTVAAPSVF IFPPSDEQLK SGTASVVCLL NNFYPREAKV QWKVDNALQS GNSQESVTEQ    180
DSKDSTYSLS STLTLSKADY EKHKVYACEV THQGLSSPVT KSFNRGEC                 228

SEQ ID NO: 41           moltype = DNA  length = 687
FEATURE                 Location/Qualifiers
misc_feature            1..687
                        note = AA6-IgG1-kappa chain
source                  1..687
                        mol_type = other DNA
                        organism = synthetic construct
SEQUENCE: 41
caactgcagc tggtagagac aggggggcggc ttagttcagc ctggagggtc tctcagactg     60
tcatgcgctg cctctggctt taccttcagt gactacgtga tgacatgggt ccgccaagct    120
ccagggaagg ggcctgagtg gatcgctact attaatacag atggcagcac aatgcgggac    180
gactccacaa aggggcggtt caccattccc agagacaacg ccaagaatac tctgtacctt    240
cagatgacca gtctgaaacc cgaggacact gctctgtact attgtgcaag aggccgggtg    300
atctctgctt ccgctatcag aggcgcagta aggggcctg aacacaagt aactgtctcg    360
agccgtacag tggctgcacc atctgtcttc atcttcccgc catctgatga gcagttgaaa    420
tctggaactg cctctgttgt gtgcctgctg aataacttct atcccagaga ggccaaagta    480
cagtggaagg tggataacgc cctccaatcg ggtaactccc aggagagtgt cacagagcag    540
gacagcaagg acagcaccta cagcctcagc agcaccctga cgctgagcaa agcagactac    600
gagaaacaca aagtctacgc ctgcgaagtc acccatcagg gcctgagctc gcccgtcaca    660
aagagcttca cagggggaga gtgttga                                        687

SEQ ID NO: 42           moltype = AA  length = 218
FEATURE                 Location/Qualifiers
REGION                  1..218
                        note = E3-IgG1-kappa chain
source                  1..218
                        mol_type = protein
                        organism = synthetic construct
SEQUENCE: 42
QVQLVESGGG LVQTGGSLRL SCASSGSIAG FETVTWSRQA PGKSLQWVAS MTKTNNEIYS     60

```
DSVKGRFIIS RDNAKNTVYL QMNSLKPEDT GVYFCKGPEL RGQGIQVTVS SRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 43             moltype = DNA   length = 657
FEATURE                   Location/Qualifiers
misc_feature              1..657
                          note = E3-IgG1-kappa chain
source                    1..657
                          mol_type = other DNA
                          organism = synthetic construct
SEQUENCE: 43
caagttcagc tggtcgaatc cggggggcgga ctggtccaga caggggggctc cctgaggctc    60
tcctgtgcat cttccggaag catcgccggc ttcgagaccg tgacctggtc tcgccaggct   120
cccgggaagt ctctgcagtg ggtcgcttcc atgactaaga ctaacaacga gatctactct   180
gactcagtga aggccgctt catcatttct agagataacg ctaaaaacac agtgtatctg   240
cagatgaata gtctcaaacc tgaagacaca ggcgtgtatt tctgtaaggg tcctgagctg   300
aggggccagg gcatccaggt aacagtctcg agccgtactg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag acagcaagg acagcaccta cagcctcagc   540
agcaccctga cgctgagcaa agcagactac gagaaacaca agtgctacgc ctgcgaagtc   600
acccatcagg gcctgagctc gcccgtcaca aagagcttca caggggagag tgttga        657

SEQ ID NO: 44             moltype = AA   length = 599
FEATURE                   Location/Qualifiers
REGION                    1..599
                          note = AH3-5D-IgG1 heavy chain
source                    1..599
                          mol_type = protein
                          organism = synthetic construct
SEQUENCE: 44
QVQLVETGGG LVQPGGSLRL SCAASGFTLD YSSIGWFRQA PGKEREGVSC ISSSGDSTKY    60
ADSVKGRFTT SRDNAKNTVY LQMNSLKPDD TAVYYCAAFR ATMCGVFPLS PYGKDDWGKG   120
TLVTVSSGGG GSGGGGSGGG GSQVQLVESG GGLVQPGGSL RLSCEASGFT LDYYGIGWFR   180
QPPGKEREAV SYISASARTI LYADSVKGRF TISRDNAKNA VYLQMNSLKR EDTAVYYCAR   240
RRFSASSVNR WLADDYDVWG RGTQAVASSA STKGPSVFPL APSSKSTSGG TAALGCLVKD   300
YFPEPVTVSW NSGALTSGVH TFPAVLQSSG LYSLSSVVTV PSSSLGTQTY ICNVNHKPSN   360
TKVDKRVEPK SCDKTHTCPP CPAPELLGGP SVFLFPPKPK DTLMISRTPE VTCVVVDVSH   420
EDPEVKFNWY VDGVEVHNAK TKPREEQYNS TYRVVSVLTV LHQDWLNGKE YKCKVSNKAL   480
PAPIEKTISK AKGQPREPQV YTLPPSREEM TKNQVSLTCL VKGFYPSDIA VEWESNGQPE   540
NNYKTTPPVL DSDGSFFLYS KLTVDKSRWQ QGNVFSCSVM HEALHNHYTQ KSLSLSPGK    599

SEQ ID NO: 45             moltype = DNA   length = 1800
FEATURE                   Location/Qualifiers
misc_feature              1..1800
                          note = AH3-5D-IgG1 heavy chain
source                    1..1800
                          mol_type = other DNA
                          organism = synthetic construct
SEQUENCE: 45
caggtacagc tggtggagac ggggggaggg ctggtacaac caggcgggtc actgaggctc    60
tcctgtgccg catctgggtt cacactggat tattcgtcca tagggtggtt tcggcaggct   120
cctggcaaag agcgtgaggg ggtctcatgt attagtagta gtggtgatag cacaaagtac   180
gccgattccg taaagggccg gtttacaacc tccaggggata atgctaagaa caccgtatat   240
ctccagatga actctctgaa gcccgacgat acggccgtat attactgtgc ggcttttcagg   300
gcgactatgt gcggcgtgtt ccctctgagc ccttacggca aggacgactg ggggcaaggggg  360
accctggtga ccgtatcctc aggcggtgga ggtctggtg ggggaggctc agggggtgga    420
ggcagccagg tgcaactggt tgaatctggg ggaggcttgg tacaacctgg ggggatccctg  480
agactctctt gcgaggcctc cggattcacc ttggactact atggcatcgg ctggttccgc   540
cagccccag ggaaggagcg ggaggccgtt tcatacatta gtgccagtgc ccggaccata   600
ctgtacgcag actctgtgaa gggacgcttt accatctcta gggacaatgc aaaaatgct   660
gtgtacctgc aaatgaacag cctgaagcgg aggataccg cagtgtacta ctgcgcgaga   720
cggcgcttct ccgcttctag cgtgaataga tggctggccg acgactacga cgtgtgggga   780
cgggcacac aggtggctgt ctcgagcgcg tcgaccaagg gcccatcggt cttcccgcta   840
gcaccctcct ccaagagcac ctctgggggc acagcggccc tgggctgcct ggtcaaggac   900
tacttccccg aacctgtgac ggtctcgtgg aactcaggcg ccctgaccag cggcgtgcac   960
accttcccgg ctgtcctaca gtcctcagga ctctactccc tcagcagcgt ggtgaccgtg  1020
ccctccagca gcttgggcac ccagacctac atctgcaacg tgaatcacaa gcccagcaac  1080
accaaggtgg acaagagagt tgagcccaaa tcttgtgaca aaactcacac atgcccaccg  1140
tgcccagcac ctgaactcct ggggggaccg tcagtcttcc tcttcccccc aaaacccaag  1200
gacaccctca tgatctcccg gacccctgag gtcacatgcg tggtggtgga cgtgagccac  1260
gaagaccctg aggtcaagtt caactggtac gtggacggcg tggaggtgca taatgccaag  1320
acaaagccgc gggaggagca gtacaacagc acgtaccgtg tggtcagcgt cctcaccgtc  1380
ctgcaccagg actggctgaa tggcaaggag tacaagtgca aggtctccaa caaagccctc  1440
ccagccccca tcgagaaaac catctccaaa gccaaagggc agccccgaga accacaggtg  1500
tacaccctgc ccccatcccg ggaggagatg accaagaacc aggtcagcct gacctgcctg  1560
gtcaaaggct tctatcccag cgacatcgcc gtggagtggg agagcaatgg gcagccggag  1620
aacaactaca agaccacgcc tcccgtgctg gactccgacg gctccttctt cctctatagc  1680
```

```
aagctcaccg tggacaagag caggtggcag caggggaacg tcttctcatg ctccgtgatg   1740
catgaggctc tgcacaacca ctacacgcag aagagcctct ccctgtcccc gggtaaatga   1800

SEQ ID NO: 46          moltype = AA  length = 354
FEATURE                Location/Qualifiers
REGION                 1..354
                       note = AA6-E3-IgG1 light chain
source                 1..354
                       mol_type = protein
                       organism = synthetic construct
SEQUENCE: 46
QLQLVETGGG LVQPGGSLRL SCAASGFTFS DYVMTWVRQA PGKGPEWIAT INTDGSTMRD    60
DSTKGRFTIS RDNAKNTLYL QMTSLKPEDT ALYYCARGRV ISASAIRGAV RGPGTQVTVS   120
SGGGGSGGGG SGGGGSQVQL VESGGGLVQT GGSLRLSCAS SGSIAGFETV TWSRQAPGKS   180
LQWVASMTKT NNEIYSDSVK GRFIISRDNA KNTVYLQMNS LKPEDTGVYF CKGPELRGQG   240
IQVTVSSRTV AAPSVFIFPP SDEQLKSGTA SVVCLLNNFY PREAKVQWKV DNALQSGNSQ   300
ESVTEQDSKD STYSLSSTLT LSKADYEKHK VYACEVTHQG LSSPVTKSFN RGEC         354

SEQ ID NO: 47          moltype = DNA  length = 1065
FEATURE                Location/Qualifiers
misc_feature           1..1065
                       note = AA6-E3-IgG1 light chain
source                 1..1065
                       mol_type = other DNA
                       organism = synthetic construct
SEQUENCE: 47
caactgcagc tggtagagac agggggcggc ttagttcagc ctggagggtc tctcagactg    60
tcatgcgctg cctctggctt taccttcagt gactacgtga tgacatgggt ccgccaagct   120
ccagggaagg ggcctgagtg gatcgctact attaatacag atggcagcac aatgcgggac   180
gactccacaa aggggcggtt caccatttcc agagacaagc ccaagaatac tctgtacctt   240
cagatgacca gtctgaaacc cgaggacact gctctgtact attgtgcaag aggccgggtg   300
atctctgctt ccgctatcag aggcgcagta aggggccctg gaacacaggt aaccgtttca   360
tccgggggag gcggttcagg cggtggggga tctggcgggg gtggatccca gttcagctg    420
gtcgaatccg ggggcggact ggtccagaca gggggctccc tgaggctctc ctgtgcatct   480
tccggaagca tcgccggctt cgagaccgtg acctggtctc gccaggctcc cgggaagtc    540
ctgcagtggg tcgcttccat gactaagact aacaacgaga tctactctga ctcagtgaaa   600
ggccgcttca tcatttctag ataacgct aaaaacacag tgtatctgca gatgaatagt    660
ctcaaacctg aagacacagg cgtgtatttc tgtaaggtc ctgagctgag gggccagggc    720
atccaggtaa cagtctcgag ccgtacggtg gctgcaccat ctgtcttcat cttcccgcca   780
tctgatgagc agttgaaatc tggaactgcc tctgttgtgt gcctgctgaa taacttctat   840
cccagagagg ccaaagtaca gtggaaggtg gataacgccc tccaatcggg taactccag   900
gagagtgtca cagagcagga cagcaaggac agcacctaca gcctcagcag caccctgacg   960
ctgagcaaag cagactacga gaaacacaaa gtctacgcct gcgaagtcac ccatcaggcc  1020
ctgagctcgc ccgtcacaaa gagcttcaac aggggagagt gttga                  1065

SEQ ID NO: 48          moltype = AA  length = 127
FEATURE                Location/Qualifiers
REGION                 1..127
                       note = VHH peptide monomer 5D
source                 1..127
                       mol_type = protein
                       organism = synthetic construct
SEQUENCE: 48
QVQLVESGGG LVQPGGSLRL SCEASGFTLD YYGIGWFRQP PGKEREAVSY ISASARTILY    60
ADSVKGRFTI SRDNAKNAVY LQMNSLKRED TAVYYCARRR FSASSVNRWL ADDYDVWGRG   120
TQVAVSS                                                             127

SEQ ID NO: 49          moltype = DNA  length = 381
FEATURE                Location/Qualifiers
misc_feature           1..381
                       note = VHH peptide monomer 5D
source                 1..381
                       mol_type = other DNA
                       organism = synthetic construct
SEQUENCE: 49
caggtgcagc tcgtggagtc aggtggaggc ttggtgcagc ctgggggtc tctgagactc    60
tcctgtgaag cctctggatt cactttggat tattatggta taggctggtt ccgccagccc   120
ccagggaagg agcgcgaggc ggtctcatat attagtgcca gtgcccgtac gatattgtat   180
gcagattccg tgaagggccg atttaccatc tccagagaca acgcaagcgt ggtgtac ca   240
ctacaaatga acagcctgaa acgtgaggac acggctgtct attactgtgc gaggcggcga   300
ttctccgcgt ctagtgttaa tagatggctt gccgacgact atgacgtctg ggtcggggg    360
acccaggtcg cggtgtcctc a                                             381

SEQ ID NO: 50          moltype = AA  length = 111
FEATURE                Location/Qualifiers
REGION                 1..111
                       note = VHH peptide monomer E3
source                 1..111
                       mol_type = protein
```

```
                                 organism = synthetic construct
SEQUENCE: 50
QVQLVESGGG LVQTGGSLRL SCASSGSIAG FETVTWSRQA PGKSLQWVAS MTKTNNEIYS   60
DSVKGRFIIS RDNAKNTVYL QMNSLKPEDT GVYFCKGPEL RGQGIQVTVS S           111

SEQ ID NO: 51           moltype = DNA  length = 333
FEATURE                 Location/Qualifiers
misc_feature            1..333
                        note = VHH peptide monomer E3
source                  1..333
                        mol_type = other DNA
                        organism = synthetic construct
SEQUENCE: 51
caggtgcagc tcgtggagtc gggcggaggc ttggtgcaga ctgggggtc tctgagactc    60
tcctgtgcat cctctggaag tatcgccggt ttcgaaaccg tgacctggtc ccgccaggct  120
cctgaaagt cgctccagtg ggtcgcatcg atgactaaaa ctaataacga gatctattca   180
gactccgtga agggccgatt catcatctcc agagacaacg ccaagaatac ggtgtatcta  240
caaatgaaca gcctgaaacc tgaggacaca ggcgtctatt tttgtaaagg tcctgagttg  300
aggggccagg ggatccaggt caccgtctcc tcg                                333

SEQ ID NO: 52           moltype = AA  length = 121
FEATURE                 Location/Qualifiers
REGION                  1..121
                        note = VHH peptide monomer AA6
source                  1..121
                        mol_type = protein
                        organism = synthetic construct
SEQUENCE: 52
QLQLVETGGG LVQPGGSLRL SCAASGFTFS DYVMTWVRQA PGKGPEWIAT INTDGSTMRD   60
DSTKGRFTIS RDNAKNTLYL QMTSLKPEDT ALYYCARGRV ISASAIRGAV RGPGTQVTVS  120
S                                                                  121

SEQ ID NO: 53           moltype = DNA  length = 363
FEATURE                 Location/Qualifiers
misc_feature            1..363
                        note = VHH peptide monomer AA6
source                  1..363
                        mol_type = other DNA
                        organism = synthetic construct
SEQUENCE: 53
cagttgcagc tcgtggagac aggggagggc ttggtgcagc ctgggggtc tctgagactc    60
tcctgtgcag cctctggatt cacgttcagt gactacgtca tgacctgggt ccgccaggct  120
ccaggaaagg ggcccgaatg gatcgcaact attaatacgg acggtagcac gatgcgtgat  180
gactccacaa aaggccgatt caccatctcc agagacaacg ccaagaacac actgtatctg  240
caaatgacca gcctgaaacc ggaggacacg gccctgtatt actgtgcgag aggccgcgtg  300
atctccgcct ccgcgataag aggggcggtt aggggcccgg ggacccaggt caccgtctcc  360
tca                                                                363

SEQ ID NO: 54           moltype = AA  length = 126
FEATURE                 Location/Qualifiers
REGION                  1..126
                        note = VHH peptide monomer AH3
source                  1..126
                        mol_type = protein
                        organism = synthetic construct
SEQUENCE: 54
QVQLVETGGL VQPGGSLRLS CAASGFTLDY SSIGWFRQAP GKEREGVSCI SSSGDSTKYA   60
DSVKGRFTTS RDNAKNTVYL QMNSLKPDDT AVYYCAAFRA TMCGVFPLSP YGKDDWGKGT  120
LVTVSS                                                             126

SEQ ID NO: 55           moltype = DNA  length = 378
FEATURE                 Location/Qualifiers
misc_feature            1..378
                        note = VHH peptide monomer AH3
source                  1..378
                        mol_type = other DNA
                        organism = synthetic construct
SEQUENCE: 55
caggtgcagc tcgtggagac gggggggcttg gtgcagcctg ggggtctct gagactctcc   60
tgtgcagcct ctggattcac tttgattat tcgtccatag ctggttccg ccaggcccca   120
gggaaggagc gtgagggggt ctcatgtatt agtagtagtg gtgatagcac aaagtatgca  180
gactccgtga agggccgatt caccacctcc agagacaacg ccaagaacac ggtgtatctg  240
caaatgaaca gcctgaaacc tgacgacaca gccgtttatt actgtgcagc ttttagggcg  300
actatgtgcg gcgtgttccc ccttagcccc tacggcaagg acgactgggg caaagggacc  360
ctggtcaccg tctcctca                                                378

SEQ ID NO: 56           moltype = AA  length = 15
FEATURE                 Location/Qualifiers
REGION                  1..15
```

```
                         note = Flexible linker 1
source                   1..15
                         mol_type = protein
                         organism = synthetic construct
SEQUENCE: 56
GGGGSGGGGS GGGGS                                                        15

SEQ ID NO: 57            moltype = DNA  length = 45
FEATURE                  Location/Qualifiers
misc_feature             1..45
                         note = Flexible linker 1
source                   1..45
                         mol_type = other DNA
                         organism = synthetic construct
SEQUENCE: 57
ggcggtggtg gctctggtgg cggcggttcc ggtggcggtg gcagc                       45

SEQ ID NO: 58            moltype = AA  length = 15
FEATURE                  Location/Qualifiers
REGION                   1..15
                         note = Flexible linker 2
source                   1..15
                         mol_type = protein
                         organism = synthetic construct
SEQUENCE: 58
GGGGSGGGGS GGGGS                                                        15

SEQ ID NO: 59            moltype = DNA  length = 45
FEATURE                  Location/Qualifiers
misc_feature             1..45
                         note = Flexible linker 2
source                   1..45
                         mol_type = other DNA
                         organism = synthetic construct
SEQUENCE: 59
ggtggaggcg gttcaggcgg aggtggctct ggcggtggcg gttcc                       45

SEQ ID NO: 60            moltype = AA  length = 15
FEATURE                  Location/Qualifiers
REGION                   1..15
                         note = Flexible linker 3
source                   1..15
                         mol_type = protein
                         organism = synthetic construct
SEQUENCE: 60
GGGGSGGGGS GGGGS                                                        15

SEQ ID NO: 61            moltype = DNA  length = 45
FEATURE                  Location/Qualifiers
misc_feature             1..45
                         note = Flexible linker 3
source                   1..45
                         mol_type = other DNA
                         organism = synthetic construct
SEQUENCE: 61
ggcggtggtg gctctggtgg cggcggttcc ggtggcggtg gcagc                       45

SEQ ID NO: 62            moltype = AA  length = 259
FEATURE                  Location/Qualifiers
REGION                   1..259
                         note = 5D-E3 heterodimer
source                   1..259
                         mol_type = protein
                         organism = synthetic construct
SEQUENCE: 62
QVQLVESGGG LVQPGGSLRL SCEASGFTLD YYGIGWFRQP PGKEREAVSY ISASARTILY       60
ADSVKGRFTI SRDNAKNAVY LQMETNSLKR EDTAVYYCAR RRFSASSVNR WLADDYDVWG      120
RGTQVAVSSG GGGSGGGGSG GGGSQVQLVE SGGGLVQTGG SLRLSCASSG SIAGFETVTW      180
SRQAPGKSLQ WVASMETTKT NNEIYSDSVK GRFIISRDNA KNTVYLQMET NSLKPEDTGV      240
YFCKGPELRG QGIQVTVSS                                                   259

SEQ ID NO: 63            moltype = DNA  length = 759
FEATURE                  Location/Qualifiers
misc_feature             1..759
                         note = 5D-E3 heterodimer
source                   1..759
                         mol_type = other DNA
                         organism = synthetic construct
SEQUENCE: 63
```

```
caggtgcagc tcgtggagtc aggtggaggc ttggtgcagc ctgggggtc  tctgagactc   60
tcctgtgaag cctctggatt cactttggat tattatggta taggctggtt ccgccagccc  120
ccagggaagg agcgcgaggc ggtctcatat attagtgcca gtgcccgtac gatattgtat  180
gcagattccg tgaagggccg atttaccatc tccagagaca tgccaagaa  cgcggtgtat  240
ctacaaatga acagcctgaa acgtgaggac acggctgtct attactgtgc gaggcggcga  300
ttctccgcgt ctagtgttaa tagatggctt gccgacgact atgacgtctg gggtcggggg  360
acccaggtcg cggtgtcctc aggcggtggt ggctctggtg gcggcggttc cggtggcggt  420
ggcagccagg tgcagctcgt ggagtcgggc ggaggcttgg tgcagactgg ggggtctctg  480
agactctcct gtgcatcctc tggaagtatc gccggtttcg aaaccgtgac ctggtcccgc  540
caggctcctg gaaagtcgct ccagtgggtc gcatcgatga ctaaaactaa taacgagatc  600
tattcagact ccgtgaaggg ccgattcatc atctccagag acaacgccaa gaatacggtg  660
tatctacaaa tgaacagcct gaaacctgag gacacaggcg tctatttttg taaaggtcct  720
gagttgaggg gccaggggat ccaggtcacc gtctcctcg               759

SEQ ID NO: 64              moltype = AA   length = 272
FEATURE                    Location/Qualifiers
REGION                     1..272
                           note = AH3-AA6 heterodimer
source                     1..272
                           mol_type = protein
                           organism = synthetic construct
SEQUENCE: 64
QVQLVETGGL VQPGGSLRLS CAASGFTLDY SSIGWFRQAP GKEREGVSCI SSSGDSTKYA   60
DSVKGRFTTS RDNAKNTVYL QMETNSLKPD DTAVYYCAAF RATMETCGVF PLSPYGKDDW  120
GKGTLVTVSS GGGGSGGGGS GGGGSQLQLV ETGGGLVQPG GSLRLSCAAS GFTFSDYVME  180
TTWVRQAPGK GPEWIATINT DGSTMETRDD STKGRFTISR DNAKNTLYLQ METTSLKPED  240
TALYYCARGR VISASAIRGA VRGPGTQVTV SS                                272

SEQ ID NO: 65              moltype = DNA   length = 786
FEATURE                    Location/Qualifiers
misc_feature               1..786
                           note = AH3-AA6 heterodimer
source                     1..786
                           mol_type = other DNA
                           organism = synthetic construct
SEQUENCE: 65
caggtgcagc tcgtggagac gggggggcttg gtgcagcctg gggggtctct gagactctcc   60
tgtgcagcct ctggattcac tttggattat tcgtccatag gctggttccg ccaggcccca  120
gggaaggagc gtgaggggt ctcatgtatt agtagtagtg gtgatagcac aaagtatgca  180
gactccgtga agggccgatt caccacctcc agagacaacg ccaagaacac ggtgtatctg  240
caaatgaaca gcctgaaacc tgacgacaca gccgtttatt actgtgcagc ttttagggcg  300
actatgtgcg gcgtgttccc ccttagcccc tacggcaagg acgactgggg caaagggacc  360
ctggtcaccg tctcctcagg cggtggtggc tcggtggact cggttccggtggtgcggt       420
agccagttgc agctcgtgga gacaggggga ggcttggtgc agcctggggg gtctctgaga  480
ctctcctgtg cagcctctgg attcacgttc agtgactacg tcatgacctg ggtccgccag  540
gctccaggaa aggggcccga atggatcgca actattaata cggacggtag cacgatgcgt  600
gatgactcca caaaaggccg attcaccatc tccagagaca accaagaa  cacactgtat  660
ctgcaaatga ccagcctgaa accggaggac acgccctgt  attactgtgc gagaggccgc  720
gtgatctccg cctccgcgat aagaggggcg gttagggggcc cggggaccca ggtcaccgtc  780
tcctca                                                                                 786

SEQ ID NO: 66              moltype = AA   length = 6
FEATURE                    Location/Qualifiers
REGION                     1..6
                           note = six-histidine tag
source                     1..6
                           mol_type = protein
                           organism = synthetic construct
SEQUENCE: 66
HHHHHH                                                                                   6

SEQ ID NO: 67              moltype = AA   length = 13
FEATURE                    Location/Qualifiers
REGION                     1..13
                           note = E-tag for protein purification
source                     1..13
                           mol_type = protein
                           organism = synthetic construct
SEQUENCE: 67
GAPVPYPDPL EPR                                                                          13

SEQ ID NO: 68              moltype = DNA   length = 6985
FEATURE                    Location/Qualifiers
misc_feature               1..6985
                           note = Plasmid pD1214-FAKS-His-hABAB-D7
source                     1..6985
                           mol_type = other DNA
                           organism = synthetic construct
SEQUENCE: 68
```

```
tcagaattgg ttaattggtt gtaacactga cccctatttg tttattttc taaatacatt    60
caaatatgta tccgctcatg agacaataac cctgataaat gcttcaataa tattgaaaaa   120
ggaagaatat gagtattcaa catttccgtg tcgcccttat tcccttttt gcggcatttt   180
gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacggatggc atgacagtaa   480
gagaattatg cagtgctgcc ataaccatga gtgataacac tgcggccaac ttacttctga   540
caacgatcgg aggaccgaag gagctaaccg cttttttgca caacatgggg gatcatgtaa   600
ctcgccttga tcgttgggaa ccggagctga atgaagccat accaaacgac gagcgtgaca   660
ccacgatgcc tgtagcgatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatccgga gccggtgagc   840
gtggttctcg cggtatcatc gcagcgctgg ggccagatgg taagccctcc cgtatcgtag   900
ttatctacac gacggggagt caggcaacta tggatgaacg aaatagacag atcgctgaga   960
taggtgcctc actgattaag cattggtaac tcatgaccaa aatcccttaa cgtgagttac  1020
gcgcgtcg ttccactgag cgtcagaccc cgtagaaaag atcaaaggat cttcttgaga   1080
tcctttttt ctgcgcgtaa tctgctgctt gcaaacaaaa aaaccaccgc taccagcggt  1140
ggtttgtttg ccggatcaag agctaccaac tcttttccg aagtaactg gcttcagcag  1200
agcgcagata ccaaatactg ttcttctagt gtagccgtag ttagcccacc acttcaagaa  1260
ctctgtagca ccgcctacat acctcgctct gctaatcctg ttaccagtgg ctgctgccag  1320
tggcgataag tcgtgtctta ccgggttgga ctcaagacga tagttaccgg ataaggcgca  1380
gcggtcgggc tgaacggggg gttcgtgcac acagcccagc ttggagcgaa cgacctacac  1440
cgaactgaga tacctacagc gtgagctatg agaaagcgcc acgcttcccg aagggagaaa  1500
ggcggacagg tatccggtaa gcggcagggt cggaacagga gggagcttcc  1560
agggggaaac gcctggtatc tttatagtcc tgtcgggttt cgccacctct gacttgagcg  1620
tcgatttttg tgatgctcgt cagggggcg gagcctatgg aaaaacgcca gcaacgcggc  1680
cttttacgg ttcctggcct tttgctgcc ttttgctcac atgttctttc ctgcgttatc  1740
ccctgattct gtggataacc gtattaccgc ctttgagtga gctgataccg ctcggggtcg  1800
tgcaggtata gcttcaaaat gtttctactc cttttttact cttccagatt ttctcggact  1860
ccgcgcatcg ccgtaccact tcaaaacacc caagcacagc atactaaatt tccctctttt  1920
cttcctctag ggtgtcgtta attcccgta ctaaaggttt ggaaagaaa aaagtgaccg  1980
cctcgttttct ttttcttcgt cgaaaaaggc aataaaaatt tttatcacgt ttctttttct  2040
tgaaaatttt ttttttgat tttttctct ttcgatgacc tcccattgat atttaagtta  2100
ataaacggac ttcaatttct caagtttcag tttcatttt cttgttctat tacaactttt  2160
tttacttctt gctcattaga aagaaagcat agcaatctaa tctaagttta aatgagattc  2220
ccatctattt tcaccgctgt cttgttcgct gcctcctctg cattggctgc ccctgttaac  2280
actaccactg aagacgagac tgctcaaatt ccagctgaag cagttatcgg ttactctgac  2340
cttgagggtg atttcgacgt cgctgttttg ccttttctcta actccactaa caacggtttg  2400
ttgttcatta acaccactat cgcttccatt gctgctaagg aagagggtgt ctctctcgag  2460
aaaagagagg ccgaagctat gcatcatcat catcatcatc aggtacagct ggtggagacg  2520
ggggaggtg tggtacaacc aggcgggtca ctgaggcttt cctgtgccgc atctggggtc  2580
acactggatt attcgtccat agggtggttt cggcaggctc ctggcaaaga gcgtgagggg  2640
gtctcatgta ttagtagtag tggtgatagc acaaagtacg ccgattccgt aaagggccgg  2700
tttacaacct ccagggataa tgctaagaac accgtatatc tccagatgaa ctctctgaag  2760
cccgacgata cggccgtata ttactgtgcg gctttcaggg cgactatgtg cggcgtgttc  2820
cctctgagcc cttacggcaa ggacgactgg ggcaaggga ccctggtgac cgtatcctca  2880
ggcggtggag ggtctggtgg gggaggctca ggggtggag cagccaggt gcaactggtt  2940
gaatctgggg gaggcttggt acaacctggg ggatccctga actctcttg cgaggcctcc  3000
ggattcacct tggactacta tggcatcggc tggttccgcc agccccccagg gaaggagcgg  3060
gaggccgttt catacattag tgccagtgcc cggaccatac tgtacgcaga ctctgtgaag  3120
ggacgcttta ccatctctag ggacaatgcc aaaaatgctg tgtacctgca aatgaacagc  3180
ctcaagcggg aggataccgc agtgtactac tgcgcgagac ggcgcttctc cgcttctagc  3240
gtgaatagat ggctggccga cgactacgac gtgtggggcc ggggcacaca ggtggctgtg  3300
tcttccggtg gcggaagcgg aggggggcagc ggggtggga gcggtggggg cagccaactg  3360
cagctggtag agacagggg cggcttagtt cagcctggag ggtctctcag actgtcatgc  3420
gctgcctctg gctttacctt cagtgactac gtgatgacat gggtccgcca agctccaggg  3480
aaggggcctg agtggatcgc tactattaat acagatggca gcacaatgcg ggacgactcc  3540
acaaagggc ggttcaccat ttccagagac aacgccaaga atactctga ccttcagatg  3600
accagtctga aacccgagga cactgctctg tactattgtg caagaggccg ggtgatctct  3660
gcttccgcta tcagaggcgc agtaagggg cctggaacac aggtaaccgt ttcatccggg  3720
ggaggcggtt caggcggtgg gggatctggc ggggtggat cccaagttca gctggtcgaa  3780
tccggggggg gactggtcca gacaggggc tccctgtgc atcttcagga  3840
agcatcgccg gcttcgagac cgtgacctgg tctcgccagg ctcccgggaa gtctctgcag  3900
tgggtcgctt ccatgactaa gactaacaac gagatctact ctgactcagt gaaaggccgc  3960
ttcatcattt ctagagataa cgctaaaaac acagtgtatc tgcagatgaa tagtctcaaa  4020
cctgaagaca caggcgtgta tttctgtaag ggtcctgagc tgaggggcca gggcatccag  4080
gtaacagtct cgagtgctcc tacaaaagcc aacggacgg tggtccagag agagaagca  4140
taataaggtt gaatcatgta attagttatg tcacgcttac attcacgccc tccccccaca  4200
tccgctctaa ccgaaaagga aggagttaga caacctgaag tctaggtccc tatttatttt  4260
tttatagtta tgttagtatt aagaacgtta tttatttc aaattttct tttttttctg  4320
tacagacgcg tgtacgcatg taacattata ctgaaaccct tgcttgagaa ggtttttggga  4380
cgctcgaagg ctttaatttg cggccctca cctgcacgca aaagcttttt caattcaatt  4440
catcatttt ttttattct ttttttgat ttcggtttct ttgaaatttt tttgattcgg  4500
taatctccga acagaaggaa gaacgaagga aggagcacag acttagattg gtatatatac  4560
gcatatgtag tgttgaagaa acatgaaatt gcccagtatt cttaacccaa ctgcacagaa  4620
caaaaaccag caggaaacga agataaatca tgtcgaaagc tacatataag gaacgtgctg  4680
ctactcatcc tagtcctgtt gctgccaagc tatttaatat catgcacgaa aagcaaacaa  4740
```

```
acttgtgtgc ttcattggat gttcgtacca ccaaggaatt actggagtta gttgaagcat    4800
taggtcccaa aatttgttta ctaaaaacac atgtggatat cttgactgat ttttccatgg    4860
agggcacagt taagccgcta aaggcattat ccgccaagta caattttta ctcttcgaag     4920
atagaaaatt tgctgacatt ggtaatacag tcaaattgca gtactctgcg ggtgtataca    4980
gaatagcaga atgggcagac attacgaatg cacacgggtg ggtgggccca ggtattgtta    5040
gcggtttgaa gcaggcggca gaagaagtaa caaggaacc tagaggcctt ttgatgttaa     5100
cagaattgtc atgcaagggc tcccatctca ctggagaata tactaagggg actgttgaca    5160
ttgcgaaaag cgacaaagat tttgttatcg gctttattgc tcaaagagac atgggtggaa    5220
gagatgaagg ttacgattgg ttgattatga cacccggtgt gggtttagat gacaagggag    5280
atgcattggg tcaacagtat agaaccgtgg atgatgttgt ctctacagga tctgacatta    5340
ttattgttgg aagaggacta tttgcaaagg gaagggatgc taaggtagag ggtgaacgtt    5400
acagaaaagc aggctgggaa gcatatttga gaagatgcgg ccagcaaaac taaaaactg     5460
tattataagt aaatgcatgt atactaaact cacaaattga agcttcaatt taattatatc    5520
agttattacc cacgctatga tccaatatca aaggaaatga tagcattgaa ggatgagact    5580
aatccaattg aggagtggca gcatatagaa cagctaaagg gtagtgctga aggaagcata    5640
cgatacccg catggaatgg gataatatca caggaggtac tagactacct ttcatcctac     5700
ataaatagac gcatataagt acgcatttaa gcataaacat gcactatgcc gttcttctca    5760
tgtatatata tacacaggca acacgcagat ataggtcgca cgtgaacagt gagctgtatg    5820
tgcgcagctc gcgttgcatt ttcggaagcg ctcgttttcg gaaacgcttt gaagttccta    5880
ttccgaagtt cctattctct agaaagtata ggaacttcag agcgcttttg aaaaccaaaa    5940
gcgctctgaa gtcgcacttt caaaaaacca aaaacgcacc ggactgtaac gagctactaa    6000
aatattgcga ataccgcttc cacaaacatt gctcaaaagt atctctttgc tatatatctc    6060
tgtgctatat ccctatataa cctacccatc caccttcgc tccttgaact tgcatctaaa     6120
ctcgacctct acatttttta tgtttatctc tagtattact ctttagacaa aaaaattgta    6180
gtaagaacta ttcatagagt gaatcgaaaa caatacgaaa atgtaaacat ttcctatacg    6240
tagtatatag agacaaaata gaagaaaccg ttcataattt tctgaccaat gaagaatcat    6300
caacgctatc actttctgtt cacaaagtat gcgcaatcca catcggtata gaatataatc    6360
ggggatgcct ttatcttgaa aaaatgcacc cgcagcttcg ctagtaatca gtaaacgcgg    6420
gaagtggagt caggcttttt ttatggaaga gaaatagac accaaagtag ccttcttcta     6480
accttaacgg acctacagtg caaaaagtta tcaagagact gcattataga gcgcacaaag    6540
gagaaaaaaa gtaatctaag atgctttgtt agaaaaatag cgctctcggg atgcatttt     6600
gtagaacaaa aagaagtat agattctttg ttggtaaaat agcgctctcg cgttgcattt     6660
ctgttctgta aaaatgcagc tcagattctt tgtttgaaaa attagcgctc tcgcgttgca    6720
tttttgtttt acaaaaatga agcacagatt cttcgttggt aaaatagcgc tttcgcgttg    6780
catttctgtt ctgtaaaaat gcagctcaga ttctttgttt gaaaaattag cgctctcgcg    6840
ttgcattttt gttctacaaa atgaagcaca gatgcttcgt tcaggtggca cttttcgggg    6900
aaatgtgcgc ggaacccta tttgtttatt tttctaaata cattcaaata tgtatccgct     6960
catgagacaa taaccctgat attgg                                          6985
```

| | | |
|---|---|---|
| SEQ ID NO: 69 | moltype = DNA length = 6916 | |
| FEATURE | Location/Qualifiers | |
| misc_feature | 1..6916 | |
| | note = Plasmid pD1214-FAKS-hABAB | |
| source | 1..6916 | |
| | mol_type = other DNA | |
| | organism = synthetic construct | |

```
SEQUENCE: 69
tcagaattgg ttaattggtt gtaacactga cccctatttg tttatttttc taaatacatt      60
caaatatgta tccgctcatg agacaataac cctgataaat gcttcaataa tattgaaaaa     120
ggaagaatat gagtattcaa catttccgtg tcgcccttat tcccttttt gcggcatttt      180
gccttcctgt ttttgctcac ccagaaacgc tggtgaaagt aaaagatgct gaagatcgat     240
tgggtgcacg agtgggttac atcgaactgg atctcaacag cggtaagatc cttgagagtt     300
ttcgccccga agaacgtttt ccaatgatga gcactttaa agttctgcta tgtggcgcgg     360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca aacatgggg gatcatgtaa     600
ctcgccttga tcgttgggaa ccggagctga atgaagccat accaaacgac gagcgtgaca    660
ccacgatgcc tgtagcgatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatccgga gccggtgagc    840
gtggttctcg cggtatcatc gcagcgctgg ggccagatgg taagccctcc cgtatcgtag    900
ttatctacac gacggggagt caggcaacta tggatgaacg aaatagacag atcgctgaga    960
taggtgcctc actgattaag cattggtaac tcatgaccaa aatcccttaa cgtgagtta    1020
gcgcgcgtcg ttcactgag cgtcagaccc cgtagaaaag atcaaaggat cttcttgaga    1080
tccttttttt ctgcgcgtaa tctgctgctt gcaaacaaaa aaaccaccgc taccagcggt    1140
ggtttgtttg ccggatcaag agctaccaac tcttttttcg aaggtaactg gcttcagcag    1200
agcgcagata ccaaatactg ttcttctagt gtagccgtag ttagcccacc acttcaagaa    1260
ctctgtagca ccgcctacat acctcgctct gctaatcctg ttaccagtgg ctgctgccag    1320
tggcgataag tcgtgtctta ccgggttgga ctcaagacga tagttaccgg ataaggcgca    1380
gcggtcgggc tgaacggggg gttcgtgcac acagcccagc ttggagcgaa cgacctacac    1440
cgaactgaga tacctacagc gtgagctatg agaaagcgcc acgcttcccg aagggagaaa    1500
ggcggacagg tatccggtaa gcggcagggt cggaacagga gagcgcacga gggagcttcc    1560
agggggaaac gcctggtatc tttatagtc cgtgatttt cgccacctct gacttgagcg    1620
tcgatttttg tgatgctcgt caggggcg gagcctatgg aaaaacgcca gcaacgcggc     1680
cttttacgg ttcctggcct tttgctggc ttttgctcac atgttcttc ctgcgttatc     1740
ccctgattct gtggataacc gtattaccgc ctttgagtga gctgataccg ctcgggtcg    1800
tgcaggtata gcttcaaaat gtttctactc ttttttact cttccagatt ttctcggact    1860
ccgcgcatcg ccgtaccact tcaaaacacc caagcacagc atactaaatt tcccctcttt    1920
```

```
cttcctctag ggtgtcgtta attacccgta ctaaaggttt ggaaaagaaa aaagtgaccg   1980
cctcgtttct ttttcttcgt cgaaaaaggc aataaaaatt tttatcacgt ttctttttct   2040
tgaaaatttt ttttttttgat ttttttctct ttcgatgacc tcccattgat atttaagtta   2100
ataaacggac ttcaatttct caagtttcag tttcattttt cttgttctat tacaactttt   2160
tttacttctt gctcattaga aagaaagcat agcaatctaa tctaagttta aatgagattc   2220
ccatctattt tcaccgctgt cttgttcgct gcctcctctg cattggctgc ccctgttaac   2280
actaccactg aagacgagac tgctcaaatt ccagctgaag cagttatcgg ttactctgac   2340
cttgagggtg atttcgacgt cgctgttttg cctttctcta actccactaa caacggtttg   2400
ttgttcatta acaccactat cgcttccatt gctgctaagg aagagggtgt ctctctcgag   2460
aaaagagagg ccgaagctat gcaggtacag ctggtgggga cgggggagg gctggtacaa   2520
ccaggcgggt cactgaggct ttcctgtgcc gcatctgggt tcacactgga ttattcgtcc   2580
ataggtggt ttcggcaggc tcctggcaaa gagcgtgagg gggtctcatg tattagtagt   2640
agtggtgata gcacaaagta cgccgattcc gtaaagggcc ggtttacaac ctccagggat   2700
aatgctaaga acaccgtata tctccagatg aactctctga agcccgacga tacggccgta   2760
tattactgtg cggctttcag ggcgactatg tgcggcgtgt tccctctgag cccttacggc   2820
aaggacgact ggggcaaggg gaccctggtg accgtatcct caggcggtgg agggtctggt   2880
gggggaggct caggggtgg aggcagccag gtgcaactgt tgaatctgg gggaggcttg   2940
gtacaacctg ggggatccct gagactctct tgcgaggcct ccggattcac cttggactac   3000
tatggcatcg gctggttccg ccagccccca gggaaggagc gggaggccgt ttcatacatt   3060
agtgccagtg cccggaccat actgtacgca gactctgtga agggacgctt taccatctct   3120
agggacaatg ccaaaaatgc tgtgtacctg caaatgaaca gcctcaagcg ggaggatacc   3180
gcagtgtact actgcgcgag acggcgcttc tccgcttcta gcgtgaatag atggctgagc   3240
gacgactacg acgtgtgggg acggggcaca caggtggctg tgtcttccgg tggcggaagc   3300
ggaggggggca gcggggtgg gagcggtggg ggcagccaac tgcagctggt agagacaggg   3360
ggcggcttag ttcagcctgg agggtctctc agactgtcat gcgctgcctc tggctttacc   3420
ttcagtgact acgtgatgac gtgggtccgc caagctcacg ggaagggggcc tgagtggatc   3480
gctactatta atacagatgg cagcacaatg cgggacgact ccacaaaggg gcggttcacc   3540
atttccagag acaacgccaa gaatactctg taccttcaga tgaccagtct gaaacccgag   3600
gacactgctc tgtactattg tgcaagaggc cgggtgatct ctgcttccgc tatcagaggc   3660
gcagtaaggg gccctggaac acaggtaacc gtttcatccg ggaggaggcg ttcaggcggt   3720
ggggggatctg gcggggtgg atcccaagtt cagctggtcg aatccggggg cggactggtc   3780
cagacagggg gctccctgag gctctcctgt gcatcttccg gaagcatcgc cggcttcgag   3840
accgtgacct ggtctcgcca ggctcccggg aagtctctgc agtgggtcgc ttccatgact   3900
aagactaaca acgagatcta ctctgactca gtgaaaggcc gcttcatcat ttctagagat   3960
aacgctaaaa acacagtgta tctgcagatg aatagtctca aacctgaaga cacaggcgtg   4020
tatttctgta agggtcctga gctgagggc cagggcatcc aggtaacagt ctcgagtggt   4080
tgaatcatgt aattagttat gtcacgctta cattcacgcc ctccccccac atccgctcta   4140
accgaaaagg aaggagttag acaacctgaa gtctaggtcc ctatttattt ttttatagtt   4200
atgttagtat taagaacgtt attatattt caaattttttc ttttttttct gtacagacgt   4260
gtgtacgcat gtaacattat actgaaaacc ttgcttgaga aggttttggg acgctcgaag   4320
gctttaattt tcggccccctc acctgcacgc aaaaagcttt tcaattcaat tcatcatttt   4380
tttttttattc ttttttttga tttcggtttc tttgaaattt ttttgattcg gtaatctccg   4440
aacagaagga agaacgaagg aaggagcaca gacttagatt ggtatatata cgcatatgta   4500
gtgttgaaga aacatgaaat tgcccagtat tcttaaccca actgcacaga acaaaaacca   4560
gcaggaaacg aagataaatc atgtcgaaag ctacatataa ggaacgtgct gctactcatc   4620
ctagtcctgt tgctgccaag ctatttaata tcatgcacga aaagcaaaca aacttgtgtg   4680
cttcattgga tgttcgtacc accaaggaat tactggagt agttgaagca ttaggtccca   4740
aaatttgttt actaaaaaca catgtgggata tcttgactga tttttccatg gagggcacag   4800
ttaagccgct aaaggcatta tccgccaagt acaatttttt actcttcgaa gatagaaaat   4860
ttgctgacat tggtaataca gtcaaattgc agtactctgc gggtgtatac agaatagcag   4920
aatgcgaaga cattacgaat gcacacggtg tggtgggccc aggtattgtt agcggtttga   4980
agcaggcggc agaagaagta acaaaggaac ctagaggcct tttgatgtta gcagaattgt   5040
catgcaaggg ctcccctatct actgcgagaat atactaaggg tactgttgac attgcgaaaa   5100
gcgacaaaga ttttgtttatc ggcttttattg ctcaaagaga catgggtgga agagatgaag   5160
gttacgattg gttgattatg acacccggtg tgggtttaga tgacaaggga gatgcattgg   5220
gtcaacagta tagaaccgtg gatgatgttg tctctacagg atctgacatt attattgttg   5280
gaagaggact atttgcaaag ggaagggatg ctaaggtaga gggtgaacgt tacagaaaag   5340
caggctggga agcatatttg agaagatgcg gccagcaaaa ctaaaaaact gtattataag   5400
taaatgctat tatactaaac tcacaaatta gagcttcaat ttaattatat cagttattac   5460
ccacgctatg atccaatatc aaaggaaatg atagcattga aggatgagac taatccaatt   5520
gaggagtggc agcatataga acagctaaag ggtagtgctg aaggaagcat acgataccccc   5580
gcatggaatg ggataaatc acaggaggta ctagactacc tttcatccta cataaataga   5640
cgcatataag tacgcattta agcataaaca cgcactatgc cgttcttctc atgtatatat   5700
atatacaggc aacacgcaga tataggtgcg acgtgaacag tgctgtat gtgcgcagct   5760
cgcgttgcat tttcggaagc gctcgttttc ggaaacgctt tgaagttcct attccgaagt   5820
tcctattctc tagaaagtat aggaacttca gagcgctttt gaaaaccaaa agcgctctga   5880
agtcgcactt tcaaaaaacc aaaaacgcac cggactgtaa cgagctacta aaatattgcg   5940
aataccgctt ccacaaacat tgctcaaaag tatctctttg ctatatatct ctgtgctata   6000
tccctatata acctacccat ccaccttttcg ctccttgaac ttgcatctaa actcgacctc   6060
tacatttttt atgtttatct ctagtattac tcttttagaca aaaaaattgt agtaagaact   6120
attcatagag tgaatcgaaa acaatacgaa aatgtaaaca tttcctatac gtagtatata   6180
gagacaaaat agaagaaacc gttcataatt ttctgaccaa tgaagaatca tcaacgctat   6240
cactttctgt tcacaaagta tgcgcaatcc acatcggtat agaatataat cggggatgcc   6300
tttatctga aaaatgcac ccgcagcttc gctagtaatc agtaagacgg ggaagtgagg   6360
tcaggctttt tttatggaag agaaaataga caccaaagta gccttcttct aaccttaacg   6420
gacctacagt gcaaaaagtt atcaagagac tgcattatag agcgcacaaa ggagaaaaaa   6480
agtaatctaa gatgctttgt tagaaaaata gcgctctcgg gatgcatttt tgtagaacaa   6540
aaaagaagta tagattcttt gttggtaaaa tagcgctctc gcgttgcatt tctgttctgt   6600
aaaaatgcag ctcagattct ttgtttgaaa aattagcgct ctcgcgttgc attttttgttt   6660
```

```
tacaaaaatg aagcacagat tcttcgttgg taaaatagcg ctttcgcgtt gcatttctgt   6720
tctgtaaaaa tgcagctcag attctttgtt tgaaaaatta gcgctctcgc gttgcatttt   6780
tgttctacaa aatgaagcac agatgcttcg ttcaggtggc actttctggg gaaatgtgcg   6840
cggaacccct atttgtttat ttttctaaat acattcaaat atgtatccgc tcatgagaca   6900
ataaccctga tattgg                                                   6916
```

| | | |
|---|---|---|
| SEQ ID NO: 70 | moltype = DNA length = 6833 | |
| FEATURE | Location/Qualifiers | |
| misc_feature | 1..6833 | |
| | note = Plasmid pD1214-AKS-hABAB | |
| source | 1..6833 | |
| | mol_type = other DNA | |
| | organism = synthetic construct | |

SEQUENCE: 70

```
ggttaaatca tgtaattagt tatgtcacgc ttacattcac gccctccccc cacatccgct     60
ctaaccgaaa aggaaggagt tagacaacct gaagtctagg tccctattta ttttttata    120
gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300
ttttttttta ttcttttttt tgatttcggt ttctttgaaa ttttttttgat tcggtaatct  360
ccgaacagaa ggaagaacga aggaaggagc acagacttag attggtatat atacgcatat   420
gtagtgttga agaaacatga aattgcccag tattcttaac ccaactgcac agaacaaaaa   480
ccagcaggaa acgaagataa atcatgtcga aagctacata taaggaacgt gctgctactc   540
atcctagtcc tgttgctgcc aagctattta atatcatgca cgaaaagcaa acaaacttgt   600
gtgcttcatt ggatgttcgt accaccaagg aattactgga gttagttgaa gcattaggtc   660
ccaaaatttg tttactaaaa acacatgtgg atatcttgac tgattttttcc atggagggca  720
cagttaagcc gctaaaggca ttatccgcca agtacaattt tttactcttc gaagatagaa   780
aatttgctga cattggtaat acagtcaaat gcagtactc tgcgggtgta tacagaaatag  840
cagaatgggc agacattacg aatgcacacg gtgtggtggg cccaggtatt gttagcggtt   900
tgaagcaggc ggcagaagaa gtaacaaagg aacctagagg ccttttgatg ttagcagaat   960
tgtcatgcaa gggctcccta tctactggaa aatatactaa gggtactgtt gacattgcga  1020
aaagcgacaa agattttgtt atcggcttta ttgctcaaag agacatgggt ggaagagatg  1080
aaggttacga ttggttgatt atgacacccg tgtgggtttt agatgacaag ggagatgcat  1140
tgggtcaaca gtatagaacc gtgatgatg ttgtctctac aggatctgac attattattg   1200
ttggaagagg actatttgca aagggaaggg atgctaaggt agagggtgaa cgttacagaa  1260
aagcaggctg ggaagcatat ttgagaagat gcggccagca aaactaaaaa actgtattat  1320
aagtaaatgc atgtatacta aactcacaaa ttagagcttc aatttaatta tatcagttat   1380
tacccacgct atgatccaat atcaaaggaa atgatagcat tgaaggatga gactaatcca  1440
attgaggagt ggcagcatat agaacagcta aagggtagtg ctgaaggaag catacgatac  1500
cccgcatgga atgggataat atcacaggag gtactagact accttctcatc ctacataaat  1560
agacgcatat aagtacgcat ttaagcataa acacgcacta tgccgttctt ctcatgtata   1620
tatatataca ggcaacacgc agatataggt gcgacgtgaa cagtgagctg tatgtgcgca   1680
gctcgtcgtt cattttcgga agcgctcgtt ttccgaaacg ctttgaagtt cctattccga  1740
agttcctatt ctctagaaag tataggaact tcagagcgct tttgaaaacc aaaagcgctc   1800
tgaagtcgca ctttcaaaaa accaaaaacg caccggactg taacgagcta ctaaaatatt  1860
gcgaataccg cttccacaaa cattgctcaa aagtatctct ttgctatata tctctgtgct  1920
atatccctat ataacctacc catccaccttt tcgctccttg aacttgcatc taaactcgac   1980
ctctacattt tttatgttta tctctagtat tactctttag acaaaaaat tgtagtaaga   2040
actattcata gagtgaatcg aaaacaatac gaaaatgtaa acatttccta tacgtagtat  2100
atagagacaa aatagaagaa accgttcata attttctgac caatgaagaa tcatcaacgc  2160
tatcactttc tgttcacaaa gtatgcgcaa tccacatcgt tataagaatat aatcgggtat  2220
gcctttatct tgaaaaaatg cacccgcagc ttcgctagta atcagtaaac gcggaagtg    2280
gagtcaggct ttttttatgg aagagaaaat agacaccaaa gtagccttct tctaacctta   2340
acggacctac agtgcaaaaa gttatcaaga gactgcatta tagagcgcac aaaggagaaa  2400
aaaagtaatc taagatgctt tgttagaaaa atagcgctct cgggatgcat ttttgtagaa  2460
caaaaaagaa gtagattct tttgttggta aaatagcgct ctcgcgttgc atttctgttc   2520
tgtaaaaatg cagctcagat tctttgtttg aaaaattagc gctctcgcgt tgcatttttg  2580
ttttacaaaa atgaagcaca gattcttcgt tggtaaaata gcgctttcgc gttgcatttc   2640
tgttctgtaa aaatgcagct cagattcttt gtttgaaaaa ttagcgctct cgcgttgcat  2700
ttttgttcta caaaatgaag cacagatgct tcgttcaggt ggcactttc ggggaaatgt   2760
gcgcggaacc cctatttgtt tatttttcta aatacattca aatatgtatc cgctcatgag   2820
acaataaccc tgatattggt cagaattggt taattggttg taacactgac ccctatttgt  2880
ttattttcct aaatacattc aaatatgtat ccgctcatga gacaataacc ctgataaatg   2940
cttcaataat attgaaaaag gaagaatatg agtattcaac atttccgtgt cgcccttatt   3000
cccttttttg cggcatttg ccttcctgtt tttgctcacc cagaaacgct ggtgaaagta    3060
aaagatgctg aagatcagtt gggtgcacga gtgggttaca tcgaactgga tctcaacagc  3120
ggtaagatcc ttgagagttt tcgccccgaa gaacgttttc caatgatgag cacttttaaa   3180
gttctgctat gtggcgcggt attatcccgt attgacgccg gcaagagca actccggtcgc   3240
cgcatacact attctcagaa tgacttggtt gagtactcac cagtcagaaa agcatcttt   3300
acggatggca tgacagtaag agaattatgc agtgctgcca taaccatgag tgataacact   3360
gcggccaact tacttctgac aacgatcgga ggaccgaagg agctaaccgc ttttttgcac   3420
aacatggggg atcatgtaac tcgccttgat cgttgggaac cggagctgaa tgaagccata   3480
ccaaacgacg agcgtgacac cacgatgcct gtagcgatgg caacaacgtt gcgcaaacta   3540
ttaactggcg aactacttac tctagcttcc cggcaacaat taatagactg gatggaggcg   3600
gataaagttg caggaccact tctgcgctcg gcccttccgg ctggctggtt tattgctgat   3660
aaatccggag ccgtgagcg tggttctcgc ggtatcatcg cagcgctggg gccagatggt    3720
aagccctccc gtatcgtagt tatctacacg acggggagtc aggcaactat ggatgaacga   3780
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
```

```
tcaaaggatc ttcttgagat ccttttttc tgcgcgtaat ctgctgcttg caaacaaaaa    3960
aaccaccgct accagcggtg gtttgtttgc cggatcaaga gctaccaact cttttttccga   4020
aggtaactgg cttcagcaga gcgcagatac caaatactgt tcttctagtg tagccgtagt   4080
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacgggggg ttcgtgcaca cagcccagct   4260
tggagcgaac gacctacacc gaactgagat acctacagcg tgagctatga gaaagcgcca   4320
cgcttcccga agggagaaag gcggacaggt atccggtaag cggcagggtc ggaacaggag   4380
agcgcacgag ggagcttcca gggggaaacg cctggtatct ttatagtcct gtcgggtttc   4440
gccacctctg acttgagcgt cgatttttgt gatgctcgtc aggggggcgg agcctatgga   4500
aaaacgccag caacgcggcc ttttttacggt tcctggcctt ttgctggcct tttgctcaca   4560
tgttctttcc tgcgttatcc cctgattctg tggataaccg tattaccgcc tttgagtgag   4620
ctgataccgc tcggggtcgt gcaggtatag cttcaaaatg tttctactcc tttttttactc   4680
ttccagattt tctcggactc cgcgcatcgc cgtaccactt caaaacaccc aagcacagca   4740
tactaaattt ccccctcttt ttcctctagg gtgtcgttaa ttacccgtac taaaggtttg   4800
gaaaagaaaa aagtgaccgc ctcgtttctt tttcttcgtc gaaaaaggca ataaaaattt   4860
ttatcacgtt tctttttctt gaaaattttt tttttgatt tttttctctt tcgatgacct   4920
cccattgata tttaagttaa taaacggact tcaatttctc aagtttcagt ttcattttc    4980
ttgttctatt acaactttt ttacttcttg ctcattagaa agaaagcata gcaatctaat    5040
ctaagtttaa aatgagattt ccttcaattt ttactgctgt tttattcgca gcatcctccg   5100
cattagctgc tccagtcaac actacaacag aagatgaatt agaaggggat ttcgatgttg   5160
ctgttttgcc attttccgcc agcattgctg ctaaagaaga aggggtatct ctcgagaaaa   5220
gagaggctga agccatgcag gtacagctgg tggagacggg ggggagggctg gtacaaccag   5280
gcgggtcact gaggctttcc tgtgccgcat ctgggttcac actggattat cgtccatag    5340
ggtggtttcg gcaggctcct ggcaaagagc gtgaggggt ctcatgtatt agtagtagtg    5400
gtgatagcac aaagtacgcc gattccgtaa agggccggtt tacaacctcc agggataatg   5460
ctaagaacac cgtatatctc cagatgaact ctctgaagcc cgacgatacg gccgtatatt   5520
actgtgcggc tttcagggcg actatgtgcg gcgtgttccc tctgagccct tacggcaagg   5580
acgactgggg caagggggacc ctggtgaccg tatcctcagg cggtggaggg tctggtgggg   5640
gaggctcagg gggtggaggc agccaggtgc aactggttga atctgggggga ggcttggtac   5700
aacctggggg atccctgaga ctctcttgcg aggcctccgg attcaccttg gactactatg   5760
gcatcggctg gttccgccag ccccagggaa aggagcggga ggccgtttca tacattagtg   5820
ccagtgcccg gaccatactg tacgcagact ctgtgaaggg acgctttacc atctctaggg   5880
acaatgccaa aaatgctgtg tacctgcaaa tgaacagcct caagcgggag gataccgcag   5940
tgtactactg cgcgagacgg cgcttctccg cttctagcgt gaatagatgg ctggccgacg   6000
actacgacgt gtggggacgg ggcacacagg tggctgtgtc ttccggtggc ggaagcggag   6060
ggggcagcgg gggtgggagc ggtggggca gccaactgca gctggtagag acaggggcg    6120
gcttagttca gcctggaggg tctctcagac tgtcatgcgc tgcctctggc tttaccttca   6180
gtgactacgt gatgacatgg gtccgccaag ctccagggaa aggcccctga tggatcgcta   6240
ctattaatac agatgcagc acaatgcggg acgactccac aaaggggcgg ttcaccattt    6300
ccagagacaa cgccaagaat actctgtacc ttcagatgac cagtctgaaa cccgaggaca   6360
ctgctctgta ctattgtgca agaggccggg tgatctctgc ttccgctatc agaggcgcag   6420
taaggggccc tggaacacag gtaaccgttt catccgggg aggcggttca ggcggtgggg    6480
gatctggcgg gggtggatcc caagttcagc tggtcgaatc cgggggcgga ctggtccaga   6540
cagggggctc cctgaggctc tcctgtgcat cttccggaag catcgccggc ttcgagaccg   6600
tgacctggtc tcgccaggct cccggaagt ctctgcagtg ggtcgcttcc atgactaaga   6660
ctaacaacga gatctactct gactcagtga aaggccgctt catcatttct agagataacg   6720
ctaaaaacac agtgtatctg cagatgaata gtctccaaacc tgaagacaca ggcgtgtatt   6780
tctgtaaggg tcctgagctg aggggccagg gcatccaggt aacagtctcg agt           6833
```

SEQ ID NO: 71             moltype = DNA   length = 6821
FEATURE                   Location/Qualifiers
misc_feature              1..6821
                          note = Plasmid pD1214-AK-hABAB
source                    1..6821
                          mol_type = other DNA
                          organism = synthetic construct
SEQUENCE: 71

```
ggttaaatca tgtaattagt tatgtcacgc ttacattcac gccctccccc cacatccgct     60
ctaaccgaaa aggaaggagt tagacaacct gaagtctagg tccctattta tttttttata    120
gttatgttag tattaagaac gttatttata tttcaaattt ttcttttttt tctgtacaga    180
cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300
ttttttttta ttcttttttt tgatttcggt ttctttgaaa tttttttgat tcggtaatct    360
ccgaacagaa ggaagaacga aggaaggagc acagacttag attggtatat atacgcatat    420
gtagtgttga agaaacatga aattgcccag tattcttaac ccaactgcac agaacaaaaa    480
ccagcaggaa acgaagataa atcatgtcga aagctacata taaggaacgt gctgctactc    540
atcctagtcc tgttgctgcc aagctatttta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgattttccc atggagggca    720
cagttaagcc gctaaaggca ttatccgcca agtacaattt tttactcttc gaagatagaa    780
aatttgctga cattggtaat acagtcaaat tgcagtactc tgcgggtgta tacagaatag    840
cagaatgggc agacattacg aatgcacacg tgtggtggg cccaggtatt gttagcggtt    900
tgaagccagg gcagaagaa gtaacaaagg aacctttttgatg ttagcagaat                960
tgtcatgcaa gggctcccta tctactggag aatatactaa gggtactgtt gacattgcga   1020
aaagcgacaa agattttgtt atcggcttta ttgctcaaag agacatgggt ggaagagatg   1080
aaggttacga ttggttgatt atgacacccg gtgtgggttt agatgacaag ggagatgcat   1140
tgggtcaaca gtatagaacc gtggatgatg ttgtctctac aggatctgac attattattg   1200
ttggaagagg actatttgca aagggaaggg atgctaaggt agagggtgaa cgttacgaa    1260
```

```
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg cttttgaagtt cctattccga    1740
agttcctatt ctctagaaag tataggaact tcagagcgct tttgaaaacc aaaagcgctc    1800
tgaagtcgca cttttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct tttttttatgg aagagaaaat agacaccaaa gtagccttct tctaaccttta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460
caaaaaagaa gtatagattc tttgttggta aaatagcgct ctcgcgttgc atttctgttc    2520
tgtaaaaatg cagctcagat tctttgtttg aaaaattagc gctctcgcgt tgcatttttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaaatgaag cacagatgct tcgttcaggt ggcactttttc ggggaaatgt    2760
gcgcggaacc cctatttgtt tatttttcta aatacattca aatatgtatc cgctcatgag    2820
acaataaccc tgatattggt cagaattggt taattggttg taacactgac ccctatttgt    2880
ttattttttct aaatacattc aaatatgtat ccgctcatga caataaacc ctgataaatg    2940
cttcaataat attgaaaaag gaagaatatg agtattcaac atttccgtgt cgcccttatt    3000
cccttttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat ccttttttttc tgcgcgtaat ctgctgcttg caaacaaaaa    3960
aaccaccgct accagcggtg gtttgtttgc cggatcaaga gctaccaact cttttttccga    4020
aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggggg ttcgtgcaca cagcccagct    4260
tggagcgaac gacctacacc gaactgagat acctacagcg tgagctatga gaaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc aggggggcgg agcctatgga    4500
aaaacgccag caacgcggcc tttttacggt tcctggcctt ttgctggcct tttgctcaca    4560
tgttctttcc tgcgttatcc cctgattctg tggataaccg tattaccgcc tttgagtgag    4620
ctgataccgc tcgggtcgt gcaggtatag cttcaaaatg tttctactcc tttttttactc    4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tctttttctt gaaaattttt ttttttgatt tttttctctt tcgatgacct    4920
cccattgata tttaagttaa taaacggact tcaatttctc aagtttcagt ttcattttttc    4980
ttgttctatt acaactttttt ttacttcttg ctcattagaa agaaagcata gcaatctaat    5040
ctaagtttaa aatgagattt ccttcaattt ttactgctgt tttattcgca gcatcctccg    5100
cattagctgc tccagtcaac actacaacag aagatgaatt agaagggat ttcgatgttg    5160
ctgttttgcc attttccgcc agcattgctc taaagaaga aggggtatct ctcgagaaaa    5220
gaatgcaggt acagctggtg gagacgggggg gagggctggt acaaccaggc gggtcactga    5280
ggctttcctg tgccgcatct gggttcacac tggattattc gtccataggg tggtttcggc    5340
aggctcctgg caaagagcgt gaggggtct catgtagtggt gatagcacaa    5400
agtacgccga ttccgtaaag ggccggttta caacctccag ggataatgct aagaacaccg    5460
tatatctcca gatgaactct ctgaagcccg acgatacggc cgtatattac tgtgcggctt    5520
tcagggcgac tatgtgcggc gtgttccctc tgagccctta cggcaaggac gactgggca    5580
aggggaccct ggtgaccgta tcctcaggcg gtggaggggtc tggtggggga ggctcagggg    5640
gtggaggcag tcaaggtcaa ctggttgaat ctgggggagg cttgtacaa cctggggagt    5700
ccctgagact ctcttgcgag gcctccgat tcacctttgga ctactatggc atcggctggt    5760
tccgccagcc cccagggaag gagcgggagg ccgtttcata cattagtgcc agtgcccgga    5820
ccatactgta cgcagactct gtgaagggac gctttaccat ctctagggac aatgccaaaa    5880
atgctgtgta cctgcaaatg aacagcctca agcggggaga taccgcagtg tactactgcg    5940
cgagacggcg cttctccgct tctagcgtga atagatggct ggccgacgac tacgacgtgt    6000
```

```
gggggacgggg cacacaggtg gctgtgtctt ccggtggcgg aagcggaggg ggcagcgggg    6060
gtggggagcgg tggggggcagc caactgcagc tggtagagac aggggggcggc ttagttcagc    6120
ctggagggtc tctcagactg tcatgcgctg cctctggctt taccttcagt gactacgtga    6180
tgacatgggt ccgccaagct ccagggaagg ggcctgagtg gatcgctact attaatacag    6240
atggcagcac aatgcgggac gactccacaa aggggcggtt caccattttcc agagacaacg    6300
ccaagaatac tctgtacctt cagatgacca gtctgaaacc cgaggacact gctctgtact    6360
attgtgcaag aggccgggtg atctctgctt ccgctatcag aggcgcagta aggggccctg    6420
gaacacaggt aaccgtttca tccggggggag gcggttcagg cggtggggga tctggcgggg    6480
gtggatccca agttcagctg gtcgaatccg ggggcggact ggtccagaca gggggctccc    6540
tgaggctctc ctgtgcatct tccggaagca tcgccggctt cgagaccgtg acctggctc    6600
gccaggctcc cgggaagtct ctgcagtggg tcgcttccat gactaagact aacaacgaga    6660
tctactctga ctcagtgaaa ggccgcttca tcatttctag agataacgct aaaaacacag    6720
tgtatctgca gatgaatagt ctcaaacctg aagcacaggg cgtgtatttc tgtaagggtc    6780
ctgagctgag gggccaggggc atccaggtaa cagtctcgag t    6821

SEQ ID NO: 72          moltype = DNA   length = 6707
FEATURE                Location/Qualifiers
misc_feature           1..6707
                       note = Plasmid pD1214-AT-hABAB
source                 1..6707
                       mol_type = other DNA
                       organism = synthetic construct
SEQUENCE: 72
ggttaaatca tgtaattagt tatgtcacgc ttacattcac gccctccccc cacatccgct    60
ctaaccgaaa aggaaggagt tagacaacct gaagtctagg tccctattta ttttttttata    120
gttatgttag tattaagaac gttatttata tttcaaattt ttctttttt tctgtacaga    180
cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300
tttttttta ttctttttt tgatttcggt ttctttgaaa ttttttgat tcggtaatct    360
ccgaacagaa ggaagaacga aggaaggagc acagacttag attggtatat atacgcatat    420
gtagtgttga agaaacatga aattgccag tattcttaac ccaactgcac agaacaaaaa    480
ccagcaggaa acgaagataa atcatgtcga aagctacata taaggaacgt gctgctactc    540
atcctagtcc tgttgctgcc aagctatttta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgatttttcc atggaggggca    720
cagttaagcc gctaaaggca ttatccgcca agtacaattt tttactcttc gaagatagaa    780
aatttgctga cattggtaat acagtcaaat tgcagtactc tgcgggtgta tacagaatag    840
cagaatgggc agacattacg aatgcacacg tgtgtggtggg cccaggtatt gttagcggtt    900
tgaagcaggc ggcagaagaa gtaacaaagg aacctttgat gttagcagaat    960
tgtcatgcaa gggctcccta tctactggag aatatactaa gggtactgtt gacattgcga    1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtataagaacc gtggatgatg ttgtctctac aggatctgac attattattg    1200
ttggaagagg actatttgca aagggaaggg atgctaaggt agagggtgaa cgttacagaa    1260
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat tcaaaagaaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact accttttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg ctttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagacagaa aatagaagaa accgttcata attttctgac caatgaagaa tcatcaacgc    2160
tatcactttc tgttcacaaa gtatgcgcaa tccacatcgg tatagaatat aatcggggat    2220
gccttttatct tgaaaaaatg cacccgcagc ttcgctagta atcagtaaac gcgggaagtg    2280
gagtcaggct ttttttatgg aagagaaaat agacaccaaa gtagccttct tctaaccttaa    2340
acggacctac agtgcaaaaa gttatcaaga gactgcatta tagagcgcac aaaggagaaa    2400
aaaagtaatc taagatgctt tgttagaaaaa atagcgctct cgggatgcat ttttgtagaa    2460
caaaaaagaa gtagattcc tttgttggta aaatagcgct ctcgcgttgc atttctgttc    2520
tgtaaaaatg cagctcagat tctttgtttg aaaaattagc gctctcgcgt tgcattttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaaatgaag tcgttcaggt cgttcaggt tcgttcaggt gggaaaatgt    2760
gcgcggaacc cctatttgtt tatttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga acaataaacc ctgataaatg    2940
cttcaataat attgaaaaag gaagaatatg agtattcaac atttccgtgt cgcccttatt    3000
cccttttttg cggcatttttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
```

```
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctcacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat ccttttttc tgcgcgtaat ctgctgcttg caaacaaaaa    3960
aaccaccgct accagcggtg gtttgtttgc cggatcaaga gctaccaact cttttttccga   4020
aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacgggggg ttcgtgcaca cagcccagct    4260
tggagcgaac gacctacacc gaactgagat acctacagcg tgagctatga aaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc agggggggcgg agcctatgga    4500
aaaacgccag caacgcggcc ttttttacggt tcctggcctt ttgctggcct tttgctcaca    4560
tgttctttcc tgcgttatcc cctgattctg tggataaccg tattaccgcc tttgagtgag    4620
ctgataccgc tcgggggtga gcaggtatag cttcaaaatg tttctactcc ttttttactc    4680
ttccagattt tctcggactc cgcgcatcgc cgtaccactt caaaacaccc aagcacagca    4740
tactaaattt ccctcttttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttttctt gaaaatttt ttttttgatt tttttctctt tcgatgacct    4920
cccattgata tttaagttaa taacgggact tcaattctc aagtttcagt ttcatttttc    4980
ttgttctatt acaactttt ttacttcttg ctcattagaa agaaagcata gcaatctaat    5040
ctaagtttaa aatgagattt ccttcaattt ttactgctgt tttattcgca gcatcctccg    5100
cattagctat gcaggtacag ctggtggaga cgggggggag gctggtacaa ccagcgggt    5160
cactgaggct ttcctgtgcc gcatctgggt tcacactgga ttattcgtcc ataggtggt    5220
ttcggcaggc tcctggcaaa gagcgtgagg gggtctcatg tattagtagt agtggtgata    5280
gcacaaagta cgccgattcc gtaaagggcc ggtttacaac ctccagggat aatgctaaga    5340
acaccgtata tctccagatg aactctctga agcccgacga tacggccgta tattactgtg    5400
cggctttcag ggcgactatg tgcggcgtgt tccctacgag cccttacggc aaggacgact    5460
ggggcaaggg gaccctggtg accgtatcct caggcggtgg agggtctggt gggggaggct    5520
caggggggtgg aggcagccag gtgcaactgg ttgaatctgg gggaggcttg gtacaacctg    5580
ggggatccct gagactctct tgcgaggcct ccggattcac cttggactac tatggcatcg    5640
gctggttccg ccagcccca gggaaggagc ggaggccgt ttcatacatt agtgccagtg    5700
cccggaccat actgtacgca gactctgtga agggacgctt taccatctct gggacaatg    5760
ccaaaaatgc tgtgtacctg caaatgaaca gcctcaagcg ggaggatacc gcagtgtact    5820
actgcgcgag acggcgcttc tccgcttcta gcgtgaatag atggctggcc gacgactacg    5880
acgtgtgggg acggggcaca caggtggctg tgtcttccgg tggcggaagc ggagggggca    5940
gcggggggtgg gagcggtggg ggcagccaac tgcagctggt agagacaggg ggcggcttag    6000
ttcagcctgg agggtctctc agactgtcat gcgctgcctc tggctttacc ttcagtgact    6060
acgtgatgac atgggtccgc caagctccag ggaagggggcc tgagtggatc gctactatta    6120
atacagatgg cagcacaatg cgggacgact ccacaaaggg acggttcacc atttccagag    6180
acaacgccaa gaatactctg taccttcaga tgaccagtct gaaacccgag gacactgctc    6240
tgtactattg tgcaagagc cgggtgatct ctgcttccgc tatcagaggc gcagtaaggg    6300
gccctggaac acaggtaacc gtttcatccg ggggaggcgg ttcaggcggt gggggatctg    6360
gcggggggtgg atcccaagtt cagctggtcg aatccgggg cggactgtc cagacagggg    6420
gctccctgag gctctcctgt gcatcttccg gaagcatcgc cggcttcgag accgtgacct    6480
ggtctcgcca ggctcccggg aagtctctgc agtgggtcgc ttcatgact aagactaaca    6540
acgagatcta ctctgactca gtgaaaggcc gcttcatcat ttctagagat aacgctaaaa    6600
acacagtgta tctgcagatg aatagtctca aacctgaaga cacaggcgtg tatttctgta    6660
agggtcctga gctgaggggc cagggcatcc aggtaacagt ctcgagt            6707
```

SEQ ID NO: 73  moltype = DNA length = 6710
FEATURE     Location/Qualifiers
misc_feature   1..6710
        note = Plasmid pD1214-AA-hABAB
source      1..6710
        mol_type = other DNA
        organism = synthetic construct
SEQUENCE: 73

```
ggttaaatca tgtaattagt tatgtcacgc ttacattcac gccctccccc cacatccgct      60
ctaaccgaaa aggaaggagt tagacaacct gaagtctagg tccctatta tttttttata    120
gttatgttag tattaagaac gttatttata tttcaaattt ttcttttttc tctgtacaga    180
cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300
tttttttta ttctttttt tgatttcggt ttctttgaaa ttttttttgat tcggtaatct    360
ccgaacagaa ggaagaacga aggaaggagc acagacttag attggtatat atacgcatat    420
gtagtgttga agaaacatga aattgccag tattcttaac ccaactgcac agaacaaaaa    480
ccagcaggaa acgaagataa atcatgtcga aagctacata taaggaacgt gctgctactc    540
atcctagtcc tgttgctgcc aagctatta atatcatgca cgaaaagcaa acaaactgt    600
gtgcttcatt ggatgttcgt accaccaagg aattactgga gttagttgaa gcattaggtc    660
ccaaaatttt tttactaaaa acacatgtgg atatcttgac tgatttttcc atggagggca    720
cagttaagcc gctaaaggca ttatccgcca agtacaattt tttactcttc gaagatagaa    780
aatttgctga cattggtaat acagtcaaat tgcagtactc tgcgggtgta tacagaatag    840
```

```
cagaatgggc agacattacg aatgcacacg gtgtggtggg cccaggtatt gttagcggtt   900
tgaagcaggc ggcagaagaa gtaacaaagg aacctagagg cctttttgatg ttagcagaat   960
tgtcatgcaa gggctcccta tctactggag aatatactaa gggtactgtt gacattgcga  1020
aaagcgacaa agattttgtt atcggcttta ttgctcaaag agacatgggt ggaagagatg  1080
aaggttacga ttggtttgatt atgacacccg gtgtgggttt agatgacaag ggagatgcat  1140
tgggtcaaca gtatagaacc gtggatgatg ttgtctctac aggatctgac attattattg  1200
ttggaagagg actatttgca aagggaaggg atgctaaggt agagggtgaa cgttacagaa  1260
aagcaggctg ggaagcatat ttgagaagat gcggccagca aaactaaaaa actgtattat  1320
aagtaaatgc atgtatacta aactcacaaa ttagagcttc aatttaatta tatcagttat  1380
tacccacgct atgatccaat atcaaaggaa atgatagcat tgaaggatga gactaatcca  1440
attgaggagt ggcagcatat agaacagcta aagggtagtg ctgaaggaag catacgatac  1500
cccgcatgga atgggataat atcacaggag gtactagact acctttcatc ctacataaat  1560
agacgcatat aagtacgcat ttaagcataa acacgcacta tgccgttctt ctcatgtata  1620
tatatataca ggcaacacgc agatataggt gcgacgtgaa cagtgagctg tatgtgcgca  1680
gctcgcgttg cattttcgga agcgctcgtt ttcggaaacg ctttgaagtt cctattccga  1740
agttcctatt ctctagaaag tataggaact tcagagcgct tttgaaaacc aaaagcgctc  1800
tgaagtcgca ctttcaaaaa accaaaaacg caccggacta taacgagcta ctaaaatatt  1860
gcgaataccg cttccacaaa cattgctcaa aagtatctct ttgctatata tctctgtgct  1920
atatccctat ataacctacc catccaccttt tcgctccttg aacttgcatc taaactcgac  1980
ctctacattt tttatgttta tctcctagtat tactctttag acaaaaaaat tgtagtaaga  2040
actattcata gagtgaatcg aaaacaatac gaaaatgtaa acatttccta tacgtagtat  2100
atagaacaaa aatagaagaa accgttcata attttctgac caatgaagaa tcatcaacgc  2160
tatcactttc tgttcacaaa gtatgcgcaa tccacatcgg tatagaatat aatcggggat  2220
gcctttatct tgaaaaaatg cacccgcagc ttcgctagta atcagtaaac gcgggaagtg  2280
gagtcaggct ttttttatgg aagagaaaat agacaccaaa gtagccttct tctaaccttta  2340
acggacctac agtgcaaaaa gttatcaaga gactgcatta tagagcgcac aaaggagaaa  2400
aaaagtaatc taagatgctt tgttagaaaa atagcgctct cgggatgcat tttttgtagaa  2460
caaaaaagaa gtatagattc tttgttggta aaatagcgct ctcgcgttgc atttctgttc  2520
tgtaaaaatg cagctcagat tctttgtttg aaaaattagc gctctcgcgt tgcattttttg  2580
ttttacaaaa atgaagcaca gattcttcgt tggtaaaata gcctttcgc gttgcatttc  2640
tgttctgtaa aaatgcagct cagattcttt gtttgaaaaa ttagcgctct cgcgttgcat  2700
ttttgttcta caaatgaag cacagatgct tcgttcaggt ggcactttttc ggggaaatgt  2760
gcgcggaacc cctatttgtt tattttttcta aatacattca aatatgtatc cgctcatgag  2820
acaataaccc tgatattggt caagaattggt taattggttg taacactgac ccctatttgt  2880
ttatttttct aaatacattc aaatatgtat ccgctcatga gacaataacc ctgataaatgt  2940
cttcaataat attgaaaaag gaagaatatg agtattcaac atttccgtgt cgcccttatt  3000
ccctttttttg cggcattttg ccttcctgtt tttgctcacc cagaaacgct ggtgaaagta  3060
aaagatgctg aagatcagtt gggtgcacga gtgggttaca tcgaactgga tctcaacagc  3120
ggtaagatcc ttgagagttt tcgccccgaa gaacgtttcc caatgatgag cactttttaaa  3180
gttctgctat gtggcgcggt attatcccgt attgacgccg ggcaagagca actcggtcgc  3240
cgcatacact attctcagaa tgacttggtt gagtactcac cagtcacaga aaagcatctt  3300
acggatggca tgacagtaag agaattatgc agtgctgcca taaccatgag tgataacact  3360
gcggccaact tacttctgac aacgatcgga ggaccgaagg agctaaccgc ttttttgcac  3420
aacatggggg atcatgtaac tcgccttgat cgttgggaac cggagctgaa tgaagccata  3480
ccaaacgacg agcgtgacac cacgatgcct gtagcgatgg caacaacgtt gcgcaaacta  3540
ttaactggcg aactacttac tctagcttcc cggcaacaat taatagactg gatggaggcg  3600
gataaagttg caggaccact tctgcgctcg gcccttccgg ctggctgttt tattgctgat  3660
aaatccggag ccggtgagcg tggttctcgc ggtatcatcg cagcgctggg gccagatggt  3720
aagccctccc gtatcgtagt tatctacacg acggggagtc aggcaactat ggatgaacga  3780
aatagacaga tcgctgagat aggtgcctca ctgattaagc attggtaact catgaccaaa  3840
atcccttaac gtgagttacg cgcgcgtcgt tccactgagc gtcagacccc gtagaaaaga  3900
tcaaaggatc ttcttgagat cctttttttc tgcgcgtaat ctgctgcttg caaacaaaaa  3960
aaccaccgct accagcggtg gtttgtttgc cggatcaaga gctaccaact ctttttccga  4020
aggtaactgg cttcagcaga gcgcagatac caaatactgt tcttctagtg tagccgtagt  4080
tagcccacca cttcaagaac tctgtagcac cgcctacata cctcgctctg ctaatcctgt  4140
taccagtggc tgctgccagt ggcgataagt cgtgtcttac cgggttggac tcaagacgat  4200
agttaccgga taaggcgcag cggtcgggct gaacggggggg ttcgtgcaca cagcccagct  4260
tggagcgaac gacctacacc gaactgagat acctacagcg tgagctatga gaaagcgcca  4320
cgcttcccga aggagaaag gcggacaggt atccggtaag cggcagggtc ggaacaggag  4380
agcgcacgag ggagcttcca gggggaaacg cctggtatct ttatagtcct gtcgggtttc  4440
gccacctctg acttgagcgt cgatttttgt gatgctcgtc aggggggcgg agcctatgga  4500
aaaacgccag caacgcggcc tttttacggt tcctggcctt ttgctggcct tttgctcaca  4560
tgttctttcc tgcgttatcc cctgattctg tggataaccg tattaccgcc tttgagtgag  4620
ctgataccgc tcgggggtcgt gcaggtatag ctctcaaaatg ttttctactcc ttttttactc  4680
ttccagattt tctcggactc cgcgcatcgc cgtaccactt caaaacaccc aagcacagca  4740
tactaaattt cccctctttc ttcctctagg gtgtcgttaa ttacccgtac taaaggtttg  4800
gaaaagaaaa aagtgaccgc ctcgtttctt tttcttcgtc gaaaaaggca ataaaaattt  4860
ttatcacgtt tctttttttctt gaaaattttt tttttttgatt ttttctctt tcgatgacct  4920
cccattgata tttaagttaa taaacggact tcaatttcgt aagtttcagt tcatttttc  4980
ttgttctatt acaactttttt ttacttcttg ctcattagaa agaaagcata gcaatctaat  5040
ctaagtttaa aatggttgcc tggtggtccc ttttcctgta cggtttacaa gtcgctgctc  5100
ctgcattggc aatgcaggta cagctggtgg agacgggggg agggctggta caaccaggcg  5160
ggtcactgag gctttcctgt gccgcatctg ggttcacact ggattattcg tccataggggt  5220
ggtttccgca ggctcctggc aaagagcgtg aggggtcctc atgattattagt agtagtggtg  5280
atagcacaaa gtacgccgat tccgtaaagg gccggtttac aacctccagg gataatgcta  5340
agaacaccgt atatctccag atgaactctc tgaagcccga cgatacgcc gtatattact  5400
gtgcggcttt cagggcgact atgtgcgcg tgttccctct gagcccttac ggcaaggacg  5460
actggggcaa ggggaccctg gtgaccgtat cctcaggcgg tggagggtct ggtggggag  5520
gctcaggggg tggaggcagc caggtgcaac tggttgaatc tgggggaggc ttggtacaac  5580
```

```
ctgggggatc cctgagactc tcttgcgagg cctccggatt cacccttggac tactatggca  5640
tcggctggtt ccgccagccc ccagggaagg agcgggaggc cgtttcatac attagtgcca  5700
gtgcccggac catactgtac gcagactctg tgaaggacg  ctttaccatc tctagggaca  5760
atgccaaaaa tgctgtgtac ctgcaaatga acagcctcaa gcgggaggat accgcagtgt  5820
actactgcgc gagacggcgc ttctccgctt ctagcgtaga tagatggctg gccgacgact  5880
acgacgtgtg gggacggggc acacaggtgg ctgtgtcttc cggtggcgga agcggagggg  5940
gcagcggggg tgggagcggt gggggcagcc aactgcagct ggtagagaca ggggggcggct  6000
tagttcagcc tggagggtct ctcagactgt catgcgctgc ctctggcttt accttcagtg  6060
actacgtgat gacatgggtc cgccaagctc cagggaaggg gcctgagtgg atcgctacta  6120
ttaatacaga tggcagcaca atgcgggacg actccacaaa ggggcggttc accatttcca  6180
gagacaacgc caagaatact ctgtaccttc agatgaccag tctgaaaccc gaggacactg  6240
ctctgtacta ttgtgcaaga ggccgggtga tctctgcttc cgctatcaga ggcgcagtaa  6300
ggggccctgg aacacaggta accgtttcat ccggggggagg cggttcaggc ggtggggggat  6360
ctggcggggg tggatcccaa gttcagctgg tcgaatccgg gggcggactg gtccagacag  6420
ggggctccct gaggctctcc tgtgcatctt ccggaagcat cgccggcttc gagaccgtga  6480
cctggtctcg ccaggctccc gggaagtctc tgcagtgggt cgcttccatg actaagacta  6540
acaacgagat ctactctgac tcagtgaaag gccgcttcat catttctaga gataacgcta  6600
aaaacacagt gtatctgcag atgaatagtc tcaaacctga agacacaggc gtgtatttct  6660
gtaagggtcc tgagctgagg ggccagggca tccaggtaac agtctcgagt              6710

SEQ ID NO: 74           moltype = DNA  length = 6704
FEATURE                 Location/Qualifiers
misc_feature            1..6704
                        note = Plasmid pD1214-GA-hABAB
source                  1..6704
                        mol_type = other DNA
                        organism = synthetic construct
SEQUENCE: 74
ggttaaatca tgtaattagt tatgtcacgc ttacattcac gccctccccc cacatccgct    60
ctaaccgaaa aggaaggagt tagacaacct gaagtctagg tccctatttta ttttttttata  120
gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300
ttttttttta ttcttttttt tgatttcggt ttctttgaaa ttttttgat tcggtaatct   360
ccgaacagaa ggaagaacga aggaaggagc acagacttag attggtatat atacgcatat   420
gtagtgttga agaaacatga aattgcccag tattcttaac ccaactgcac agaacaaaaa   480
ccagcaggaa acgaagataa atcatgtcga aagctcacata taaggaacgt gctgctactc   540
atcctagtcc tgttgctgcc aagctattta atatcatgca cgaaaagcaa acaaacttgt   600
gtgcttcatt ggatgttcgt accaccaagg aattactgga gttagttgaa gcattaggtc   660
ccaaaatttg tttactaaaa acacatgtgg atatcttgac tgatttttcc atggagggca   720
cagttaagcc gctaaaggca ttatccgcca agtacaattt tttactcttc gaagatagaa   780
aatttgctga cattggtaat acagtcaaat gcagtactc  tgcgggtgta tacagaatag   840
cagaatgggc agacattacg aatgcacacg gtgtggtggg cccaggtatt gttagcgatt   900
tgaagcaggc ggcagaagaa gtaacaaagg aacctagagg cctttgatg ttagcagaat   960
tgtcatgcaa gggctcccta tctactggag aatatactaa gggtactgtt gacattgcga  1020
aaagcgacaa agattttgtt atcggcttta ttgctcaaag agacatgggt ggaagagatg  1080
aaggttacga ttggttgatt atgacacccg gtgtgggttt agatgacaag ggagatgcat  1140
tgggtcaaca gtatagaacc gtggatgatg ttgtctctac aggatctgac attattattg  1200
ttggaagagg actatttgca aagggaaggg atgctaaggt agagggtgaa cgttacagaa  1260
aagcaggctg ggaagcatat ttgagaagat gcggccagca aaactaaaaa actgtattat  1320
aagtaaatgc atgtatacta aactcacaaa ttagagcttc aatttaatta tatcagttat  1380
tacccacgct atgatccaat atcaaaggaa atgatagcat tgaaggatga gactaatcca  1440
attgaggagt ggcagcatat agaacagcta aagggtagtg ctgaaggaag catacgatac  1500
cccgcatgga atgggataat atcacaggag gtactagact accttttcatc ctacataaat  1560
agacgcatat aagtacgcat ttaagcataa acacgcatca tgccgttctt ctcatgtata  1620
tatatataca ggcaacacgc agatataggt gcgacgtgaa cagtgagctg tatgtgcgca  1680
gctcgcgttg cattttcgga agcgctcgtt tcggaaacg  ctttgaagtt cctattccga  1740
agttcctatt ctctagaaag tataggaact tcagagcgct tttgaaaacc aaaagcgctc  1800
tgaagtcgca ctttcaaaaa accaaaaacg caccggactg taacgagcta ctaaaatatt  1860
gcgaataccg cttccacaaa cattgctcaa aagtatctct ttgctatata tctctgtgct  1920
atatccctat ataacctacc catccaccctt tcgctccttg aacttgcatc taaactcgac  1980
ctctacattt tttatgttta tctctagtat tactcttta  acaaaaaaat tgtagtaaga  2040
actattcata gagtgaatcg aaaacaatac gaaaatgtaa acatttccta tacgtagtat  2100
atagagacaa aatagaagaa accgttcata attttctgac caatgaagaa tcatcaacgc  2160
tatcactttc tgttcacaaa gtatgcgcaa tccacatcgg tatagaatat aatcgggat   2220
gcctttatct tgaaaaaatg cacccgcagc ttcgctagta atcagtaaac gcgggaagtg  2280
gagtcaggct ttttttatgg aagagaaaat agacaccaaa gtagccttct tctaacctta  2340
acggacctac agtgcaaaaa gttatcaaga gactgcatta tagagcgcac aaaggagaaa  2400
aaaagtaatc taagatgctt tgttagaaaa atagcgctct cgggatgcat ttttgtagaa  2460
caaaaaagaa gtagagattc tttgttggta aaatagcgct ctcgcgttgc atttctgttc  2520
tgtaaaaatg cagctcagat tctttgtttg aaaaattagc gctctcgcgt tgcatttttg  2580
ttttacaaaa atgaagcaca gattcttcgt tggtaaaata gcgctttcgc gttgcatttc  2640
tgttctgtaa aaatgcagct cagattcttt gtttgaaaaa ttagcgctct cgcgttgcat  2700
ttctgttcta caaaatgaag cacagatgct tcgttcaggt ggcactttcg gggaaatgt   2760
gcgcggaacc cctatttgtt tattttcta  aatacattca aatatgtatc cgctcatgag  2820
acaataaccc tgatattggt cagaattggt taattggttg taacactgac ccctatttgt  2880
ttattttttct aaatacattc aaatatgtat ccgctcatga caataaacc  ctgataaatg  2940
cttcaataat attgaaaaag gaagaatatg agtattcaac atttccgtgt cgcccttatt  3000
cccttttttg cggcattttg ccttcctgtt tttgctcacc cagaaacgct ggtgaaagta  3060
```

```
aaagatgctg aagatcagtt gggtgcacga gtgggttaca tcgaactgga tctcaacagc   3120
ggtaagatcc ttgagagttt tcgcccgaa gaacgttttc caatgatgag cactttttaaa   3180
gttctgctat gtggcgcggt attatcccgt attgacgccg ggcaagagca actcggtcgc   3240
cgcatacact attctcagaa tgacttggtt gagtactcac cagtcacaga aaagcatctt   3300
acggatggca tgacagtaag agaattatgc agtgctgcca taaccatgag tgataacact   3360
gcggccaact tacttctgac aacgatcgga ggaccgaagg agctaaccgc ttttttgcac   3420
aacatggggg atcatgtaac tcgccttgat cgttgggaac cggagctgaa tgaagccata   3480
ccaaacgacg agcgtgacac cacgatgcct gtagcgatgg caacaacgtt gcgcaaacta   3540
ttaactggcg aactacttac tctagcttcc cggcaacaat aatagactg gatggaggcg   3600
gataaagttg caggaccact tctgcgctcg ccccttccgg ctggctggtt tattgctgat   3660
aaatccggag ccgtgagcg tggttctcgc ggtatcatcg cagcgctggg gccagatggt   3720
aagccctccc gtatcgtagt tatctacacg acggggagtc aggcaactat ggatgaacga   3780
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
tcaaaggatc ttcttgagat ccttttttc tgcgcgtaat ctgctgcttg caaacaaaaa   3960
aaccaccgct accagcggtg gtttgtttgc cggatcaaga gctaccaact cttttttccga   4020
aggtaactgg cttcagcaga gcgcagatac caaatactgt tcttctagtg tagccgtagt   4080
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacgggggg ttcgtgcaca cagcccagct   4260
tggagcgaac gacctacacc gaactgagat acctacagcg tgagctatga gaaagcgcca   4320
cgcttcccga agggagaaa gcggacaggt atccggtaag cggcagggtc ggaacaggag   4380
agcgcacgag ggagcttcca gggggaaacg cctggtatct ttatagtcct gtcgggtttc   4440
gccacctctg acttgagcgt cgatttttgt gatgctcgtc agggggggcgg agcctatgga   4500
aaaacgccca caacgcggcc ttttacggt tcctggcctt ttgctggcct tttgctcaca   4560
tgttcttttcc tgcgttatcc cctgattctg tggataaccg tattaccgcct ttgagtgag   4620
ctgataccgc tcgggtcgt gcaggtatag cttcaaaatg tttctactcc ttttttactc   4680
ttccagattt tctcggactc cgcgcatcgc cgtaccactt caaaacaccc aagcacagca   4740
tactaaattt ccctctcttc ttcctctagg gtgtcgttaa ttacccgtac taaaggtttg   4800
gaaaagaaaa aagtgaccgc ctcgtttctt ttctttcgtc gaaaaaaggca ataaaattt   4860
ttatcacgtt tctttttcct gaaaattttt tttttgatt ttttttctctt tcgatgacct   4920
cccattgata tttaagttaa taaacggact tcaattcttc aagtttcagt ttcatttttc   4980
ttgttctatt acaactttt ttacttcttg ctcattagaa agaaagcata gcaatctaat   5040
ctaagtttaa aatgtcttt agatcacttt tagctctgtc cggtttggtt tgtagtggat   5100
tggcaatgca ggtacagctg gtggagacg ggggagggct ggtacaacca ggcgggtcac   5160
tgaggctttc ctgtgccgca tctgggttca cactggatta ttcgtccata gggtggtttc   5220
ggcaggctcc tggcaaagag cgtgagggg tctcatgtat tagtagtagt ggtgatagca   5280
caaagtacgc cgattccgta aagggccggt ttacaacctc cagggataat gctaagaaca   5340
ccgtatatct ccagatgaac tctctgaagc cgacgatac tgctgtatat tactgtgcgg   5400
cttttcagggc gactatgtgc ggcgtgttcc ctctgagccc ttacggcaag acgactggg   5460
gcaaggggac cctggtgacc gtatcctcag gcggtgagg gtctggtggg ggaggctcag   5520
ggggtggagg cagccaggtg caactggttg aatctggggg aggcttggta caacctgggg   5580
gatccctgag actctcttgc gaggcctccg gattcaccttt ggactctat ggcatcgact   5640
ggttccgcca gccccagg aaggagcggg aggccgtttc atacattagt gccagtgccc   5700
ggaccatact gtacgcagac tctgtgaagg gacgctttac catctctagg gacaatgcca   5760
aaaatgctgt gtacctgcaa atgaacagcc tcaagcggga ggataccgca gtgtactact   5820
gcgcgaaggg gcgcttctcc gcttctagcg tgaatagatg gctggccgac gactacgacg   5880
tgtggggacg gggcacacag gtggctgtgt cttccggtgg cggaagcgga ggggcagcg   5940
ggggtggag cggtggggc agccaactgc agctggtaga gacaggggc ggcttagttc   6000
agcctggagg gtctctcaga ctgtcatgcg ctgcctctgg ctttaccttc agtgactacg   6060
tgatgacatg ggtccgccaa gctccaggga aggggcctga gtggatcgct actattaata   6120
cagatggcag cacaatgcgg gacgactcca caaaggggcg gttcaccatt tccagagaca   6180
acgccaagaa tactctgtac cttcagatga ccagtctgaa accgaggac actgctctgt   6240
actattgtgc aagaggccgg gtgatctctg cttccgctat cagaggcgca gtaaggggcc   6300
ctggaacaca ggtaaccgtt tcatccgggg gaggcggttc aggcggttgg ggatctggcg   6360
ggggtggatc ccaagttcag ctggtcgaat ccggggggcgg actggtccag acagggggct   6420
ccctgaggct ctcctgtgca tcttccggaa gcatcgccgg cttcgagacc gtgacctggt   6480
ctcgccaggc tcccgggaag tctctgcagt gggtcgcttc catgactaag actaacaacg   6540
agatctactc tgactcagtg aaaggccgct tcatcatttc tagagataac gctaaaaaca   6600
cagtgtatct gcagatgaat agtctcaaac tgaagacac aggctgtat ttctgtaagg   6660
gtcctgctgc agggggccag ggcatccagg taacgctctc gagt          6704
```

```
SEQ ID NO: 75          moltype = DNA  length = 6698
FEATURE                Location/Qualifiers
misc_feature           1..6698
                       note = Plasmid pD1214-IN-hABAB
source                 1..6698
                       mol_type = other DNA
                       organism = synthetic construct
SEQUENCE: 75
ggttaaatca tgtaattagt tatgtcacgc ttacattcac gccctccccc cacatccgct    60
ctaaccgaaa aggaaggagt tagacaacct gaagtctagg tccctatta ttttttttata   120
gttatgttag tattaagaac gttattata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300
tttttttta ttctttttt tgatttcggt ttctttgaaa tttttttgat tcggtaatct   360
ccgaacagaa ggaagaacga aggaaggagc acagacttag attggtatat atacgcatat   420
gtagtgttga agaaacatga aattgcccag tattcttaac ccaactgcac agaacaaaaa   480
ccagcaggaa acgaagataa atcatgtcga aagctacata taaggaacgt gctgctactc   540
```

```
atcctagtcc tgttgctgcc aagctattta atatcatgca cgaaaagcaa acaaacttgt   600
gtgcttcatt ggatgttcgt accaccaagg aattactgga gttagttgaa gcattaggtc   660
ccaaaatttg tttactaaaa acacatgtgg atatcttgac tgatttttcc atggagggca   720
cagttaagcc gctaaaggca ttatccgcca agtacaattt tttactcttc gaagatagaa   780
aatttgctga cattggtaat acagtcaaat tgcagtcatc tgcgggtgta tacagaatag   840
cagaatgggc agacattacg aatgcacacg gtgtggtggg cccaggtatt gttagcggtt   900
tgaagcaggc ggcagaagaa gtaacaaagg aacctagagg cctttgatg ttagcagaat    960
tgtcatgcaa gggctcccta tctactggag aatatactaa gggtactgtt gacattgcga  1020
aaagcgacaa agattttgtt atcggcttta ttgctcaaag agacatgggt ggaagagata  1080
aaggttacga ttggttgatt atgacacccg gtgtgggttt agatgacaag ggagatgcat  1140
tgggtcaaca gtatagaacc gtggatgatg ttgtctctac aggatctgac attattattg  1200
ttggaagagg actatttgca aagggaaggg atgctaaggt agagggtgaa cgttacagaa  1260
aagcaggctg ggaagcatat ttgagaagat gcggccagca aaactaaaaa actgtattat  1320
aagtaaatgc atgtatacta aactcacaaa ttagagcttc aatttaatta tatcagttat  1380
tacccacgct atgatccaat atcaaaggaa atgatagcat tgaaggatga gactaatcca  1440
attgaggagt ggcagcatat agaacagcta aagggtagtg ctgaaggaag catacgatac  1500
cccgcatgga atgggataat atcacaggag gtactagact acctttcatc ctacatanaat 1560
agacgcatat aagtacgcat ttaagcataa acacgcacta tgccgttctt ctcatgtata  1620
tatatataca ggcaacacgc agatataggt gcgacgtgaa cagtgagctg tatgtgcgca  1680
gctcgcgttg cattttcgga agcgctcgtt ttcggaaacg ctttgaagtt cctattccga  1740
agttcctatt ctctagaaag tataggaact tcagagcgct tttgaaaacc aaaagcgctc  1800
tgaagtcgca ctttcaaaaa accaaaaacg caccggactg taacgagcta ctaaaatatt  1860
gcgaataccg cttccacaaa cattgctcaa aagtatctct ttgctatata tctctgtgct  1920
atatccctat ataacctacc catccaactt tcgctccttg aacttgcatc taaactcgac  1980
ctctacattt tttatgttta tctctagtat tactctttag acaaaaaaat tgtagtaaga  2040
actattcata gagtgaatcg aaaacaatac gaaaatgtaa acattcctaa tacgtagtat  2100
atagagacaa aatagaagaa accgttcata attttctgac caatgaagaa tcatcaacgc  2160
tatcactttc tgttcacaaa gtatgcgcaa tccacatcgg tatagaatat aatcggggat  2220
gccttttatct tgaaaaatg cacccgcagc ttcgctagta atcagtaaac gcgggaagtg   2280
gagtcaggct ttttttatgg aagagaaaat agacaccaaa gtagccttct tctaacctta  2340
acggacctac agtgcaaaag gttatcaaga gactgcatta tagagcgcac aaaggagaaa  2400
aaaagtaatc taagatgctt tgttagaaaa atagcgctct cgggatgcat ttttgtagaa  2460
caaaaaagaa gtatagattc tttgttggta aaatagcgct ctcgcgttgc atttctgttc  2520
tgtaaaaatg cagctcagat tctttgtttg aaaaattagc gctctcgcgt tgcattttg   2580
ttttacaaaa atgaagcaca gattcttcgt tggtaaaata gcgctttcgc gttgcatttc  2640
tgttctgtaa aaatgcagct cagattcttt gtttgaaaaa ttagcgctct cgcgttgcat  2700
ttttgttcta caaatgaag cacagatgct tcgttcaggt ggcacttttc ggggaaatgt    2760
gcgcggaacc cctatttgtt tatttttcta aatacattca aatatgtatc cgctcatgag  2820
acaataaccc tgatattggt cagaattggt taattggttg taacactgac ccctatttgt  2880
ttatttttct aaatacattc aaatatgtat ccgctcatga gacaataacc ctgataaatg  2940
cttcaataat attgaaaaag gaagaatatg agtattcaac atttccgtgt cgcccttatt  3000
ccctttttg cggcatttg ccttcctgtt tttgctcacc cagaaacgct ggtgaaagta     3060
aaagatgctg aagatcagtt gggtgcacga gtgggttaca tcgaactgga tctcaacagc  3120
ggtaagatcc ttgagagttt tcgccccgaa gaacgttttc caatgatgag cacttttaaa  3180
gttctgctat gtggcgcggt attatcccgt attgacgccg gcaagagcaa actcggtcgc  3240
cgcatacact attctcagaa tgacttggtt gagtactcac cagtcacaga aaagcatctt  3300
acggatggca tgacagtaag agaattatgc agtgctgcca taaccatgag tgataacact  3360
gcggccaact tacttctgac aacgatcgga ggaccgaagg agctaaccgc ttttttgcac  3420
aacatggggg atcatgtaac tcgccttgat cgttgggaac cggagctgaa tgaagccata  3480
ccaaacgacg agcgtgacac cacgatgcct gtagcgatgg caacaacgtt gcgcaaacta  3540
ttaactggcg aactacttac tctagcttcc cggcaacaat taatagactg gatgaggcg   3600
gataaagttg caggaccact tctgcgctcg gcccttccgg ctggctggtt tattgctgat  3660
aaatccggag ccggtgagcg tggttctcgc ggtatcatcg cagcgctggg gccagatggt  3720
aagccctccc gtatcgtagt tatctacacg acggggagtc aggcaactat ggatgaacga  3780
aatagacaga tcgctgagat aggtgcctca ctgattaagc attggtaact catgaccaaa  3840
atcccttaac gtgagttacg cgcgcgtcgt tccactgagc gtcagacccc gtagaaaaga  3900
tcaaaggatc ttcttgagat cctttttttc tgcgcgtaat ctgctgcttg caaacaaaaa  3960
aaccaccgct accagcggtg gtttgtttgc cggatcaaga gctaccaact cttttttcga  4020
aggtaactgg cttcagcaga gcgcagatac caaatactgt tcttctagtg tagccgtagt  4080
tagcccacca cttcaagaac tctgtagcac cgcctacata cctcgctctg ctaatcctgt  4140
taccagtggc tgctgccagt ggcgataagt cgtgtcttac cgggttggac tcaagacgat  4200
agttaccgga taaggcgcag cggtcgggct gaacggggg ttcgtgcaca cagcccagct   4260
tggagcgaac gacctacacc gaactgagat acctacagcg tgagctatga gaaagcgcca  4320
cgcttcccga agggagaaag gcggacaggt atccggtaag cggcagggtc ggaacaggag  4380
agcgcacgag ggagcttcca gggggaaacg cctggtatct ttatagtcct gtcgggtttc  4440
gccacctctg acttgagcgt cgatttttgt gatgctcgtc aggggggcgg agcctatgga  4500
aaaacgccag caacgcggcc tttttacggt tcctggcctt ttgctggcct tttgctcaca  4560
tgttctttcc tgcgttatcc cctgattctg tggataacgt gtataccgcc tttgagtgag  4620
ctgataccgc tcgggggtcgt gcaggtatag ctttcaaaatg tttctactcc tttttttactc 4680
ttccagattt tctcggactc cgcgcatcgc cgtaccactt caaaacaccc aagcacagca  4740
tactaaattt cccctctttc ttcctctagg gtgtcgttaa ttacccgtac taaaggttg   4800
gaaaagaaaa aagtgaccgc ctcgtttctt tttcttcgtc gaaaaggca ataaaaattt    4860
ttatcacgtt tctttttctt gaaattttt ttttttgatt tttttctctt tcgatgacct    4920
cccattgata tttaagttaa taaacggact tcaatttcagt ttcattttc                4980
ttgttctatt acaactttt ttacttcttg ctcattagaa agaaagcata gcaatcaat     5040
ctaagtttaa aatgaaactt gcttactctc tgttgttacc attggccggt gtttccgcaa  5100
tgcaggtaca gctggtggag acgggggggag ggctggtaca accaggcggg tcactgaggc  5160
tttcctgtgc cgcatctggg ttcacactgg attattcgtc cataggtgg tttcggcagg    5220
ctcctggcaa agagcgtgag ggggtctcat gtattagtag tagtggtgat agcacaaagt  5280
```

```
acgccgattc cgtaaagggc cggtttacaa cctccaggga taatgctaag aacaccgtat   5340
atctccagat gaactctctg aagcccgacg atacggccgt atattactgt gcggctttca   5400
gggcgactat gtgcggcgtg ttccctctga gcccttacgg caaggacgac tggggcaagg   5460
ggaccctggt gaccgtatcc tcaggcggtg gagggtctgg tggggaggc tcaggggtg    5520
gaggcagcca ggtgcaactg gttgaatctg ggggaggctt ggtacaacct ggggatccc    5580
tgagactctc ttgcgaggcc tccggattca ccttggacta ctatggcatc ggctggttcc   5640
gccagccccc agggaaggag cgggaggccg tttcatacat tagtgccagt gcccggacca   5700
tactgtacgc agactctgtg aagggacgct ttaccatctc tagggacaat gccaaaaatg   5760
ctgtgtacct gcaaatgaac agcctcaagc gggaggatac cgcagtgtac tactgcgcga   5820
gacggcgctt ctccgcttct agcgtgaata gatggctggc cgacgactac gacgtgtggg   5880
gacggggcac acaggtggct gtgtcttccg gtgcggaag cggaggggc agcggggtg     5940
ggagcggtgg gggcagccaa ctgcagctgg tagagacagg gggcggctta gttcagcctg   6000
gagggtctct cagactgtca tgcgctgcct ctggctttac cttcagtgac tacgtgatga   6060
catgggtccg ccaagctcca gggaaggggc ctgagtggat cgctactatt aatacagatg   6120
gcagcacaat gcgggacgac tccacaaagg ggcggttcac catttccaga gacaacgcca   6180
agaatactct gtaccttcag atgaccagtc tgaaacccga ggacactgct ctgtactatt   6240
gtgcaagagg ccgggtgatc tctgcttccg ctatcagagg cgcagtaagg ggccctgaa    6300
cacaggtaac cgtttcatcc gggggagcg gttcaggcgg tggggatct ggcgggggtg    6360
gatcccaagt tcagctggtc gaatccgggg gcggactggt ccagacaggg ggctccctga   6420
ggctctcctg tgcatcttcc ggaagcatcc ccggcttcga gaccgtgacc tggtctcgcc   6480
aggctcccgg gaagtctctg cagtgggtcg cttccatgac taagactaac aacgagatct   6540
actctgactc agtgaaaggc cgcttcatca ttttctagaga taacgctaaa aacacagtgt   6600
atctgcagat gaatagtctc aaacctgaag acacaggcgt gtatttctgt aagggtcctg   6660
agctgagggg ccagggcatc caggtaacag tctcgagt                          6698
```

SEQ ID NO: 76          moltype = DNA   length = 6707
FEATURE                Location/Qualifiers
misc_feature           1..6707
                       note = Plasmid pD1214-IVS-hABAB
source                 1..6707
                       mol_type = other DNA
                       organism = synthetic construct SEQUENCE: 76
```
ggttaaatca tgtaattagt tatgtcacgc ttacattcac gccctccccc cacatccgct     60
ctaaccgaaa aggaaggagt tagacaacct gaagtctagg tccctatta tttttttata    120
gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300
tttttttta ttcttttttt tgatttcggt ttctttgaaa tttttttgat tcggtaatct   360
ccgaacagaa ggaagaacga aggaaggagc acagacttag attggtatat atacgcatat   420
gtagtgttga agaaacatga aattgcccag tattcttaac ccaactgcac agaacaaaaa   480
ccagcaggaa acgaagataa atcatgtcga agctacata taaggaacgt gctgctactc   540
atcctagtcc tgttgctgcc aagctattta atatcatgca cgaaaagcaa acaaacttgt   600
gtgcttcatt ggatgttcgt accaccaagg aattactgca gttagttgaa gcattaggtc   660
ccaaaatttg tttactaaaa acacatgtgg atatcttgac tgattttttcc atggagggca   720
cagttaagcc gctaaaggca ttatccgcca agtacaattt tttactcttc gaagatagaa   780
aatttgctga cattggtaat acagtcaaat tgcagtactc tgcgggtgta tacagaaatg   840
cagaatgggc agacattacg aatgcacacg gtgtggtggg cccagtgtatt gttagcggtt   900
tgaagcaggc ggcagaagaa gtaacaaagg aacctagagg cctttttgatg ttagcagaat   960
tgtcatgcaa gggctcccta tctactggag aatatactaa gggtactgtt gacattgcga   1020
aaagcgacaa agattttgtt atcggctta ttgctcaaaa agacatgggt ggaagaagta   1080
aaggttacga ttggttgatt atgacacccg gtgtgggttt agatgacaag ggagatgcat   1140
tgggtcaaca gtatagaacc gtgatgatg ttgtctctac aggatctgac attattattg   1200
ttggaagagg actatttgca aagggaaggg atgctaaggt agagggtgaa cgttacagaa   1260
aagcaggctg ggaagcatat ttgagaagat gcggccagca aaactaaaaa actgtattat   1320
aagtaaatgc atgtatacta aactcacaaa ttagagcttc aatttaatta tatcagttat   1380
tacccacgct atgatccaat atcaaaggaa atgatagcat tgaaggatga gactaatcca   1440
attgaggagt ggcagcatat agaacagcta agggtagtg ctgaaggaag catacgatac   1500
cccgcatgga ggggataat atcacaggag gtactagact acctttcatc ctacataaat   1560
agacgcatat aagtacgcat ttaagcataa acacgcacta tgccgttctt ctcatgtata   1620
tatatataca ggcaacacgc agatataggt gcgacgtgaa cagtgagctg tatgtgcgca   1680
gctcgcgttg cattttcgga agcgctcgtt tcggaaacg ctttgaagtt cctattccga   1740
agttcctatt ctctagaaag tataggaact tcagagcgct tttgaaaacc aaaagcgctc   1800
tgaagtcgca ctttcaaaaa accaaaaacg caccggactg taacgagcta ctaaaatatt   1860
gcgaataccg cttccacaaa cattgctcaa aagtatctct ttgctatata tctctgtgct   1920
atatccctat ataacctacc catccacctt cgctccttg aacttgcatc taaactcgac   1980
ctctacattt tttatgttta tctctagtat tactctttag acaaaaaaat tgtagtaaga   2040
actattcata gagtgaatcg aaaacaatac gaaaatgtaa acatttccta tacgtagtat   2100
atagagacaa aatagaagaa accgttcata attttctgac caatgaagaa tcatcaacgc   2160
tatcactttc tgttcacaaa gtatgcgcaa tccacatcgg tatagaatat aatcggggat   2220
gcctttatct tgaaaaaatg cacccgcagc ttcgctagta atcagtaaac gcgggaagtg   2280
gagtcaggct tttttttatgg aagagaaaat agacaccaaa gtagccttct ctaaccttaa   2340
acggacctac agtgcaaaaa gttatcaaga gactgcatta tagagcgcac aaaggagaaa   2400
aaaagtaatc taagatgctt tgttagaaaa atagcgctct cgggatgcat tttttgtagaa   2460
caaaaaagaa gtatagattc tttgttggta aaatagcgct ctcgcgttgc atttctgttc   2520
tgtaaaaatg cagctcagat tctttgtttg aaaaattagc gctctcgcgt tgcatttttg   2580
ttttacaaaa atgaagcaca gattcttcgt tggtaaaata gcgctttcgc gttgcatttc   2640
tgttctgtaa aaatgcagct cagattcttt gtttgaaaaa ttagcgctct cgcgttgcat   2700
ttttgttcta caaaatgaag cacagatgct tcgttcaggt ggcacttttc ggggaaatgt   2760
```

```
gcgcggaacc cctatttgtt tattttcta aatacattca aatatgtatc cgctcatgag  2820
acaataaccc tgatattggt cagaattggt taattggttg taacactgac ccctatttgt  2880
ttattttct aaatacattc aaatatgtat ccgctcatga caataaacc ctgataaatg  2940
cttcaataat attgaaaaag gaagaatatg agtattcaac atttccgtgt cgcccttatt  3000
ccctttttg cggcattttg ccttcctgtt tttgctcacc cagaaacgct ggtgaaagta  3060
aaagatgctg aagatcagtt gggtgcacga gtgggttaca tcgaactgga tctcaacagc  3120
ggtaagatcc ttgagagttt tcgccccgaa gaacgttttc caatgatgag cacttttaaa  3180
gttctgctat gtggcgcggt attatccgt attgacgccg ggcaagagca actcggtcgc  3240
cgcatacact attctcagaa tgacttggtt gagtactcac cagtcacaga aaagcatctt  3300
acggatggca tgacagtaag agaattatgc agtgctgcca taaccatgag tgataacact  3360
gcggccaact tacttctgac aacgatcgga ggaccgaagg agctaaccgc ttttttgcac  3420
aacatggggg atcatgtaac tcgccttgat cgttgggaac cggagctgaa tgaagccata  3480
ccaaacgacg agcgtgacac cacgatgcct gtagcgatgg caacaacgtt gcgcaaacta  3540
ttaactggcg aactacttac tctagcttcc cggcaacaat aatagactgg atggaggcg  3600
gataaagttg caggaccact tctgcgctcg gcccttccgg ctggctggtt tattgctgat  3660
aaatccggag ccggtgagcg tggttctcgc ggtatcatcg cagcgctggg gccagatggt  3720
aagccctccc gtatcgtagt tatctacacg acggggagtc aggcaactat ggatgaacga  3780
aatagacaga tcgctgagat aggtgcctca ctgattaagc attggtaact catgaccaaa  3840
atcccttaac gtgagttacg cgcgcgtcgt tccactgagc gtcagacccc gtagaaaaga  3900
tcaaaggatc ttcttgagat cctttttttc tgcgcgtaat ctgctgcttg caaacaaaaa  3960
aaccaccgct accagcggtg gtttgtttgc cggatcaaga gctaccaact cttttttcga  4020
aggtaactgg cttcagcaga gcgcagatac caaatactgt tcttctagtg tagccgtagt  4080
tagcccacca cttcaagaac tctgtagcac cgcctacata cctcgctctg ctaatcctgt  4140
taccagtggc tgctgccagt ggcgataagt cgtgtcttac cgggttggac tcaagacgat  4200
agttaccgga taaggcgcag cggtcgggct gaacggggg ttcgtgcaca cagcccagct  4260
tggagcgaac gacctacacc gaactgagat acctacagcg tgagctatga gaaagcgcca  4320
cgcttcccga agggagaaag gcggacaggt atccggtaag cggcagggtc ggaacaggag  4380
agcgcacgag ggagcttcca gggggaaacg cctggtatct ttatagtcct gtcgggtttc  4440
gccacctctg acttgagcgt cgatttttgt gatgctcgtc agggggggcgg agcctatgga  4500
aaaacgccag caacgcggcc tttttacggt tcctggcctt ttgctggcct tttgctcaca  4560
tgttctttcc tgcgttatcc cctgattctg tggataaccg tattaccgcc tttgagtgag  4620
ctgataccgc tcgggtcgt gcaggtatag cttcaaaatg tttctactcc ttttttactc  4680
ttccagattt tctcggactc cgcgcatcgc cgtaccactt caaaacaccc aagcacagca  4740
tactaaattt cccctctttc ttcctctagg gtgtcgttaa ttacccgtac taaaggtttg  4800
gaaaagaaaa aagtgaccgc ctcgtttctt tttcttcgtc gaaaaaggca ataaaaattt  4860
ttatcacgtt tcttttcttt gaaaattttt tttttgatt tttttctctt tcgatgacct  4920
cccattgata tttaagttaa taaacggact tcaatttctc aagtttcagt ttcatttttc  4980
ttgttctatt acaacttttt ttacttcttg ctcattagaa agaaagcata gcaatctaat  5040
ctaagtttaa aatgttactt caagtttctt tgttcctgtt ggctggtttt gccgcaaaaa  5100
tctccgcaat gcaggtacag ctggtggaga cgggggagg gctggtacaa ccaggcgggt  5160
cactgaggct ttcctgtgcc gcatctgggt tcacactgga ttattcgtcc ataggtggt  5220
ttcggcaggc tcctggcaaa gagcgtgagg gggtctcatg tattagtagt agtggtgata  5280
gcacaaagta cgccgattcc gtaaagggcc ggtttacaac ctccagggat gctaaga  5340
acaccgtata tctccagatg aactctctga agcccgacga tacggccgta ttactactgt  5400
cggctttcag ggcgactatg tgcggcgtgt tccctctgag cccttacggc aaggacgact  5460
ggggcaaggg gaccctggtg accgtatcct caggcggtgg gggtctggt gggggaggct  5520
caggggggtgg agcagccag gtgcaactgg ttgaatctgg ggaggcttg gtacaacctg  5580
ggggatccct gagactctct gcgaggcct ccgattcac cttggactac tatggcatcg  5640
gctggttccg ccagccccca gggaaggagc gggaggccgt tcatacatt agtgccagtg  5700
cccgaccat actgtacgca gactctgtga agggacgctt taccatctct agggacaatg  5760
ccaaaaatgc tgtgtacctg caaatgaaca gcctcaagcg ggaggatacc gcagtgtact  5820
actgcgcgag acggcgcttc tccgcttcta gcgtgaatag atggctggcc gacgactacg  5880
acgtgtgggg acggggcaca caggtggctg tgtcttccgg tggcggaagc ggaggggca  5940
gcggggggtgg gagcggtggg ggcagccaac tgcagctggt agagacaggg ggcggcttag  6000
ttcagcctgg aggtctctc agactgtcat gcgctgcctc tggctttacc ttcagtgact  6060
acgtgatgac atgggtccgc caagctccag ggaaggggcc tgagtggatc gctactatta  6120
atacagatgg cagcacaatg cgggacgact ccacaaaggg gcggttcacc atttccagag  6180
acaacgccaa gaatactctg taccttcaga tgaccagtct gaaacccgag gacactgctc  6240
tgtactattg tgcaagaggc cgggtgatct ctgcttccgc tatcagaggc gcagtaaggg  6300
gccctggaac acaggtaacc gtttcatccg gggaggcggg ttcaggcggt gggggatctg  6360
gcggggggtgg atcccaagtt cagctggtcg aatccggggg cggactggtc cagacagggg  6420
gctccctgag gctctcctgt gcatcttccg gaagcatcgc cggcttcgag accgtgacct  6480
ggtctcgcca ggctcccggg aagtctctgc agtgggtcgc ttccatgact aagactaaca  6540
acgagatcta ctctgactca gtgaaaggcc gcttcatcat ttctagaagat caggataaaa  6600
acacagtgta tctgcagatg aatagtctca aacctgaaga cacaggcgtg tatttctgta  6660
agggtcctga gctgagggc cagggcatcc aggtaacagt ctcgagt             6707
```

```
SEQ ID NO: 77          moltype = DNA   length = 6728
FEATURE                Location/Qualifiers
misc_feature           1..6728
                       note = Plasmid pD1214-KP-hABAB
source                 1..6728
                       mol_type = other DNA
                       organism = synthetic construct
SEQUENCE: 77
ggttaaatca tgtaattagt tatgtcacgc ttacattcac gccctccccc cacatccgct   60
ctaaccgaaa aggaaggagt tagacaacct gaagtctagg tccctatttta ttttttata  120
gttatgttaa tattaagaac gttatttata tttcaaattt ttcttttttt tctgtacaga  180
cgcgtgtacg catgtaacat tatactgaaa accttgcttg agaaggtttt gggacgctcg  240
```

-continued

```
aaggctttaa tttgcggccc ctcacctgca cgcaaaaagc ttttcaattc aattcatcat 300
ttttttttta ttcttttttt tgatttcggt ttctttgaaa ttttttttgat tcggtaatct 360
ccgaacagaa ggaagaacga aggaaggagc acagacttag attggtatat atacgcatat 420
gtagtgttga agaaacatga aattgcccag tattcttaac ccaactgcac agaacaaaaa 480
ccagcaggaa acgaagataa atcatgtcga aagctacata taaggaacgt gctgctactc 540
atcctagtcc tgttgctgcc aagctattta atatcatgca cgaaaagcaa acaaacttgt 600
gtgcttcatt ggatgttcgt accaccaagg aattactgga gttagttgaa gcattaggtc 660
ccaaaatttg tttactaaaa acacatgtgg atatcttgac tgatttttcc atggagggca 720
cagttaagcc gctaaaggca ttatccgcca agtacaattt tttactcttc gaagataaga 780
aatttgctga cattggtaat acagtcaaat tgcagtactc tgcgggtgta tacagaatag 840
cagaatgggc agacattacg aatgcacacg gtgtggtggg cccaggtatt gttagcggtt 900
tgaagcaggc ggcagaagaa gtaacaaagg aacctagagg ccttttgatg ttagcagaat 960
tgtcatgcaa gggctcccta tctactggag aatatactaa gggtactgtt gacattgcga 1020
aaagcgacaa agattttgtt atcggcttta ttgctcaaag aggagagatg ggaagagatg 1080
aaggttacga ttggttgatt atgacacccg gtgtgggttt agatgacaag ggagatgcat 1140
tgggtcaaca gtatagaacc gtggatgatg ttgtctctac aggatctgac attattattg 1200
ttggaagagg actatttgca aagggaaggg atgctaaggt agagggtgaa cgttacagaa 1260
aagcaggctg ggaagcatat ttgagaagat gcggccagca aaactaaaaa actgtattat 1320
aagtaaatgc atgtatacta aactcacaaa ttagagcttc aatttaatta tatcagttat 1380
tacccacgct atgatccaat atcaaaggaa atgatagcat tgaaggatga gactaatcca 1440
attgaggagt ggcagcatat agaacagcta aagggtagtg ctgaaggaag catacgatac 1500
cccgcatgga attgggataat atcacaggag gtactagact acctttcatc ctacataaat 1560
agacgcatat aagtacgcat ttaagcataa acacgcacta tgccgttctt ctcatgtata 1620
tatatataca ggcaacacgc agatataggt gcgacgtgaa cagtgagctg tatgtgcgca 1680
gctcgcgttc cattttcgga agcgctcgtt ttcgaaacg ctttgaagtt cctattccga 1740
agttcctatt ctctagaaag tataggaact tcagagcgct tttgaaaacc aaaagcgctc 1800
tgaagtcgca ctttcaaaaa accaaaaacg caccggactg taacgagcta ctaaaatatt 1860
gcgaataccg cttccacaaa cattgctcaa aagtatctct ttgctatata tctctgtgct 1920
atatccctat ataacctacc catccaccttt tcgctccttg aacttgcatc taaactcgac 1980
ctctacattt tttatgttta tctctagtat tactcttag acaaaaaaat tgtagtaaga 2040
actattcata gagtgaatcg aaaacaatac gaaatgtaa acatttccta tacgtagtat 2100
atagagacaa aatagaagaa accgttcata attttctgac caatgaagaa tcatcaacgc 2160
tatcactttc tgttcacaaa gtatgcgcaa tccacatcgg tatagaatat aatcggggat 2220
gcctttatct tgaaaaaatg cacccgcagc ttcgctagta atcagtaaac gcgggaagtg 2280
gagtcaggct ttttttatgg aagagaaaat agacaccaaa gtagccttct tctaaccta 2340
acggacctac agtgcaaaaa gttatcaaga gactgcatta tagagcgcac aaaggagaaa 2400
aaaagtaatc taagatgctt tgttagaaaa atagcgctct cgggatgcat ttttgtagaa 2460
caaaaagaa gtatagattc tttgttggta aaatagcgct ctcgcgttgc atttctgttc 2520
tgtaaaaatg cagctcagat tctttgtttg aaaaattagc gctctcgcgt tgcattttta 2580
ttttacaaaa atgaagcaca gattcttcgt tggtaaaata gcgctttcgc gttgcatttc 2640
tgttctgtaa aaatgcagct cagattcttt gtttgaaaaa ttagcgctct cgcgttgcat 2700
ttttgttcta caaaatgaag cacagatgct tcgttcaggt ggcactttc gggaaatgt 2760
gcgcggaacc cctatttgtt tatttttcta aatacattca aatatgtatc cgctcatgag 2820
acaataaccc tgatattggt cagaattggt taattggttg taacactgac ccctatttgt 2880
ttattttcct aaatacattc aaatatgtat ccgctcatga caataaacc ctgataaatg 2940
cttcaataat attgaaaaag gaagaatatg agtattcaac atttccgtgt cgcccttatt 3000
ccctttttg cggcattttg ccttcctgtt tttgctcacc cagaaacgct ggtgaaagta 3060
aaagatgctg aagatcagtt gggtgcacga gtgggttaca tcgaactgga tctcaacagc 3120
ggtaagatcc ttgagagttt tcgccccgaa gaacgttttc caatgatgag cacttttaaa 3180
gttctgctat gtggcgcggt attatcccgt attgacgccg ggcaagagca actcggtcgc 3240
cgcatacact attctcagaa tgacttggtt gagtactcac cagtcacaga aaagcatctt 3300
acggatggca tgacagtaag agaattatgc agtgctgcca taaccatgag tgataacact 3360
gcggccaact tacttctgac aacgatcgga ggaccgaagg agctaaccgc ttttttgcac 3420
aacatggggg atcatgtaac tcgccttgat cgttgggaac cggagctgaa tgaagccata 3480
ccaaacgacg agcgtgacac cacgatgcct gtagcgatgg caacaacgtt gcgcaaacta 3540
ttaactggcg aactacttac tctagcttcc cggcaacaat taatagactg gatggaggcg 3600
gataaagttg caggaccact tctgcgctcg gcccttccgg ctggctggtt tattgctgat 3660
aaatccggag ccggtgagcg tggttctcgc ggtatcatcg cagcgctggg gccagatggt 3720
aagccctccc gtatcgtagt tatctacacg acggggagtc aggcaactat ggatgaacga 3780
aatagacaga tcgctgagat aggtgcctca ctgattaagc attggtaact catgaccaaa 3840
atcccttaac gtgagttacg cgcgcgtcgt tccactgagc gtcagacccc gtagaaaaga 3900
tcaaaggatc ttcttgagat cctttttttc tgcgcgtaat ctgctgcttg caaacaaaaa 3960
aaccaccgct accagcggtg gtttgtttgc cggatcaaga gctaccaact ctttttccga 4020
aggtaactgg cttcagcaga gcgcagatac caaatactgt tcttctagtg tagccgtagt 4080
tagcccacca cttcaagaac tctgtagcac cgcctacata cctcgctctg ctaatcctgt 4140
taccagtggc tgctgccagt ggcgataagt cgtgtcttac cgggttggac tcaagacgat 4200
agttaccgga taaggcgcag cggtcgggct gaacggggggg ttcgtgcaca cagcccagct 4260
tggagcgaac gacctacacc gaactgagat acctacagcg tgagctatga gaaagcgcca 4320
cgcttcccga agggagaaag gcggacaggt atccggtaag cggcagggtc ggaacaggag 4380
agcgcacgag ggagcttcca gggggaaacg cctggtatct ttatagtcct gtcgggtttc 4440
gccacctctg acttgagcgt cgatttttgt gatgctcgtc aggggggcgg agcctatgga 4500
aaaacgccag caacgcggcc tttttacggt tcctggcctt ttgctggcct tttgctcaca 4560
tgttctttcc tgcgttatcc cctgattctg tggataaccg tattaccgcc tttgagtgag 4620
ctgataccgc tcgccgcagc cgaacgaccg agcgcagcga gtcagtgagc gaggaagcgg 4680
ttccagattt tctcggactc cgcgcatcgc cgtaccactt caaaacaccc aagcacagca 4740
tactaaattt cccctctttc ttcctctagg gtgtcgttaa ttacccgtac taaaggtttg 4800
gaaaagaaaa aagtgaccgc ctcgtttctt tttcttcgtc gaaaaaggca ataaaaattt 4860
ttatcacgtt tcttttttctt gaaaattttt tttttgatt tttttctctt tcgatgacct 4920
cccattgata tttaagttaa taaacggact tcaatttctc aagtttcagt ttcatttttc 4980
```

```
ttgttctatt acaactttt ttacttcttg ctcattagaa agaaagcata gcaatctaat   5040
ctaagtttaa aatgacaaaa ccaacccaag tcttggtgag atctgtatcc attctttcct   5100
ttatcacttt attgcatctg gttgttgcta tgcaggtaca gctggtggag acggggggag   5160
ggctggtaca accaggcggg tcactgaggc ttcctgtgc cgcatctggg ttcacactgg   5220
attattcgtc catagggtgg tttcggcagg ctcctggcaa agagcgtgag gggtctcat   5280
gtattagtag tagtggtgat agcacaaagt acgccgattc cgtaaagggc cggtttacaa   5340
cctccaggga taatgctaag aacaccgtat atctccagat gaactctctg aagcccgacg   5400
atacggccgt atattactgt gcggctttca gggcgactat gtgcggcgtg ttccctctga   5460
gcccttacgg caaggacgac tggggcaagg ggacctggt gaccgtatcc tcaggcggtg   5520
gagggtctgg tgggggaggc tcaggggtg gaggcagcca ggtgcaactg gttgaatctg   5580
gggaggctt ggtacaacct gggggatccc tgagactctc ttgcgaggcc tccggattca   5640
ccttggacta ctatggcatc ggctggttcc gccagcccc agggaaggag cgggaggccg   5700
tttcatacat tagtgccagt gcccggacca tactgtacgc agactctgtg aagggacgct   5760
ttaccatctc tagggacaat gccaaaaatg ctgtgtacct gcaaatgaac agcctcaagc   5820
gggaggatac cgcagtgtac tactgcgcga cacggcgctt ctccgcttct agcgtgaata   5880
gatggctggc cgacgactac gacgtgtggg gacggggcac acaggtggct gtgtcttccg   5940
gtggcggaag cggaggggc agcggggtg ggagcggtgg gggcagccaa ctgcagctgg   6000
tagaacagg gggcggctta gttcagcctg gagggtctct cagactgtca tgcgctgcct   6060
ctggctttac cttcagtgac tacgtgatga catgggtccg ccaagctcca gggaaggggc   6120
ctgagtggat cgctactatt aatacagatg gcagcacaat gcgggacgac tccacaaagg   6180
ggcggttcac cattcaga gacaacgcca agaatactct gtaccttcag atgaccagtc   6240
tgaaacccga ggacactgct ctgtactatt gcaagagg ccgggtgatc tctgcttccg   6300
ctatcagagg cgcagtaagg ggccctgaa cacaggtaac cgtttcatcc ggggaggcg   6360
gttcaggcgg tggggatct ggcggggtg gatcccaagt tcagctggtc gaatccgggg   6420
gcggactggt ccagacaggg ggctccctga ggctctcctg tgcatcttcc ggaagcatcg   6480
ccggcttcga gaccgtgacc tggtctcgcc aggctcccgg gaagtctccg tcagtgggtcg   6540
cttccatgac taagactaac aacgagatct actctgactc agtgaaaggc cgcttcatca   6600
tttctagaga taacgctaaa aacacagtgt atctgcagat gaatagtctc aaacctgaag   6660
acacaggcgt gtatttctgt aagggtcctg agctgagggg ccaggcatc caggtaacag   6720
tctcgagt                                                          6728
```

SEQ ID NO: 78        moltype = DNA   length = 6728
FEATURE              Location/Qualifiers
misc_feature         1..6728
                     note = Plasmid pD1214-LZ-hABAB
source               1..6728
                     mol_type = other DNA
                     organism = synthetic construct
SEQUENCE: 78
```
ggttaaatca tgtaattagt tatgtcacgc ttcattcac gccctccccc cacatccgct     60
ctaaccgaaa aggaaggagt tagacaacct gaagtctagg tccctattta ttttttata    120
gttatgttaa tattaagaac gttatttata tttcaaattt ttctttttt tctgtacaga    180
cgcgtgtaca catgtaacat tatactgaaa accttgcttg agaaggtttt gggacgctg    240
aaggctttaa tttgcggccc ctcacctgca cgcaaaaagc ttttcaattc aattcatcat    300
ttttttttta ttctttttt tgatttcggt ttctttgaaa ttttttgat tcggtaatct     360
ccgaacagaa ggaagaacga aggaaggagc acagactag attggtatat atacgcatat    420
gtagtgttga agaaacatga aattgccag tattcttaac ccaactgcac agaacaaaaa    480
ccagcaggaa acgaagataa atcatgtcga aagctacata taaggaacgt gctgctactc    540
atcctagtcc tgttgctgcc aagctattta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgatttttcc atggagggca    720
cagttaagcc gctaaaggca ttatccgcca agtacaattt tttactcttc gaagatagaa    780
aatttgctga cattggtaat acagtcaaat gcagtactc tgcgggtgta tacagaatag    840
cagaatgggc agacattacg aatgcacacg gtgtggtggg cccaggtatt gttagcggtt    900
tgaagcaggc ggcagaagaa gtaacaaagg aacctagagg ccttttgatg ttagcagaat    960
tgtcatgcaa gggctcccta tctactggag aatatactaa gggtactgtt gacattgcga   1020
aaagcgacaa agattttgtt atcggcttta ttgctcaaag agacatgggt ggaagagatg   1080
aaggttacga ttggttgatt atgacacccg gtgtgggttt agatgacaag ggagatgcat   1140
tgggtcaaca gtataaagaa gtggatgatg ttgtctctac aggatctgac attattattg   1200
ttggaagagg actatttgca aagggaaggg atgctaaggt agaggggtgaa cgttacagaa   1260
aagcaggctg ggaagcatat ttgagaagat gcggccagca aaactaaaaa actgtattat   1320
aagtaaatgc atgtatacta aactcacaaa ttagagcttc aatttaatta tatcagttat   1380
tacccacgct atgatccaat tcaaaggaa atgatagcat tgaaggatga gactaatcca   1440
attgaggagt ggcagcatat agaacagcta aagggtaagtg ctgaaggaag catcgatac   1500
cccgcatgga atgggataat atcacaggag gtactagact acctttcatc ctacataaat   1560
agacgcatat aagtacgcat ttaagcataa acacgcacta tgccgttctt ctcatgtata   1620
tatatataca ggcaacacgc agatataggt gcgacgtgaa cagtgagctg tatgtgcgca   1680
gctcgcgttg cattttcgga agcgctcgtt tcggaaacg ctttgaagtt cctattccga   1740
agttcctatt ctctagaaag tataggaact tcagagcgct tttgaaaacc aaaagcgctc   1800
tgaagtcgca ctttcaaaaa accaaaaacg caccggactg taacgagcta ctaaaatatt   1860
gcgaataccg cttccacaaa cattgctcaa aagtatctct ttgctatata tctctgtgct   1920
atatccctat ataacctacc catccacctt tcgctcctg aacttgcatc taaactcgac   1980
ctctacattt tttatgttta tctctagtat tactcttag acaaaaaaat tgtagtaaga   2040
actattcata gagtgaatcg aaaacaatac gaaaatgtaa acatttccta tacgtagtat   2100
atagagacaa aatagaagaa accgttcata atttctgac caatgaagaa tcatcaacgc   2160
tatcactttc tgttcacaaa gtatgcgcaa tccacatcgg tatagaatat aatcggggat   2220
gcctttatct tgaaaaaatg cacccgcagc ttcgctagta atcagtaaac gcgggaagtg   2280
gagtcaggct ttttttatgg aagagaaaat agacaccaaa gtagccttct tctaaccttaa   2340
acggacctac agtgcaaaaa gttatcaaga gactgcatta tagagcgcac aaaggagaaa   2400
```

```
aaaagtaatc taagatgctt tgttagaaaa atagcgctct cgggatgcat ttttgtagaa 2460
caaaaaagaa gtatagattc tttgttggta aaatagcgct ctcgcgttgc atttctgttc 2520
tgtaaaaatg cagctcagat tctttgtttg aaaaattagc gctctcgcgt tgcattttg  2580
ttttacaaaa atgaagcaca gattcttcgt tggtaaaata gcgctttcgc gttgcatttc 2640
tgttctgtaa aaatgcagct cagattcttt gtttgaaaaa ttagcgctct cgcgttgcat 2700
ttttgttcta caaaatgaag cacagatgct tcgttcaggt ggcacttttc ggggaaatgt 2760
gcgcggaacc cctatttgtt tattttttcta aatacattca aatatgtatc cgctcatgag 2820
acaataaccc tgatattggt cagaattggt taattggttg taacactgac ccctatttgt 2880
ttattttttct aaatacattc aaatatgtat ccgctcatga gacaataaacc ctgataaatg 2940
cttcaataat attgaaaaag gaagaatatg agtattcaac atttccgtgt cgcccttatt 3000
ccctttttg cggcattttg ccttcctgtt tttgctcacc cagaaacgct ggtgaaagta 3060
aaagatgctg aagatcagtt gggtgcacga gtgggttaca tcgaactgga tctcaacagc 3120
ggtaagatcc ttgagagttt tcgccccgaa gaacgttttc caatgatgag cacttttaaa 3180
gttctgctat gtggcgcggt attatcccgt attgacgccg ggcaagagca actcggtcgc 3240
cgcatacact attctcagaa tgacttggtt gagtactcac cagtcacaga aaagcatctt 3300
acggatggca tgacagtaag agaattatgc agtgctgcca taaccatgag tgataacact 3360
gcggccaact tacttctgac aacgatcgga ggaccgaagg agctaaccgc ttttttgcac 3420
aacatggggg atcatgtaac tcgccttgat cgttgggaac cggagctgaa tgaagccata 3480
ccaaacgacg agcgtgacac cacgatgcct gtagcgatgg caacaacgtt gcgcaaacta 3540
ttaactggcg aactacttac tctagcttcc cggcaacaat taatagactg gatgaggcg 3600
gataaagttg caggaccact tctgcgctcg gcccttccgg ctggctggtt tattgctgat 3660
aaatccggag ccggtgagcg tggttctcgc ggtatcatcg cagcgctggg gccagatggt 3720
aagccctccc gtatcgtagt tatctacacg acggggagtc aggcaactat ggatgaacga 3780
aatagacaga tcgctgagat aggtgcctca ctgattaagc attggtaact catgaccaaa 3840
atcccttaac gtgagttacg cgcgcgtcgt tccactgagc gtcagacccc gtagaaaaga 3900
tcaaaggatc ttcttgaat cctttttttc tgcgcgtaat ctgctgcttg caaacaaaaa 3960
aaccaccgct accagcggtg gtttgtttgc cggatcaaga gctaccaact ctttttccga 4020
aggtaactgg cttcagcaga gcgcagatac caaatactgt tcttctagtg tagccgtagt 4080
tagcccacca cttcaagaac tctgtagcac cgcctacata cctcgctctg ctaatcctgt 4140
taccagtggc tgctgccagt ggcgataagt cgtgtcttac cgggttggac tcaagacgat 4200
agttaccgga taaggcgcag cggtcgggct gaacggggg ttcgtgcaca cagcccagct 4260
tggagcgaac gacctacacc gaactgagat acctacagcg tgagctatga gaaagcgcca 4320
cgcttcccga agggagaaag gcggacaggt atccggtaag cggcagggtc ggaacaggag 4380
agcgcacgag ggagcttcca gggggaaacg cctggtatct ttatagtcct gtcgggtttc 4440
gccacctctg acttgagcgt cgatttttgt gatgctcgtc aggggggcgg agcctatgga 4500
aaaacgccag caacgcggcc tttttacggt tcctggcctt ttgctggcct tttgctcaca 4560
tgttctttcc tgcgttatcc cctgattctg tggataaccg tattaccgcc tttgagtgag 4620
ctgataccgc tcggggtcgt gcaggtatag cttcaaaatg ttttctactcc tttttttactc 4680
ttccagattt tctcggactc cgcgcatcgc cgtaccactt caaaacaccc aagcacagca 4740
tactaaattt cccctctttc ttcctctagg gtgtcgttaa ttacccgtac taaaggtttg 4800
gaaaagaaaa aagtgaccgc ctcgtttctt tttcttcgtc gaaaaaggca ataaaaattt 4860
ttatcacgtt tcttttttcttt gaaaattttt tttttgattt tttttctctt tcgatgacct 4920
cccattgata tttaagttaa taaacggact tcaatttctc aagtttcagt ttcattttc  4980
ttgttctatt acaactttttt ttacttcttg ctcattagaa agaaagcata gcaatctaat 5040
ctaagtttaa aatgttaggt aaaatgatc caatgtgtct ggtgcttgtt ctgttgggtt 5100
tgactgctct attgggtatc tgccaaggaa tgcaggtaca gctggtggag acgggggag 5160
ggctggtaca accaggcggg tcactgaggc tttcctgtgc cgcatctggg ttcacactgg 5220
attattcgtc cataggggg tttcggcagg ctcctggcaa agagcgtgg ggggtctcat 5280
gtattagtag tagtggtgat agcacaaagt acgccgattc cgtaaggggc cggtttacaa 5340
cctcagggga taatgctaag aacaccgtat atctccagat gaactctctg aagcccgacg 5400
atacgccgt atattactgt gcggctttca gggcgactat gtgcgcgtt ttccctctga 5460
gcccttacgg caaggacgac tggggcaagg gaccctggt gaccgtatcc tcaggcggtg 5520
gagggtctgg tggggaggc tcaggggtg gaggcagcca ggtgcaactg gttgaatctg 5580
ggggaggctt ggtacaacct gggggatccc tgagactctc ttgcgaggcc tccgattcca 5640
ccttggacta ctatgccatc ggctggttcc gccagccccc agggaaggag cgggaggccg 5700
tttcatacat tagtgccagt gcccggacca tactgtacgc agactctgtg aagggacgct 5760
ttaccatctc tagggacaat gccaaaatg ctgtgtaccct gcaaatgaac agcctcaagc 5820
gggaggatac cgcagtgtac tactgcgcga cgcggcgctt ctccgcttct agcgtgaata 5880
gatggctggc cgacgactac gacgtgtggg gacgggcac acaggtggct gtgtcttccg 5940
gtggcggaag cggagggggc agcggggtg ggagcggtgg gggcagccaa ctgcagctgg 6000
tagagacagg gggcggctta gttcagcctg gagggtctct cagactgtca tgcgctgcct 6060
ctggctttac cttcagtgac tacgtgatga catgggtccg ccaagctcca gggaagggc 6120
ctgagtggat cgctactatt aatacagatg gcagcacaat gcgggacgac tccacaaagg 6180
ggcggttcac catttccaga gacaacgcca agaatactct gacctttcag atgaccagtc 6240
tgaaacccga ggacactgct ctgtactatt gtgcaagagg ccgggtgatc tctgcttccg 6300
ctatcagagg cgcagtaagg ggccctgaaa cacaggtaac cgtttcatcc ggggaggcg 6360
gttcaggcgg tggggatct ggcggggtg gatcccaagt tcagctggtc gaatccgggg 6420
gcggactggt ccagacaggg ggctccctga ggctctcctg tgcatcttcc ggaagcatcg 6480
ccggcttcga gaccgtgacc tggtctcgcc aggctccgg gaagtctctg cagtgggtcg 6540
cttccatgac taagactaac aacgagatct actctgactc agtgaaaggc cgcttcatca 6600
tttctagaga taacgctaaa aacacagtgt atctgcagat gaatagtctc aaacctgaag 6660
acacaggcgt gtattctgt aagggtcctg agctgagggg ccagggcatc caggtaacag 6720
tctcgagt                                                          6728
```

SEQ ID NO: 79        moltype = DNA  length = 6704
FEATURE             Location/Qualifiers
misc_feature       1..6704
                      note = Plasmid pD1214-SA-hABAB
source              1..6704 mol_type = other DNA
organism = synthetic construct

SEQUENCE: 79

```
ggttaaatca tgtaattagt tatgtcacgc ttacattcac gccctccccc cacatccgct   60
ctaaccgaaa aggaaggagt tagacaacct gaagtctagg tccctattta ttttttttata  120
gttatgttag tattaagaac gttatttata tttcaaattt ttctttttt tctgtacaga    180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300
ttttttttta ttcttttttt tgatttcggt ttctttgaaa ttttttttgat tcggtaatct  360
ccgaacagaa ggaagaacga aggaaggagc acagacttag attggtatat atacgcatat   420
gtagtgttga agaaacatga aattgccag tattcttaac ccaactgcac agaacaaaaa    480
ccagcaggaa acgaagataa atcatgtcga aagctacata taaggaacgt gctgctactc   540
atcctagtcc tgttgctgcc aagctattta atatcatgca cgaaaagcaa acaaacttgt   600
gtgctttcatt ggatgttcgt accaccaagg aattactgga gttagttgaa gcattaggtc   660
ccaaaatttg tttactaaaa acacatgtgg atatcttgac tgattttcc atggagggca    720
cagttaagcc gctaaaggca ttatccgcca agtacaattt tttactcttc gaagatagaa   780
aatttgctga cattggtaat acagtcaaat tgcagtactc tgcgggtgta tacagaatag   840
cagaatgggc agacattacg aatgcacacg gtgtggtggg cccaggtatt gttagccgtt   900
tgaagcaggc ggcagaagaa gtaacaaagg aacctagagg cctttgatg ttagcagaat    960
tgtcatgcaa gggctccta tctactggag aatatactaa gggtactgtt gacattgcga   1020
aaagcgacaa agatttgtt atcggcttta ttgctcaaag agacatgggt ggaagagatg   1080
aaggttacga ttggttgatt atgacacccg gtgtgggtt agatgacaag gggatgcat    1140
tgggtcaaca gtatagaacc gtggatgatg ttgtctctac aggatctgac attattattg   1200
ttggaagagg actatttgca aagggaaggg atgctaaggt agagggtgaa cgttacagaa   1260
aagcaggctg ggaagcatat ttgagaagat gcggccagca aaactaaaaa actgtattat   1320
aagtaaatgc atgtatacta aactcacaaa ttagagcttc aatttaatta tatcagttat   1380
tacccacgct atgatccaat atcaaaggaa atgatagcat tgaaggatga gactaatcca   1440
attgaggagt ggcagcatat agaacagcta aagggtagtg ctgaaggaag catacgatac   1500
cccgcatgga atgggataat atcacaggag gtactagact accttcatc ctacataaat   1560
agacgcatat aagtacgcat ttaagcataa acacgcacta tgccgttctt ctcatgtata   1620
tatatataca ggcaacacgc agatatagg gcgacgtgaa cagtgagctg tatgtgcgca   1680
gctcgcgttg cattttcgga agcgctcgtt ttcggaaacg ctttgaagtt cctattccga   1740
agttcctatt ctctagaaag tataggaact tcagagcgct tttgaaaacc aaaagcgctc   1800
tgaagtcgca ctttcaaaaa accaaaaacg caccgactg taacgagcta ctaaaatatt   1860
gcgaataccg cttccacaaa cattgctcaa aagtatctct ttgctatata tctctgtgct   1920
atatccctat ataacctacc catccacctt tcgctccttg aacttgcatc taaactcgac   1980
ctctacattt tttatgttta tctctagtat tactcttag acaaaaaaat tgtagtaaga   2040
actattcata gagtgaatcg aaaacaatac gaaaatgtaa acatttccta tacgtagtat   2100
atagacacaa aatagaagaa accgttcata attttctgac caatgaagaa tcatcaacgc   2160
tatcactttc tgttcacaaa gtatgcgcaa tccacatcgg tatagaatat aatcggggat   2220
gcctttatct tgaaaaaatg cacccgcagc ttcgctagta atcagtaaac gcgggaagtg   2280
gagtcaggct ttttttatgg aagagaaaat agacaccaaa gtagccttct tctaacctta   2340
acggacctac agtgcaaaaa gttatcaaga gactgcatta tagagcgcaa aaaggagaaa   2400
aaaagtaatc taagatgctt tgttagaaaa atagcgctct cgggatgcat ttttgtagaa   2460
caaaaaagaa gtatagattc tttgttggta aaatagcgct ctcgcgttgc atttctgttc   2520
tgtaaaaatg cagctcagat tctttgtttg aaaaattagc gctctcgcgt tgcatttttg   2580
ttttacaaaa atgaagcaca gattcttcgt tggtaaaata ggcttttgc gttgcatttc   2640
tgttctgtaa aaatgcagct cagattcttt gtttgaaaaa ttagcgctct cgcgttgcat   2700
ttttgttcta caaaatgaag cacagatgct tcgttcaggt ggcactttc ggggaaatgt    2760
gcgcggaacc cctatttgtt tatttttcta aatacattca aatatgtatc cgctcatgag   2820
acaataaccc tgatattggt cagaattggt taattggttg taacactgac ccctatttgt   2880
ttatttttct aaatacattc aaatatgtat ccgctcatga acaataacc ctgataaatgt    2940
cttcaataat attgaaaaag gaagaatatg agtattcaac atttccgtgt cgcccttatt   3000
ccctttttg cggcattttg ccttcctgtt tttgctcacc cagaaacgct ggtgaaagta   3060
aaagatgctg aagatcagtt gggtgcacga gtgggttaca tcgaactgga tctcaacagc   3120
ggtaagatcc ttgagagttt tcgccccgaa gaacgttttc caatgatgag cacttttaaa   3180
gttctgctat gtggcgcggt attatcccgt attgacgccg ggcaagagca actcggtcgc   3240
cgcatacact attctcagaa tgacttggtt gagtactcac cagtcacaga aaagcatctt   3300
acggatggca tgacagtaag agaattatgc agtgctgcca taaccatgag tgataacact   3360
gcggccaact tacttctgac aacgatcgga ggaccgaagg agctaaccgc ttttttgcac   3420
aacatgggg atcatgtaac tcgccttgat cgttgggaac cggagctgaa tgaagccata   3480
ccaaacgacg agcgtgacac cacgatgcct gtagcgatgg caacaacgtt gcgcaaacta   3540
ttaactggcg aactacttac tctagcttcc cggcaacaat aatagactg gatggaggcg   3600
gataaagttg caggaccact tctgcgctcg gcccttccgg ctggctgttt tattgctagt   3660
aaatccggag ccggtgagcg tggttctcgc ggtatcatcg cagcgctggg gccagatggt   3720
aagccctccc gtatcgtagt tatctacacg acggggagtc aggcaactat ggatgaacga   3780
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
tcaaaggatc ttcttgagat ccttttttc tgcgcgtaat ctgctgcttg caaacaaaaa   3960
aaccaccgct accagcggtg gtttgtttgc cggatcaaga gctaccaact cttttttccga   4020
aggtaactgg cttcagcaga gcgcagatac caaatactgt tcttctagtg tagccgtagt   4080
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacggggg ttcgtgcaca cagcccagct    4260
tggagcgaac gacctacacc gaactgagat acctacagcg tgagctatga gaaagcgcca   4320
cgcttcccga agggagaaag gcggacaggt atccggtaag cggcagggtc ggaacaggag   4380
agcgcacgag ggagcttcca gggggaaacg cctggtatct ttatagtcct gtcgggtttc   4440
gccacctctg acttgagcgt cgatttttgt gatgctcgtc agggggggcgg agcctatgga   4500
aaaacgccag caacgcggcc tttttacggt tcctggcctt tgctggcct tttgctcaca   4560
```

```
tgttctttcc tgcgttatcc cctgattctg tggataaccg tattaccgcc tttgagtgag    4620
ctgataccgc tcgggtcgt gcaggtatag cttcaaaatg tttctactcc tttttttactc    4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttttctt gaaaattttt tttttgatt tttttctctt tcgatgacct    4920
cccattgata tttaagttaa taaacggact tcaattctc aagtttcagt ttcattttttc    4980
ttgttctatt acaactttt ttacttcttg ctcattagaa agaaagcata gcaatctaat    5040
ctaagtttaa aatgaaatgt gttacttttta tctcacttttt gttcctgttc tccagcgctt    5100
actctatgca ggtacagctg gtggagacgt ggggagggct ggtacaacca ggcgggtcac    5160
tgaggctttc ctgtgccgca tctgggttca cactggatta ttcgtccata gggtggtttc    5220
ggcaggctcc tggcaaagag cgtgagggg tctcatgtat tagtagtagt ggtgatagca    5280
caaagtacgc cgattccgta aagggccggt ttacaacctc cagggataat gctaagaaca    5340
ccgtatatct ccagatgaac tctctgaagc ccgacgatac ggactatat tactgtgcga    5400
ctttcagggc gactatgtgc ggcgtgttcc ctctgagccc ttacggcaag gacgactggg    5460
gcaaggggac cctggtgacc gtatcctcag gcggtgagg gtctggtggg ggaggctcag    5520
ggggtggagg cagccaggtg caactggttg aatctggggg aggcttggta caacctggg    5580
gatccctgag actctcttgc gaggccrccg gattcaccttt ggactactat ggcatcggct    5640
ggttccgcca gccccaggg aaggagcggg aggccgtttc atacatttagt gccagtgccc    5700
ggaccatact gtacgcagac tctgtgaagg gacgctttac catctctagg gacaatgcca    5760
aaaatgctgt gtacctgcaa atgaacagcc tcaagcggga ggataccgca gtgtactact    5820
gcgcagacg gcgcttctcc gcttctagcg tgaatagatg gctggccgac gactacgacg    5880
tgtggggacg gggcacacag gtggctgtgt cttccggtgg cggaagcgga ggggcagcg    5940
ggggtgggag cggtggggc agccaactgc agctggtaga gacagggggc ggcttagttc    6000
agcctggagg gtctctcaga ctgtcatgcg ctgcctctgg ctttaccttc agtgactacg    6060
tgatgacatg ggtccgccaa gctccaggga aggggccrga gtggatcgct actattaata    6120
cagatggcag cacaatgcgg gacgactcca caaaggggcg gttcaccatt tccagagaca    6180
acgccaagaa tactctgtac cttcagatga ccagtctgaa acccgaggac actgctctgt    6240
actattgtgc aagaggccgg gtgatctctg cttccgctat cagaggcgca gtaagggcc    6300
ctgaaacaca ggtaaccgtt tcatccgggg gaggcggttc aggcggttgg ggatctggcg    6360
ggggtggatc ccaagttcag ctggtcgaat ccggggggcg actggtccga acaggggct    6420
ccctgaggct ctcctgtgca tcttccggaa gcatcgccgg cttcgagacc gtgacctggt    6480
ctcgccaggc tcccgggaag tctctgcagt gggtcgcttc catgactaag actaacaacg    6540
agatctactc tgactcagtg aaaggccgct tcatcatttc tagagataac gctaaaaaca    6600
cagtgtatct gcagatgaat agtctcaaac tgaagacac aggcgtgtat ttctgtaagg    6660
gtcctgagct gagggccag ggcatccagg taacgtctc gagt                       6704
```

```
SEQ ID NO: 80            molytype = DNA   length = 6574
FEATURE                  Location/Qualifiers
misc_feature             1..6574
                         note = Plasmid pCEV-G4-Km
source                   1..6574
                         mol_type = other DNA
                         organism = synthetic construct
SEQUENCE: 80
ggagcgacct catgctatac ctgagaaagc aacctgacct acaggaaaga gttactcaag    60
aataagaatt ttcgttttaa aacctaagag tcactttaaa atttgtatac acttattttt    120
tttataactt atttaataat aaaaatcata aatcataaga aattcgctta tttagaagtg    180
tcaacaacgt atctaccaac gatttgaccc ttttccatct tttcgtaaat ttctggcaag    240
gtagacaagc cgacaacctt gattggagac ttgaccaaac ctctggcgaa gaattgttaa    300
ttaagagctc agatcttatc gtcgtcatcc ttgtaatcca tcgatactag ttttttgatt    360
aaaattaaaa aaacttttg ttttttgtgt tattctttgt tcttagaaaa gacaagttga    420
gcttgtttgt tcttgatgtt ttattatttt acaatagctg caaatgaaga atagattcga    480
acattgtgaa gtattggcat atatcgtctc tatttatact tttttttttt cagttctagt    540
atattttgta ttttcctcct tttcattctt tcagttgcca ataagttaca ggggatctcg    600
aaagatggtg gggatttttc cttgaaagac gactttttgc catctaattt ttccttgttg    660
cctctgaaaa ttatccagca gaagcaaatg taaaagatga acctcagaag aacacgcagg    720
ggcccgaaat tgttcctacg agaagtagtg ggtcataaaa agtttattcc ctggaaaaaa    780
aattttgcgt tgcctttctg gagaatttt tcgaattagc gtgctgccac tgcatgcatt    840
tctgagaagt gtgggcattc ttccaccagt tgttcctcct aaaaaaaaaa agatttccta    900
ccccgcacaa attcctgcat acccctcatt tccacgggc cggccgcaca caccatagct    960
tcaaaatgtt tctactcctt ttttactctt ccagattttc tcggactccg cgcatcgccc    1020
taccacttca aaacacccaa gcacagcata ctaaatttcc cctctttctt cctctagggt    1080
gtcgttaatt acccgtacta aaggtttgga aagaaaaaaa gagaccgcct cgtttcttt    1140
tcttcgtcga aaaaggcaat aaaaattttt atcacgtttc ttttttcttga aaatttttt    1200
ttttgatttt tttctctttc gatgacctcc cattgatatt taagttaata aacggtcttc    1260
aattctcaa gtttcagttt cattttctt gttctattac aactttttt acttcttgct    1320
cattagaaag aaagcatagc aatctaatct aagtttaat tacaaggatc cgtaatacga    1380
ctcactatag ggcccgggcg tcgacatgga acagaagttg atttccgaag aagacctcag    1440
gtaagcttgg taccgcggct agctaagatc cgctctaacc gaaaaggaag gagttagaca    1500
acctgaagtc taggtcccta tttatttttt tatagttatg ttagtattaa gaacgttatt    1560
tatatttcaa attttttctttt ttttctgta cagacgcgtg tacgcatgta acattatact    1620
gaaaccttg cttgagaagg ttttgggacg ctcgaagatc cagctgcatt aatgaatcgg    1680
ccaacggcg ggagagcg gtttgcgtat tgggcgctct tccgcttcct cgctcactga    1740
ctcgctgcgc tcggtcgttc ggctgcggcg agcggtatca gctcactcaa aggcggtaat    1800
acggttatcc acagaatcag gggataacgc aggaaagaac atgtgagcaa aaggccagca    1860
aaaggccagg aaccgtaaaa aggccgcgtt gctggcgttt ttccataggc tccgcccccc    1920
tgacgagcat cacaaaaatc gacgctcaag tcagaggtgg cgaaacccga caggactata    1980
aagataccag gcgtttcccc ctggaagctc cctcgtgcgc tctcctgttc cgaccctgcc    2040
```

```
gcttaccgga tacctgtccg cctttctccc ttcgggaagc gtggcgcttt ctcatagctc  2100
acgctgtagg tatctcagtt cggtgtaggt cgttcgctcc aagctgggct gtgtgcacga  2160
accccccgtt cagcccgacc gctgcgcctt atccggtaac tatcgtcttg agtccaaccc  2220
ggtaagacac gacttatcgc cactggcagc agccactggt aacaggatta gcagagcgag  2280
gtatgtaggc ggtgctacag agttcttgaa gtggtggcct aactacggct acactgaag   2340
gacagtattt ggtatctgcg ctctgctgaa gccagttacc ttcggaaaaa gagttggtag  2400
ctcttgatcc ggcaaacaaa ccaccgctgg tagcggtggt ttttttgttt gcaagcagca  2460
gattacgcgc agaaaaaaag gatctcaaga agatcctttg atcttttcta cggggtctga  2520
cgctcagtgg aacgaaaact cacgttaagg gattttggtc atgagattat caaaaaggat  2580
cttcacctag atccttttaa attaaaaatg aagttttaaa tcaatctaaa gtatatatga  2640
gtaaacttgg tctgacagtt accaatgctt aatcagtgag gcacctatct cagcgatctg  2700
tctatttcgt tcatccatag ttgcctgact ccccgtcgtg tagataacta cgatacggga  2760
gggcttacca tctggcccca gtgctgcaat gataccgcga gacccacgct caccggctcc  2820
agatttatca gcaataaacc agccagcgg aagggccgag cgcagaagtg gtcctgcaac  2880
tttatccgcc tccatccagt ctattaattg ttgccgggaa gctagagtaa gtagttcgcc  2940
agttaatagt ttgcgcaacg ttgttgccat tgctacaggc atcgtggtgt cacgctcgtc  3000
gtttggtatg gcttcattca gctccggttc caacgatca aggcgagtta catgatcccc  3060
catgttgtgc aaaaaagcgg ttagctcctt cggtcctccg atcgttgtca gaagtaagtt  3120
ggccgcagtg ttatcactca tggttatggc agcactgcat aattctctta ctgtcatgcc  3180
atccgtaaga tgcttttctg tgactggtga gtactcaacc aagtcattct gagaatagtg  3240
tatgcggcga ccgagttgct cttgcccggc gtcaatacgg gataataccg cgccacatag  3300
cagaacttta aaagtgctca tcattggaaa acgttcttcg gggcgaaaac tctcaaggat  3360
cttaccgctg ttgagatcca gttcgatgta acccactcgt gcacccaact gatcttcagc  3420
atcttttact ttcaccagcg tttctgggtg agcaaaaaca ggaaggcaaa atgccgcaaa  3480
aaagggaata agggcgacac ggaaatgttg aatactcata ctcttccttt tcaatatta   3540
ttgaagcatt tatcagggtt attgtctcat gagcggatac atatttgaat gtatttagaa  3600
aaataaacaa ataggggttc cgcgcacatt tccccgaaaa gtgccacctg aacgaagcat  3660
ctgtgcttca ttttgtagaa caaaaatgca acgcgagagc gctaattttt caaacaaaga  3720
atctgagctg cattttttaca gaacagaaat gcaacgcgaa agcgctattt taccaacgaa  3780
gaatctgtgc ttcattttg taaaacaaaa atgcaacgcg agagcgctaa ttttcaaac   3840
aagaatctg agctgcattt ttacagaaca gaaatgcaac gcgagagcgc tattttacca  3900
acaaagaatc tatacttctt ttttgttcta caaaaatgca tcccgagagc gctattttc   3960
taacaaagca tcttagatta ctttttttct cctttgtgcg ctctataatg cagtctcttg  4020
ataactttt gcactgtagg tccgttaagg ttagaagaag gctactttgg tgtctatttt  4080
ctcttccata aaaaaagcct gactccactt cccgcgttta ctgattacta gcgaagctgc  4140
gggtgcattt tttcaagata aaggcatccc cgattatatt ctataccgat gtggattgcg  4200
catactttgt gaacagaaag tgatagcgtt gatgattctt cattggtcag aaaattatga  4260
acggtttctt ctattttgtc tctatatact acgtatagga aatgtttaca ttttcgtatt  4320
gttttcgatt cactcatga atagttctta ctacaatttt tttgtctaaa gagtaatact  4380
agagatacc ataaaaatg tagaggtcga gtttagatgc aagttcaagg agcgaaaggt   4440
ggatgggtag gttatatagg gatatagcac agagatatat agcaaagaga ctttttgag   4500
caatgtttgt ggaagcggta ttcgcaatat tttagtagct cgttacagtc cggtgcgttt  4560
ttggttttt gaaagtgcgt cttcagagcg ctttttggtt tcaaaagcgc tctgaagttc  4620
ctatactttc tagagaatag gaacttcgga ataggaactt caaagcgttt ccgaaaacga  4680
gcgcttccga aaatgcaacg cgagctgcgc acatacagct cactgttcac gtcgcaccta  4740
tatctgcgtg ttgcctgtat atatatatac atgaagaaga cggcatagtg cgtgtttatg  4800
cttaaatgcg tacttatatg cgtctattta tgtaggatga aaggtagtct agtacctcct  4860
gtgatattat cccattccat gcggggtatc gtatgcttcc ttcagcacta ccctttagct  4920
gttctatatg ctgccactcc tcaattggat tagtctcatc cttcaatgct atcatttcct  4980
ttgatattgg atcatggtag acaacccta atataacttc gtataatgta tgctatacga  5040
agttattagg tctagagatc tgtttagctt gcctcgtccc cgccgggtca cccggccagc  5100
gacatggagg cccagaatac cctccttgac agtcttgacg tgcgcagctc aggggcatga  5160
tgtgactgtc gcccgtacat ttagcccata catccccatg tataatcatt gcatcccata  5220
cattttgatg gccgcacggc gcgaagcaaa aattacggct cctcgctgca gacctgcgag  5280
cagggaaacg ctccctcac agacgcgttg aattgtcccc acgccgcgcc cctgtagaga  5340
aatataaaag gttaggattt gccactgagg ttcttctttc atatacttcc ttttaaaatc  5400
ttgctaggat acagttctca catcacatcc gaacataaac aaccatgggt aaggaaaaga  5460
ctcacgtttc gaggccgcga ttaaattcca acatggatgc tgatttatat gggtataaat  5520
gggctcgcga taatgtcggg caatcaggtg cgacaatcta tcgattgtat gggaagcccg  5580
atgcgccaga gttgtttctg aaacatggca aaggtagcgt tgccaatgat gttacagatg  5640
agatggtcag actaaactgg ctgacggaat ttatgcctct tccgaccatc aagcatttta  5700
tccgtactcc tgatgatgca tggttactca ccactgcgat ccccgcaaa acagcattcc   5760
aggtattaga agaatatcct gattcaggtg aaaatattgt tgatgcgctg gcagtgttcc  5820
tgcgccggtt gcattcgatt cctgtttgta attgtccttt taacagcgat cgcgtatttc  5880
gtctcgctca ggcgcaatca cgaatgaata acggtttggt tgatgcgagt gattttgatg  5940
acgagcgtaa tggctggcct gttgaacaag tctggaaaga aatgcataag cttttgccat  6000
tctcaccgga ttcagtcgtc actcatggtg atttctcact tgataacctt atttttgacg  6060
aggggaaatt aataggttgt attgatgttg gacgagtcgg aatcgcagac cgataccagg  6120
atcttgccat cctatggaac tgcctcggtg agttttctcc ttcattacag aaacggcttt  6180
ttcaaaaata tggtattgat aatcctgata tgaataaatt gcagtttcat tgatgctcg   6240
atgagttttt ctaatcagta ctgacaataa aagattcttg ttttcaagac ttgtcatt    6300
tgtatagttt ttttatattg tagttgttct atttaatca aatgttagcg tgatttatat  6360
tttttttcgc ctcgacatca tctgcccaga tgcgaagtta agtgcgcaga aagtaatatc  6420
atgcgtcaat cgtatgtgaa tgctggtcgc tatactgctg tcgattcgat actaacgccg  6480
ccatccagtg tcgaaaacga gctctcgaga accccttaata taacttcgta taatgtatgc  6540
tatacgaagt tattaggtga tatcagatcc acta                              6574

SEQ ID NO: 81          moltype = DNA  length = 8211
FEATURE                Location/Qualifiers
```

| | |
|---|---|
| misc_feature | 1..8211 |
| | note = Plasmid pCEV-G4-Km-TEF-AT-hABAB* |
| source | 1..8211 |
| | mol_type = other DNA |
| | organism = synthetic construct |

SEQUENCE: 81

```
gcctaggatg agatttcctt caattttac tgctgtttta ttcgcagcat cctccgcatt    60
agctggcgcc cacgtgatgc aggtacagct ggtggagacg gggggagggc tggtacaacc   120
aggcgggtca ctgaggcttt cctgtgccgc atctgggttc acactggatt attcgtccat   180
agggtggttt cggcaggctc ctggcaaaga gcgtgggggg gtctcatgta ttagtagtag   240
tggtgatagc acaaagtacg ccgattccgt aaagggccgg tttacaacct cagggataa    300
tgctaagaac accgtatatc tccagatgaa ctctctgaag cccgacgata cggccgtata   360
ttactgtgcg gctttcaggg cgactatgtg cggcgtgttc cctctgagcc cttacggcaa   420
ggacgactgg ggcaagggga ccctggtgac cgtatcctca ggcggtggag ggtctggtgg   480
gggaggctca gggggtggag gcagccaggt gcaactggtt gaatctgggg gaggcttggt   540
acaacctggg ggatccctga gactctcttg cgaggcctcc ggattcacct tggactacta   600
tggcatcggc tggttccgcc agcccccagg gaaggagcgg gaggccgttt catacattag   660
tgccagtgcc cggaccatac tgtacgcaga ctctgtgaag ggacgcttta ccatctctag   720
ggacaatgcc aaaaatgctg tgtacctgca aatgaacagc ctcaagcggg aggataccgc   780
agtgtactac tgcgcgagac ggcgcttctc cgcttctagc gtgaatagat ggctggccga   840
cgactacgac gtgtggggac ggggcacaca ggtggctgtg tcttccggtg gcggaagcgg   900
aggggccagc ggggggtgga gcggtggggg cagccaactg cagctggtag agacaggggg   960
cggcttagtt cagcctggag ggtctctcag actgtcatgc gctgcctctg gctttacctt  1020
cagtgactac gtgatgacat gggtccgcca agctccaggg aaggggcctg agtggatcgc  1080
tactattaat acagatggca gcacaatgcg ggacgactcc acaaagggc ggttcaccat   1140
ttccagagac aacgccaaga atactctgta ccttcagatg accagtctga aacccgagga  1200
cactgctctg tactattgtg caagaggccg ggtgatctct gcttccgcta tcagaggcgc  1260
agtaaggggc cctggaacac aggtaaccgt ttcatccggg ggaggcggtt caggcggtgg  1320
gggatctggc ggggtggat cccaagttca gctggtcgaa tccggggggcg gactggtcca   1380
gacaggggac tccctgaggc tctcctgtgc atcttccgga agcatcgccg gcttcgagac  1440
cgtgacctgg tctcgccagg ctcccgggaa gtctctgcag tgggtcgctt ccatgactaa  1500
gactaacaac gagatctact ctgactcagt gaaaggccgc ttcatcattt ctagagataa  1560
cgctaaaaac acagtgtatc tgcagatgaa tagtctcaaa cctgaagaca caggcgtgta  1620
tttctgtaag ggtcctgagc tgaggggcca gggcaccgga gtaacagtct cgagtgtcga  1680
cggtacctaa gctagctaag atccgctcta accgaaaagg aaggagttag acaacctgaa  1740
gtctaggtcc ctatttattt ttttatagtt atgttagtat taagaacgtt atttatattt  1800
caaattttc ttttttttct gtacagacgc gtgtacgcat gtaacattat actgaaaacc   1860
ttgcttgaga aggttttggg acgctcgaag atccagctgc attaatgaat cggccaacgc  1920
gcggggagag gcggtttgcg tattgggcgc tcttccgctt cctcgctcac tgactcgctg  1980
cgctcggtcg ttcggctgcg gcgagcggta tcagctcact caaaggcggt aatacggtta  2040
tccacagaat caggggataa cgcaggaaag aacatgtgag caaaaggcca gcaaaaggcc  2100
aggaaccgta aaaaggccgc gttgctggcg ttttttccata ggctccgccc cctgacgag   2160
catcaaaaaa atcgacgctc aagtcagagg tggcgaaacc cgacaggact ataaagatac  2220
caggcgtttc ccctggaagc tccctcgtgc gctctcctg ttccgaccct gccgcttacc   2280
ggatacctgt ccgcctttct cccttcggga agcgtggcgc tttctcatag ctcacgctgt  2340
aggtatctca gttcggtgta ggtcgttcgc tccaagctgg gctgtgtgca cgaaccccc   2400
gttccgcccg accgctgcgc cttatccggt aactatcgtc ttgagtccaa cccggtaaga  2460
cacgacttat cgccactggc agcagccact ggtaacagga ttagcagagc gaggtatgta  2520
ggcggtgcta cagagttctt gaagtggtgg cctaactacg gctacactag aaggacagta  2580
tttggtatct gcgctctgct gaagccagtt accttcggaa aaagagttgg tagctcttga  2640
tccggcaaac aaaccaccgc tggtagcggt ggtttttttg tttgcaagca gcagattacg  2700
cgcagaaaaa aaggatctca agaagatcct ttgatctttt ctacgggtc tgacgctcag   2760
tggaacgaaa actcacgtta agggatttg tcatgagat tatcaaaaag gatcttcacc   2820
tagatccttt taaattaaaa atgaagtttt aaatcaatct aaagtatata tgagtaaact  2880
tggtctgaca gttaccaatg cttaatcagt gaggcaccta tctcagcgat ctgtctattt  2940
cgttcatcca tagttgcctg actccccgtc gtgtagataa ctacgatacg ggagggctta  3000
ccatctggcc ccagtgctgc aatgataccg cgagacccac gctcaccggc tccagattta  3060
tcagcaataa accagccagc cggaagggcc gagcgcagaa gtggtcctgc aactttatcc  3120
gcctccatcc agtctattaa ttgttgccgg gaagctagag taagtagttc gccagttaat  3180
agtttgcgca acgttgttgc cattgctaca ggcatcgtgg tgtcacgctc gtcgtttggt  3240
atggcttcat tcagctccgg ttcccaacga tcaaggcgag ttacatgatc ccccatgttg  3300
tgcaaaaaag cggttagctc cttcggtcct ccgatcgttg tcagaagtaa gttggccgca  3360
gtgttatcac tcatggttat ggcagcactg cataattctc ttactgtcat gccatccgta  3420
agatgctttt ctgtgactgg tgagtactca accaagtcat tctgagaata gtgtatgcgg  3480
cgaccgagtt gctcttgccc ggcgtcaata cgggataata ccgcgccaca tagcagaact  3540
ttaaaagtgc tcatcattgg aaaacgttct cggggcgaaa actctcaag gatcttaccg   3600
ctgttgagat ccagttcgat gtaacccact cgtgcaccca actgatcttc agcatctttt  3660
actttcacca gcgtttctgg gtgagcaaaa acaggaaggc aaaatgccgc aaaaaaggga  3720
ataagggcga cacggaaatg ttgaatactc atactcttcc tttttcaata ttattgaagc  3780
atttatcagg gttattgtct catgagcgga tacatatttg aatgtattta gaaaaataaa  3840
caaataggg ttccgcgcac atttccccga aaagtgccac ctgaacgaag catctgtgct  3900
tcatttgta gaacaaaaat gcaacgcgag agcgctaatt tttcaaacaa gaatctgag   3960
ctgcatttt acagaacaga atgcaacgc gaaagcgcta tttaccaac gaagaatctg    4020
tgcttcattt tgtaaaaca aaatgcaac gcgagagcgc taatttttca aacaaagaat   4080
ctgagctgca ttttacaga acagaaatgc aacgcgagag cgctatttta ccaacaaaga   4140
atctatactt ctttttttgtt ctacaaaaat gcatcccgag agcgctattt ttctaacaaa  4200
gcatcttaga ttacttttttt tctccttttgt gcgctctata atgcagtctc ttgataactt  4260
tttgcactgt aggtccgtta aggttagaag aaggctactt ggtgtctat tttctcttcc   4320
ataaaaaaag cctgactcca cttcccgcgt ttactgatta ctagcgaagc tgcgggtgca   4380
```

```
tttttttcaag ataaaggcat ccccgattat attctatacc gatgtggatt gcgcatactt    4440
tgtgaacaga aagtgatagc gttgatgatt cttcattggt cagaaaatta tgaacggttt    4500
cttctatttt gtctctatat actacgtata ggaaatgttt acattttcgt attgttttcg    4560
attcactcta tgaatagttc ttactacaat ttttttgtct aaagagtaat actagagata    4620
aacataaaaa atgtagaggt cgagtttaga tgcaagttca aggagcgaaa ggtggatggg    4680
taggttatat agggatatag cacagagata tatagcaaag agatactttt gagcaatgtt    4740
tgtggaagcg gtattcgcaa tattttagta gctcgttaca gtccggtgcg ttttggttt     4800
tttgaaagtg cgtcttcaga gcgcttttgg ttttcaaaag cgctctgaag ttcctatact    4860
ttctagagaa taggaacttc ggaataggaa cttcaaagcg tttccgaaaa cgagcgcttc    4920
cgaaaatgca acgcgagctg cgcacataca gctcactgtt cacgtcgcac ctatatctgc    4980
gtgttgcctg tatatatata tacatgagaa aacggcata gtgcgtgttt atgcttaaat     5040
gcgtacttat atgcgtctat ttatgtagga tgaaaggtag tctagtacct cctgtgatat    5100
tatcccattc catgcggggt atcgtatgct tccttcagca ctacccttta gctgttctat    5160
atgctgccac tcctcaattg gattagtctc atccttcaat gctatcattt cctttgatat    5220
tggatcatgg tagacaaccc ttaatataac ttcgtataat gtatgctata cgaagttatt    5280
aggtctagag atctgtttag cttgcctcgt ccccgccggg tcacccggcc agcgacatgg    5340
aggcccagaa taccctcctt gacagtcttg acgtgcgcag ctcaggggca tgatgtgact    5400
gtcgcccgta catttagccc atacatcccc atgtataatc atttgcatcc atacattttg    5460
atggccgcac ggcgcgaagc aaaaattacg gctcctcgct gcagacctgc gagcagggaa    5520
acgctcccct cacagacgcg ttgaattgtc cccacgccgc gccctgtag agaaatataa      5580
aaggttagga tttgccactg aggttcttct ttcatatact tccttttaaa atcttgctag    5640
gatacagttc tcacatcaca tccgaacata aacaaccatg ggtaaggaaa agactcacgt    5700
ttcgaggccg cgattaaatt ccaacatgga tgctgattta tatgggtata aatgggctcg    5760
cgataatgtc gggcaatcag gtgcgacaat ctatcgattg tatgggaagc ccgatgcgcc    5820
agagttgttt ctgaaacatg gcaaaggtag cgttgccaat gatgttacag atgagatggt    5880
cagactaaac tggctgacgg aatttatgcc tcttccgacc atcaagcatt ttatccgtac    5940
tcctgatgat gcatggttac tcaccactgc gatccccggc aaaacagcat tccaggtatt    6000
agaagaatat cctgattcag gtgaaaatat tgttgatgcg ctggcagtgt tcctgcgccg    6060
gttgcattcg attcctgttt gtaattgtcc ttttaacagc gatcgcgtat ttcgtctcgc    6120
tcaggcgcaa tcacgaatga ataaccgttt ggttgatgcg agtgatttg atgacgagcg    6180
taatggctgg cctgttgaac aagtctgaaa agaaatgcat aagcttttgc cattctcacc    6240
ggattcagtc gtcactcatg gtgatttctc acttgataac cttattttg acgaggggaa    6300
attaataggt tgtattgatg ttggacgagt cggaatcgca gaccgatacc aggatcttgc    6360
catcctatgg aactgcctcg gtgagttttc tccttcatta cagaaacggc tttttcaaaa    6420
atatggtatt gataatcctg atatgaataa attgcagttt catttgatgc tcgatgagtt    6480
tttctaatca gtactgacaa taaaaagatt cttgttttca agaacttgtc atttgtatag    6540
ttttttttata ttgtagttgt tctatttaa tcaaatgtta gcgtgattta tatttttttt     6600
cgcctcgaca tcatctgccc agatgcgaag ttaagtgcgc agaaagtaat atcatgcgtc    6660
aatcgtatgt gaatgctggt cgctatactg ctgtcgattc gatactaacg ccgccatcca    6720
gtgtcgaaaa cgagctctcg agaacccttta atataacttc gtataatgta tgctatacga    6780
agttattagg tgatatcaga tccactagga gcgacctcat gctatacctg agaaagcaac    6840
ctgacctaca ggaaagagtt actcaagaat aagaattttc gttttaaaac ctaagagtca    6900
ctttaaaatt tgtatacact tattttttt ataacttatt taataataaa aatcataaat      6960
cataagaaat tcgcttattt agaagtgtca acaacgtatc taccaacgat ttgacccttt    7020
tccatctttt cgtaaatttc tggcaaggta gacaagccga caaccttgat tggagacttg    7080
accaaacctg tggcgaagaa ttgttaatta agagctcaga tcttatcgtc gtcatccttg    7140
taatccatcg atactagttt tttgattaaa attaaaaaaa ctttttgttt ttgtgtttat     7200
tctttgttct tagaaaagac aagttgagct tgtttgttct tgatgtttta ttatttaca     7260
atagctgcaa atgaagaata gattcgaaca ttgtgaagta ttggcatata tcgtctctat    7320
ttatacttt tttttttcag ttctagtata ttttgtatt tcctccttt cattcttca         7380
gttgccaata agttacaggg gatctcgaaa gatggtgggg atttttcctt gaaagacgac    7440
ttttgccat ctaatttttc cttgttgcct ctgaaaatta tccagcagaa gcaaatgtaa      7500
aagatgaacc tcagaagaac acgcaggggc ccgaaattgt tcctacgaga agtagtgggt    7560
cataaaaagt ttattccctg aaaaaaaat tttgcgttgc ctttctggag aattttttcg     7620
aattagcgtg ctgccactgc atgcattct gagaagtgtg ggcattcttc caccagttgt    7680
tcctcctaaa aaaaaaaaga tttcctaccc cgcacaaatt cctgcatacc cctcatttcc    7740
acggggccgg ccgcacacac catagcttca aaatgtttct actcctttt tactcttcca    7800
gattttctcg gactccgcgc atcgccgtac cacttcaaaa cacccaagca cagcatacta    7860
aatttcccct cttttcttcct ctagggtgtc gttaattacc cgtactaaag gtttggaaaa   7920
gaaaaaagag accgcctcgt ttcttttct tcgtcgaaaa aggcaataaa aatttttatc      7980
acgtttcttt ttcttgaaaa tttttttttt tgattttttt ctctttcgat gacctcccat     8040
tgatatttaa gttaataaac ggtcttcaat ttctcaagtt tcagtttcat ttttcttgtt    8100
ctattacaac tttttttact tcttgctcat tagaaagaaa gcatagcaat ctaatctaag    8160
ttttaattac aaggatccgt aatacgactc actatagggc ccgggcgtcg a            8211
```

SEQ ID NO: 82      moltype = DNA   length = 8202
FEATURE               Location/Qualifiers
misc_feature      1..8202
                      note = Plasmid pCEV-G4-Km-TEF-IVS-hABAB*
source                1..8202
                      mol_type = other DNA
                      organism = synthetic construct
SEQUENCE: 82

```
catgttactt caagcttttct tgttcctgtt ggctggttttt gccgcaaaaa tctccgcagg    60
cgcccacgtg atgcaggtac agctggtgga gacgggggga gggctggtac aaccaggcgg   120
gtcactgagg ctttcctgtg ccgcatctgg gttcacactg gattattcgt ccataggtg     180
gtttcggcag gctcctggca aagagcgtga gggggtctca tgtattagta gtagtggtga   240
tagcacaaag tacgccgatt ccgtaaaggg ccggtttaca acctcaggg ataatgctaa      300
gaacaccgta tatctccaga tgaactctct gaagcccgac gatacggccg tatattactg    360
```

```
tgcggctttc agggcgacta tgtgcgcgt gttccctctg agcccttacg gcaaggacga    420
ctggggcaag gggaccctgg tgaccgtatc ctcaggcggt ggagggtctg gtggggagg    480
ctcagggggt ggaggcagcc aggtgcaact ggttgaatct gggggaggct tggtacaacc   540
tgggggatcc ctgagactct cttgcgaggc ctccggattc accttggact actatgcat    600
cggctggttc cgccagcccc cagggaagga gcgggaggc gtttcataca ttagtgccag    660
tgcccggacc atactgtacg cagactctgt gaagggacgc tttaccatct ctagggacaa   720
tgccaaaaat gctgtgtacc tgcaaatgaa cagcctcaag cgggaggata ccgcagtgta   780
ctactgcgcg agacgcgct tctccgcttc tagcgtgaat agatgctgg ccgacgacta    840
cgacgtgtgg ggacggggca cacaggtggc tgtgtcttcc ggtggcggaa gcggaggggg   900
cagcgggggt gggagcggtg ggggcagcca actgcagctg gtagagacag ggggcggctt   960
agttcagcct ggagggtctc tcagactgtc atgcgctgcc tctggcttta ccttcagtga  1020
ctacgtgatg acatgggtcc gccaagctcc agggaagggg cctgagtgga tcgctactat  1080
taatacagat ggcagcacaa tgcgggacga ctccacaaag gggcggttca ccatttccag  1140
agacaacgcc aagaatactc tgtaccttca gatgaccagt ctgaaacccg aggacactgc  1200
tctgtactat tgtgcaagag gccggtgat ctctgcttcc gctatcagag gcgcagtaag   1260
gggccctgga acacaggtaa ccgtttcatc cggggaggc ggttcaggcg gtggggatc    1320
tggcgggggt ggatcccaag ttcagctggt cgaatccggg ggcggactgg tccagacagg  1380
gggctccctg aggctctcct gtgcatcttc cggaagcatc gggcgcttcg agaccgtgac  1440
ctggtctcgc caggctcccg ggaagtctct gcagtgggtc gcttccatga ctaagactaa  1500
caacgagatc tactctgact cagtgaaagg ccgcttcatc atttctagag ataacgctaa  1560
aaacacagtg tatctgcaga tgaatagtct caaacctgaa gacacaggcg tgtatttctg  1620
taagggtcct gagctgaggg gccagggcat tcaggtagca gtctcgagtt aaggtaccgc  1680
ggctagctaa gatccgctct aaccgaaaag gaaggagtta gacaacctga agtctaggtc  1740
cctatttatt ttttttatagt tatgttagta ttaagaacgt tatttatatt tcaaatttt   1800
ctttttttc tgtacagacg cgtgtacgca tgtaacatta tactgaaaac cttgcttgag   1860
aaggttttgg gacgctcgaa gatccagctg cattaatgaa tcggccaacg cgcggggaga  1920
ggcggtttgc gtattgggcg ctcttccgct tcctcgctca ctgactcgct gcgctcggtc  1980
gttcggctgc ggcgagcggt atcagctcac tcaaaggcgg taatacggtt atccacagaa  2040
tcaggggata acgcaggaaa gaacatgtga gcaaaaggcc agcaaaggc caggaaccgt   2100
aaaaaggccg cgttgctggc gtttttccat aggctccgcc ccctgacga gcatcacaaa   2160
aatcgacgct caagtcagag gtggcgaaac ccgacaggac tataaagata ccaggcgttt  2220
ccccctggaa gctccctcgt gcgctctcct gttccgaccc tgccgcttac cggatacctg  2280
tccgcctttc tcccttcggg aagcgtggcg ctttctcata gctcacgctg taggtatctc  2340
agttcggtgt aggtcgttcg ctccaagctg ggctgtgtgc acgaaccccc cgttcagccc  2400
gaccgctgcg ccttatccgg taactatcgt cttgagtcca acccggtaag cacagactta  2460
tcgccactgg cagcagccac tggtaacagg attagcagag cgaggtatgt aggcggtgct  2520
acagagttct tgaagtggtg gcctaactac ggctacacta aaggacagt atttggtatc   2580
tgcgctctgc tgaagccagt taccttcgga aaaagagttg gtagctcttg atccggcaaa  2640
caaaccaccg ctggtagcgg tggtttttt gtttgcaagc agcagattac gcgcagaaaa   2700
aaaggatctc aagaagatcc tttgatcttt tctacggggt ctgacgctca gtggaacgaa  2760
aactcacgtt aagggatttt ggtcatgaga ttatcaaaaa ggatcttcac ctagatcctt  2820
ttaaattaaa aatgaagttt taaatcaatc taaagtatat atgagtaaac ttggtctgac  2880
agttaccaat gcttaatcag tgaggcacct atctcagcga tctgtctatt tcgttcatcc  2940
atagttgcct gactcccgt cgtgtagata actacgatac gggagggctt accatctggc   3000
cccagtgctg caatgatacc gcgagaccca cgctcaccgg ctccagattt atcagcaata  3060
aaccagccag ccggaaggc cgagcgcaga agtggtcctg caactttatc cgcctccatc   3120
cagtctatta attgttgccg ggaagctaga gtaagtagtt cgccagttaa tagtttgcgc  3180
aacgttgttg ccattgctac aggcatcgtg gtgtcacgct cgtcgtttgg tatggcttca  3240
ttcagctccg gttcccaacg atcaaggcga gttacatgat cccccatgtt gtgcaaaaaa  3300
gcggttagct ccttcggtcc tccgatcgtt gtcagaagta agttggccgc agtgttatca  3360
ctcatggtta tggcagcact gcataattct cttactgtca tgccatccgt aagatgcttt  3420
tctgtgactg gtgagtactc aaccaagtca ttctgagaat agtgtatgcg gcgaccgagt  3480
tgctcttgcc cggcgtcaat acgggataat accgcgccac atagcagaac tttaaaagtg  3540
ctcatcattg gaaaacgttc ttcggggcga aaactctcaa ggatcttacc gctgttgaga  3600
tccagttcga tgtaacccac tcgtgcaccc aactgatctt cagcatcttt tactttcacc  3660
agcgtttctg ggtgagcaaa aacaggaagg caaaatgccg caaaaaaggg aataagggcg  3720
acacggaaat gttgaatact catactcttc ctttttcaat attattgaag catttatcag  3780
ggttattgtc tcatgagcgg atacatattt gaatgtattt agaaaaataa acaaataggg  3840
gttccgcgca catttccccg aaaagtgcca cctgaacgaa gcatctgtgc ttcattttgt  3900
agaacaaaaa tgcaacgcga gagcgctaat ttttcaaaca aagaatctga gctgcatttt  3960
tacagaacag aaatgcaacg cgaaagcgct attttaccaa cgaagaatct gtgcttcatt  4020
tttgtaaaac aaaaatgcaa cgcgagagcg ctaattttc aaacaaagaa tctgagctgc   4080
attttacag aacagaaatg caacgcgaga gcgctatttt accaacaaag aatctatact  4140
tcttttttgt tctacaaaaa tgcatcccga gagcgctatt tttctaacaa agcatcttag  4200
attacttttt ttctccttg tgcgctctat aatgcagtct cttgataact ttttgcactg  4260
taggtccgtt aaggttagaa gaaggctact tggtgtctca ttttctcttc cataaaaaaa  4320
gcctgactcc acttccgcg tttactgatt actagcgaag ctgcgggtgc attttttcaa   4380
gataaaggca tccccgatta tattctatac cgatgtggat tgcgcatact ttgtgaacag  4440
aaagtgatag cgttgatgat tcttcattgg tcagaaaatt atgaacggtt tcttctattt  4500
tgtctctata tactacgtat aggaaatgtt tacattttcg tattgttttc gattcactct  4560
atgaatagtt cttactacaa ttttttttgtc taaagagtaa tactagagat aaacataaaa  4620
aatgtagagg tcgagtttag atgcaagttc aaggagcgaa aggtggatgg gtaggttata  4680
tagggatata gcacagagat atatagcaaa gagatacttt tgagcaatgt ttgtggaagc  4740
ggtattcgca atattttagt agctcgttac agtccggtgc gtttttggtt ttttgaaagt  4800
gcgtcttcag agcgcttttg gttttcaaaa gcgctctgaa gttcctatac tttctagaga  4860
ataggaactt cggaatagga acttcaaagc gtttccgaaa acgagcgctt ccgaaaatgc  4920
aacgcgagct gcgcacatac agctcactgt tcacgtcgca cctatatctg cgtgttgcct  4980
gtatatatat atacatgaga agaacggcat agtgcgtgtt tatgcttaaa tgcgtactta  5040
tatgcgtcta tttatgtagg atgaaaggta gtctagtacc tcctgtgata ttatcccatt  5100
```

```
ccatgcgggg tatcgtatgc ttccttcagc actacccttt agctgttcta tatgctgcca  5160
ctcctcaatt ggattagtct catccttcaa tgctatcatt tcctttgata ttggatcatg  5220
gtagacaacc cttaatataa cttcgtataa tgtatgctat acgaagttat taggtctaga  5280
gatctgttta gcttgcctcg tccccgccgg gtcacccggc cagcgacatg gaggcccaga  5340
atacccctcct tgacagtctt gacgtgcgca gctcagggcg atgatgtgac tgtcgcccgt  5400
acatttagcc catacatccc catgtataat catttgcatc catacatttt gatggccgca  5460
cggcgcgaag caaaaattac ggctcctcgc tgcagacctg cgagcaggga aacgctcccc  5520
tcacagacgc gttgaattgt ccccacgccg cgccctgta gagaaatata aaggttagg  5580
atttgccact gaggttcttc tttcatatac ttcctttaa aatcttgcta ggatacagtt  5640
ctcacatcac atccgaacat aaacaaccat gggtaaggaa aagactcacg tttcgaggcc  5700
gcgattaaat tccaacatgg atgctgattt atatgggtat aaatgggctc gcgataatgt  5760
cgggcaatca ggtgcgacaa tctatcgatt gtatgggaag cccgatgcgc cagagttgtt  5820
tctgaaacat ggcaaaggta gcgttgccaa tgatgttaca gatgagatgg tcagactaaa  5880
ctggctgacg gaatttatgc ctcttccgac catcaagcat tttatccgta ctcctgatga  5940
tgcatggtta ctcaccactg cgatcccggg caaaacagca ttccaggtat tagaagaata  6000
tcctgattca ggtgaaaata ttgttgatgc gctggcagtg ttcctgcgcc ggttgcattc  6060
gattcctgtt tgtaattgtc cttttaacag cgatcgcgta tttcgtctcg ctcaggcgca  6120
atcacgaatg aataacggtt tggttgatgc gagtgatttt gatgacgagc gtaatggctg  6180
gcctgttgaa caagtctgga agaaaatgca taagcttttg ccattctcac cggattcagt  6240
cgtcactcat ggtgatttct cacttgataa ccttattttt gacgagggga aattaatagg  6300
ttgtattgat gttggacgag tcggaatcgc agaccgatac caggatcttg ccatcctatg  6360
gaactgcctc ggtgagtttt ctccttcatt acagaaacgg cttttttcaaa aatatggtat  6420
tgataatcct gatatgaata aattgcagtt tcatttgatg ctcgatgagt ttttctaatc  6480
agtactgaca ataaaaagat tcttgttttc aagaacttgt catttgtata gtttttttat  6540
attgtagttg ttcatttta atcaaatgtt agcgtgattt atatttttt tcgcctcgac  6600
atcatctgcc cagatgcgaa gttaagtgcg cagaaagtaa tatcatgcgt caatcgtatg  6660
tgaatgctgg tcgctatact gctgtcgatt cgatactaac gccgccatcc agtgtcgaaa  6720
acgagctctc gagaacccct aatataactt cgtataatgt atgctatacg aagttattag  6780
gtgatatcag atccactagg agcgacctca tgctatacct gagaaagcaa cctgacctac  6840
aggaaagagt tactcaagaa taagaatttt cgttttaaga cctaagagtc acttttaaaat  6900
ttgtatacac ttatttttt tataacttat ttaataataa aaatcataaa tcataagaaa  6960
ttcgcttatt tagaagtgtc aacaacgtat ctaccaacga tttgaccctt ttccatcttt  7020
tcgtaaattt ctggcaaggt agacaagccg acaaccttga ttgagactt gaccaaacct  7080
ctggcgaaga atttgttaat aagagctcag atcttatcgt cgtcatcctt gtaatccatc  7140
gatactagtt ttttgattaa aattaaaaaa acttttttgtt tttgtgttta ttctttgttc  7200
ttagaaaaga caagttgagc ttgtttgttc ttgatgtttt attattttac aatagctgca  7260
aatgaagaat agattcgaac attgtgaagt attggcatat atcgtctcta tttatacttt  7320
ttttttttca gttctagtat attttgtatt ttcctccttt tcattcttc agttgccaat  7380
aagttacagg ggatctcgaa agatggtggg gattttttct tgaaagacga cttttttgcca  7440
tctaatttt ccttgttgcc tctgaaaatt atccagcaga agcaaatgta aaagatgaac  7500
ctcagaagaa cacgcagggg cccgaaattg ttcctacgag aagtagtggg tcataaaaag  7560
tttattccct ggaaaaaaaa ttttgcgttg cctttctgga gaattttttc gaattagcgt  7620
gctgccactg catgcatttc tgagaagtgt gggcattctt ccaccagttg ttcctcctaa  7680
aaaaaaaag atttcctacc ccgcacaaat tcctgcatac ccctcatttc cacggggccg  7740
gccgcacaca ccatagcttc aaaatgtttc tactcctttt ttactcttcc agattttctc  7800
ggactccgcg catcgccgta ccacttcaaa acacccaagc acagcatact aaatttcccc  7860
tctttcttcc tctagggtgt cgttaattac ccgtactaaa ggtttggaaa agaaaaaaga  7920
gaccgcctcg tttctttttc ttcgtcgaaa aaggcaataa aaatttttat cacgtttctt  7980
tttcttgaaa atttttttttt ttgattttt tctcttcga tgacctccca ttgatattta  8040
agttaataaa cggtcttcaa tttctcaagt ttcagtttca tttttcttgt tctattacaa  8100
ctttttttac ttcttgctca ttagaaagaa agcatagcaa tctaatctaa gttttaatta  8160
caaggatccg taatacgact cactataggg cccgggcgtc ga                     8202

SEQ ID NO: 83        moltype = DNA   length = 8190
FEATURE              Location/Qualifiers
misc_feature         1..8190
                     note = Plasmid pCEV-G4-Km-TEF-AT-hABAB
source               1..8190
                     mol_type = other DNA
                     organism = synthetic construct
SEQUENCE: 83
catgagattt ccttcaattt ttactgctgt tttattcgca gcatcctccg cattagctat    60
gcaggtacag ctggtggaga cggggggagg gctggtacaa ccaggcgggt cactgaggct   120
ttcctgtgcc gcatctgggt tcacactgga ttattcgtcc ataggtggt ttcggcaggc   180
tcctggcaaa gagcgtgagg gggtctcatg tattagtagt agtggtgata gcacaaagta   240
cgccgattcc gtaaagggcc ggtttacaac ctccagggat aatgctaaga acaccgtata   300
tctccagatg aactctctga agcccgacga tacggccgta tattactgtg cggctttcag   360
ggcgactatg tgcggcgtgt tccctctgag cccttacggc aaggacgact ggggcaaggg   420
gaccctggtg accgtatcct caggcggtgg agggtcggt cagggggtgg cagggggtgg   480
aggcagccag gtgcaactgg ttgaatctgg gggaggcttg gtacaacctg gggatccct   540
gagactctct tgcgaggcct ccggattcac cttggactac tatggcatcg gctggttccg   600
ccagcccccca gggaaggagc gggaggccgt ttcatacatt agtgccagtg cccggaccat   660
actgtacgca gactctgtga agggacgctt taccatctct agggacaatg ccaaaaatgc   720
tgtgtacctg caaatgaaca gcctcaagcg ggaggatacc gcagtgtact actgcgcgag   780
acggcgcttc tccgcttcta gcgtgaatag atgctggcc gacgactacg acgtgtgggg   840
acggggcaca caggtggctg tgtcttccgg tggcggaagc ggaggggca gcggggtgg   900
gagcggtggg ggcagccaac tgcagctggt agagacaggg ggcggcttag ttcagcctgg   960
agggtctctc agactgtcat gcgctgcctc tggctttacc ttcagtgact acgtgatgac  1020
atgggtccgc caagctccag ggaaggggcc tgagtggatc gctactatta atacagatgg  1080
```

```
cagcacaatg cgggacgact ccacaaaggg gcggttcacc atttccagag acaacgccaa   1140
gaatactctg taccttcaga tgaccagtct gaaacccgag gacactgctc tgtactattg   1200
tgcaagaggc cgggtgatct ctgcttccgc tatcagaggc gcagtaaggg gccctggaac   1260
acaggtaacc gtttcatccg ggggaggcgg ttcaggcggt gggggatctg gcggggggtgg   1320
atcccaagtt cagctggtcg aatccggggg cggactggtc cagacagggg gctccctgag   1380
gctctcctgt gcatcttccg gaagcatcgc cggcttcgag accgtgacct ggtctcgcca   1440
ggctcccggg aagtctctgc agtgggtcgc ttccatgact aagactaaca acgagatcta   1500
ctctgactca gtgaaaggcc gcttcatcat ttctagagat aacgctaaaa acacagtgta   1560
tctgcagatg aatagtctca aacctgaaga cacaggcgtg tatttctgta agggtcctga   1620
gctgaggggc cagggcatcc aggtaacagt ctcgagttaa ggtaccgcgg ctagctaaga   1680
tccgctctaa ccgaaaagga aggagttaga caacctgaag tctaggtccc tatttatttt   1740
tttatagtta tgttagtatt aagaacgtta tttatatttc aaattttttct ttttttttctg   1800
tacagacgcg tgtacgcatg taacattata ctgaaaacct tgcttgagaa ggttttggga   1860
cgctcgaaga tccagctgca ttaatgaatc ggccaacgcg cggggagagg cggtttgcgt   1920
attgggcgct cttccgcttc ctcgctcact gactcgctgc gctcggtcgt tcggctgcgg   1980
cgagcggtat cagctcactc aaaggcggta atacggttat ccacagaatc aggggataac   2040
gcaggaaaga acatgtgagc aaaaggccag caaaaggcca ggaaccgtaa aaaggccgcg   2100
ttgctggcgt ttttccatag gctccgcccc cctgacgagc atcacaaaaa tcgacgctca   2160
agtcagaggt ggcgaaaccc gacaggacta taaagatacc aggcgtttcc ccctggaagc   2220
tccctcgtgc gctctcctgt tccgaccctg ccgcttaccg gatacctgtc cgcctttctc   2280
ccttcggaa gcgtggcgct ttctcatagc tcacgctgta ggtatctcag ttcggtgtag   2340
gtcgttcgct ccaagctggg ctgtgtgcac gaaccccccg ttcagcccga ccgctgcgcc   2400
ttatccggta actatcgtct gagtccaac ccggtaagac acgacttatc gccactggca   2460
gcagccactg gtaacaggat tagcagagcg aggtatgtag gcggtgctac agagttcttg   2520
aagtggtggc ctaactacgg ctacactaga aggacagtat ttggtatctg cgctctgctg   2580
aagccagtta ccttcggaaa aagagttggt agctcttgat ccggcaaaca aaccaccgct   2640
ggtagcggtg gtttttttgt ttgcaagcag cagattacgc gcagaaaaaa aggatctcaa   2700
gaagatcctt tgatcttttc tacggggtct gacgctcagt ggaacgaaaa ctcacgttaa   2760
gggattttgg tcatgagatt atcaaaaagg atcttcacct agatcctttt aaattaaaaa   2820
tgaagtttta aatcaatcta aagtatatat gagtaaactt ggtctgacag ttaccaatgc   2880
ttaatcagtg aggcacctat ctcagcgatc tgtctatttc gttcatccat agttgcctga   2940
ctccccgtcg tgtagataac tacgatacgg gagggcttac catctggccc cagtgctgca   3000
atgataccgc gagacccacg ctcaccggct ccagatttat cagcaataaa ccagccagcc   3060
ggaagggccg agcgcagaag tggtcctgca actttatccg cctccatcca gtctattaat   3120
tgttgccggg aagctagagt aagtagttcg ccagttaata gtttgcgcaa cgttgttgcc   3180
attgctacag gcatcgtggt gtcacgctcg tcgtttggta tggcttcatt cagctccggt   3240
tcccaacgat caaggcgagt tacatgatcc cccatgttgt gcaaaaaagc ggttagctcc   3300
ttcggtcctc cgatcgttgt cagaagtaag ttggccgcag tgttatcact catggttatg   3360
gcagcactgc ataattctct tactgtcatg ccatccgtaa gatgcttttc tgtgactggt   3420
gagtactcaa ccaagtcatt ctgagaatag tgtatgcggc gaccgagttg ctcttgcccg   3480
gcgtcaatac gggataatac cgcgccacat agcagaactt taaaagtgct catcattgga   3540
aaacgttctt cggggcgaaa actctcaagg atcttaccgc tgttgagatc cagttcgatg   3600
taacccactc gtgcacccaa ctgatcttca gcatctttta ctttcaccag cgtttctggg   3660
tgagcaaaaa caggaaggca aaatgccgca aaaaagggaa taagggcgac acggaaatgt   3720
tgaatactca tactcttcct ttttcaatat tattgaagca tttatcaggg ttattgtctc   3780
atgagcggat acatatttga atgtatttag aaaaataaac aaataggggt tccgcgcaca   3840
tttccccgaa aagtgccacc tgaacgaagc atctgtgctt catttttgtag aacaaaaatg   3900
caacgcgaga gcgctaattt ttcaaacaaa gaatctgagc tgcatttttta cagaacagaa   3960
atgcaacgcg aaagcgctat tttaccaacg aagaatctgt gcttcatttt tgtaaaacaa   4020
aaatgcaacg cgagagcgct aattttttcaa acaaagaatc tgagctgcat ttttacgaaa   4080
cagaaatgca acgcgagagc gctattttac caacaaagaa tctatacttc tttttttgttt   4140
tacaaaaatg catcccgaga gcgctatttt tctaacaaag catcttagat tacttttttt   4200
ctcctttgtg cgctctataa tgcagtctct tgataacttt ttgcactgta ggtccgttaa   4260
ggttagaaga aggctacttt ggtgtctatt ttctcttcca taaaaaaagc ctgactccac   4320
ttcccgcgtt tactgattac tagcgaagct gcgggtgcat tttttcaaga taaaggcatc   4380
cccgattata ttctataccg atgtggattg cgcatacttt gtgaacgaaa agtgatagcg   4440
ttgatgattc ttcattggtc agaaaattat gaacggtttc ttctattttg tctctatata   4500
ctacgtatag gaaatgttta cattttcgta ttgttttcga ttcactctat gaatagttct   4560
tactacaatt tttttgtcta aagagtaata ctagagataa acataaaaaa tgtagaggtc   4620
gagtttagat gcaagttcaa ggagcgaaag gtggatgggt aggttatata gggatatagc   4680
acagagatat atagcaaaga gatactttg agcaatgttt gtggaagcgg tattcgcaat   4740
attttagtag ctcgttacag tccggtgcgt ttttggtttt ttgaaagtgc gtcttcagag   4800
cgcttttggt tttcaaaagc gctctgaagt tcctatactt tctagagaat aggaacttcg   4860
gaataggaac ttcaaagcgt ttccgaaaac gagcgcttcc gaaaatgcaa cgcgagctgc   4920
gcacatacag ctcactgttc acgtcgcacc tatatctgcg tgttgcctgt atatatatat   4980
acatgagaag aacggcatag tgcgtgttta tgcttaaatg cgtacttata tgcgtctatt   5040
tatgtaggat gaaaggtagt ctagtacctc ctgtgatatt atcccattcc atgcgggta   5100
tcgtatgctt ccttcagcac taccctttag ctgttctata tgctgccact cctcaattgg   5160
attagtctca tccttcaatg ctatcatttc ctttgatatt ggatcatgat agacaaccct   5220
taatataact tcgtataatg tatgctatac gaagttatta ggtctagaga tctgtttagc   5280
ttgcctcgtc cccgccgggt cacccggcca gcgacatgga gcccagaat accctccttg   5340
acagtcttga cgtgcgcagc tcaggggcat gatgtgactg tcgcccgtac atttagccca   5400
tacatccca tgtataatca tttgcatcca tactttga tggccgcacg gcgcgaagca   5460
aaaattacgg ctcctcgctg cagacctgcg agcagggaaa cgctccccte acagacggtc   5520
tgaattgtcc ccacgccgcg cccctgtaga gaaatataaa aggttaggat ttgccactga   5580
ggttcttctt tcatatactt ccttttaaaa tcttgctagg atacagttct cacatcacat   5640
ccgaacataa acaaccatgg gtaaggaaaa gactcacgtt tcgaggccgc gattaaattc   5700
caacatggat gctgatttat atgggtataa atgggctcgc gataatgtcg ggcaatcagg   5760
tgcgacaatc tatcgattgt atgggaagcc cgatgcgcca gagttgtttc tgaaacatgg   5820
```

```
caaaggtagc gttgccaatg atgttacaga tgagatggtc agactaaact ggctgacgga   5880
atttatgcct cttccgacca tcaagcattt tatccgtact cctgatgatg catggttact   5940
caccactgcg atccccggca aaacagcatt ccaggtatta gaagaatatc ctgattcagg   6000
tgaaatatt gttgatgcgc tggcagtgtt cctgcgccgg ttgcattcga ttcctgtttg    6060
taattgtcct tttaacagcg atcgcgtatt tcgtctcgct caggcgcaat cacgaatgaa   6120
taacggtttg gttgatgcga gtgattttga tgacgagcgt aatggctggc ctgttgaaca   6180
agtctggaaa gaaatgcata agcttttgcc attctcaccg gattcagtcg tcactcatgg   6240
tgatttctca cttgataacc ttattttga cgaggggaaa ttaataggtt gtattgatgt    6300
tggacgagtc ggaatcgcag accgatacca ggatcttgcc atcctatgga actgcctcgg   6360
tgagttttct ccttcattac agaaacggct ttttcaaaaa tatggtattg ataatcctga   6420
tatgaataaa ttgcagtttc atttgatgct cgatgagttt ttctaatcag tactgacaat   6480
aaaaagattc ttgttttcaa gaacttgtca tttgtatagt tttttatat tgtagttgtt     6540
ctatttttaat caaatgttag cgtgatttat attttttttc gcctcgacat catctgccca   6600
gatgcgaagt taagtgcgca gaaagtaata tcatgcgtca atcgtatgtg aatgctggtc    6660
gctatactgc tgtcgattcg atactaacgc cgccatccag tgtcgaaaac gagctctcga   6720
gaaccccttaa tataacttcg tataatgtat gctatacgaa gttattaggt gatatcagat   6780
ccactaggag cgacctcatg ctatacctga gaaagcaacc tgacctacag gaaagagtta   6840
ctcaagaata agaattttcg ttttaaaacc taagagtcac tttaaaattt gtatacactt   6900
atttttttta taacttattt aataataaaa atcataaatc ataagaaatt cgcttattta   6960
gaagtgtcaa caacgtatct accaacgatt tgacccttt ccatcttttc gtaaatttct    7020
ggcaaggtag acaagccgac aaccttgatt ggagacttga ccaaacctct ggcgaagaat   7080
tgttaattaa gagctcagat cttatcgtcg tcatcctttat aatccatcga tactagtttt   7140
ttgattaaaa ttaaaaaaac ttttttgtttt tgtgttattt ctttgttctt agaaaagaca   7200
agttgagctt gtttgttctt gatgttttat tattttacaa tagctgcaaa tgaagaatag   7260
attcgaacat tgtgaagtat tggcatatat cgtctctatt tatactttt tttttcagt     7320
tctagtatat tttgtatttt cctcctttc atttttcag ttgccaataa gttacagggg     7380
atctcgaaag atggtgggga ttttttcctg aaagacgact ttttgccatc taatttttcc   7440
ttgttgcctc tgaaaattat ccagcagaag caaatgtaaa agatgaacct cagaagaaca   7500
cgcaggggcc cgaaattgtt cctacgaaa gtagtgggtc ataaaagtt tattccctgg     7560
aaaaaaaatt ttgcgttgcc tttctggaga atttttcga attagcgtgc tgccactgca   7620
tgcatttctg agaagtgtgg gcattcttcc accagttgtt cctcctaaaa aaaaaaagat   7680
ttcctaccc gcacaaattc ctgcataccc ctcatttcca cggggccggc cgcacacacc    7740
atagcttcaa aatgttcta ctccttttt actcttccag attttctcgg actccgcgca     7800
tcgccgtacc acttcaaaac acccaagcac agcatactaa attttcccctc ttttcttcctc  7860
tagggtgtcg ttaattaccc gtactaaagg tttggaaaag aaaaagaga ccgcctcgtt    7920
tcttttttctt cgtcgaaaaa ggcaataaaa attttttatca cgtttctttt tcttgaaaat   7980
ttttttttttt gatttttttc tctttcgatg acctcccatt gatatttaag ttaataaacg   8040
gtcttcaatt tctcaagttt cagtttcatt tttcttgttc tattacaact ttttttactt   8100
cttgctcatt agaaagaaag catagcaatc taatctaagt tttaattaca aggatccgta   8160
atacgactca ctataggggcc cgggcgtcga                                   8190

SEQ ID NO: 84          moltype = DNA  length = 8190
FEATURE                Location/Qualifiers
misc_feature           1..8190
                       note = Plasmid pCEV-G4-Km-TEF-AT-yABAB
source                 1..8190
                       mol_type = other DNA
                       organism = synthetic construct
SEQUENCE: 84
ggagcgacct catgctatac ctgagaaagc aacctgacct acaggaaaga gttactcaag    60
aataagaatt ttcgttttaa aacctaagag tcactttaaa atttgtatac acttattttt   120
tttataactt atttaataat aaaaatcata atcataaga aattcgctta tttagaagtg   180
tcaacaacgt atctaccaac gatttgaccc ttttccatct tttcgtaaat ttctggcaag   240
gtagacaagc cgacaacctt gattggagac ttgaccaaac ctctggcgaa gaattgttaa   300
ttaagagctc agatcttatc gtcgtcatcc tgtaatcca tcgatactag tttttttgatt   360
aaaattaaaa aaacttttttg ttttttgtgtt tattctttgt tcttagaaaa gacaagttga   420
gcttgtttgt tcttgatgtt ttattattttt acaatagctg caaatgaaga atagattcga   480
acattgtgaa gtattggcat atatcgtctc tattttatact ttttttttt cagttctagt   540
atattttgta ttttcctcct tttcattctt tcagttgcca ataagttaca ggggatctcg   600
aaagatggtg ggaatttttc cttgaaagac gacttttgc catctcaattt ttccttgttg   660
cctctgaaaa ttatccagca gaagcaaatg taaaagatga acctcagaag aacacgcagg   720
ggcccgaaat tgttcctacg agaagtagtg gtcataaaa agtttattcc ctggaaaaaa   780
aattttgcgt tgccttttctg gagaattttt tcgaattagc gtgctgccac tgcatgcatt   840
tctgagaagt gtgggcattc ttccaccagt tgttcctcct aaaaaaaaaa agattttccta   900
ccccgcacaa attcctgcat accctcatt tccacgggggc cggccgcaca ccatagct    960
tcaaaatgtt tctactcctt ttttactctt ccagattttc tcggactccg cgcatcgccg   1020
taccacttca aaacacccaa gcacagcata ctaaattttcc cctcttttctt cctctagggt   1080
gtcgttaatt acccgtacta aaggtttgga aagaaaaa gagaccgcct cgtttctttt   1140
tcttcgtcga aaaaggcaat aaaaatttttt atcacgtttc ttttcttgaa aatttttttt   1200
ttttgatttt tttctctttc gatgacctcc cattgatatt taagttaata aacggtcttc   1260
aatttctcaa gtttcagttt cattttcttt gtcttattac aactttttttt acttcttgct   1320
cattagaaag aagcatagc aatctaatct aagttaat acaaggatc cgtaatacga    1380
ctcactata ggcccgggcg tcgacatgag atttccttca atttactg ctgttttatt    1440
cgcagcatcc tccgcattag ctatgcaagt acaattggtt gaaaccggtg gtgttttagt   1500
tcaaccaggt ggtagtttga gattatcttg tgctgcatca ggtttacat ggattattc    1560
ttcaataggt tggttcagac aagctcctgg taaagaaaga gaaggtgttt cttgcatatc   1620
cagttctggt gactcaacta aatatgctga ctccgttaag ggtagattca ctacttcaag   1680
agataacgct aaaaatacag tctacttgca aatgaactca ttaaagccag atgacacagc   1740
agtctattac tgtgccgctt ttagagccac catgtgcggt gtattcccat tgtctccta   1800
```

```
cggtaaagat gactgggta aaggtacttt agttactgtc tcatccggtg gtggtggttc   1860
cggtggtggt ggtagtggtg gtggtggttc tcaagttcaa ttagtagaat ccggtggtgg   1920
tttagtccaa cctggtggta gtttaagatt atcctgcgaa gcaagtggtt ttacattaga   1980
ttattacggt atcggttggt ttagacaacc acctggtaaa gaaagagaag ctgtctctta   2040
tattccgct agtgcaagaa ctatattgta cgcagattct gtaaagggta gattcacaat   2100
ttcaagagac aatgccaaga acgctgtttta tttgcaaatg aactctttga agagagaaga   2160
caccgcagtt tattactgtg ccagaagaag attttctgct tcttcagtca acagatggtt   2220
agcagacgat tatgatgttt ggggtagagg tacacaagtc gccgtaagtt ctggtggtgg   2280
ttccggtggt ggtagtggtg gtggttctgg tggtggttca caattgcaat tagtagaaac   2340
tggtggtggt ttggttcaac caggtggttc cttgagatta agttgtgctg catctggttt   2400
tactttctct gattacgtta tgacatgggt cagacaagct ccaggtaaag gtcctgaatg   2460
gatcgctaca attaataccg acggttccac aatgagagat gacagtacca agggtagatt   2520
cactatttca agagataacg ctaagaacac attgtactta caaatgaccc tctttgaaacc   2580
agaagacacc gcattatatt actgtgccag aggtagagtc atatccgcca gtgctatcag   2640
aggtgcagta agaggtcctg gtactcaagt tacagtctct tcaggtggcg gcggtagtgg   2700
cggcggcggt tctggcggtg gtggttcaca agtccaattg gtagaatctg gtggtggttt   2760
agttcaaact ggtggttcat tgagattatc ctgcgcttcc agtggttcca ttgcaggttt   2820
cgaaactgtt acatggtcaa gacaagctcc aggtaaatct ttgcaatggg tcgcctcaat   2880
gaccaagact aacaacgaaa tctattctga ttcagttaag ggtagattca ttatttcaag   2940
agataatgct aaaaacaccg tttatttgca aatgaactca ttgaagccag aagatactgg   3000
tgtttacttc tgcaagggtc ctgaattaag aggtcaaggt attcaagtaa cagtttcttc   3060
ataaggtacc gcggctagct aagatccgtc ctaaccgaaa agaaggagt tagacaacct   3120
gaagtctagg tccctattta ttttttttata gttatgttag tattaagaac gttatttata   3180
tttcaaattt ttcttttttt tctgtacaga cgcgtgtacg catgtaacat tatactgaaa   3240
accttgcttg agaaggtttt gggacgctcg aagatccagc tgcattaatg aatcggccaa   3300
cgcgcgggga gaggcggttt gcgtattggg cgctcttccg cttcctcgct cactgactcg   3360
ctgcgctcgg tcgttcggct gcggcgagcg gtatcagctc actcaaaggc ggtaatacgg   3420
ttatccacag aatcagggga taacgcagga aagaacatgt gagcaaaagg ccagcaaaag   3480
gccaggaacc gtaaaaaggc cgcgttgctg gcgtttttcc ataggctccg ccccctgac   3540
gagcatcaca aaaatcgacg ctcaagtcag aggtggcgaa acccgacagg actataaaga   3600
taccaggcgt ttccccctgg aagctccctc gtgcgctctc ctgttccgac cctgccgctt   3660
accggatacc tgtccgcctt tctcccttcg ggaagcgtgg cgctttctca tagctcacgc   3720
tgtaggtatc tcagttcggt gtaggtcgtt cgctccaagc tgggctgtgt gcacgaaccc   3780
cccgttcagc ccgaccgctg cgccttatcc ggtaactatc gtcttgagtc caacccggta   3840
agacacgact tatcgccact ggcagcagcc actggtaaca ggattagcag agcgaggtat   3900
gtaggcggtg ctacagagtt cttgaagtgg tggcctaact acggctacac tagaaggaca   3960
gtatttggta tctgcgctct gctgaagcca gttaccttcg gaaaaagagt tggtagctct   4020
tgatccggca aacaaaccac cgctggtagc ggtggttttt ttgtttgcaa gcagcagatt   4080
acgcgcagaa aaaaaggatc tcaagaagat cctttgatct tttctacggg gtctgacgct   4140
cagtggaacg aaaactcacg ttaagggatt ttggtcatga gattatcaaa aaggatcttc   4200
acctagatcc ttttaaatta aaaatgaagt tttaaatcaa tctaaagtat atatgagtaa   4260
acttggtctg acagttacca atgcttaatc agtgaggcac ctatctcagc gatctgtcta   4320
tttcgttcat ccatagttgc ctgactcccc gtcgtgtaga taactacgat acgggagggc   4380
ttaccatctg gccccagtgc tgcaatgata ccgcgagacc cacgctcacc ggctccagat   4440
ttatcagcaa taaaccagcc agccggaagg gccgagcgca gaagtggtcc tgcaacttta   4500
tccgcctcca tccagtctat taattgttgc cgggaagcta gagtaagtag ttcgccagtt   4560
aatagtttgc gcaacgttgt tgccattgct acaggcatcg tggtgtcacg ctcgtcgttt   4620
ggtatggctt cattcagctc cggttcccaa cgatcaaggc gagttacatg atcccccatg   4680
ttgtgcaaaa aagcggttag ctccttcggt cctccgatcg ttgtcagaag taagttggcc   4740
gcagtgttat cactcatggt tatggcagca ctgcataatt ctcttactgt catgccatcc   4800
gtaagatgct tttctgtgac tggtgagtac tcaaccaagt cattctgaga atagtgtatg   4860
cggcgaccga gttgctcttg cccggcgtca atacgggata ataccgcgcc acatagcaga   4920
actttaaaag tgctcatcat tggaaaacgt tcttcggggc gaaaactctc aaggatctta   4980
ccgctgttga gatccagttc gatgtaaccc actcgtgcac ccaactgatc ttcagcatct   5040
tttactttca ccagcgtttc tgggtgagca aaaacaggaa ggcaaaatgc cgcaaaaaag   5100
ggaataaggg cgacacggaa atgttgaata ctcatactct tcctttttca atattattga   5160
agcatttatc agggttattg tctcatgagc ggatacatat ttgaatgtat ttagaaaaat   5220
aaacaaatag gggttccgcg cacatttccc cgaaaagtgc cacctgaacg aagcatctgt   5280
gcttcatttt gtagaacaaa aatgcaacgc gagagcgcta attttcaaa caaagaatct   5340
gagctgcatt tttacagaac agaaatgcaa cgcgaaagcg ctattttacc aacgaagaat   5400
ctgtgcttca tttttgtaaa acaaaaatgc aacgcgagag cgctaatttt tcaaacaaag   5460
aatctgagct gcattttac agaacagaaa tgcaacgcga gagcgctatt ttaccaacaa   5520
agaatctata cttctttttt gttctacaaa aatgcatccc gagagcgcta tttttctaac   5580
aaagcatctt agattacttt ttttctcctt tgtgcgctct ataatgcagt ctcttgataa   5640
cttttttgcac tgtaggtccg ttaaggttag aagaaggcta cttttggtgtc tattttctct   5700
tccataaaaa aagcctgact ccacttcccg cgtttactga ttactagcga agctgcgggt   5760
gcattttttc aagataaagg catcccgat tatattctat accgatgtgg attgcgcata   5820
ctttgtgaac agaaagtgat agcgttgatg attcttcatt ggtcagaaaa ttatgaacgg   5880
tttcttctat tttgtctcta tatactacgt ataggaaatg tttacatttt cgtattgttc   5940
tcgattcact ctatgaatag ttcttactac aattttttg tctaaagagt aatactagag   6000
ataaacataa aaaatgtaga ggtcgagttt agatgcaagt tcaggagcg aaaggtggat   6060
gggtaggtta tatagggata tagcacagag atatatagca aagagatact tttgagcaat   6120
gtttgtggaa gcggtattcg caatatttta gtagctcgtt acagtccggt gcgttttgg   6180
tttttttgaaa gtgcgtcttc agagcgcttt tggttttcaa aagcgctctg aagttcctat   6240
actttctaga aataggaac ttcggaatag gaacttcaaa gcgttccga aaacgagcgc   6300
ttccgaaaat gcaacgcgag ctgcgcacat acagctcact gttcacgtcg cacctatatc   6360
tgcgtgttgc ctgtatatat atatacatga gaagaacggc atagtgcgtg tttatgctta   6420
aatgcgtact tatatgcgtc tatttatgta ggatgaaagg tagtctagta cctcctgtga   6480
tattatccca ttccatgcgg ggtatcgtat gcttccttca gcactaccct ttagctgttc   6540
```

-continued

```
tatatgctgc cactcctcaa ttggattagt ctcatccttc aatgctatca tttcctttga 6600
tattggatca tggtagacaa cccttaatat aacttcgtat aatgtatgct atacgaagtt 6660
attaggtcta gagatctgtt tagcttgcct cgtccccgcc gggtcacccg gccagcgaca 6720
tggaggccca gaataccctc cttgacagtc ttgacgtgcg cagctcaggg gcatgatgtg 6780
actgtcgccc gtacatttag cccatacatc cccatgtata atcatttgca tccatacatt 6840
ttgatggccg cacggcgcga agcaaaaatt acggctcctc gctgcagacc tgcgagcagg 6900
gaaacgctcc cctcacagac gcgttgaatt gtccccacgc cgcgcccctg tagagaaata 6960
taaaaggtta ggatttgcca ctgaggttct tctttcatat acttccttt aaaatcttgc 7020
taggatacag ttctcacatc acatccgaac ataaacaacc atgggtaagg aaaagactca 7080
cgtttcgagg ccgcgattaa attccaacat ggatgctgat ttatatgggt ataaatgggc 7140
tcgcgataat gtcgggcaat caggtgcgac aatctatcga ttgtatggga agcccgatgc 7200
gccagagttg tttctgaaac atggcaaagg tagcgttgcc aatgatgtta cagatgagat 7260
ggtcagacta aactggctga cggaatttat gcctcttccg accatcaagc attttatccg 7320
tactcctgat gatgcatggt tactcaccac tgcgatcccc ggcaaaacag cattccaggt 7380
attagaagaa tatcctgatt caggtgaaaa tattgttgat gcgctggcag tgttcctgcg 7440
ccggttgcat tcgattcctg tttgtaattg tccttttaac agcgatcgcg tatttcgtct 7500
cgctcaggcg caatcacgaa tgaataacgg tttggttgat gcgagtgatt ttgatgacga 7560
gcgtaatggc tggcctgttg aacaagtctg gaaagaaatg cataagcttt tgccattctc 7620
accggattca gtcgtcactc atggtgattt ctcacttgat aaccttattt ttgacgaggg 7680
gaaattaata ggttgtattg atgttggacg agtcggaatc gcagaccgat accaggatct 7740
tgccatccta tggaactgcc tcggtgagtt ttctccttca ttacagaaac ggcttttca 7800
aaaatatggt attgataatc ctgatatgaa taaattgca tttcatttga tgctcgatga 7860
gttttctaa tcagtactga caataaaaag attcttgttt tcaagaactt gtcatttgta 7920
tagtttttt atattgtagt tgttctattt taatcaaatg ttagcgtgat ttatattttt 7980
tttcgcctcg acatcatctg cccagatgcg aagtaagtg cgcagaaagt aatatcatgc 8040
gtcaatcgta tgtgaatgct ggtcgctata ctgctgtcga ttcgatacta acgccgccat 8100
ccagtgtcga aaacgagctc tcgagaaccc ttaatataac ttcgtataat gtatgctata 8160
cgaagttatt aggtgatatc agatccacta                                   8190
```

SEQ ID NO: 85        moltype = DNA  length = 8202
FEATURE              Location/Qualifiers
misc_feature         1..8202
                     note = Plasmid pCEV-G4-Km-TEF-X40-AT-yABAB
source               1..8202
                     mol_type = other DNA
                     organism = synthetic construct

SEQUENCE: 85

```
ggagcgacct catgctatac ctgagaaagc aacctgacct acaggaaaga gttactcaag 60
aataagaatt ttcgttttaa aacctaagag tcactttaaa atttgtatac acttattttt 120
tttataactt atttaataat aaaaatcata aatcataaga aattcgctta tttagaagtg 180
tcaacaacgt atctaccaac gatttgaccc ttttccatct tttcgtaaat ttctggcaag 240
gtagacaagc cgacaacctt gattggagac ttgaccaaac ctctggcgaa gaattgttaa 300
ttaagagctc agatcttatc gtcgtcatcc ttgtaatcca tcgatactag tttttgatt 360
aaaattaaaa aaactttttg ttttttgtgtt tattctttgt tcttagaaaa gacaagttga 420
gcttgtttgt tcttgatgtt ttattatttt acaatagctg caaatgaaga atagattcga 480
acattgtgaa gtattggcat atatcgtctc tatttatact tttttttttt cagttctagt 540
atattttgta ttttcctcct tttcattctt tcagttgcca ataagttaca ggggatctgg 600
aaagatggtg gggattttc cttgaaagac gactttttgc catctaattt ttccttgttg 660
cctctgaaaa ttatccagca gaagcaaatg taaaagatga acctcagaag aacacgcagg 720
ggcccgaaat tgttcctacg agaagtagtg ggtcataaaa agtttattcc ctggaaaaaa 780
aattttgcgt tgccttttctg gagaattttt tcgaattagc gtgctgccac tgcatgcatt 840
tctgagaagt gtgggcattc ttccaccagt tgttcctcct aaaaaaaaaa agatttccta 900
ccccgcacaa attcctgcat acccctcatt ccacggggc cggccgcaca caccatagct 960
tcaaaatgtt tctactcctt ttttactctt ccagattttc tcggactccg cgcatcgccg 1020
taccacttca aaacacccaa gcacagcata ctaaattttc cctcttttct cctctagggt 1080
gtcgttaatt acccgtacta aaggtttgga aaagaaaaaa gagaccgcct cgtttctttt 1140
tcttcgtcga aaaaggcaat aaaaattttt atcacgtttc ttttttcttga aaatttttt 1200
ttttgatttt tttctctttc gatgacctcc cattgatatt taagttaata aacggtcttc 1260
aatttctcaa gtttcagttt catttttctt gttctattac aactttttct acttcttgtt 1320
cattagaaag aaagcatagc aatctaatct aagttttaat tacaaggatc catgagattt 1380
ccttcaattt ttactgctgt tttattcgca gcatcctccg cattagctat gcaagtacaa 1440
ttggttgaaa ccggtggtgg tttagttcaa ccaggtggta gtttgagatt atcttgtgct 1500
gcatcaggtt ttacattgga ttattcttca ataggttggt tcagcaagc tcctggtaaa 1560
gaaagagaag gtgtttcttg catatccagt tctggtgact caactaaata tgctgactcc 1620
gttaagggta gattcactac ttcaagagat aacgctaaaa atacagtcta cttgcaaatg 1680
aactcattaa agccagatga cacagcagtc tattactgtg ccgcttttag agccaccatg 1740
tgcggtgtat tccattgtc tccttacggt aaagatgact ggggtaaagg tactttagtt 1800
actgtctcat ccggtggtgg tggttccggt ggtggtggta gtggtggtgg tggttctcaa 1860
gttcaattag tagaatccgg tggtggttta gtccaacctg gtggtagttt aagattatcc 1920
tgcgaagcaa gtggttttac attagattat tacggtatcg gttggtttag acaaccacct 1980
ggtaaagaaa gagaagctgt ctcttatatt ccgctagtg caagaactat attgtacgca 2040
gattctgtaa agggtagatt cacaatttca agagacaatg ccaagaacgc tgtttatttg 2100
caaatgaact cttttgaagag agaagacacc gcagtttatt actgtgccag aagaagattt 2160
tctgcttctt cagtcaacag atgttagca gacgattatg atgtttaggt tagaggtaca 2220
caagtcgccc taagtctgg tggtggttcc ggtggtggta gtggtggtgg ttctggtggt 2280
ggtcacaat tgcaattagt agaaactggt ggtggttttg ttcaaccagg tggttccttg 2340
agattaagtt gtgctgcatc tggttttact ttctctgatt acgttatgac atgggtcaga 2400
caagctccag gtaaaggtcc tgaatggatc gctacaatta ataccgacgg ttccacaatg 2460
agagatgaca gtaccaaggg tagattcact attttcaaag ataacgctaa gaacacattg 2520
```

```
tacttacaaa tgacctcttt gaaaccagaa gacaccgcat tatattactg tgccagaggt    2580
agagtcatat ccgccagtgc tatcagaggt gcagtaagag gtcctggtac tcaagttaca    2640
gtctcttcag gtggcggcgg tagtggcggc ggcggttctg gcggtggtgg ttcacaagtc    2700
caattggtag aatctggtgg tggtttagtt caaactggtg gttcattgag attatcctgc    2760
gcttccagtg gttccattgc aggtttcgaa actgttacat ggtcaagaca agctccagtt    2820
aaatctttgc aatgggtcgc ctcaatgacc aagactaaca acgaaatcta ttctgattca    2880
gttaagggta gattcattat ttcaagagat aatgctaaaa acaccgttta tttgcaaatg    2940
aactcattga agccagaaga tactggtgtt tacttctgca agggtcctga attaagaggt    3000
caaggtattc aagtaacagt ttcttcagtc gacatggaac agaagttgat ttccgaagaa    3060
gacctcgagt aagcttggta ccgcggctag ctaagatccg ctctaaccga aaaggaagga    3120
gttagacaac ctgaagtcta ggtcccctatt tattttttta tagttatgtt agtattaaga    3180
acgttattta tatttcaaat ttttctttt tttctgtaca dacgcgtgta cgcatgtaac     3240
attatactga aaaccttgct tgagaaggtt ttgggacgct cgaagatcca gctgcattaa    3300
tgaatcggcc aacgcgcggg gagaggcggt ttgcgtattg ggcgctcttc cgcttcctcg    3360
ctcactgact cgctgcgctc ggtcgttcgg ctgcggcgag cggtatcagc tcactcaaag    3420
gcggtaatac ggttatccac agaatcaggg gataacgcag gaaagaacat gtgagcaaaa    3480
ggccagcaaa aggccaggaa ccgtaaaaag gccgcgttgc tggcgttttt ccataggctc    3540
cgccccctg acgagcatca caaaaatcga cgctcaagtc agaggtggcg aaacccgaca    3600
ggactataaa gataccaggc gtttccccct ggaagctccc tcgtgcgctc tcctgttccg    3660
accctgccgc ttaccggata cctgtccgcc tttctccctt cgggaagcgt ggcgctttct    3720
catagctcac gctgtaggta tctcagttcg gtgtaggtcg ttcgctccaa gctgggctgt    3780
gtgcacgaac cccccgttca gcccgaccgc tgcgccttat ccgtcttgag    3840
tccaacccgg taagacacga cttatcgcca ctggcagcag ccactggtaa caggattagc    3900
agagcgaggt atgtaggcgg tgctacagag ttcttgaagt ggtggcctaa ctacggctac    3960
actagaagga cagtatttgg tatctgcgct ctgctgaagc cagttacctt cggaaaaaga    4020
gttggtagct cttgatccgg caaacaaacc accgctggta gcggtggttt ttttgtttgc    4080
aagcagcaga ttacgcgcag aaaaaaagga tctcaagaag atcctttgat cttttctacg    4140
gggtctgacg ctcagtggaa cgaaaactca cgttaaggga ttttggtcat gagattatca    4200
aaaaggatct tcacctagat ccttttaaat taaaatgaa gttttaaatc aatctaaagt    4260
atatatgagt aaacttggtc tgacagttac caatgcttaa tcagtgaggc acctatctca    4320
gcgatctgtc tatttcgttc atccatagtt gcctgactcc ccgtcgtgta gataactacg    4380
atacgggagg gcttaccatc tggccccagt gctgcaatga taccgcgaga cccacgctca    4440
ccggctccag atttatcagc aataaaccag ccagccggaa gggccgagcg cagaagtggt    4500
cctgcaactt tatccgcctc catccagtct attaattgtt gccgggaagc tagagtaagt    4560
agttcgccag ttaatagttt gcgcaacgtt gttgccattg ctacaggcat cgtggtgtca    4620
cgctcgtcgt ttggtatggc ttcattcagc tccggttccc aacgatcaag gcgagttaca    4680
tgatccccca tgttgtgcaa aaaagcggtt agctccttcg gtcctccgat cgttgtcaga    4740
agtaagttgg ccgcagtgtt atcactcatg gttatggcag cactgcataa ttctcttact    4800
gtcatgccat ccgtaagatg cttttctgtg actggtgagt actcaaccaa gtcattctga    4860
gaatagtgta tgcggcgacc gagttgctct tgcccggcgt caatacggga taataccgcg    4920
ccacatagca gaactttaaa agtgctcatc attggaaaac gttcttcggg gcgaaaactc    4980
tcaaggatct taccgctgtt gagatccagt tcgatgtaac ccactcgtgc acccaactga    5040
tcttcagcat cttttacttt caccagcgtt tctgggtgag caaaaacagg aaggcaaaat    5100
gccgcaaaaa agggaataag ggcgacacgg aaatgttgaa tactcatact cttcctttt    5160
caatattatt gaagcattta tcagggttat tgtctcatga gcggatacat atttgaatgt    5220
atttagaaaa ataaacaaat aggggttccg cgcacatttc cccgaaaagt gccacctgaa    5280
cgaagcatct gtgcttcatt ttgtagaaca aaaatgcaac gcgagagcgc taattttca    5340
aacaaagaat ctgagctgca tttttacaga acagaaatgc aacgcgaaag cgctatttta    5400
ccaacgaaga atctgtgctt cattttttgta aacaaaaat gcaacgcgag agcgctaatt    5460
tttcaaacaa agaatctgag ctgcattttt acagaacaga aatgcaacgc gagagcgcta    5520
ttttaccaac aaagaatcta tacttctttt ttgttctaca aaatgcatc ccgagagcga    5580
tattttcta caaagcatc ttagattact tttttttctcc tttgtgcgct ctataatgca    5640
gtctcttgat aacttttgc actgtaggtc cgttaaggtt agaagaaggc tactttggtg    5700
tctatttctct cttccataaa aaaagcctga ctccacttcc cgcgtttact gattactagc    5760
gaagctgcgg gtgcatttt tcaagataaa ggcatcccg attatattct ataccgatgt    5820
ggattgcgca tactttgtga acagaaagtg atagcgttga tgattcttca ttggtcagaa    5880
aattatgaac ggtttcttct attttgtctc tatatactac gtataggaaa tgtttacatt    5940
ttcgtattgt tttcgattca ctctatgaat agttcttact acaattttt tgtctaaaga    6000
gtaatactag agataaacat aaaaaatgta gaggtcgagt ttagatgcaa gttcaaggag    6060
cgaaaggtgg atgggtaggt tatatagggg atatagcacag agatatatag caaagagata    6120
cttttgagca atgtttgtgg aagcggtatt cgcaatattt tagtagctcg ttacagtccg    6180
gtgcgttttt ggttttttga aagtgcgtct tcagagcgct tttggttttc aaaagcgctc    6240
tgaagttcct atacttcta gagaatagga acttcggaat aggaacttca aagcgtttcc    6300
gaaaacgagc gcttccgaaa atgcaacgcg agctgcgcac atacagctca ctgttcacgt    6360
cgcacctata tctgcgtgtt gcctgtatat atatatacat gagaagaacg gcatagtgcg    6420
tgtttatgct taaatgcgta cttatatgcg tctatttatg taggatgaaa ggtagtctag    6480
tacctcctgt gatattatcc cattccatgc ggggtatcgt atgcttcctt cagcactacc    6540
ctttagctgt tctatatgct gccactcctc aattggatta gtctcatcct tcaatgctat    6600
catttccttt gatattggat catggtagac aaccctaat ataacttcgt ataatgtatg    6660
ctatacgaag ttattaggtc tagagatctg tttagcttgc ctcgtccccg ccgggtcacc    6720
cggcagcga catggaggcc cagaataccc tccttgacag tcttgacgtg cgcagctcag    6780
gggcatgatg tgactgtcgc ccgtacattt agcccataca tccccatgta taatcatttg    6840
catccataca ttttgatggc cgcacggcgc gaagcaaaaa ttacggctcc tcgctgcaga    6900
cctgcgagca gggaaacgct cccctcacag acgcgttgaa ttgtccccac gccgcgcccc    6960
tgtagagaaa tataaaaggt taggatttgc cactgaggtt cttctttcat atacttcctt    7020
ttaaaatctt gctaggatac agttctcaca tcacatccga acataaacaa ccatgggtaa    7080
ggaaaagact cacgtttcga ggccgcgatt aaattccaac atggatgctg atttatatgg    7140
gtataaatgg gctcgcgata atgtcgggca atcaggtgcg acaatctatc gattgtatgg    7200
gaagcccgat gcgccagagt tgtttctgaa acatggcaaa ggtagcgttg ccaatgatgt    7260
```

```
tacagatgag atggtcagac taaactggct gacggaattt atgcctcttc cgaccatcaa   7320
gcattttatc cgtactcctg atgatgcatg gttactcacc actgcgatcc ccggcaaaac   7380
agcattccag gtattagaag aatatcctga ttcaggtgaa aatattgttg atgcgctggc   7440
agtgttcctg cgccggttgc attcgattcc tgtttgtaat tgtcctttta acagcgatcg   7500
cgtatttcgt ctcgctcagg cgcaatcacg aatgaataac ggtttggttg atgcgagtga   7560
ttttgatgac gagcgtaatg gctggcctgt tgaacaagtc tggaaagaaa tgcataagct   7620
tttgccattc tcaccggatt cagtcgtcac tcatgtgtat ttctcacttg ataaccttat   7680
ttttgacgag gggaaattaa taggttgtat tgatgttgga cgagtcggaa tcgcagaccg   7740
ataccaggat cttgccatcc tatggaactg cctcggttgg ttttctcctt cattacagaa   7800
acggcttttt caaaaatatg gtattgataa tcctgatatg aataaattgc agtttcattt   7860
gatgctcgat gagtttttct aatcagtact gacaataaaa agattcttgt tttcaagaac   7920
ttgtcatttg tatagttttt ttatattgta gttgttctat tttaatcaaa tgttagcgtg   7980
atttatattt ttttttcgcct cgacatcatc tgcccagatg cgaagttaag tgcgcagaaa   8040
gtaatatcat gcgtcaatcg tatgtgaatg ctggtcgcta tactgctgtc gattcgatac   8100
taacgccgcc atccagtgtc gaaaacgagc tctcgagaac ccttaatata acttcgtata   8160
atgtatgcta tacgaagtta ttaggtgata tcagatccac ta                      8202

SEQ ID NO: 86           moltype = DNA   length = 6151
FEATURE                 Location/Qualifiers
misc_feature            1..6151
                        note = Plasmid pCEV-G4-Ph
source                  1..6151
                        mol_type = other DNA
                        organism = synthetic construct
SEQUENCE: 86
ggagcgacct catgctatac ctgagaaagc aacctgacct acaggaaaga gttactcaag   60
aataagaatt ttcgttttaa aacctaagag tcacttttaaa atttgtatac acttattttt   120
tttataactt atttaataat aaaaatcata aatcataaga aattcgctta tttagaagtg   180
tcaacaacgt atctaccaac gatttgaccc ttttccatct tttcgtaaat ttctggcaag   240
gtagacaagc cgacaacctt gattggagac ttgaccaaac ctctggcgaa gaattgttaa   300
ttaagagctc agatcttatc gtcgtcatcc ttgtaatcca tcgatactag tttttttgatt   360
aaaattaaaa aaacttttg ttttttgtgtt tattctttgt tcttagaaaa gacaagttga   420
gcttgtttgt tcttgatgtt ttattatttt acaatagctg caaatgaaga atagattcga   480
acattgtgaa gtattggcat atatcgtctc tatttatact ttttttttt cagttctagt   540
atattttgta ttttcctcct tttcattctt tcagttgcca ataagttaca ggggatctcg   600
aaagatggtg gggattttc cttgaaagac gactttttgc catctaattt ttccttgttg   660
cctctgaaaa ttatccagca gaagcaaatg taaaagatga acctcagaag aacacgcagg   720
ggcccgaaat tgttcctacg agaagtagtg ggtcataaaa agttgtattcc ctggaaaaaa   780
aattttgcgt tgccttttctg gagaattttt tcgaattagc gtgctgccac tgcatgcatt   840
tctgagaagt gtgggcattc ttccaccagt tgttcctcct aaaaaaaaaa agatttccta   900
ccccgcacaa attcctgcat accccctcatt tccacggggc cggccgcaca caccatagct   960
tcaaaatgtt tctactcctt ttttactctt ccagattttc tcggactccg cgcatcgccg   1020
taccacttca aaacacccaa gcacagcata ctaaattcc cctctttctt cctctagggt   1080
gtcgttaatt acccgtacta aaggtttgga aaagaaaaaa gagaccgcct cgtttctttt   1140
tcttcgtcga aaaggcaat aaaaaatttt atcacgtttc ttttttcttga aatttttttt   1200
ttttgatttt tttctctttc gatgacctcc cattgatatt taagttaata aacggtcttc   1260
aatttctcaa gtttcagttt catttttctt gttctattac aactttttt acttcttgct   1320
cattagaaag aaagcatagc aatctaatct aagttttaat tacaaggatc cgtaatacga   1380
ctcactatag ggcccgggcg tcgacatgga acagaagttg atttccgaag aagacctcga   1440
gtaagcttgg taccgcggct agctaagatc cgctctaacc gaaaaggaag gagttagaca   1500
acctgaagtc taggtcccta tttattttt tatagttatg ttagtattaa gaacgttatt   1560
tatatttcaa attttttctt ttttttctgta cagacgcgtg tacgcatgta acattatact   1620
gaaaaccttg cttgagaagg ttttgggacg ctcgaagatc cagctgcatt aatgaatcgg   1680
ccaacgcgcg gggagaggcg gtttgcgtat tgggcgctct tccgcttcct cgctcactga   1740
ctcgctgcgc tcggtcgttc ggctgcggcg agcggtatca gctcactcaa aggcggtaat   1800
acggttatcc acagaatcag gggataacgc aggaaagaac atgtgagcaa aaggccagca   1860
aaaggccagg aaccgtaaaa aggccgcgtt gctggcgttt ttccataggc tccgcccccc   1920
tgacgagcat cacaaaaatc gacgctcaag tcagaggtgg cgaaacccga caggactata   1980
aagataccag gcgtttcccc ctggaagctc cctcgtgcgc tctcctgttc cgaccctgcc   2040
gcttaccgga tacctgtccg cctttctccc ttcgggaagc gtggcgcttt ctcatagctc   2100
acgctgtagg tatctcagtt cggtgtaggt cgttcgctcc aagctgggct gtgtgcacga   2160
accccccgtt cagcccgacc gctgcgcctt atccggtaac tatcgtcttg agtccaaccc   2220
ggtaagacac gacttatcgc cactggcagc agccactggt aacaggatta gcagagcgag   2280
gtatgtaggc ggtgctacag agttcttgaa gtggtggcct aactacggct acactagaag   2340
gacagtattt ggtatctgcg ctctgctgaa gccagttacc ttcggaaaaa gagttggtag   2400
ctcttgatcc ggcaaacaaa ccaccgctgg tagcggtggt ttttttgttt gcaagcagca   2460
gattacgcgc agaaaaaaag gatctcaaga agatcctttg atcttttcta cggggtctga   2520
cgctcagtgg aacgaaaact cacgttaagg gattttggtc atgagattat caaaaaggat   2580
cttcacctag atccttttaa attaaaaatg aagttttaaa tcaatctaaa gtatatatga   2640
gtaaacttgg tctgacagtt accaatgctt aatcagtgag gcacctatct cagcgatctg   2700
tctatttcgt tcatccatag ttgcctgact ccccgtcgtg tagataacta cgatacggga   2760
gggcttacca tctggcccca gtgctgcaat gataccgcga cccacgct caccggctcc   2820
agatttatca gcaataaacc agccagccgg aaggccgagc gcagaagtg gtcctgcaac   2880
tttatccgcc tccatccagt ctattaattg ttgccggaa gctagagtaa gtagttcgcc   2940
agttaatagt ttgcgcaacg ttgttgccat tgctacaggc atcgtggtgt cacgctcgtc   3000
gtttggtatg gcttcattca gctccggttc ccaacgatca aggcgagtta catgatcccc   3060
catgttgtgc aaaaaagcgg ttagctcctt cggtcctccg atcgttgtca gaagtaagtt   3120
ggccgcagtg ttatcactca tggttatggc agcactgcat aattctctta ctgtcatgcc   3180
atccgtaaga tgcttttctg tgactggtga gtactcaacc aagtcattct gagaatagtg   3240
```

```
tatgcggcga ccgagttgct cttgcccggc gtcaatacgg gataataccg cgccacatag 3300
cagaactttta aaaagtgctca tcattggaaa acgttcttcg gggcgaaaac tctcaaggat 3360
cttaccgctg ttgagatcca gttcgatgta acccactcgt gcacccaact gatcttcagc 3420
atcttttact ttcaccagcg tttctgggtg agcaaaaaca ggaaggcaaa atgccgcaaa 3480
aaagggaata agggcgacac ggaaatgttg aatactacta ctcttccttt tcaatatta 3540
ttgaagcatt tatcagggtt attgtctcat gagcggatac atatttgaat gtatttagaa 3600
aaataaacaa atagggggttc cgcgcacatt tccccgaaaa gtgccacctg aacgaagcat 3660
ctgtgcttca ttttgtagaa caaaatgca acgcgagagc gctaattttt caaacaaaga 3720
atctgagctg cattttttaca gaacagaaat gcaacgcgaa agcgctattt taccaacgaa 3780
gaatctgtgc ttcattttttg taaaacaaaa atgcaacgcg agagcgctaa ttttttcaaac 3840
aaagaatctg agctgcattt ttacagaaca gaaatgcaac gcgagagcgc tattttacca 3900
acaaagaatc tatacttctt ttttgttcta caaaaatgca tcccgagagc gctattttc 3960
taacaaagca tcttagatta ctttttttct cctttgtgcg ctctataatg cagtctcttg 4020
ataacttttt gcactgtagg tccgttaagg ttagaagaag gctactttgg tgtctatttt 4080
ctcttccata aaaaaagcct gactccactt cccgcgttta ctgattacta gcgaagctgc 4140
gggtgcattt tttcaagata aaggcatccc cgattatatt ctataccgat gtggattgcg 4200
catactttgt gaacagaaag tgatagcgtt gatgattctt cattggtcag aaaattatga 4260
acggtttctt ctatttttgtc tctatatact acgtatagga aatgtttaca ttttcgtatt 4320
gttttcgatt cactctatga atagttctta ctacaatttt tttgtctaaa gagtaatact 4380
agagataaac ataaaaaatg tagaggtcga gtttagatgc aagttcaagg agcgaaaggt 4440
ggatgggtag gttatatagg gatatagcac agagatatat agcaaagaga tacttttgag 4500
caatgttgt ggaagcggta ttcgcaatat tttagtagct cgttacagtc cggtgcgttt 4560
ttggttttttt gaaagtgcgt cttcagagcg ctttttggttt tcaaaagcgc tctgaagttc 4620
ctatactttc tagagaatag gaacttcgga ataggaactt caaagcgttt ccgaaaacga 4680
gcgcttccga aaatgcaacg cgagctgcgc acatacagct cactgttcac gtcgcaccta 4740
tatctgcgtg ttgcctgtat atatatatac atgagaagaa cggcatagtg cgtgtttatg 4800
cttaaatgcg tacttatatg cgtctattta tgtaggatga aaggtagtct agtacctcct 4860
gtgatattat cccattccat gcggggtatc gtatgcttcc ttcagcacta cccttttagct 4920
gttctatatg ctgccactcc tcaattggat tagtctcatc cttcaatgct atcatttcct 4980
ttgatattgg atcatggtag acaacccta atataacttc gtataatgta tgctatacga 5040
agttattagg tctagagatc tgtttagctt gcctcgtccc cgccgggtca cccggccagc 5100
gacatggagg cccagaatac cctccttgac agtcttgacg tgcgcagctc aggggcatga 5160
tgtgactgtc gcccgtacat ttagcccata catccccatg tataatcatt gcatccata 5220
cattttgatg gccgcacggc gcgaagcaaa aattacggct cctcgctgca gacctgcgag 5280
cagggaaacg ctccccctcac agacgcgttg aattgtcccc acgccgcgcc cctgtagaga 5340
aatataaaag gttaggatttt gccactgagg ttcttcttc atatacttcc ttttaaaatc 5400
ttgctaggat acagttctca catcacatcc gaacataaac aaccatgggg atgaccgacc 5460
aagcgacgcc caacctgcca tcacgagatt tcgatcccac cgccgccttc tatgaaaggt 5520
tgggctttcgg aatcgttttc cgggacgccg gctggatgat cctccagcgc ggggatctca 5580
tgctggagtt cttcgcccac cccgggctcg atccctcgc gagttggttc agctgctgcc 5640
tgaggctgga cgacctcgcg gagttctacc ggcagtgcaa atccgtcggc atccaggaaa 5700
ccagcagcgg ctataccgcgc atccatgccc ccgaactgca ggagtgggga ggcacgatgg 5760
ccgcttttggt cgacccggac gggacgctcc tgcgcctgat acagaacgaa ttgcttgcag 5820
gcatctcatg atcagtactg acaataaaaa gattcttgtt ttcaagaact tgtcatttgt 5880
atagtttttt tatattgtag ttgttctatt taatcaaat gttagcgtga tttatatttt 5940
ttttcgcctc gacatcatct gcccagatgc gaagttaagt gcgcagaaag taatatcatg 6000
cgtcaatcgt atgtgaatgc tggtcgctat actgctgtcg attcgatact aacgccgcca 6060
tccagtgtcg aaaacgagct ctcgagaacc cttaatataa cttcgtataa tgtatgctat 6120
acgaagttat taggtgatat cagatccact a                              6151
```

SEQ ID NO: 87          moltype = DNA   length = 6861
FEATURE                Location/Qualifiers
misc_feature           1..6861
                       note = Plasmid pBIS-GALkFLP-URA3
source                 1..6861
                       mol_type = other DNA
                       organism = synthetic construct
SEQUENCE: 87

```
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcgggctgg cttaactatg cggcatcaga gcagattgta ctgagagtgc 180
accataccac agcttttcaa ttcaattcat cattttttt ttattctttt ttttgatttc 240
ggtttctttg aaatttttttt gattcggtaa tctccgaaca gaaggaagaa cgaaggaagg 300
agcacagact tagattggta tatatacgca tatgtagtgt tgaagaaaca tgaaattgcc 360
cagtattctt aacccaactg cacagaacaa aaacctgcag gaaacgaaga taatcatgtg 420
cgaaagctac atataaggaa cgtgctgcta ctcatcctag tcctgttgct gccaagctat 480
ttaatatcat gcacgaaaag caaacaaact tgtgtgcttc attggatgtt cgtaccacca 540
aggaattact ggagttagtt gaagcattag tcccaaaat tgtttacta aaaacacatg 600
tggatatctt gactgatttt tccatggagg gcacagttaa gccgctaaag gcattatccg 660
ccaagtacaa ttttttactc ttcgaagaca gaaaatttgc tgacattggt aatacagtca 720
aattgcagta ctctgcgggt gtatacgaaa gcagaatg gcagacatt acgaatgcac 780
acggtgtggt gggcccaggt attgttagcg gtttgaagca ggcggcagaa gaagtaacaa 840
aggaacctag aggcctttg atgttagcag aattgtcatg caagggctcc ctatctactg 900
gagaatatac taagggtact gttgacattg cgaagagcga caaagatttt gttatcggct 960
ttattgctca aagagacatg ggtggaagag atgaaggtta cgattggttg attatgacac 1020
ccggtgtggg tttagatgac aagggagacg cattgggtca acagtataga accgtggatg 1080
atgtggtctc tacaggatct gacattatta ttgttggaag aggactattt gcaagggaa 1140
gggatgctaa ggtagagggt gaacgttaca gaaaagcagg ctgggaagca tatttgagaa 1200
gatgcggcca gcaaaactaa aaaactgtat tataagtaaa tgcatgtata ctaaactcac 1260
```

```
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa ttttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact ataggggcgaa ttgggtaccg gccccccct cgaggtcgac ggtatcgata   2040
agcttgatat cgaattcctg cagcccgggg gatccaaaaa tcatcgcttc gctgattaat   2100
taccccagaa ataaggctaa aaaactaatc gcattatcat cctatggttg ttaatttgat   2160
tcgttcattt gaaggtttgt ggggccaggt tactgccaat ttttcctctt cataaccata   2220
aaagctagta ttgtagaatc tttattgttc ggagcagtgc ggcgcgaggc acatctgcgt   2280
ttcaggaacg cgaccggtga agacgggac gcacggagga gagtcttcct tcggagggct   2340
gtcacccgct cggcggcttc taatccgtac ttcaatatag caatgagcag ttaagcgtat   2400
tactgaaagt tccaaagaga aggtttttt aggctaagat aatgggggctc tttacatttc   2460
cacaacatat aagtaagatt agatatggat atgtatatgg atatgtatat ggtggtaatg   2520
ccatgtaata tgattattaa acttcttttgc gtccatccaa aaaaaaagta agaatttttg   2580
ggtcgacatg ccacaatttg gtatattatg taaaacacca cctaaggtgc ttgttcgtca   2640
gtttgtggaa aggtttgaaa gaccttcagg tgagaaaata gcattatgtg ctgctgaact   2700
aacctattta tgttggatga ttacacataa cggaacagca atcaagagag ccacattcat   2760
gagctataat actatcataa gcaattcgct gagtttcgat attgtcaata aatcactcca   2820
gtttaaatac aagacgcaaa aagcaacaat tctggaagcc tcattaaaga aattgattcc   2880
tgcttgggaa tttacaatta ttccttacta tggacaaaaa catcaatctg atatcactga   2940
tattgtaagt agtttgcaat tacagttcga atcatcggaa gaagcagata agggaaatag   3000
ccacagtaaa aaaatgctta aagcacttct aagtgagggt gaaaagcatct gggagatcac   3060
tgagaaaata ctaaattcgt ttgagtatac ttcgagattt acaaaaacaa aaactttata   3120
ccaattcctc ttcctagcta ctttcatcaa ttgtggaaga ttcagcgata ttaagaacgt   3180
tgatccgaaa tcatttaaat tagtccaaaa taagtatctg ggagtaataa tccagtgttt   3240
agtgacagag acaaagacaa gcgttagtag gcacatatac ttctttagcg caaggggtag   3300
gatcgatcca cttgtatatt tggatgaatt tttgaggaat tctgaaccag tcctaaaacg   3360
agtaaatagg accggcaatt cttcaagcaa taaacaggaa taccaattat taaaagataa   3420
cttagtcaga tcgtacaata aagctttgaa gaaaatgcg ccttattcaa tctttgctat   3480
aaaaaatggc ccaaaatctc tcattggaag acatttgatg acctcattc tttcaatgaa   3540
gggcctaacg gagttgacta atgttgtggg aaattggagc gataagcgtg cttctgccgg   3600
ggccaggaca acgtatactc atcagataac agcaatacct gatcactact tcgcactagt   3660
ttctcggtac tatgcatatg atccaatatc aaggaaatg atagcattga aggatgagac   3720
taatccaatt gaggagtggc agcatataga acagctaaag ggtagtgctg aaggaagcat   3780
acgataccc gcatggaatg ggataatatc acaggaggta ctagactacc tttcatccta   3840
cataaataga cgcatataag tacgcattta agcataaaca cgcactatgc cgttcttctc   3900
atgtatatat atatacaggc aacacgcaga tataggtgcg acgtgaacag tgagctgtat   3960
gtgcgcagct cgcgttgcat tttcggaagc gctcgttttc ggaaacgctt tgaagttcct   4020
attccgaagt tcctattctc tagttctaga gcggccgcca ccgcggtgga gctccagctt   4080
ttgttccctt tagtgagggt taattgcgcg cttggcgtaa tcatggtcat agctgtttcc   4140
tgtgtgaaat tgttatccgc tcacaattcc acacaacata ggagccggaa gcataaagtg   4200
taaagcctgg ggtgcctaat gagtgaggta actcacatta attgcgttgc gctcactgcc   4260
cgctttccag tcgggaaacc tgtcgtgcca gctgcattaa tgaatcgcgg gaggcgggt   4320
gagaggcggt ttgcgtattg ggcgctcttc cgcttcctcg ctcactgact cgctgcgctc   4380
ggtcgttcgg ctgcggcgag cggtatcagc tcactcaaag gcggtaatac ggttatccac   4440
agaatcaggg gataacgcag gaaagaacat gtgagcaaaa ggccagcaaa aggccaggaa   4500
ccgtaaaaag gccgcgttgc tggcgttttt ccataggctc cgccccctg acgagcatca   4560
caaaaatcga cgctcaagtc agaggtggcg aaacccgaca ggactataaa gataccaggc   4620
gtttccccct ggaagctccc tcgtgcgctc tcctgttccg accctgccgc ttaccggata   4680
cctgtccgcc tttctccctt cgggaagcgt ggcgctttct catagctcac gctgtaggta   4740
tctcagttcg gtgtaggtcg ttcgctccaa gctgggctgt gtgcacgaac cccccgttca   4800
gcccgaccgc tgcgccttat ccggtaacta tcgtcttgag tccaacccgg taagacacga   4860
cttatcgcca ctggcagcag ccactggtaa caggattagc agagcgaggt atgtaggcgg   4920
tgctacagag ttcttgaagt ggtggcctaa ctacggctac actagaagga cagtatttgg   4980
tatctgcgct ctgctgaagc cagttacctt cggaaaaaga gttggtagct cttgatccgg   5040
caaacaaacc accgctggta gcggtggttt ttttgtttgc aagcagcaga ttacgcgcag   5100
aaaaaaagga tctcaagaag atcctttgat cttttctacg gggtctgacg ctcagtggaa   5160
cgaaaactca cgttaaggga ttttggtcat gagattatca aaaaggatct tcacctagat   5220
ccttttaaat taaaaatgaa gttttaaatc aatctaaagt atatatgagt aaacttggtc   5280
tgacagttac caatgcttaa tcagtgaggc acctatctca gcgatctgtc tatttcgttc   5340
atccatagtt gcctgactcc ccgtcgtgta gataactacg atacgggagg gcttaccatc   5400
tggccccagt gctgcaatga taccgcgaga cccacgctca ccggctccag atttatcagc   5460
aataaaccag ccagccggaa gggccgagcg cagaagtggt cctgcaactt tatccgcctc   5520
catccagtct attaattgtt gccgggaagc tagagtaagt agttcgccag ttaatagttt   5580
gcgcaacgtt gttgccattg ctacaggcat cgtggtgtca cgctcgtcgt ttggtatggc   5640
ttcattcagc tccggttccc aacgatcaag gcgagttaca tgatccccca tgttgtgcaa   5700
aaaagcggtt agctccttcg gtcctccgat cgttgtcaga agtaagttgg ccgcagtgtt   5760
atcactcatg gttatggcag cactgcataa ttctcttact gtcatgccat ccgtaagatg   5820
cttttctgtg actggtgagt actcaaccaa gtcattctga gaatagtgta tgcggcgacc   5880
gagttgctct tgcccggcgt caatacggga taataccgcg ccacatagca gaactttaaa   5940
agtgctcatc attggaaaac gttcttcggg gcgaaaactc tcaaggatct taccgctgtt   6000
```

```
gagatccagt tcgatgtaac ccactcgtgc acccaactga tcttcagcat cttttacttt   6060
caccagcgtt tctgggtgag caaaaacagg aaggcaaaat gccgcaaaaa agggaataag   6120
ggcgacacgg aaatgttgaa tactcatact cttcctttt caatattatt gaagcattta    6180
tcagggttat tgtctcatga gcggatacat atttgaatgt atttagaaaa ataaacaaat   6240
aggggttccg cgcacatttc cccgaaaagt gccacctggg tccttttcat cacgtgctat   6300
aaaaataatt ataatttaaa tttttaata taaatatata aattaaaaat agaaagtaaa    6360
aaaagaaatt aaagaaaaaa tagttttttgt tttccgaaga tgtaaaagac tctaggggga   6420
tcgccaacaa atactccctt ttatcttgct cttcctgctc tcaggtatta atgccgaatt   6480
gtttcatctt gtctgtgtag aagaccacac acgaaaatcc tgtgatttta catttactt   6540
atcgttaatc gaatgtatat ctatttaatc tgcttttctt gtctaataaa tatatatgta   6600
aagtacgctt tttgttgaaa ttttttaaac ctttgtttat tttttttct tcattccgta    6660
actcttctac cttctttatt tactttctaa aatccaaata caaaacataa aaataaataa   6720
acacagagta aattcccaaa ttattccatc attaaaagat acgaggcgcg tgtaagttac   6780
aggcaagcga tccgtcctaa gaaaccatta ttatcatgac attaacctat aaaaataggc   6840
gtatcacgag gccctttcgt c                                             6861

SEQ ID NO: 88          moltype = DNA  length = 6857
FEATURE                Location/Qualifiers
misc_feature           1..6857
                       note = Plasmid pCEV-URA3-TEF-AT-yABAB-cMyc
source                 1..6857
                       mol_type = other DNA
                       organism = synthetic construct
SEQUENCE: 88
agcttttcaa ttcaattcat catttttttt ttattcttt ttttgatttc ggtttctttg    60
aaatttttt gattcggtaa tctccgaaca gaaggaagaa cgaaggaagg agcacagact   120
tagattggta tatatacgca tatgtagtgt tgaagaaaca tgaaattgcc cagtattctt   180
aacccaactg cacagaacaa aaaccagcag gaaacgaaga taaatcatgt cgaaagctac   240
atataaggaa cgtgctgcta ctcatcctag tcctgttgct gccaagctat ttaatatcat   300
gcacgaaaag caaacaaact tgtgtgcttc attggatgtt cgtaccacca aggaattact   360
ggagttagtt gaagcattag gtcccaaaat ttgttacta aaaacacatg tggatatctt   420
gactgatttt tccatggagg gcacagttaa gccgctaaag gcattatccg ccaagtacaa   480
ttttttactc ttcgaagata gaaaatttgc tgacattggt aatacagtca aattgcagta   540
ctctgcgggt gtatacagaa tagcagaatg ggcagacatt acgaatgcac acggtgtggt   600
gggcccaggt attgttagcg gtttgaagca ggcggcagaa gaagtaacaa aggaacctaa   660
aggcctttg atgttagcag aattgtcatg caagggctcc ctatctactg agaatatac    720
taagggtact gttgacattg cgaaaagcga caaagatttt gttatcggct ttattgctca   780
aagagacatg ggtggaagag atgaaggtta cgattggttg attatgacac ccggtgtggg   840
tttagatgac aagggagatg cattgtgtca acagtataga accgtggatg atgttgctc    900
tacaggatct gacattatta ttgttggaag aggactattt gcaaagggaa gggatgctaa   960
ggtagagggt gaacgttaca gaaaagcagg ctgggaagca tatttgagaa gatgcggcca   1020
gcaaaactaa aaaactgtat tataagtaaa tgcatgtata ctaaactcac aaattagagc   1080
ttcaatttaa ttatatcagt tattaccccg gccgcacaca catagcttc aaaatgtttc   1140
tactcctttt ttactcttcc agattttctc ggactccgcg catcgccgta ccacttcaaa   1200
acacccaagc acagcatact aaatttcccc tcttttcttcc ctagggtgt cgttaattac   1260
ccgtactaaa ggtttggaaa agaaaaaaga gaccgcctcg tttcttttc ttcgtcgaaa    1320
aaggcaataa aaatttttat cacgtttctt tttcttgaaa attttttttt ttgatttttt   1380
tctctttcga tgacctccca ttgatattta agtaataaa cggtcttcaa tttctccaagt   1440
ttcagttca ttttttcttgt tctattacaa ctttttttac ttcttgctca ttagaaagaa    1500
agcatagcaa tctaatctaa gttttaatta caaggatcca tgagattcc ttcaattttt    1560
actgctgttt tattcgcagc atcctccgca ttagctatgc aagtacaatt ggttgaaacc   1620
ggtggtggtt tagttcaacc aggtggtagt ttgagattat cttgtgctgc atcaggtttt   1680
acattggatt attcttcaat aaggttggttc agacaagctc ctggtaaaga aagagaaggt   1740
gtttcttgca tatccagttc tggtgactca actaaatatg ctgactccgt taagggtaga   1800
ttcactactt caagagataa cgctaaaaat acagtctact tgcaaatgaa ctcattaaag   1860
ccagatgaca cagcagtcta ttactgtgcc gcttttagag ccaccatgtg cggtgtattc   1920
ccattgtctc cttacggtaa agatgactgg ggtaaaggta cttagttac tgtctcatcc   1980
ggtggtggtg gttccggtgg tggtggtagt ggtggtggtg gttctcaagt tcaattagta   2040
gaatccggtg gtggtttagt ccaacctggt ggtagtttaa gattatcct cgaagcaagt   2100
ggttttacat tagattatta cggtatcggt tggtttagac aaccacctgg taaagaaaga   2160
gaagctgtct cttatatttc cgctagtgca agaactatat gtacgcaga ttctgtaaag    2220
ggtagattca caatttcaag agacaatgcc aagaacgctg tttatttgca aatgaactct   2280
ttgaagagag aagacaccgc agtttattac tgtgccagaa gaagattttc tgcttcttca   2340
gtcaacagat ggttagcaga cgattatgat gtttggggta gaggtacaca agtcgccgta   2400
agttctggtg gtggttccgg tggtggtagt ggtggtggtg ctggtggtgg ttcacaattg   2460
caattagtag aaactggtgg tggttttgtt caaccaggtg gttccttgag attaagttgt   2520
gctgcatctg gttttactt ctctgattac gttatgacat gggtcagaca agctccaggt    2580
aaaggtcctg aatggatcgc tacaattaat accgacggtt ccacaatgag agatgacagt   2640
accaagggta gattcactat ttcaagagat aacgctaaga acacattgta cttacaaatg   2700
acctctttga aaccagaaga caccgcatta tattactgtg ccagaggtag agtcatatcc   2760
gccagtgcta tcagaggtgc agtaagaggt cctggtactc aagttacagt ctcttcaggt   2820
ggcggcggta gtggcggcgg cggttctggc ggtggtggtt cacaagtcca attggtagaa   2880
tctggtggtg gtttagttca aactggtggt tcattgagat tatcctgcgc ttccagtggt   2940
tccattgcag gtttcgaaac tgttacatgg tcaagacaag ctccaggtaa atctttgcaa   3000
tgggtcgcct caatgaccaa gactaacaac gaaatctatt ctgattcagt aagggtaga   3060
ttcattattt caagagataa tgctaaaaac accgttatt tgcaaatgaa ctcattgaag    3120
ccagaagata ctggtgttta cttctgcaag ggtcctgaat taagggtca aggtattcaa   3180
gtaacagttt cttcagtcga catggaacag aagttgattt ccgaagaaga cctcgagtaa   3240
gcttggtacc gcggctagct aagatccgct ctaaccgaaa aggaaggagt tagacaacct   3300
```

```
gaagtctagg tccctattta ttttttttata gttatgttag tattaagaac gttatttata   3360
tttcaaattt ttcttttttt tctgtacaga cgcgtgtacg catgtaacat tatactgaaa   3420
accttgcttg agaaggtttt gggacgctcg aagatccagc tgcattaatg aatcggccaa   3480
cgcgcgggga gaggcggttt gcgtattggg cgctcttccg cttcctcgct cactgactcg   3540
ctgcgctcgg tcgttcggct gcggcgagcg gtatcagctc actcaaaggc ggtaatacgg   3600
ttatccacag aatcagggga taacgcagga agaacatgt gagcaaaagg ccagcaaaag   3660
gccaggaacc gtaaaaaggc cgcgttgctg gcgtttttcc ataggctccg ccccccctgac  3720
gagcatcaca aaaatcgacg ctcaagtcag aggtggcgaa acccgacagg actataaaga   3780
taccaggcgt ttccccctgg aagctccctc gtgcgctctc ctgttccgac cctgccgctt   3840
accggatacc tgtccgcctt tctcccttcg ggaagcgtgg cgctttctca tagctcacgc   3900
tgtaggtatc tcagttcggt gtaggtcgtt cgctccaagc tgggctgtgt gcacgaaccc   3960
cccgttcagc ccgaccgctg cgccttatcc ggtaactatc gtcttgagtc caacccggta   4020
agacacgact tatcgccact ggcagcagcc actggtaaca ggattagcag agcgaggtat   4080
gtaggcggtg ctacagagtt cttgaagtgg tggcctaact acggctacac tagaaggaca   4140
gtatttggta tctgcgctct gctgaagcca gttaccttcg gaaaaagagt tggtagctct   4200
tgatccggca aacaaaccac cgctggtagc ggtggttttt ttgtttgcaa gcagcagatt   4260
acgcgcagaa aaaaaggatc tcaagaagat cctttgatct tttctacggg gtctgacgct   4320
cagtggaacg aaaactcacg ttaagggatt ttggtcatga gattatcaaa aaggatcttc   4380
acctagatcc ttttaaatta aaaatgaagt tttaaatcaa tctaaagtat atatgagtaa   4440
acttggtctg acagttacca atgcttaatc agtgaggcac ctatctcagc gatctgtcta   4500
tttcgttcat ccatagttgc ctgactcccc gtcgtgtaga taactacgat acgggagggc   4560
ttaccatctg gccccagtgc tgcaatgata ccgcgagacc cacgctcacc ggctccagat   4620
ttatcagcaa taaaccagcc agccggaagg gccgagcgca gaagtggtcc tgcaacttta   4680
tccgcctcca tccagtctat taattgttgc cgggaagcta gagtaagtag ttcgccagtt   4740
aatagtttgc gcaacgttgt tgccattgct acaggcatcg tggtgtcacg ctcgtcgttt   4800
ggtatggctt cattcagctc cggttcccaa cgatcaaggc gagttacatg atcccccatg   4860
ttgtgcaaaa aagcggttag ctccttcggt cctccgatcg ttgtcagaag taagttggcc   4920
gcagtgttat cactcatggt tatggcagca ctgcataatt ctcttactgt catgccatcc   4980
gtaagatgct tttctgtgac tggtgagtac tcaaccaagt cattctgaga atagtgtatg   5040
cggcgaccga gttgctcttg cccggcgtca atacgggata ataccgcgcc acatagcaga   5100
actttaaaag tgctcatcat tggaaaacgt tcttcgggc gaaaactctc aaggatctta   5160
ccgctgttga gatccagttc gatgtaaccc actcgtgcac ccaactgatc ttcagcatct   5220
tttactttca ccagcgtttc tgggtgagca aaaacaggaa ggcaaaatgc cgcaaaaaag   5280
ggaataaggg cgacacggaa atgttgaata ctcatactct tcctttttca atattattga   5340
agcatttatc agggttattg tctcatgagc ggatacatat ttgaatgtat ttagaaaaat   5400
aaacaaatag gggttccgcg cacatttccc cgaaaagtgc cacctgaacg aagcatctgt   5460
gcttcatttt gtagaacaaa aatgcaacgc gagagcgcta attttcaaa caaagaatct   5520
gagctgcatt tttacagaac agaaatgcaa cgcgaaagcg ctattttacc aacgaagaat   5580
ctgtgcttca ttttgtaaa acaaaaatgc aacgcgagcg cgctaatttt tcaaacaaag   5640
aatctgagct gcattttttac agaacagaaa tgcaacgcga gagcgctatt ttaccaacaa   5700
agaatctata cttctttttt gttctacaaa aatgcatccc gagagcgcta tttttctaac   5760
aaagcatctt agattacttt ttttctcctt tgtgcgctct ataatgcagt ctcttgataa   5820
cttttttgcac tgtaggtccg ttaaggttag aagaaggcta ctttggtgtc tattttctct   5880
tccataaaaa aagcctgact ccacttcccg cgtttactga ttactagcga agctgcgggt   5940
gcatttttc aagataaagg catccccgat tatattctat accgatgtgg attgcgcata   6000
ctttgtgaac agaaagtgat agcgttgatg attcttcatt ggtcagaaaa ttatgaacgg   6060
tttcttctat tttgtctcta tatactacgt ataggaaatg tttacatttt cgtattgttt   6120
tcgattcact ctatgaatag ttcttactac aatttttttg tctaaagagt aatactagag   6180
ataaacataa aaaatgtaga ggtcgagttt agatgcaagt tcaaggagcg aaaggtggat   6240
gggtaggtta tatagggata tagcacagag atatatagca aagagatact tttgagcaat   6300
gtttggaa gcggtattcg caatattta gtagctcgtt acagtccggt gcgttttgga   6360
tttttgaaa gtgcgtcttc agagcgcttt tggttttcaa aagcgctctg aagttcctat   6420
actttctaga aataggaac ttcggaatag gaacttcaaa gcgttccga aaacgagcgc   6480
ttccgaaaat gcaacgcgag ctgcgcacat acagctcact gttcacgtcg cacctatatc   6540
tgcgtgttgc ctgtatatat atacatga gaagaaccgc atatgcgtg ttatgctta    6600
aatgcgtact tatatgcgtc tatttatgta ggatgaaagg tagtctagta cctcctgtga   6660
tattatccca ttcatgcgg ggtatcgtat gcttccttca gcactaccct ttagctgttc   6720
tatatgctgc cactcctcaa ttggattagt ctcatccttc aatgctatca tttcctttga   6780
tattggatca tggtagacaa cccttaatat aacttcgtat aatgtatgct atacgaagtt   6840
attaggtcta gagatct                                                  6857
```

SEQ ID NO: 89        moltype = DNA   length = 5199
FEATURE              Location/Qualifiers
misc_feature         1..5199
                     note = Plasmid pCEV-URA3-TEF-cMyc
source               1..5199
                     mol_type = other DNA
                     organism = synthetic construct
SEQUENCE: 89

```
agcttttcaa ttcaattcat catttttttt ttattctttt ttttgatttc ggtttctttg     60
aaatttttt gattcggtaa tctccgaaca gaaggaagaa cgaaggaagg agcacagact    120
tagattggta tatatacgca tatgtagtgt tgaagaaaca tgaaattgcc cagtattctt    180
aacccaactg cacagaacaa aaaccagcag gaaacgaaga taaatcatgt cgaaagctac    240
atataaggaa cgtgctgcta ctcatcctag tcctgttgct gccaagctat ttaatatcat    300
gcacgaaaag caaacaaact tgtgtgcttc attggatgtt cgtaccacca aggaattact    360
ggagttagtt gaagcattag gtcccaaaat ttgtttacta aaaacacatg tggatatctt    420
gactgatttt tccatggagg gcacagttaa gccgctaaag gcattatccg ccaagtacaa    480
ttttttactc ttcgaagata gaaaatttgc tgacattggt aatacagtca aattgcagta    540
ctctgcgggt gtatacagaa tagcagaatg ggcagacatt acgaatgcac acggtgtggt    600
```

```
gggcccaggt attgttagcg gtttgaagca ggcggcagaa gaagtaacaa aggaacctag    660
aggcctttg atgttagcag aattgtcatg caagggctcc ctatctactg gagaatatac    720
taagggtact gttgacattg cgaaaagcga caaagatttt gttatcggct ttattgctca    780
aagagacatg ggtggaagag atgaaggtta cgattggttg attatgacac ccggtgtggg    840
tttagatgac aagggagatg cattggtca acagtataga accgtggatg atgttgtctc    900
tacaggatct gacattatta ttgttggaag aggactattt gcaagggaa gggatgctaa    960
ggtagagggt gaacgttaca gaaaagcagg ctgggaagca tatttgagaa gatgcggcca   1020
gcaaaactaa aaaactgtat tataagtaaa tgcatgtata ctaaactcac aaattagagc   1080
ttcaatttaa ttatatcagt tattaccccg gccgcacaca ccatagcttc aaaatgtttc   1140
tactccttt ttactcttcc agattttctc ggactccgcg catcgccgta ccacttcaaa   1200
acacccaagc acagcatact aaatttcccc tctttcttcc tctagggtgt cgttaattac   1260
ccgtactaaa ggtttggaaa agaaaaaaga gaccgcctcg tttcttttc ttcgtcgaaa    1320
aaggcaataa aaattttat cacgtttctt tttcttgaaa atttttttt ttgatttttt    1380
tctctttcga tgacctccca ttgatattta agttaataaa cggtcttcaa tttctcaagt   1440
ttcagtttca tttttcttgt tctattacaa cttttttac ttcttgctca ttagaaagaa   1500
agcatagcaa tctaatctaa gttttaatta caaggatctc gacatggaac agaagttgat   1560
ttccgaagaa gacctcgagt aagcttgta ccgcggctag ctaagatccg ctctaaccga   1620
aaaggaagga gttagacaac ctgaagtcta ggtccctatt tatttttta tagttatgtt   1680
agtattaaga acgttattta tatttcaaat ttttcttttt tttctgtaca gacgcgtgta   1740
cgcatgtaac attatactga aaaccttgct tgagaaggtt ttgggacgct cgaagatcca   1800
gctgcattaa tgaatcggcc aacgcgcggg gagaggcggt ttgcgtattg ggcgctcttc   1860
cgcttcctcg ctcactgact cgctgcgctc ggtcgttcgg ctgcggcgag cggtatcagc   1920
tcactcaaag gcggtaatac ggttatccac agaatcaggg gataacgcag gaaagaacat   1980
gtgagcaaaa ggccagcaaa aggccaggaa ccgtaaaaag gccgcgttgc tggcgttttt   2040
ccataggctc cgcccccctg acgagcatca caaaaatcga cgctcaagtc agaggtggcg   2100
aaacccgaca ggactataaa gataccaggc gtttccccct ggaagctccc tcgtgcgctc   2160
tcctgttccg accctgccgc ttaccggata cctgtccgcc tttctccctt cgggaagcgt   2220
ggcgctttct catagctcac gctgtaggta tctcagttcg gtgtaggtcg ttcgctccaa   2280
gctgggctgt gtgcacgaac cccccgttca gcccgaccgc tgcgccttat ccggtaacta   2340
tcgtcttgag tccaacccgg taagacacga cttatcgcca ctggcagcag ccactggtaa   2400
caggattagc agagcgaggt atgtaggcgg tgctacagag ttcttgaagt ggtggcctaa   2460
ctacggctac actagaagga cagtatttgg tatctgcgct ctgctgaagc cagttacctt   2520
cggaaaaaga gttggtagct cttgatccgg caaacaaacc accgctggta gcggtggttt   2580
ttttgtttgc aagcagcaga ttacgcgcag aaaaaaagga tctcaagaag atcctttgat   2640
cttttctacg gggtctgacg ctcagtggaa cgaaaactca cgttaaggga ttttggtcat   2700
gagattatca aaaaggatct tcacctagat ccttttaaat taaaaatgaa gttttaaatc   2760
aatctaaagt atatatgagt aaacttggtc tgacagttac caatgcttaa tcagtgaggc   2820
acctatctca gcgatctgtc tatttcgttc atccatagtt gcctgactcc ccgtcgtgta   2880
gataactacg atacgggagg gcttaccatc tggccccagt gctgcaatga taccgcgaga   2940
cccacgctca ccggctccag atttatcagc aataaaccag ccagccggaa gggccgagcg   3000
cagaagtggt cctgcaactt tatccgcctc catccagtct attaattgtt gccgggaagc   3060
tagagtaagt agttcgccag ttaatagttt gcgcaacgtt gttgccattg ctacaggcat   3120
cgtggtgtca cgctcgtcgt ttggtatggc ttcattcagc tccggttccc aacgatcaag   3180
gcgagttaca tgatccccca tgttgtgcaa aaaagcggtt agctccttcg gtcctccgat   3240
cgttgtcaga agtaagttgg ccgcagtgtt atcactcatg gttatggcag cactgcataa   3300
ttctcttact gtcatgccat ccgtaagatg cttttctgtg actggtgagt actcaaccaa   3360
gtcattctga gaatagtgta tgcggcgacc gagttgctct tgcccggcgt caatacggga   3420
taataccgcg ccacatagca gaactttaaa agtgctcatc attggaaaac gttcttcggg   3480
gcgaaaactc tcaaggatct taccgctgtt gagatccagt tcgatgtaac ccactcgtgc   3540
acccaactga tcttcagcat cttttactt caccagcgtt tctgggtgag caaaaacagg   3600
aaggcaaaat gccgcaaaaa agggaataag ggcgacacgg aaatgttgaa tactcatact   3660
cttcctttt caatattatt gaagcattta tcagggttat tgtctcatga gcggatacat   3720
atttgaatgt atttagaaaa ataaacaaat aggggttccg cgcacatttc cccgaaaagt   3780
gccacctgaa cgaagcatct gtgcttcatt ttgtagaaca aaaatgcaac gcgagagcgc   3840
taatttttca aacaaagaat ctgagctgca ttttacaga acagaaatgc aacgcgaaag   3900
cgctatttta ccaacgaaga atctgtgctt cattttttgta aaacaaaaat gcaacgcgag   3960
agcgctaatt tttcaaacaa agaatctgag ctgcattttt acagaacaga atgcaacgc   4020
gagagcgcta ttttaccaac aaagaatcta tacttctttt tgttctaca aaaatgcatc   4080
ccgagagcgc tatttttcta acaaagcatc ttagattact tttttctcc tttgtgcgct   4140
ctataatgca gtctcttgat aacttttgc actgtaggtc cgttaaggtt agaagaaggc   4200
tactttggtg tctattttct cttccataaa aaagcctga ctccacttcc cgcgtttact   4260
gattactagc gaagctgcgg gtgcatttt tcaagataaa ggcatcccg attatattct   4320
ataccgatgt ggattgcgca tactttgtga acagaaagtg atagcgttga tgattcttca   4380
ttggtcagaa aattatgaac ggtttcttct attttgtcta tatactac gtataggaaa   4440
tgtttacatt ttcgtattgt tttcgattca ctctatgaat agttcttact acaattttt   4500
tgtctaaaga gtaatactag agataaacat aaaaaatgta gaggtcgagt ttagatgcaa   4560
gttcaaggag cgaaaggtgg atgggtaggt tatataggga tatagcacag agatatatag   4620
caaagagata cttttgagca atgtttgtgg aagcggtatt cgcaatattt tagtagctcc   4680
ttacagtccg gtgcgttttt ggttttttga aagtgcgtct tcagagcgct tttggttttc   4740
aaaagcgctc tgaagttcct atactttcta gagaatagga acttcggaat aggaacttca   4800
aagcgtttcc gaaaacgagc gcttccgaaa atgcaacgcg agctgcgcac atacagctca   4860
ctgttcacgt cgcacctata tctgcgtgtt gcctgtatat atatacat gagaagaacg   4920
gcatagtgcg tgtttatgct taaatgcgta cttatgcg tctatttatg taggatgaaa   4980
ggtagtctag tacctcctgt gatattatcc cattccatgc gggtgatcgt atgcttcctt   5040
cagcactacc ctttagctgt tctatatgct gccactcctc aattggatta gtctcatcct   5100
tcaatgctat catttccttt gatattggat catggtagac aacccttaat ataacttcgt   5160
ataatgtatg ctatacgaag ttattaggtc tagagatct                          5199
```

SEQ ID NO: 90  moltype = DNA  length = 7208

```
FEATURE              Location/Qualifiers
misc_feature         1..7208
                     note = Plasmid pCEV-G4-Km-TEF-AT-yABAB hAA6T83N-tagless
source               1..7208
                     mol_type = other DNA
                     organism = synthetic construct
SEQUENCE: 90
cacacaccat agcttcaaaa tgtttctact ccttttttac tcttccagat tttctcggac    60
tccgcgcatc gccgtaccac ttcaaaacac ccaagcacag catactaaat ttcccctctt   120
tcttcctcta gggtgtcgtt aattaccgt actaaaggtt tggaaaagaa aaaagagacc    180
gcctcgtttc ttttcttcg tcgaaaaagg caataaaaat ttttatcacg tttctttttc    240
ttgaaaattt ttttttttga ttttttttctc tttcgatgac ctcccattga tatttaagtt   300
aataaacggt cttcaatttc tcaagtttca gtttcatttt tcttgttcta ttacaacttt   360
ttttacttct tgctcattag aaagaaagca tagcaatcta atctaagttt taattacaag   420
gatccatgag atttccttca attttttactg ctgttttatt cgcagcatcc tccgcattag   480
ctatgcaagt acaattggtt gaaaccggtg gtggtttagt tcaaccaggt ggtagtttga   540
gattatcttg tgctgcatca ggtttacat tggattattc ttcaataggt tggttcagac    600
aagctcctgg taaagaaaga gaaggtgttt cttgcatatc cagttctggt gactcaacta   660
aatatgctga ctccgttaag ggtagattca ctacttcaag agataacgct aaaaatacag   720
tctacttgca aatgaactca ttaaagccag atgacacagc agtctattac tgtgccgctt   780
ttagagccac catgtgcggt gtattcccat tgtctcctta cggtaaagat gactgggta    840
aaggtacttt agttactgtc tcatccggtg gtggtggtgt ggtggtggt ggtagtggtg   900
gtggtggttc tcaagttcaa ttagtagaat ccggtggtgg tttagtccaa cctggtggta   960
gtttaagatt atcctgcgaa gcaagtggtt ttacattaga ttattacggt atcggttggt  1020
ttagacaacc acctggtaaa gaaagagaag ctgtctctta tatttccgct agtgcaagaa  1080
ctatattgta cgcagattct gtaaagggta gattcacaat ttcaagagac accgcagtt   1140
acgctgttta tttgcaaatg aactctttga agagagaaga caccgcagtt tattactgtg  1200
ccagaagaag attttctgct tcttcagtca acagatggtt agcagacgat tatgatgttt  1260
ggggtagagg tacacaagtc gccgtaagtt ctggtggtgg ttccggtggt ggtagtggtg  1320
gtggttctgg tggtggttca cagctgcagc tggtggagac cggggagggc ttagttcaga  1380
ctgggggtc cctgagactc tcctgtgcag cctctggatt caccttcagt gactacgtga   1440
tgacctgggt ccgccaagct ccagggaagg ggcctgagtg gatcgcaact attaatactg  1500
atgggagcac aatgcgcgac gactccacaa agggccggtt caccatctcc agagacaacg  1560
ccaagaacac tctgtatctg caaatgaaca gtctgaaacc cgaggacact gctctgtatt  1620
actgtgcaag aggccgggtg atctctgctt ccgctatcag aggcgcagtc agaggccctg  1680
gaacccaggt caccgtctcg agcggtggcg gcggtagtgg cggcggcggt tctggcggtg  1740
gtggttcaca agtccaattg gtagaatctg gtggtgttt agttcaaact ggtggttcat   1800
tgagattatc ctgcgcttcc agtggttcca ttgcaggttt cgaactgtt acatggtcaa    1860
gacaagctcc aggtaaatct ttgcaatggg tcgcctcaat gaccaagact aacaacgaaa  1920
tctattctga ttcagttaag ggtagattca ttatttcaag agataatgct aaaaacaccg   1980
tttatttgca aatgaactca ttgaagccag aagatactgg tgtttacttc tgcaagggtc  2040
ctgaattaag aggtcaaggt attcaagtaa cagtttcttc agtcgacgcg gctagctaag  2100
atccgtctca accgaaaagg aaggagttag acaacctgaa gtctaggtcc ctatttattt  2160
tttttatagtt atgttagtat taagaacgtt atttatattt caaattttt ttttttttct   2220
gtacagacgc gtgtacgcat gtaacattat actgaaaacc ttgcttgaga aggttttggg  2280
acgctcgaag atccagctgc attaatgaat cggccaacgc gcggggagag gcggtttgcg  2340
tattggcgc tcttccgctt cctcgctcac tgactcgctg cgctcggtcg ttcggctgcg   2400
gcgagcggta tcagctcact caaaggcggt aatacggtta ccacagaat caggggataa   2460
cgcaggaaag aacatgtgag caaaaggcca gcaaaaggcc aggaaccgta aaaaggccgc  2520
gttgctggcg tttttccata ggctccgccc cctgacgag catcacaaaa atcgacgctc   2580
aagtcaggat tggcgaaacc cgacaggact ataaagatac caggcgttc cccctggaag  2640
ctccctcgtg cgctctcctg ttccgaccct gccgcttacc ggatacgt ccgccttct    2700
ccttcggga agcgtggcgc tttctcatag ctcacgctgt aggtatctca gttcggtgta   2760
ggtcgttcgc tccaagctgg gctgtgtgca cgaaccccc gttcagccc accgctgcgc    2820
cttatccggt aactatcgtc ttgagtccaa cccggtaaga cacgacttat cgccactggc  2880
agcagccact ggtaacagga ttagcagagc gaggtatgta ggcggtgcta cagagttctt  2940
gaagtggtgg cctaactacg gctacactag aaggacagta tttggtatct gcgctctgct  3000
gaagccagtt accttcggaa aaagagttgg tagctcttga tccggcaaac aaaccaccgc  3060
tggtagcggt ggtttttttg tttgcaagca gcagattacg cgcagaaaaa aaggatctca  3120
agaagatcct ttgatctttt ctacgggtc tgacgctcag tggaacgaaa actcacgtta   3180
agggattttg gtcatgagat tatcaaaaag gatcttcacc tagatccttt taaattaaaa  3240
atgaagtttt aaatcaatct aaagtatata tgagtaaact tggtctgaca gttaccaatg  3300
cttaatcagt gaggcaccta tctcagcgat ctgtctattt cgttcatcca tagttgcctg  3360
actccccgtc gtgtagataa cacgacg gagggcttta ccatctggcc ccagtgctgc    3420
aatgataccg cgagacccac gctcaccggc tccagattta tcagcaataa accagccagc   3480
cggaagggcc gagcgcagaa gtggtcctgc aactttatcc gcctccatcc agtctattaa   3540
ttgttgccgg gaagctagag taagtagttc gccagttaat agtttgcgca acgttgttgc   3600
cattgctaca ggcatcgtgg tgtcacgctc gtcgtttggt atggcttcat tcagctccgg   3660
ttcccaacga tcaaggcgag ttacatgatc ccccatgttg tgcaaaaaag cggttagctc   3720
cttcggtcct ccgatcgttg tcagaagtaa gttggccgca gtgttatcac tcatggttat   3780
ggcagcactg cataattctc ttactgtcat gccatccgta agatgctttt ctgtgactgg   3840
tgagtactca accaagtcat tctgagaata gtgtatgcgg cgaccgagtt gctcttgccc   3900
ggcgtcaata cgggataata ccgcgccaca tagcagaact ttaaaagtgc tcatcattgg   3960
aaaacgttct tcggggcgaa aactctcaag gatcttaccg ctgttgagat ccagttcgat   4020
gtaacccact cgtgcaccca actgatcttc agcatctttt actttcacca gcgtttctgg   4080
gtgagcaaaa acaggaaggc aaaatgccgc aaaaagggaa taagggcga cacggaaatg   4140
ttgaatactc atactcttcc ttttttcaata ttattgaagc atttatcagg gttattgtct   4200
catgagcgga tacatatttg aatgtattta gaaaaataaa caataggggg ttccgcgcac   4260
atttccccga aagtgccac ctgaacgaag catctgtgct tcatttttgta gaacaaaaat   4320
```

-continued

```
gcaacgcgag agcgctaatt tttcaaacaa agaatctgag ctgcattttt acagaacaga  4380
aatgcaacgc gaaagcgcta ttttaccaac gaagaatctg tgcttcattt ttgtaaaaca  4440
aaaatgcaac gcgagagcgc taatttttca aacaaagaat ctgagctgca tttttacaga  4500
acagaaatgc aacgcgagag cgctatttta ccaacaaaga atctatactt ctttttgtt   4560
ctacaaaaat gcatcccgag agcgctattt tctaacaaa gcatcttaga ttactttttt   4620
tctcctttgt gcgctctata atgcagtctc ttgataactt tttgcactgt aggtccgtta  4680
aggttagaag aaggctactt tggtgtctat tttctcttcc ataaaaaaag cctgactcca  4740
cttcccgcgt ttactgatta ctagcgaagc tgcgggtgca tttttcaag ataaaggcat   4800
ccccgattat attctatacc gatgtggatt gcgcatactt tgtgaacaga aagtgatagc  4860
gttgatgatt cttcattggt cagaaaatta tgaacggttt cttctatttt gtctctatat  4920
actacgtata ggaaatgttt acattttcgt attgttttcg attcactcta tgaatagttc  4980
ttactacaat ttttttgtct aaagagtaat actagagata aacataaaaa atgtagaggt  5040
cgagtttaga tgcaagttca aggagcgaaa ggtggatggg taggttatat agggatatag  5100
cacagagata tatagcaaag agatacttt gagcaatgtt tgtggaagcg gtattcgcaa  5160
tattttagta gctcgttaca gtccggtgcg ttttttggttt tttgaaagtg cgtcttcaga  5220
gcgcttttgg ttttcaaaag cgctctgaag ttcctatact ttctagagaa taggaacttc  5280
ggaataggaa cttcaaagcg tttccgaaaa cgagcgcttc cgaaaatgca acgcgagctg  5340
cgcacataca gctcactgtt cacgtcgcac ctatatcgtg cgttgcctg tatatatata   5400
tacatgagaa gaacggcata gtgcgtgttt atgcttaaat gcgtacttat atgcgtctat  5460
ttatgtagga tgaaaggtag tctagtacct cctgtgatat tatcccattc catgcggggt  5520
atcgtatgct tccttcagca ctacccttta gctgttctat atgctgccac tcctcaattg  5580
gattagtctc atccttcaat gctatcattt cctttgataat tggatcatgg tagacaaccc  5640
ttaatataac ttcgtataat gtatgctata cgaagttatt aggtctagag atctgtttag  5700
cttgcctcgt cccggcgggg tcacccggcc agcgacatgg aggcccagaa tacccctctt  5760
gacagtcttg acgtgcgcag ctcaggggca tgatgtgact gtcgcccgta catttagccc  5820
atacatcccc atgtataatc atttgcatcc atacatttg atggcccgcac ggcgcgaagc  5880
aaaaattacg gctcctcgct gcagacctgc gagcagggaa acgctcccct cacagacgcg  5940
ttgaattgtc cccacgccgc gcccctgtag agaaatataa aaggttagga tttgccactg  6000
aggttcttct ttcatatact tccttttaaa atcttgctag gatacagttc tcacatcaca  6060
tccgaacata aacaaccatg ggtaaggaaa agactcacgt ttcgaggccg cgattaaatt  6120
ccaacatgga tgctgattta tatgggtata aatgggctcg cgataatgtc gggcaatcag  6180
gtgcgacaat ctatcgattg tatgggaagc ccgatgcgcc agagttgttt ctgaaacatg  6240
gcaaaggtag cgttgccaat gatgttacag atgagatggt cagactaaac tggctgacgg  6300
aatttatgcc tcttccgacc atcaagcatt ttatccgtac tcctgatgat gcatggttac  6360
tcaccactgc gatcccgggc aaaacagcat tccaggtatt agaagaatat cctgattcag  6420
gtgaaaatat tgttgatgcg ctggcagtgt tcctgcgccg gttgcattcg attcctgttt  6480
gtaattgtcc ttttaacagc gatcgcgtat ttcgtctcgc tcaggcgcaa tcacgaatga  6540
ataacggttt ggttgatgcg agtgatttg atgacgagcg taatggctgg cctgttgaac   6600
aagtctgaa agaaatgcat aagcttttgc cattctcacc ggattcagtc gtcactcatg  6660
gtgatttctc acttgataac cttatttttg acgaggggaa attaataggt tgtattgatg  6720
ttggacgagt cggaatcgca gaccgatacc aggatcttgc catcctatgg aactgcctcg  6780
gtgagttttc tccttcatta cagaaacggc ttttcaaaa atatggtatt gataatcctg   6840
atatgaataa attgcagttt catttgatgc tcgatgagtt ttctaatca gtactgacaa  6900
taaaaagatt cttgttttca agaacttgtc atttgtatag ttttttata ttgtagttgt   6960
tctattttaa tcaaatgtta gcgtgattta tatttttttt cgcctcgaca tcatctgccc  7020
agatgcgaag ttaagtgcgc agaaagtaat atcatgcgtc aatcgtatgt gaatgctggt  7080
cgctatactg ctgtcgattc gatactaacg ccgccatcca gtgtcgaaaa cgagctctcg  7140
agaaccctta atataacttc gtataatgta tgctatacga agttattagg tgatatcaga  7200
tccactag                                                          7208
```

SEQ ID NO: 91  moltype = DNA length = 10379
FEATURE  Location/Qualifiers
misc_feature  1..10379
  note = Plasmid pCRI-Sb-delta1
source  1..10379
  mol_type = other DNA
  organism = synthetic construct
SEQUENCE: 91

```
tcgcgcgaac ccaactgcac agaacaaaaa cctgcaggaa acgaagataa atcatgtcga    60
aagctacata taaggaacgt gctgctactc atcctagtcc tgttgctgcc aagctattta   120
atatcatgca cgaaaagcaa acaaacttgt gtgcttcatt ggatgttcgt accaccaagg   180
aattactgga gttagttgaa gcattaggtc ccaaaatttg tttactaaaa acacatgtgg   240
atatcttgac tgatttttcc atggagggca cagttaagcc gctaaaggca ttatccgcca   300
agtacaattt tttactcttc gaagacagaa aatttgctga cagttgtaat acagtcaaat   360
tgcagtactc tgcgggtgta tacagaatag cagaatgggc agacattacg aatgcacacg   420
gtgtggtggg cccaggtatt gttagcggtt tgaagcaggc ggcagaagaa gtaacaaagg   480
aacctagagg ccttttgatg ttagcagaat tgtcatgcaa gggctcccta tctactggag   540
aatatactaa gggtactgtt gacattgcga gagcgcaaa agattttgtt atcggcttta   600
ttgctcaaag agacatgggt ggaagagatg aagttacga ttggttgatt atgacaccg    660
gtgtgggttt agatgacaag ggagacgcat gggtcaaca gtatagaacc gtggatgatg   720
tcgtttctac aggatctgac attattattg ttggaagagg actatttgca aagggaaggg   780
atgctaaggt agagggtgaa cgttacgaaa agcaggctg ggaagcatat ttgagaagat   840
gcggccagca aaactaaaaa actgtattat aagtaaatgc atgtatacta aactcacaaa   900
ttagagcttc aatttaatta tatcagttat taccctgtc gagtcttt gaaaagataa    960
tgtatgatta tgctttcact catatttata cagaaacttg atgttttctt tcgagtatat  1020
acaaggtgat tacatgtacg tttgaagtac aactctagat tttgtagtgc cctcttgggc  1080
tagcggtaaa ggtgcgcatt ttttcacacc ctacaatgtt ctgttcaaaa gattttggtc  1140
aaacgctgta gaagtgaaag ttggtgcgca tgtttcggcg ttcgaaactt ctccgcagtg  1200
aaagataaat gatcgggttt tagagctatg ctgttttgaa tggtcccaaa actactagta  1260
```

```
tattatcata tagttttaga gctatgctgt tttgaatggt cccaaaactt tttttgtttt  1320
ttatgtctgc atagcttcaa aatgtttcta ctccttttt  actcttccag attttctcgg  1380
actccgcgca tcgccgtacc acttcaaaac acccaagcac agcatactaa atttcccctc  1440
tttcttcctc tagggtgtcg ttaattaccc gtactaaagg tttggaaaag aaaaaagagg  1500
ccgcctcgtt tcttttctt  cgtcgaaaaa ggcaataaaa attttatca cgtttcttt   1560
tcttgaaaat ttttttttt  gatttttttc tctttcgatg acctcccatt gatatttaag  1620
ttaataaacg gtcttcaatt tctcaagttt cagtttcatt tttcttgttc tattacaact  1680
tttttactt  cttgctcatt agaaagaaag catagcaatc taatctaagt tttctagatg  1740
gattataaag atgacgatga caaacctcca aaaaagaaga gaaaggtcga taagaaatac  1800
tcaataggct tagatatcgg cacaaatagc gtcggatggg cggtgatcac tgatgaatat  1860
aaggttccgt ctaaaaagtt caaggttctg gaaatacag  accgccacag tatcaaaaaa  1920
aatcttatag gggctctttt atttgacagt ggagagacag cggaagcgac tcgtctcaaa  1980
cggacagctc gtagaaggta tacacgtcgg aagaatcgta tttgttatct acaggagatt  2040
ttttcaaatg agatggcgaa agtagatgat agtttcttc  atcgacttga agagtcttt   2100
ttggtggaag aagacaagaa gcatgaacgt catcctattt ttggaaatat agtagatgaa  2160
gttgcttatc atgagaaata tccaactatc tatcatctgc gaaaaaaatt ggtagattct  2220
acttataaag cggatttgcg cttaatctat ttggccttag cgcatatgat taagtttcgt  2280
ggtcatttt  tgattgaggg agatttaaat cctgataata gtgatgtgga caaactattt  2340
atccagttgg tacaaaccta caatcaatta tttgaagaaa accctattaa cgcaagtgga  2400
gtagatgcta aagcgattct ttctgcacga ttgagtaaat caagacgatt agaaaatctc  2460
attgctcagc tccccggtga gaagaaaaat ggcttatttg gaatctcat  tgctttgtca  2520
tgggtttga  cccctaattt taaatcaaat tttgatttgg cagaagatgc taaattacag  2580
cttttcaaaag atacttacga tgatgattta gataatttat tggcgcaaat tggagatcaa  2640
tatgctgatt tgtttttggc agctaagaat ttatcagatg ctattttact ttcagatatc  2700
ctaagagtaa atactgaaat aactaaggct cccctatcag cttcaatgat taaacgctac  2760
gatgaacatc atcaagactt gactcttta  aaagtcttaa ttcgacaaca acttccagaa  2820
aagtataaag aaatctttt  tgatcaatca aaaaacggat atgcaggtta tattgatggg  2880
ggagctagcc aagaagaatt ttataaattt atcaaaccaa ttttagaaaa aatggatggt  2940
actgaggaat tattggtgaa actaaatcgt gaagatttgc tgcgcaagca acggaccttt  3000
gacaacggct ctattaccca tcaaattcac ttgggtgagc tgcatgctat tttgagaaga  3060
caagaagact tttatccatt tttaaaagac aatcgtgaga agattgaaaa aatcttgact  3120
tttcgaattc cttattatgt tggtccattg gcgcgtggca atagtcgttt tgcatggatg  3180
actcggaagt ctgaagaaac aattaccca  tggaattttg aagaagttgt cgataaaggt  3240
gcttcagctc aatcatttat tgaacgcatg acaaactttg ataaaaatct tccaaatgaa  3300
aaagtactac caaaacatag tttgctttat gagtattta  cggtttataa cgaattgaca  3360
aaggtcaaat atgttactga aggaatgcga aaaccagcat ttctttcagg tgaacagaag  3420
aaagccattg ttgatttact cttcaaaaca aatcgaaaag taaccgttaa gcaattaaaa  3480
gaagattatt tcaaaaaaat agaatgtttt gatagtgttg aaatttcagg agttgaagat  3540
agatttaatg cttcattagg tacctaccat gatttgctaa aaattattaa agataaagat  3600
tttttggata atgaagaaaa tgaagatatc ttagaggata ttgtttaac  attgaccta   3660
tttgaagata gggagatgat tgaggaaaga cttaaaacat atgctcacct ctttgatgat  3720
aaggtgatga aacagcttaa acgtcgccgt tatactggtt ggggacgttt gtctcgaaaa  3780
ttgattaatg gtattaggga taagcaatct ggcaaaacaa tattagattt tttgaaatca  3840
gatggttttg ccaatcgcaa ttttatgcag ctgatccatg atgatagttt gacatttaaa  3900
gaagacattc aaaaagcaca agtgtctgga caaggcgata gtttacatga acatattgca  3960
aatttagctg gtagccctgc tattaaaaaa ggtattttac agactgtaaa agttgttgat  4020
gaattggtca aagtaatggg gcggcataag ccagaaaata tcgttattga aatggcacgt  4080
gaaaatcaga caactcaaaa gggccagaaa aattcgcgag agcgtatgaa acgaatcgaa  4140
gaaggtatca aagaattagg aagtcagatt cttaaagagc atcctgttga aaatactcaa  4200
ttgcaaaatg aaaagctcta tctctattat ctccaaaatg gaagagacat gtatgtggac  4260
caagaattag atattaatcg tttaagtgat tatgatgtcg atcacattgt tccacaaagt  4320
ttccttaaag acgattcaat agacaataag gtcttaacgc gttctgataa aaatcgtggt  4380
aaatcggata acgttccaag tgaagaagta gtcaaaagga tgaaaaacta ttggagacaa  4440
cttctaaacg ccaagttaat cactcaacgt aagtttgata atttaacgaa agctgaacgt  4500
ggaggtttga gtgaacttga taaagctggt tttatcgaac gccaattggt tgaaactcgc  4560
caaatcacta agcatgtggc acaaattttg gatagtcgca tgaatactaa atacgatgaa  4620
aatgataaac ttattcgaga ggttaaagtg attaccttaa aatctaaatt agtttctgac  4680
ttccgaaaag atttccaatt ctataaagta cgtgagatta caattacca  tcatgcccat  4740
gatgcgtatc taaatgccgt cgttggaact gctttgatta agaaatatcc aaaacttgaa  4800
tcggagtttg tctatggtga ttataagtt  tatgatgttc gtaaaatgat tgctaagtct  4860
gagcaagaaa taggcaaagc aaccgcaaaa tatttctttt actctaatat catgaacttc  4920
ttcaaaacag aaattacact tgcaaatgga gagattcgca aacgccctct aatcgaaact  4980
aatgggaaa  ctggagaaat tgtctgggat aaagggcgag attttgccac agtgcgcaaa  5040
gtattgtcca tgcccaagt  caatattgtc aagaaaacag aagtacagac aggcggattc  5100
tccaaggagt caattttacc aaaaagaaat tcggacaagc ttattgctcg taaaaaagac  5160
tgggatccaa aaaaatatgg tggttttgat agtccaacgg tagcttattc agtcctagtg  5220
gttgctaagt ggaaaaagg  gaaatcgaag aagttaaaat ccgttaaaga gttactaggg  5280
atcacaatta tggaaagaag ttcctttgaa aaaatccga  ttgactttt  agaagctaaa  5340
ggatataagg aagttaaaaa agacttaatc attaaactac ctaaatatag tcttttgag   5400
ttagaaaacg gtcgtaaacg gatgctggct agtgccggag aattacaaaa aggaaatgag  5460
ctggctctgc caagcaaata tgtgaatttt ttatatttag ctagtcatta tgaaaagttg  5520
aagggtagtc cagaagataa cgaacaaaaa caattgtttg tggagcagca taagcattat  5580
ttagatgaga ttattgagca aatcagtgaa ttttctaagc gtgttatttt agcagatgcc  5640
aatttagata aagttcttag tgcatataac aaacatagag acaaaccaat acgtgaacaa  5700
gcagaaaata ttattcattt atttacgttg acgaatcttg gagctcccgc tgcttttaaa  5760
tattttgata caacaattga tcgtaaacga tatacgtcta caaaagaagt tttagatgcc  5820
actcttatcc atcaatccat cactggtctt tatgaaacac gcattgattt gagtcagcta  5880
ggaggtgacc ctccaaaaaa gaagagaaag gtctgagcgg atctcttatg tctttacgat  5940
ttatagtttt cattatcaag tatgcctata ttagtatata gcatctttag atgacagtgt  6000
```

```
tcgaagtttc acgaataaaa gataatattc tacttttgc tcccaccgcg tttgctagca  6060
cgagtgaaca ccatccctcg cctgtgagtt gtacccattc ctctaaactg tagacatggt  6120
agcttcagca gtgttcgtta tgtacggcat cctccaacaa acagtcggtt atagtttgtc  6180
ctgctcctct gaatcgagtc cctcgatatt tctcatacta gttctagaga tctgccaatt  6240
gaacataaca tggtagttac atatactagt aaatatggttc ggcacacatt aaaagtataa  6300
aaactatctg aattacgaat tacatatatt ggtcataaaa atcaatcaat catcgtgtgt  6360
tttatatgtc tcttatctaa gtataagaat atccatagtt aatattcact tacgctacct  6420
tttaacctgt aatcattgtc aacaggatat gttaacgacc cacattgata aacgctagta  6480
tttcttttc ctcttcttat tggccggctg tctctatact ccctatagt ctgtttcttt  6540
tcgtttcgat tgttttacgt ttgaggcctc gtgcgcaca tggtacgctg tggtgctcgc  6600
ggctgggaac gaaactctgg gagctgcgat tggcaggaac cattcaaaac agcatagcaa  6660
gttaaaataa ggctagtccg ttatcaactt gaaaaagtgg caccgagtcg gtgcttttt  6720
tccatatcca acttccaatt taatctttct tttttaattt tcacttattt gcgatacaga  6780
aagaccctgc aggcatgcaa gcttggcgta atcatggtca tagctgtttc ctgtgtgaaa  6840
ttgttatccg ctcacaattc cacacaacat acgagccgga agcataaagt gtaaagcctg  6900
gggtgcctaa tgagtgagct aactcacatt aattgcgttg cgctcactgc ccgctttcca  6960
gtcgggaaac ctgtcgtgcc agctgcatta atgaatcggc caacgcgcgg ggagaggcgg  7020
tttgcgtatt gggcgctctt ccgcttcctc gctcactgac tcgctgcgct cggtcgttcg  7080
gctgcggcga gcggtatcag ctcactcaaa ggcggtaata cggttatcca cagaatcagg  7140
ggataacgca ggaaagaaca tgtgagcaaa aggccagcaa aaggccagga accgtaaaaa  7200
ggccgcgttg ctggcgtttt tccataggct ccgcccccct gacgagcatc acaaaaatcg  7260
acgctcaagt cagaggtggc gaaacccgac aggactataa agataccagg cgtttccccc  7320
tggaagctcc ctcgtgcgct ctcctgttcc gaccctgccg cttaccggat acctgtccgc  7380
ctttctccct tcgggaagcg tggcgctttc tcatagctca cgctgtaggt atctcagttc  7440
ggtgtaggtc gttcgctcca agctgggctg tgtgcacgaa ccccccgttc agcccgaccg  7500
ctgcgcctta tccggtaact atcgtcttga gtccaacccg gtaagacacg acttatcgcc  7560
actggcagca gccactggta acaggattag cagagcgagg tatgtaggcg gtgctacaga  7620
gttcttgaag tggtggccta actacggcta cactagaaga acagtatttg gtatctgcgc  7680
tctgctgaag ccagttacct tcggaaaaag agttggtagc tcttgatccg gcaaacaaac  7740
caccgctggt agcggtggtt tttttgtttg caagcagcag attacgcgca gaaaaaaagg  7800
atctcaagaa gatcctttga tcttttctac ggggtctgac gctcagtgga acgaaaactc  7860
acgttaaggg attttggtca tgagattatc aaaaaggatc ttcacctaga tccttttaaa  7920
ttaaaaatga agttttaaat caatctaaag tatatatgag taaacttggt ctgacagtta  7980
ccaatgctta atcagtgagg cacctatctc agcgatctgt ctatttcgtt catccatagt  8040
tgcctgactc cccgtcgtgt agataactac gatacgggag ggcttaccat ctggccccag  8100
tgctgcaatg ataccgcggc tccacgctc accggctcca gatttatcag caataaacca  8160
gccagccgga agggccgagc gcagaagtgg tcctgcaact ttatccgcct ccatccagtc  8220
tattaattgt tgccgggaag ctagagtaag tagttcgcca gttaatagtt tgcgcaacgt  8280
tgttgccatt gctacaggca tcgtggtgtc acgctcgtcg tttggtatgg cttcattcag  8340
ctccggttcc caacgatcaa ggcgagttac atgatccccc atgttgtgca aaaaagcggt  8400
tagctccttc ggtcctccga tcgttgtcag aagtaagttg gccgcagtgt tatcactcat  8460
ggttatggca gcactgcata attctcttac tgtcatgcca tccgtaagat gcttttctgt  8520
gactgagtga gtactcaacca agtcattctg agaatagtgt atgcggcgac cgagttgctc  8580
ttgcccggcg tcaatacggg ataataccgc gccacatagc agaactttaa aagtgctcat  8640
cattggaaaa cgttcttcgg ggcgaaaact ctcaaggatc ttaccgctgt tgagatccag  8700
ttcgatgtaa ccccactcgtg cacccaactg atcttcagca tcttttactt tcaccagcgt  8760
ttctgggtga gcaaaaacag gaaggcaaaa tgccgcaaaa aagggaataa gggcgacacg  8820
gaaatgttga atactcatac tcttccttt tcaatattat tgaagcattt atcagggtta  8880
ttgtctcatg agcggataca tatttgaatg tatttagaaa aataaacaaa tagggggttcc  8940
gcgcacattt ccccgaaaag tgccacctga cgaagcatc tgtgcttcat tttgtagaac  9000
aaaaatgcaa cgcgagagcg ctaattttc aaacaaagaa tctgagctgc attttacag  9060
aacagaaatg caacgcgaaa gcgctatttt accaacgaag aatctgtgct tcattttgt  9120
aaaacaaaaa tgcaacgcga gagcgctaat tttcaaaca aagaatctga gctgcattt  9180
tacagaacag aaatgcaacg cgagagcgct attttaccaa caagaatct atacttcttt  9240
tttgttctac aaaaatgcat cccgagagcg ctattttct aacaaagcat cttagattac  9300
ttttttctc ctttgtgcgc tctataatgc agtctcttga taactttttg cactgtaggt  9360
ccgttaaggt tagaagaagg ctactttggt gtctatttc tcttccataa aaaaagcctg  9420
actccacttc ccgcgtttac tgattactag cgaagctgcg ggtgcatttt ttcaagataa  9480
aggcatcccc gattatattc tataccgatg tggattgcgc atactttgtg aacagaaagt  9540
gatagcgttg atgattcttc attggtcaga aaattatgaa cggtttcttc tatttttgtct  9600
ctatatacta cgtataggaa atgtttacat ttcgtattg tttcgattc actctatgaa  9660
tagttcttac tacaattttt ttgtctaaag agtaatacta gagataaaca taaaaaatgt  9720
agaggtcgag tttagatgca agttcaagga gcgaaaggtg gatgggtagg ttatataggg  9780
atatagcaca gagatatata gcaaagagat acttttgagc agatgtttgt gaagcggtat  9840
tcgcaatatt ttagtagctc gttacagtcc ggtgcgtttt tggttttttg aaagtgcgtc  9900
ttcagagcgc ttttggttt caaagcgct ctgaagttcc tatactttct agagaatagg  9960
aacttcggaa taggaacttc aaagcgtttc cgaaaacgag cgcttccgaa aatgcaacgc  10020
gagctgcgca catacagctc actgttcacg tcgcacctat atctgcgtgt tgcctgtata  10080
tatatataca tgagaagaac ggcatagtgc gtgtttatgc ttaaatgcgt acttatatgc  10140
gtctatttat gtaggatgaa aggtagtcta gtacctcctg tgatattatc ccattccatg  10200
cggggtatcg tatgcttcct tcagcactac ccttagctg ttctatatgc tgccactcct  10260
caattggatt agtctcatcc ttcaatgcta tcatttcctt tgatattgga tcatctaaga  10320
aaccattatt atcatgacat taacctataa aaataggcgt atcacgaggc cctttcgtc   10379

SEQ ID NO: 92       moltype = DNA   length = 10379
FEATURE             Location/Qualifiers
misc_feature        1..10379
                    note = Plasmid pCRI-Sb-delta2
source              1..10379
``` mol_type = other DNA
organism = synthetic construct

SEQUENCE: 92

```
tcgcgcgaac ccaactgcac agaacaaaaa cctgcaggaa acgaagataa atcatgtcga    60
aagctacata taaggaacgt gctgctactc atcctagtcc tgttgctgcc aagctattta   120
atatcatgca cgaaaagcaa acaaacttgt gtgcttcatt ggatgttcgt accaccaagg   180
aattactgga gttagttgaa gcattaggtc ccaaaatttg tttactaaaa acacatgtgg   240
atatcttgac tgattttttcc atggagggca cagttaagcc gctaaaggca ttatccgcca   300
agtacaattt tttactcttc gaagacagaa aatttgctga cattggtaat acagtcaaat   360
tgcagtactc tgcgggtgta tacagaatag cagaatgggc agacattacg aatgcacacg   420
gtgtggtggg cccaggtatt gttagcggtt gaagcaggc ggcagaagaa gtaacaaagg   480
aacctagagg cctttttgatg ttagcagaat tgtcatgcaa gggctcccta tctactggag   540
aatatactaa gggtactgtt gacattgcga agagcgacaa agattttgtt atcggcttta   600
ttgctcaaag agacatgggt ggaagagatg aaggttacga ttggttgatt atgacacccg   660
gtgtgggttt agatgacaag ggagacgcat tgggtcaaca gtatagaacc gtggatgatg   720
tcgtttctac aggatctgac attattattg ttggaagagg actatttgca aagggaaggg   780
atgctaaggt agagggtgaa cgttacgaaa aagcaggctg gaagcatat ttgagaagat   840
gcggccagca aaactaaaaa actgtattat aagtaaatgc atgtatacta aactcacaaa   900
ttagagcttc aatttaatta tatcagttat taccctgtgc tcgagtcttt gaaaagataa   960
tgtatgatta tgctttcact catatttata cagaaacttg atgttttctt tcgagtatat  1020
acaaggtgat tacatgtacg tttgaagtac aactctagat tttgtagtgc cctcttgggc  1080
tagcgtaaa ggtgcgcatt ttttcacacc ctacaatgct ctgttcaaaa gattttggtc  1140
aaacgctgta gaagtgaaag ttggtgcgca tgtttcggcg ttcgaaactt ctccgcagtg  1200
aaagataaat gatcgggttt tagagctatg ctgttttgaa tggtcccaaa actatggatt  1260
cctaaatcct cggttttaga gctatgctgt tttgaatggt cccaaaactt ttttttgttt  1320
ttatgtctgc atagcttcaa aatgtttcta ctccttttt actcttccag attttctcgg  1380
actccgcgca tcgccgtacc acttcaaaac acccaagcac agcatactaa atttccctc  1440
tttcttcctc tagggtgtcg ttaattaccc gtactaaagg tttggaaaag aaaaaagagg  1500
ccgcctcgtt tcttttttctt cgtcgaaaaa ggcaataaaa attttttatca cgtttcttttt  1560
tcttgaaaat ttttttttttc gattttttttc tctttcgatg acctcccatt gatatttaag  1620
ttaataaacg gtcttcaatt tctcaagttt cagtttcatt tttcttgttc tattacaact  1680
ttttttactt cttgctcatt agaaagaaag catagcaatc taatctaagt tttctagatg  1740
gattataaag atgacgatga caaacctcca aaaaagaaga gaaggtcga taagaaatac  1800
tcaataggct tagatatcgg cacaaatagc gtcggatggg cggtgatcac tgatgaatat  1860
aaggttccgt ctaaaaagtt caaggttctg ggaaatacag accgccacag tatcaaaaaa  1920
aatcttatag gggctctttt atttgacagt ggagagacag cggaagcgac tcgtctcaaa  1980
cggacagctc gtagaaggta tacacgtcgg aagaatcgta tttgttatct acaggagatt  2040
tttttcaaatg agatggcgaa agtagatgat agtttctttc atcgacttga agagtctttt  2100
ttggtggaag aagcaagaa gcatgaacgt catcctattt ttggaaatat agtagatgaa  2160
gttgcttatc atgagaaata tccaactatc tatcatctgc gaaaaaaatt ggtagattct  2220
acttataaag cggatttgcg cttaatctat ttggccttag cgcatatgat taagtttcgt  2280
ggtcattttt tgattgaggg agatttaaat cctgataata gtgatgtgga caaactattt  2340
atccagttgg tacaaaccta caatcaatta tttgaagaaa accctattaa cgcaagtgga  2400
gtagatgcta aagcgattct ttctgcacga ttgagtaaat caagacgatt agaaaatctc  2460
attgctcagc tccccggtga agaaaaaat ggcttatttg gaatctcat tgctttgtca  2520
ttgggtttga cccctaattt taaatcaaat tttgatttgg cagaagatgc taaattacag  2580
cttttcaaaag atacttacga tgatgattta gataatttat tggcgcaaat tggagatcaa  2640
tatgctgatt tgtttttggc agctaagaat ttatcagatg ctatttttact ttcagatatc  2700
ctaagagtaa atactgaaat aactaaggct cccctatcag cttcaatgat taaacgctac  2760
gatgaacatc atcaagactt gactctttta aaagcttag ttcgacaaca acttccagaa  2820
aagtataaag aaatcttttt tgatcaatca aaaaacggat atgcaggtta tattgatggg  2880
ggagctagcc aagaagaatt ttataaattt atcaaaccaa ttttagaaaa aatggatggt  2940
actgaggaat tattggtgaa actaaatcgt gaagatttgc tgcgcaagca acggaccttt  3000
gacaacggct ctattaccca tcaaattcac ttgggtgagc tgcatgctat ttgagaaga  3060
caagagact tttatccatt tttaaaagac aatcgtgaga agattgaaaa aatcttgact  3120
tttcgaattc cttattatgt tggtccattg gcgcgtggca atagtcgttt tgcatgatg  3180
actcggaagt ctgaagaaac aattacccca tggaattttg aagaagttgt cgataaaggt  3240
gcttcagctc aatcatttat tgaacgcatg acaaactttg ataaaaatct tccaaatgaa  3300
aaagtactac caaaacatag tttgctttat gagtatttta cggttataa cgaattgaca  3360
aaggtcaaat atgttactga aggaatgcga aaaccagcat ttctttcagg tgaacagaag  3420
aaagccattg ttgatttact cttcaaaaca aatcgaaaag taaccgttaa gcaattaaaa  3480
gaagattatt tcaaaaaaat agaatgtttt gatagtgttg aaatttcagg agttgaagat  3540
agatttaatg cttcattagg tacctaccat gatttgctaa aaattattaa agataaagat  3600
ttttggata atgaagaaaa tgaagatatc ttagaggata ttgttttaac attgacctta  3660
tttgaagata gggagatgat tgaggaaaga cttaaaacat atgctcacct cttttgatgat  3720
aaggtgatga aacagcttaa acgtgccgt tatactggtt ggggacgttt gtctgaaaaa  3780
ttgattaatg gtattaggga taagcaatct ggcaaaacaa tattagattt tttgaaatca  3840
gatggttttg ccaatcgcaa tttttatgcag ctgatccatg atgatagttt gacatttaaa  3900
gaagacattc aaaaagcaca agtgtctgga caaggcgata gtttacatga acatattgca  3960
aatttagctg gtagccctgc tattaaaaaa ggtattttac agactgtaaa agttgttgat  4020
gaattggtca aagtaatggg gcggcataag ccagaaaata tcgttattga aatggcacgt  4080
gaaaatcaga caactcaaaa gggccagaaa aattcgcgag agcgtatgaa acgaatcgaa  4140
gaaggtatca aagaattagg aagtcagatt cttaaagagc atcctgttga aaatactcaa  4200
ttgcaaaatg aaaagctcta tctctattat ctccaaaatg gaagagacat gtatgtggac  4260
caagaattag atattaatcg tttaagtgat tatgatgtcg atcacattgt tccacaaagt  4320
ttccttaaag acgattcaat agacaataag gtcttaacgc gttctgataa aaatcgtggt  4380
aaatcggata acgttccaag tgaagaagta gtcaaaaaga tgaaaactta ttggagacaa  4440
cttctaaacg ccaagttaat cactcaacgt aagtttgata atttaacgaa agctgaacgt  4500
ggaggtttga gtgaacttga taaagctggt tttatcaaac gccaattggt tgaaactcgc  4560
```

```
caaatcacta agcatgtggc acaaattttg gatagtcgca tgaatactaa atacgatgaa  4620
aatgataaac ttattcgaga ggttaaagtg attaccttaa aatctaaatt agtttctgac  4680
ttccgaaaag atttccaatt ctataaagta cgtgagatta acaattacca tcatgcccat  4740
gatgcgtatc taaatgccgt cgttggaact gctttgatta gaaatatcc aaaacttgaa   4800
tcggagtttg tctatggtga ttataaagtt tatgatgttc gtaaaatgat tgctaagtct  4860
gagcaagaaa taggcaaagc aaccgcaaaa tatttctttt actctaatat catgaacttc  4920
ttcaaaacag aaattacact tgcaaatgga gagattcgca aacgccctct aatcgaaact  4980
aatgggaaa ctggagaaat tgtctgggat aagggcgag attttgccac agtgcgcaaa    5040
gtattgtcca tgccccaagt caatattgtc aagaaaacag aagtacagac aggcggattc  5100
tccaaggagt caattttacc aaaaagaaat tcggacaagc ttattgctcg taaaaaagac  5160
tgggatccaa aaaaatatgg tggttttgat agtccaacgg tagcttattc agtcctagtg  5220
gttgctaagg tggaaaaagg gaaatcgaag aagttaaaat ccgttaaaga gttactaggg  5280
atcacaatta tggaaagaag ttcctttgaa aaaaatccga ttgactttt agaagctaaa   5340
ggatataagg aagttaaaaa agacttaatc attaaactac ctaaatatag tcttttgag   5400
ttagaaaacg gtcgtaaacg gatgctggct agtgccggag aattacaaaa aggaaatgag  5460
ctggctctgc caagcaaata tgtgaatttt ttatatttag ctagtcatta tgaaaagttg  5520
aagggtagtc cagaagataa cgaacaaaaa caattgtttg tggagcagca taagcattat  5580
ttagatgaga ttattgagca aatcagtgaa ttttctaagc gtgttatttt agcagatgcc  5640
aatttagata aagttcttag tgcatataac aaacatagag acaaaccaat acgtgaacaa  5700
gcagaaaata ttattcattt atttacgttg acgaatcttg gagctcccgc tgcttttaaa  5760
tatttgata caacaattga tcgtaaacga tatacgtcta caaagaagt tttagatgcc   5820
actcttatcc atcaatccat cactgttctt tatgaaacac gcattgattt gagtcagcta  5880
ggaggtgacc ctccaaaaaa gaagagaaag gtctgagcgg atctcttatg tctttacgat  5940
ttatagtttt cattatcaag tatgcctata ttagtatata gcatctttag atgacagtgt  6000
tcgaagtttc acgaataaaa gataatattc tacttttgc tcccaccgcg tttgctagca    6060
cgagtgaaca ccatccctcg cctgtgagtt gtacccattc ctctaaactg tagacatggt  6120
agcttcagca gtgttcgtta tgtacggcat cctccaacaa acagtcggtt atagtttgtc  6180
ctgctcctct gaatcgagtc cctcgatatt tctcatacta gttctagaga tctgccaatt  6240
gaacataaca tggtagttac atatactagt aatatggttc ggcacacatt aaaagtataa  6300
aaactatctg aattacgaat tacatatatt ggtcataaaa atcaatcaat catcgtgtaa  6360
tttatatgtc tcttatctaa gtataagaat atccatagtt aatattcact tacgctacct  6420
tttaacctgt aatcattgtc aacaggatat gttaacgacc cacattgata aacgctagta  6480
tttctttttc ctcttcttat tggccggctg tctctatact cccctatagt ctgtttcttt  6540
tcgttttcgat tgtttttacgt ttgaggcctc gtggcgcaca tggtacgctg tggtgctcgc 6600
ggctgggaac gaaactcgtg gagctgcgat tggcagaac cattcaaaac agcatagcaa    6660
gttaaaataa ggctagtccg ttatcaactt gaaaaagtgg caccgagtcg gtgcttttt    6720
tccatatcca acttccaatt taatctttct tttttaattt tcacttattt gcgatacaga  6780
aagaccctgc aggcatgcaa gcttggcgta atcatggtca tagctgtttc ctgtgtgaaa  6840
ttgttatccg ctcacaattc cacacaacat acgagccgga agcataaagt gtaaagcctg  6900
gggtgcctaa tgagtgagct aactcacatt aattgcgttg cgctcactgc ccgctttcca  6960
gtcgggaaac ctgtcgtgcc agctgcatta atgaatcggc caacgcgcgg ggagaggcgg  7020
tttgcgtatt gggcgctctt ccgcttcctc gctcactgac tcgctgcgct cggtcgttcg  7080
gctgcggcga gcggtatcag ctcactcaaa ggcggtaata cggttatcca cagaatcagg  7140
ggataacgca ggaaagaaca tgtgagcaaa aggccagcaa aaggccagga accgtaaaaa  7200
ggccgcgttg ctggcgtttt tccataggct ccgcccccct gacgagcatc acaaaaatcg  7260
acgctcaagt cagaggtggc gaaacccgac aggactataa agataccagg cgtttccccc  7320
tggaagctcc ctcgtgcgct ctcctgttcc gaccctgccg cttaccggat acctgtccgc  7380
ctttctccct tcgggaagcg tggcgctttc tcatagctca cgctgtaggt atctcagttc  7440
ggtgtaggtc gttcgctcca agctgggctg tgtgcacgaa ccccccgttc agcccgaccg  7500
ctgcgcctta tccggtaact atcgtcttga gtccaacccg gtaagacacg acttatcgcc  7560
actggcagca gccactggta acaggattag cagagcgagg tatgtaggcg gtgctacaga  7620
gttcttgaag tggtggccta actacggcta cactagaaga acagtatttg gtatctgcgc  7680
tctgctgaag ccagttacct tcggaaaaag agttggtagc tcttgatccg gcaaacaaac  7740
caccgctggt agcggtggtt ttttttgttt caagcagcag attacgcgca gaaaaaaagg  7800
atctcaagaa gatcctttga tcttttctac ggggtctgac gctcagtgga acgaaaactc  7860
acgttaaggg attttggtca tgagattatc aaaaaggatc ttcacctaga tccttttaaa  7920
ttaaaaatga agttttaaat caatctaaag tatatatgag taaacttggt ctgacagtta  7980
ccaatgctta atcagtgagg cacctatctc agcgatctgt ctatttcgtt catccatagt  8040
tgcctgactc cccgtcgtgt agataactac gatacgggag ggcttaccat ctggccccag  8100
tgctgcaatg ataccgcggc tcccacgctc accggctcca gatttatcag caataaacca  8160
gccagccgga agggccgagc gcagaagtgg tcctgcaact ttatccgcct ccatccagtc  8220
tattaattgt tgccgggaag ctagagtaag tagttcgcca gttaatagtt tgcgcaacgt  8280
tgttgccatt gctacaggca tcgtggtgtc acgctcgtcg tttggtatgg cttcattcag  8340
ctccggttcc caacgatcaa ggcgagttac atgatccccc atgttgtgca aaaaagcggt  8400
tagctccttc ggtcctccga tcgttgtcag aagtaagttg gccgcagtgt tatcactcat  8460
ggttatggca gcactgcata attctcttac tgtcatgcca tccgtaagat gcttttctgt  8520
gactggtgag tactcaacca agtcattctg agaatagtgt atgcggcgac cgagttgctc  8580
ttgcccggcg tcaatacggg ataataccgc gccacatagc agaactttaa aagtgctcat  8640
cattggaaaa cgttcttcgg ggcgaaaact ctcaaggatc ttaccgctgt tgagatccgt  8700
ttcgatgtaa cccactcgtg cacccaactg atcttcagca tcttttactt tcaccagcgt  8760
ttctgggtga gcaaaaacag gaaggcaaaa tgccgcaaaa aagggaataa gggcgacacg  8820
gaaatgttga atactcatac tcttcctttt tcaatattat tgaagcattt atcagggtta  8880
ttgtctcatg agcggataca tatttgaatg tatttagaaa aataaacaaa tagggggtcc  8940
gcgcacattt ccccgaaaag tgccacctga acgaagcatc tgtgcttcat tttgtagaac  9000
aaaaatgcaa cgcgagagcg ctaatttttc aaacaaagaa tctgagctgc attttttacag 9060
aacagaaatg caacgcgaaa gcgctatttt accaacgaag aatctgtgct tcattttgt   9120
aaaacaaaaa tgcaacgcga gagcgctaat ttttcaaaca agaatctga gctgcatttt   9180
tacagaacag aaatgcaacg cgagagcgct attttaccaa caaagaatct atacttcttt  9240
tttgttctac aaaaatgcat cccgagagcg ctattttct aacaaagcat cttagattac    9300
```

```
ttttttctc ctttgtgcgc tctataatgc agtctcttga taactttttg cactgtaggt   9360
ccgttaaggt tagaagaagg ctactttggt gtctattttc tcttccataa aaaaagcctg   9420
actccacttc ccgcgtttac tgattactag cgaagctgcg ggtgcatttt ttcaagataa   9480
aggcatcccc gattatattc tataccgatg tggattgcgc atactttgtg aacagaaagt   9540
gatagcgttg atgattcttc attggtcaga aaattatgaa cggtttcttc tattttgtct   9600
ctatatacta cgtataggaa atgtttacat tttcgtattg ttttcgattc actctatgaa   9660
tagttcttac tacaattttt ttgtctaaag agtaatacta gagataaaca taaaaaatgt   9720
agaggtcgag tttagatgca agttcaagga gcgaaaggtg gatgggtagg ttatataggg   9780
atatagcaca gagatatata gcaaagagat acttttgagc aatgtttgtg gaagcggtat   9840
tcgcaatatt ttagtagctc gttacagtcc ggtgcgtttt tggttttttg aaagtgcgtc   9900
ttcagagcgc ttttggtttt caaaagcgct ctgaagttcc tatactttct agagaatagg   9960
aacttcggaa taggaacttc aaagcgtttc cgaaaacgag cgcttccgaa aatgcaacgc  10020
gagctgcgca catacagctc actgttcacg tcgcacctat atctgcgtgt tgcctgtata  10080
tatatataca tgaagaagaac ggcatagtgc gtgtttatgc ttaaatgcgt acttatatgc  10140
gtctatttat gtaggatgaa aggtagtcta gtacctcctg tgatattatc ccattccatg  10200
cggggtatcg tatgcttcct tcagcactac ccttttagctg ttctatatgc tgccactcct  10260
caattggatt agtctcatcc ttcaatgcta tcatttcctt tgatattgga tcatctaaga  10320
aaccattatt atcatgacat taacctataa aaataggcgt atcacgaggc cctttcgtc  10379

SEQ ID NO: 93          moltype = DNA   length = 126
FEATURE                Location/Qualifiers
source                 1..126
                       mol_type = other DNA
                       organism = Saccharomyces boulardii
SEQUENCE: 93
tgttggaata aaaatcaact atcatctact aactagtatt tacgttacta gtatatattc    60
atatacggtg ttagaagatg acgcaaatga tgagaaatag tcatctaaat tagtggaagc   120
tgaaac                                                              126

SEQ ID NO: 94          moltype = DNA   length = 105
FEATURE                Location/Qualifiers
source                 1..105
                       mol_type = other DNA
                       organism = Saccharomyces boulardii
SEQUENCE: 94
aatatttata gaattgtgta gaattgcaga ttcccttta tggattccta aatcctcgag     60
gagaacttct agtatatcta catacctaat attatagcct taatc                   105

SEQ ID NO: 95          moltype = DNA   length = 6919
FEATURE                Location/Qualifiers
misc_feature           1..6919
                       note = Plasmid pPL5071_TEF1-Cre_URA3
misc_feature           2382
                       note = n is a, c, g, or t
source                 1..6919
                       mol_type = other DNA
                       organism = synthetic construct
SEQUENCE: 95
agaaaccatt attatcatga cattaaccta taaaaatagg cgtatcacga ggccctttcg    60
tctcgcgcgt ttcggtgatg acggtgaaaa cctctgacac atgcagctcc cggagacggt   120
cacagcttgt ctgtaagcgg atgccgggag cagacaagcc cgtcagggcg cgtcagcggg   180
tgttggcggg tgtcggggct ggcttaacta tgcggcatca gagcagattg tactgagagt   240
gcaccatacc acagctttc aattcaattc atcattttt ttttattctt ttttttgatt    300
tcggtttctt tgaaattttt ttgattcggt aatctccgaa cagaaggaag aacgaaggaa   360
ggagcagaca cttagattgg tatatatacg catatgtagt gttgaagaaa catgaaattg   420
cccagtattc ttaacccaac tgcacagaac aaaaacctgc aggaaacgaa gataaatcat   480
gtcgaaagct acatataagg aacgtgctgc tactcatcct agtcctgttg ctgccaagct   540
atttaatatc atgcacgaaa agcaaacaaa cttgtgtgct tcattggatg ttcgtaccac   600
caaggaatta ctggagttag ttgaagcatt aggtcccaaa atttgtttac taaaaacaca   660
tgtggatatc ttgactgatt tttccatgga gggcacagtt aagccgctaa aggcattatc   720
cgccaagtac aattttttac tcttcgaaga cagaaaattt gctgacattg gtaatacagt   780
caaattgcag tactctgcgg gtgtatacag aatagcagaa tgggcagaca ttacgaatgc   840
acacggtgtg gtgggcccag gtattgttag cggtttgaag caggcggcag aagaagtaac   900
aaaggaacct agaggccttt tgatgttagc agaattgtca tgcaagggct ccctatctac   960
tggagaatat actaagggta ctgttgacat tgcgaagagc gacaaagatt ttgttatcgg  1020
ctttattgct caaagagaca tgggtggaag agatgaaggt tacgattggt tgattatgac  1080
acccggtgtg ggtttagatg acaagggaga cgcattgggt caacagtata gaaccgtgga  1140
tgatgtggtc tctacaggat ctgacattat tattgttgga agaggactaa ttgcaaaggg  1200
aagggatgct aaggtagagg gtgaacgtta cagaaaagcg ggctgggaag catatttgag  1260
aagatgcggc cagcaaaaact aaaaaactgt attataagta aatgcatgta tactaaactc  1320
acaaattaga gcttcaattt aattatatca gttattaccc tatgcggtgt gaaataccgc  1380
acagatgcgt aaggagaaaa taccgcatca ggaaattgta aacgttaata ttttgttaaa  1440
attcgcgtta aattttgtt aaatcagctc attttttaac caataggccg aaatcggcaa  1500
aatcccttat aaatcaaaag aatagaccga gatagggttg agtgttgttc cagtttggaa  1560
caagagtcca ctattaaaga acgtggactc caacgtcaaa gggcgaaaaa ccgtctatca  1620
gggcgatggc ccactacgtg aaccatcacc ctaatcaagt ttttttgggt cgaggtgccg  1680
taaagcacta aatcggaacc ctaaagggag cccccgattt agagcttgac ggggaaagcc  1740
ggcgaacgtg gcgagaaagg aagggaagaa agcgaaagga gcgggcgcta gggcgctggc  1800
aagtgtagcg gtcacgctgc gcgtaaccac cacacccgcc gcgcttaatg cgccgctaca  1860
```

```
gggcgcgtcg cgccattcgc cattcaggct gcgcaactgt tgggaagggc gatcggtgcg   1920
ggcctcttcg ctattacgcc agctggcgaa aggggggatgt gctgcaaggc gattaagttg   1980
ggtaacgcca gggttttccc agtcacgacg ttgtaaaacg acggccagtg agcgcgcgta   2040
atacgactca ctatagggcg aattgggtac cggccgcaaa ttaaagcctt cgagcgtccc   2100
aaaaccttct caagcaaggt tttcagtata atgttacatg cgtacacgcg tctgtacaga   2160
aaaaaaagaa aaatttgaaa tataaataac gttcttaata ctaacataac tataaaaaaa   2220
taaataggga cctagacttc aggttgtcta actccttcct tttcggttag agcggatgtg   2280
gggggagggc gtgaatgtaa gcgtgacata actaattaca tgactcgagg tcgacaattc   2340
caaccttacc caagagttcg ccaaactcag acatcacttt angcaaaacc gcgccgtgct   2400
tcttcctcgg tggcattcat cacgaaatgt tcagcactac gcatacttt gacaggaaac    2460
gcaacggata ttgagtcaat atcaggcatt ctatcgctca gctttacagt gacaatgacg   2520
gctggcgact gaatattagt gcttacagac agcactacat attttccgtc gatgttgaaa   2580
tcctttctca tatgtcacca taaatatcaa ataattatag caatcattta cgcgttaatg   2640
gctaatcgcc atcttccagc aggcgcacca ttgcccctgt ttcactatcc agggtacgga   2700
tatagttcat gacaatattt acattggtcc agccaccagc ttgcatgatc tccggtattg   2760
aaactccagc gcgggccata tctcgcgcgg ctccgacacg ggcactgtgt ccagaccagg   2820
ccaggtatct ctgaccagag tcatccttag cgccgtaaat caatcgatga gttgcttcaa   2880
aaatcccttc cagggcgcga gttgatagct ggctggtggc agatggcgcg gcaacaccat   2940
tttttctgac ccggcaaaac aggtagttat tcggatcatc agctacacca gagacggaaa   3000
tccatcgctc gaccagttta gttaccccca ggctaagtgc cttctctaca cctgcggtgc   3060
taaccagcgt tttcgttctg ccaatatgga ttaacattct cccaccgtca gtacgtgaga   3120
tatctttaac cctgatcctg gcaatttcgg ctatacgtaa cagggtgtta taagcaatcc   3180
ccagaaatgc cagattacgt atatcctggc agcgatcgct attttccatg agtgaacgaa   3240
cctggtcgaa atcagtgcgt tcgaacgcta gagcctgttt tgcacgttca ccggcatcaa   3300
cgttttcttt tcggatccgc cgcataacca gtgaaacagc attgctgtca cttggtcgtg   3360
gcagcccgga ccgacgatga agcatgttta gctggcccaa atgttgctgg atagtttta    3420
ctgccagacc gcgcgcctga agatatagaa gataatcgcg aacatcttca ggttctgcgg   3480
gaaaccattt ccgttattc aacttgcacc atgccgccca cgaccggcaa acggacagaa     3540
gcattttcca ggtatgctca gaaaacgcct ggcgatcct gaacatgtcc atcaggttct    3600
tgcgaacctc atcactcgtt gcatcgaccg gtaatgcagg caaattttgg tgtacggtca   3660
gtaaattgga catttaacac tcagataatg gttttaagta aagtgtacag gatcggctct   3720
gcccctcgac ggtatcgata agcttgatat cgaattcctg cagcccgggg gatccactag   3780
tttttgtaat taaaacttag attagattgc tatgctttct ttccaatgag caagaagtaa   3840
aaaaagttgt aatagaacag gaaaaatgaa gctgaaactt gagaaattga agacccgtttg  3900
ttaactcaaa tatcaatggg aggtcgtcga aagagaacaa aatcgaaaaa aaagttttca   3960
agagaaagaa acgtgataaa aatttttatt gccttctccg acgaagaaaa agggacgagg   4020
cggtctcttt ttccttttcc aaacctttag tacgggtaat taacggcacc ctagaggaag   4080
gaggaggggg aatttagtat gctgtgcttg ggtgttttga agtggtacgg cggtgcgcgg   4140
agtccgagaa aatctggaag agtaaaaaag gagtagagac attttgaagc tatccagctt   4200
ttgttccctt tagtgagggt taattgcgcg cttggcgtaa tcatggtcat agctgtttcc   4260
tgtgtgaaat tgttatccgc tcacaattcc acacaacata ggagccggaa gcataaagtg   4320
taaagcctgg ggtgcctaat gagtgaggta actcacatta ttgcgttgc gctcactgcc    4380
cgctttccag tcgggaaacc tgtcgtgcca gctgcattaa tgaatcggcc aacgcgcggg   4440
gagaggcggt ttgcgtattg ggcgctcttc cgcttcctcg ctcactgact cgctgcgctc   4500
ggtcgttcgg ctgcggcgag cggtatcagc tcactcaaag gcggtaatac ggttatccac   4560
agaatcaggg gataacgcag gaaagaacat gtgagcaaaa ggccagcaaa aggccaggaa   4620
ccgtaaaaag gccgcgttgc tggcgttttt ccataggctc cgcccccctg acgagcatca   4680
caaaaatcga cgctcaagtc agaggtggcg aaacccgaca ggactataaa gataccaggc   4740
gtttccccct ggaagctccc tcgtgcgctc tcctgttccg accctgccgc ttaccggata   4800
cctgtccgcc tttctccctt cgggaagcgt ggcgctttct catagctcac gctgtaggta   4860
tctcagttcg gtgtaggtcg ttcgctccaa gctgggctgt gtgcacgaac cccccgttca   4920
gcccgaccgc tgcgccttat ccggtaacta tcgtcttgag tccaacccgg taagacacga   4980
cttatcgcca ctggcagcag ccactggtaa caggattagc agagcgaggt atgtaggcgg   5040
tgctacagag ttcttgaagt ggtggcctaa ctacggctac actagaagga cagtatttgg   5100
tatctgcgct ctgctgaagc cagttacctt cggaaaaaga gttggtagct cttgatccgg   5160
caaacaaacc accgctggta gcggtggttt ttttgtttgc aagcagcaga ttacgcgcag   5220
aaaaaaagga tctcaagaag atcctttgat cttttctacg gggtctgacg ctcagtggaa   5280
cgaaaactca cgttaaggga ttttggtcat gagattatca aaaaggatct tcacctagat   5340
ccttttaaat taaaaatgaa gttttaaatc aatctaaagt atatatgagt aaacttggtc   5400
tgacagttac caatgcttaa tcagtgaggc acctatctca gcgatctgtc tatttcgttc   5460
atccatagtt gcctgactcc ccgtcgtgta gataactacg atacgggagg cttaccatc    5520
tggcccagt gctgcaatga taccgcgaga cccacgctca ccggctccag atttatcagc    5580
aataaaccag ccagccggaa gggccgagcg cagaagtggt cctgcaactt tatccgcctc   5640
catccagtct attaattgtt gccgggaagc tagagtaagt agttcgccag ttaatagttt   5700
gcgcaacgtt gttgccattg ctacaggcat cgtggtgtca cgctcgtcgt ttggtatggc   5760
ttcattcagc tccggttccc aacgatcaag gcgagttaca tgatccccca tgttgtgcaa   5820
aaaagcggtt agctccttcg gtcctccgat cgttgtcaga agtaagttgg ccgcagtgtt   5880
atcactcatg gttatggcag cactgcataa ttctcttact gtcatgccat ccgtaagatg   5940
cttttctgtg actggtgagt actcaaccaa gtcattctga gaatagtgta tgcggcgacc   6000
gagttgctct tgcccggcgt caatacggga taataccgcg ccacatagca gaactttaaa   6060
agtgctcatc attggaaaac gttcttcggg gcgaaaactc tcaaggatct taccgctgtt   6120
gagatccagt tcgatgtaac ccactcgtgc acccaactga tcttcagcat cttttacttt   6180
caccagcgtt tctgggtgag caaaaacagg aaggcaaaat gccgcaaaaa agggaataag   6240
ggcgacacgg aaatgttgaa tactcatact cttcctttc caatattatt gaagcattta   6300
tcagggttat tgtctcatga gcggatacat atttgaatgt atttagaaaa ataaacaaat   6360
aggggttccg cgcacatttc cccgaaaagt gccacctggg tccttttcat cacgtgctat   6420
aaaaataatt ataatttaaa ttttttaata taaatatata aattaaaaat agaaagtaaa   6480
aaaagaaatt aaagaaaaaa tagttttgt tttccgaaga tgtaaaagac tctaggggga    6540
tcgccaacaa atactacctt ttatcttgct cttcctgctc tcaggtatta atgccgaatt   6600
```

```
gtttcatctt gtctgtgtag aagaccacac acgaaaatcc tgtgatttta catttttactt    6660
atcgttaatc gaatgtatat ctatttaatc tgcttttctt gtctaataaa tatatatgta    6720
aagtacgctt tttgttgaaa ttttttaaac ctttgtttat ttttttttct tcattccgta    6780
actcttctac cttctttatt tactttctaa aatccaaata caaacataa aaataaataa     6840
acacagagta aattcccaaa ttattccatc attaaaagat acgaggcgcg tgtaagttac    6900
aggcaagcga tccgtccta                                                 6919
```

```
SEQ ID NO: 96            moltype = AA   length = 89
FEATURE                  Location/Qualifiers
source                   1..89
                         mol_type = protein
                         organism = Saccharomyces cerevisiae
SEQUENCE: 96
MRFPSIFTAV LFAASSALAA PVNTTTEDET AQIPAEAVIG YSDLEGDFDV AVLPFSNSTN    60
NGLLFINTTI ASIAAKEEGV SLEKREAEA                                      89

SEQ ID NO: 97            moltype = AA   length = 61
FEATURE                  Location/Qualifiers
source                   1..61
                         mol_type = protein
                         organism = Saccharomyces cerevisiae
SEQUENCE: 97
MRFPSIFTAV LFAASSALAA PVNTTTEDEL EGDFDVAVLP FSASIAAKEE GVSLEKREAE    60
A                                                                    61

SEQ ID NO: 98            moltype = AA   length = 57
FEATURE                  Location/Qualifiers
source                   1..57
                         mol_type = protein
                         organism = Saccharomyces cerevisiae
SEQUENCE: 98
MRFPSIFTAV LFAASSALAA PVNTTTEDEL EGDFDVAVLP FSASIAAKEE GVSLEKR       57

SEQ ID NO: 99            moltype = AA   length = 19
FEATURE                  Location/Qualifiers
source                   1..19
                         mol_type = protein
                         organism = Saccharomyces cerevisiae
SEQUENCE: 99
MRFPSIFTAV LFAASSALA                                                 19

SEQ ID NO: 100           moltype = AA   length = 20
FEATURE                  Location/Qualifiers
source                   1..20
                         mol_type = protein
                         organism = Aspergillus niger
SEQUENCE: 100
MVAWWSLFLY GLQVAAPALA                                                20

SEQ ID NO: 101           moltype = AA   length = 18
FEATURE                  Location/Qualifiers
source                   1..18
                         mol_type = protein
                         organism = Aspergillus awamorii
SEQUENCE: 101
MSFRSLLALS GLVCSGLA                                                  18

SEQ ID NO: 102           moltype = AA   length = 16
FEATURE                  Location/Qualifiers
source                   1..16
                         mol_type = protein
                         organism = Kluyveromyces marxianus
SEQUENCE: 102
MKLAYSLLLP LAGVSA                                                    16

SEQ ID NO: 103           moltype = AA   length = 19
FEATURE                  Location/Qualifiers
source                   1..19
                         mol_type = protein
                         organism = Saccharomyces cerevisiae
SEQUENCE: 103
MLLQAFLFLL AGFAAKISA                                                 19

SEQ ID NO: 104           moltype = AA   length = 26
FEATURE                  Location/Qualifiers
source                   1..26
                         mol_type = protein
                         organism = Saccharomyces cerevisiae
SEQUENCE: 104
```

```
MTKPTQVLVR SVSILFFITL LHLVVA                                          26

SEQ ID NO: 105          moltype = AA   length = 26
FEATURE                 Location/Qualifiers
source                  1..26
                        mol_type = protein
                        organism = Gallus gallus
SEQUENCE: 105
MLGKNDPMCL VLVLLGLTAL LGICQG                                          26

SEQ ID NO: 106          moltype = AA   length = 18
FEATURE                 Location/Qualifiers
source                  1..18
                        mol_type = protein
                        organism = Homo sapiens
SEQUENCE: 106
MKWVTFISLL FLFSSAYS                                                   18

SEQ ID NO: 107          moltype = AA   length = 566
FEATURE                 Location/Qualifiers
REGION                  1..566
                        note = ABAB binding protein expressed from plasmid
source                  1..566
                        mol_type = protein
                        organism = synthetic construct
SEQUENCE: 107
MRFPSIFTAV LFAASSALAM QVQLVETGGG LVQPGGSLRL SCAASGFTLD YSSIGWFRQA      60
PGKEREGVSC ISSSGDSTKY ADSVKGRFTT SRDNAKNTVY LQMNSLKPDD TAVYYCAAFR     120
ATMCGVFPLS PYGKDDWGKG TLVTVSSGGG GSGGGGSGGG GSQVQLVESG GGLVQPGGSL     180
RLSCEASGFT LDYYGIGWFR QPPGKEREAV SYISASARTI LYADSVKGRF TISRDNAKNA     240
VYLQMNSLKR EDTAVYYCAR RRFSASSVNR WLADDYDVWG RGTQVAVSSG GGSGGGSGGG     300
SGGGSQLQLV ETGGGLVQPG GSLRLSCAAS GFTFSDYVMT WVRQAPGKGP EWIATINTDG     360
STMRDDSTKG RFTISRDNAK NTLYLQMTSL KPEDTALYYC ARGRVISASA IRGAVRGPGT     420
QVTVSSGGGG SGGGGSGGGG SQVQLVESGG GLVQTGGSLR LSCASSGSIA GFETVTWSRQ     480
APGKSLQWVA SMTKTNNEIY SDSVKGRFII SRDNAKNTVY LQMNSLKPED TGVYFCKGPE     540
LRGQGIQVTV SSVDMEQKLI SEEDLE                                         566

SEQ ID NO: 108          moltype = DNA  length = 1701
FEATURE                 Location/Qualifiers
misc_feature            1..1701
                        note = Polynucleotide sequence encoding ABAB binding
                        protein expressed from plasmid
source                  1..1701
                        mol_type = other DNA
                        organism = synthetic construct
SEQUENCE: 108
atgagatttc cttcaatttt tactgctgtt ttattcgcag catcctccgc attagctatg      60
caagtacaat tggttgaaac cggtggtggt ttagttcaac aggtggtag tttgagatta     120
tcttgtgctg catcaggttt tacattggat tattcttcaa taggttggtt cagacaagct     180
cctggtaaag aaagagaagg tgtttcttgc atatccagtt ctggtgactc aactaaatat     240
gctgactccg ttaagggtag attcactact tcaagagata acgctaaaaa tacagtctac     300
ttgcaaatga actcattaaa gccagatgac acagcagtct attactgtgc cgcttttaga     360
gccaccatgt gcggtgtatt cccattgtct ccttacggta agatgactg gggtaaaggt     420
actttagtta ctgtctcatc cggtggtggt ggttccggtg gtggtggtag tggtggtggt     480
ggttctcaag ttcaattagt agaatccggt ggtggttag tccaacctgg tgtagttta     540
agattatcct gcgaagcaag tggttttaca ttagattatt acggtatcgg ttggtttaga     600
caaccacctg gtaaagaaag agaagctgtc tcttatattt ccgctagtgc aagaactata     660
ttgtacgcag attctgtaaa gggtagattc acaatttcaa gagacaatgc caagaacgct     720
gttttatttg caaatgaactc tttgaagaga gaagacaccg cagtttatta ctgtgccaga     780
agaagatttt ctgcttcttc agtcaacaga tggttagcag acgatatga tgtttgggat     840
agaggtacac aagtcgccgt aagttctggt ggtggttccg gtggtggtag tggtggtggt     900
tctggtggtg gttcacaatt gcaattagta gaaactggtg gtggtttggt tcaaccaggt     960
ggttccttga gattaagttg tgctgcatct ggttttactt tctctgatta cgttatgaca    1020
tgggtcagac aagctccagg taaaggtcct gaatggatcg ctacaattaa taccgacggt    1080
tccacaatga gagatgacag taccaagggt agattcacta tttcaagaga taacgctaag    1140
aacacattgt acttacaaat gacctctttg aaaccagaag acaccgcatt atattactgt    1200
gccagaggta gagtcatatc cgccagtgct atcagaggtg cagtaagagg tcctggtact    1260
caagttacag tctcttcagg tggcggcggt agtggcggcg gcggttctgg cggtggtggt    1320
tcacaagtcc aattggtaga atctggtggt ggtttagttc aaactggtga    1380
ttatcctgcg cttccagtgg ttccattgca ggtttcgaaa ctgttacatg gtcaagacaa    1440
gctccaggta atctttgca atgggtcgcc tcaatgacca agactaacaa cgaaatctat    1500
tctgattcag ttaagggtag attcattatt tcaagagata tgctaaaaa caccgtttat    1560
ttgcaaatga actcattgaa gccagaagat actggtgttt acttctgcaa gggtcctgaa    1620
ttaagaggtc aaggtattca agtaacagtt tcttcagtcg acatggaaca gaagttgatt    1680
tccgaagaag acctcgagta a                                              1701

SEQ ID NO: 109          moltype = AA   length = 557
FEATURE                 Location/Qualifiers
REGION                  1..557
```

```
                        note = ABAB binding protein expressed from chromosomal
                          integration
source                  1..557
                        mol_type = protein
                        organism = synthetic construct
SEQUENCE: 109
MRFPSIFTAV LFAASSALAM QVQLVETGGG LVQPGGSLRL SCAASGFTLD YSSIGWFRQA   60
PGKEREGVSC ISSSGDSTKY ADSVKGRFTT SRDNAKNTVY LQMNSLKPDD TAVYYCAAFR  120
ATMCGVFPLS PYGKDDWGKG TLVTVSSGGG GSGGGGSGGG GSQVQLVESG GGLVQPGGSL  180
RLSCEASGFT LDYYGIGWFR QPPGKEREAV SYISASARTI LYADSVKGRF TISRDNAKNA  240
VYLQMNSLKR EDTAVYYCAR RRFSASSVNR WLADDYDVWG RGTQVAVSSG GGSGGGSGGG  300
SGGGSQLQLV ETGGGLVQPG GSLRLSCAAS GFTFSDYVMT WVRQAPGKGP EWIATINTDG  360
STMRDDSTKG RFTISRDNAK NTLYLQMNSL KPEDTALYYC ARGRVISASA IRGAVRGPGT  420
QVTVSSGGGG SGGGGSGGGG SQVQLVESGG GLVQTGGSLR LSCASSGSIA GFETVTWSRQ  480
APGKSLQWVA SMTKTNNEIY SDSVKGRFII SRDNAKNTVY LQMNSLKPED TGVYFCKGPE  540
LRGQGIQVTV SSVDAAS                                                557

SEQ ID NO: 110          moltype = DNA   length = 1674
FEATURE                 Location/Qualifiers
misc_feature            1..1674
                        note = Polynucleotide sequence encoding ABAB binding
                          protein expressed from chromosomal integration
source                  1..1674
                        mol_type = other DNA
                        organism = synthetic construct
SEQUENCE: 110
atgagatttc cttcaatttt tactgctgtt ttattcgcag catcctccgc attagctatg   60
caagtacaat tggttgaaac cggtggtggt ttagttcaac aggtggtag tttgagatta  120
tcttgtgctg catcaggttt tacattggat tattcttcaa taggttggtt cagacaagct  180
cctgctaaag aaagagaagg tgtttcttgc atatccgtt ctggtgactc aactaaatat  240
gctgactccg ttaagggtag attcactact tcaagagata cgctaaaaa tacagtctac  300
ttgcaaatga actcattaaa gccagatgac acagcagtct attactgtgc cgcttttaga  360
gccaccatgt gcggtgtatt cccattgtct ccttacggta agatgactg ggtaaaggt  420
actttagtta ctgtctcatc cggtggtggt ggttccggtg gtggtggtag tggtggtggt  480
ggttctcaag ttcaattagt agaatccggt ggtggtttaa tccaacctgg tggtagttta  540
agattatcct gcgaagcaag tggttttaca ttagattatt acggtatcgg ttggtttaga  600
caaccacctg gtaaagaaag agaagctgtc tcttatattt ccgctagtgc aagaactata  660
ttgtacgcag attctgtaaa gggtagattc acaatttcaa gagacaatgc caagaacgct  720
gtttatttgc aaatgaactc tttgaagaga gaagacacca cagtttatta ctgtgccaga  780
agaagatttt ctgcttcttc agtcaacaga tggttagcag acgattatga tgtttggggt  840
agaggtacac aagtcgccgt aagttctggt ggtggttccg gtggtggtag tggtggtggt  900
tctggtggtg gttcacagct gcagctggtg agaccggggg aggcttagt tcagcctggg  960
gggtccctga gactctcctg tgcagcctct ggattcacct cagtgacta cgtgatgacc 1020
tgggtccgcc aagctccagg aaggggcct gagtggatcg caactattaa tactgatggg 1080
agcacaatgc gcgacgactc cacaaagggc cggttcacca ctccagaga caacgccaag 1140
aacactctgt atctgcaaat gaacagtctg aaacccgagg acactgctct gtattactgt 1200
gcaagaggcc gggtgatctc tgcttccgct atcagagcag cagtcagagg ccctggaacc 1260
caggtcaccg tctcgagcgg tggcggcggt agtggcggcg gcggttctgg cggtggtggt 1320
tcacaagtcc aattggtaga atctggtggt ggtttagttc aaactggtgg ttcattgaga 1380
ttatcctgcg cttccagtgg ttccattgca ggttcgaaa ctgttacatg gtcaagacaa 1440
gctccaggta aatctttgca atgggtcgcc tcaatgacca agactaacaa cgaaatctat 1500
tctgattcag ttaagggtag attcattatt tcaagagata atgctaaaaa caccgtttat 1560
ttgcaaatga actcattgaa gccagaagat actggtgttt acttctgcaa gggtcctgaa 1620
ttaagaggtc aaggtattca agtaacagtt cttcagtcg acgcggctag ctaa        1674

SEQ ID NO: 111          moltype = AA   length = 549
FEATURE                 Location/Qualifiers
REGION                  1..549
                        note = ABA binding agent
source                  1..549
                        mol_type = protein
                        organism = synthetic construct
SEQUENCE: 111
QVQLVETGGL VQPGGSLRLS CAASGFTLDY SSIGWFRQAP GKEREGVSCI SSSGDSTKYA   60
DSVKGRFTTS RDNAKNTVYL QMNSLKPDDT AVYYCAAFRA TMCGVFPLSP YGKDDWGKGT  120
LVTVSSEPKT PKPQPTSGGG GSGGGGSGGG GSQVQLVESG GGLVQTGGSL RLSCASSGSI  180
AGFETVTWSR QAPGKSLQWV ASMTKTNNEI YSDSVKGRFI ISRDNAKNTV YLQMNSLKPE  240
DTGVYFCKGP ELRGQGIQVT VSSEPKTPKP QTSAIAGGGG SGGGGSGGGG SLQAMAAASQ  300
VQLVESGGGL VQTGGSLRLS CASSGSIAGF ETVTWSRQAP GKSLQWVASM TKTNNEIYSD  360
SVKGRFIISR DNAKNTVYLQ MNSLKPEDTG VYFCKGPELR GQGIQVTVSS GGGGSGGGGS  420
GGGGSWAAQL QLVETGGGLV QPGGSLRLSC AASGFTFSDY VMTWVRQAPG KGPEWIATIN  480
TDGSTMRDDS TKGRFTISRD NAKNTLYLQM TSLKPEDTAL YYCARGRVIS ASAIRGAVRG  540
PGTQVTVSS                                                          549

SEQ ID NO: 112          moltype = AA   length = 15
FEATURE                 Location/Qualifiers
REGION                  1..15
                        note = D7 tag
source                  1..15
```

-continued

```
                        mol_type = protein
                        organism = synthetic construct
SEQUENCE: 112
APTKAKRRVV QREKT                                                     15

SEQ ID NO: 113          moltype = AA  length = 553
FEATURE                 Location/Qualifiers
REGION                  1..553
                        note = His-hABAB-D7 binding agent
source                  1..553
                        mol_type = protein
                        organism = synthetic construct
SEQUENCE: 113
HHHHHHQVQL VETGGGLVQP GGSLRLSCAA SGFTLDYSSI GWFRQAPGKE REGVSCISSS     60
GDSTKYADSV KGRFTTSRDN AKNTVYLQMN SLKPDDTAVY YCAAFRATMC GVFPLSPYGK    120
DDWGKGTLVT VSSGGGGSGG GGSGGGGSQV QLVESGGGLV QPGGSLRLSC EASGFTLDYY    180
GIGWFRQPPG KEREAVSYIS ASARTILYAD SVKGRFTISR DNAKNAVYLQ MNSLKREDTA    240
VYYCARRRFS ASSVNRWLAD DYDVWGRGTQ VAVSSGGGSG GGSGGGSGGG SQLQLVETGG    300
GLVQPGGSLR LSCAASGFTF SDYVMTWVRQ APGKGPEWIA TINTDGSTMR DDSTKGRFTI    360
SRDNAKNTLY LQMTSLKPED TALYYCARGR VISASAIRGA VRGPGTQVTV SSGGGGSGGG    420
GSGGGGSQVQ LVESGGGLVQ TGGSLRLSCA SSGSIAGFET VTWSRQAPGK SLQWVASMTK    480
TNNEIYSDSV KGRFIISRDN AKNTVYLQMN SLKPEDTGVY FCKGPELRGQ GIQVTVSSAP    540
TKAKRRVVQR EKT                                                      553

SEQ ID NO: 114          moltype = DNA  length = 1665
FEATURE                 Location/Qualifiers
misc_feature            1..1665
                        note = Polynucleotide sequence encoding His-hABAB-D7
                         binding agent
source                  1..1665
                        mol_type = other DNA
                        organism = synthetic construct
SEQUENCE: 114
catcatcatc atcatcatca ggtacagctg gtggagacgg ggggagggct ggtacaacca     60
ggcgggtcac tgaggctttc ctgtgccgca tctgggttca cactggatta ttcgtccata    120
gggtggtttc ggcaggctcc tggcaaagag cgtgaggggg tctcatgtat tagtagtagt    180
ggtgatagca caaagtacgc cgattccgta aagggccggt ttacaacctc agggataat     240
gctaagaaca ccgtatatct ccagatgaac tctctgaagc ccgacgatac ggccgtatat    300
tactgtgcgg ctttcagggc gactatgtgc ggcgtgttcc ctctgagccc ttacggcaag    360
gacgactggg gcaaggggac cctggtgacc gtatcctcag gcggtggagg gtctggtggg    420
ggaggctcag gggtggagg cagccaggtg caactggttg aatctggggg aggcttggta    480
caacctgggg gatccctgag actctcttgc gaggcctccg gattcacctt ggactactat    540
ggcatcggct ggttccgcca gccccccaggg aaggagcggg aggtttc atacattagt    600
gccagtgccc ggaccatact gtacgcagac tctgtgaagg gacgctttac catctctagg    660
gacaatgcca aaaatgctgt gtacctgcaa atgaacagcc tcaagcggga ggataccgca    720
gtgtactact gcgcgagacg gcgcttctcc gcttctagcg tgaatagatg gctggccgac    780
gactacgaca tgtggggcag gggcacacag gtggctgtgt cttccggtgg cggaagcgga    840
gggggcagcg ggggtgggag cggtgggggc agccaactgc agctggtaga gacagggggc    900
ggcttagttc agcctggagg gtctctcaga ctgtcatgcg ctgcctctgg ctttaccttc    960
agtgactacg tgatgacatg ggtccgccaa gctccaggga aggggcctga gtggatcgct   1020
actattaata cagatggcag cacaatgcgg gacgactcca caaaggggcg gttcaccatt   1080
tccagagaca acgccaagaa tactctgtac cttcagatga ccagtctgaa acccgaggac   1140
actgctctgt actattgtgc aagaggccgg gtgatctctg cttccgctat cagaggcgca   1200
gtaaggggcc ctgaacaca ggtaaccgtt tcatccgggg gaggcggttc aggcggtggg   1260
ggatctggcg ggggtggatc ccaagttcag ctggtcgaat ccgggggcag actggtccag   1320
acaggggcct ccctgaggct ctcctgtgca tcttccggaa gcatcgccgg cttcgagacc   1380
gtgacctggt ctcgccaggc tcccgggaag tctctgcagt gggtcgcttc catgactaag   1440
actaacaacg agatctactc tgactcagtg aaaggccgct tcatcatttc tagagataac   1500
gctaaaaaca cagtgtatct gcagatgaat agtctcaaac tgaagacac aggcgtgtat   1560
ttctgtaagg gtcctgagct gagggggccag ggcatccagg taacagtctc gagtgctcct   1620
acaaaagcca aacggagagt ggtccagaga gagaagacct aataa                  1665

SEQ ID NO: 115          moltype = DNA  length = 7257
FEATURE                 Location/Qualifiers
misc_feature            1..7257
                        note = Plasmid pCEV-G4-Km-TEF-AT-RSyABAB
source                  1..7257
                        mol_type = other DNA
                        organism = synthetic construct
SEQUENCE: 115
cacacaccat agcttcaaaa tgtttctact cctttttta tcttccagat tttctcggac     60
tccgcgcatc gccgtaccac ttcaaaacac ccaagcacag catactaaat ttcccctctt    120
tcttcctcta gggtgtcgtt aattacccgt actaaaggtt tggaaagaa aaaagagacc    180
gcctcgtttc ttttttcttcg tcgaaaaagg caataaat ttttctttt                240
ttgaaaattt tttttttga ttttttctc tttcgatgac ctcccattga tatttaagtt     300
aataaacggt cttcaatttc tcaagtttca gtttcatttt tcttgttcta ttacaacttt    360
ttttacttct tgctcattag aaagaaagca tagcaacta atctaagttt taattacaag    420
gatccatgag atttccttca attttttactg ctgttttatt cgcagcatcc tccgcattag    480
ctatgcaagt acaattggtt gaaaccggtg gtggtttagt tcaaccaggt ggtagtttga    540
```

```
gattatcttg tgctgcatca ggttttacat tggattattc ttcaataggt tggttcagac    600
aagctcctgg taaagaaaga gaaggtgttt cttgcatatc cagttctggt gactcaacta    660
aatatgctga ctccgttaag ggtagattca ctacttcaag agataacgct aaaaatacag    720
tctacttgca aatgaactca ttaaagccag atgacacagc agtctattac tgtgccgctt    780
ttagagccac catgtgcggt gtattcccat tgtctcctta cggtaaagat gactggggta    840
aaggtacttt agttactgtc tcatccggtg gtggtggttc cggtggtggt ggtagtggtg    900
gtggtggttc tcaagttcaa ttagtagaat ccggtggtgg tttagtccaa cctggtggta    960
gtttaagatt atcctgcgaa gcaagtggtt ttacattaga ttattacggt atcggttggt   1020
ttagacaacc acctggtaaa gaaagagaag ctgtctctta tatttccgct agtgcaagaa   1080
ctatattgta cgcagattct gtaaagggta gattcacaat ttcaagagac aatgccaaga   1140
acgctgttta tttgcaaatg aactctttga agagagaaga caccgcagtt tattactgtg   1200
ccagaagaag atttttctgct tcttcagtca acagatggtt agcagacgat tatgatgttt   1260
ggggtagagg tacacaagtc gccgtaagtt ctggtggtgg ttccggtggt ggtagtggtg   1320
gtggttctgg tggtggttca cagctgcagc tggtggagac cgggggaggc ttagttcagc   1380
ctgggggggtc cctgagactc tcctgtgcag cctctggatt caccttcagt gactacgtga   1440
tgacctgggt ccgccaagct ccagggaagg gcctgagtg gatcgcaact attaatactg   1500
atgggagcac aatgcgcgac gactccacaa agggccggtt caccatctcc agagacaacg   1560
ccaagaacac tctgtatctg caaatgaaca gtctgaaacc cgaggacact gctctgtatt   1620
actgtgcaag aggccgggtg atctctgctt ccgctatcag aggcgcagtc agaggccctg   1680
gaacccaggt caccgtctcg agcggtggcg cggtagtgg cggcggcggt tctggcggtg   1740
gtggttcaca agtccaattg gtagaatctg gtggtggttt agttcaaact ggtggttcat   1800
tgagattatc ctgcgcttcc agtgtttcca ttgcaggttt cgaaactgtt acatggtcaa   1860
gacaagctcc aggtaaatct ttgcaatggg tcgcctcaat gaccaagact aacaacgaaa   1920
tctattctga ttcagttaag ggtagattca ttatttcaag agataatgct aaaaacaccg   1980
tttatttgca aatgaactca ttgaagccag aagatactgg tgtttacttc tgcaagggtc   2040
ctgaattaag aggtcaaggt attcaagtaa cagtttcttc atctcgacatg aacagaagt   2100
tgatttccga agaagacctc gagtaagctt ggtaccgcgg ctagctaaga tccgctctaa   2160
ccgaaaagga aggagttaga caacctgaag tctaggtccc tatttatttt tttatagtta   2220
tgttagtatt aagaacgtta tttatatttc aaatttttct ttttttttctg tacagacgcg   2280
tgtacgcatg taacattata ctgaaaacct tgcttgagaa ggttttggga cgctcgaaga   2340
tccagctgca ttaatgaatc ggccaacgcg cggggagagg cggtttgcgt attgggcgct   2400
cttccgcttc ctcgctcact gactcgctgc gctcggtcgt tcggctgcgg cgagcggtat   2460
cagctcactc aaaggcggta atacggttat ccacagaatc aggggataac gcaggaaaga   2520
acatgtgagc aaaaggccag caaaaggcca ggaaccgtaa aaaggccgcg ttgctggcgt   2580
ttttccatag gctccgcccc cctgacgagc atcacaaaaa tcgacgctca agtcagaggt   2640
ggcgaaaccc gacaggacta taaagatacc aggcgtttcc ccctggaagc tccctcgtgc   2700
gctctcctgt tccgaccctg ccgcttaccg gatacctgtc cgcctttctc ccttcgggaa   2760
gcgtggcgct ttctcatagc tcacgctgta ggtatctcag ttcggtgtag tcgttcgct   2820
ccaagctggg ctgtgtgcac gaaccccccg ttcagcccga ccgctgcgcc ttatccggta   2880
actatcgtct tgagtccaac ccggtaagac acgacttatc gccactggca gcagccactg   2940
gtaacaggat tagcagagcg aggtatgtag gcggtgctac agagttcttg aagtggtggc   3000
ctaactacgg ctacactaga aggacagtat ttggtatctg cgctctgctg aagccagtta   3060
ccttcggaaa aagagttggt agctcttgat ccggcaaaca aaccaccgct ggtagcggtg   3120
gtttttttgt ttgcaagcag cagattacgc gcagaaaaaa aggatctcaa gaagatcctt   3180
tgatcttttc tacggggtct gacgctcagt ggaacgaaaa ctcacgttaa gggattttgg   3240
tcatgagatt atcaaaaagg atcttcacct agatcctttt aaattaaaaa tgaagtttta   3300
aatcaatcta aagtatatat gagtaaactt ggtctgacag ttaccaatgc ttaatcagtg   3360
aggcacctat ctcagcgatc tgtctatttc gttcatccat agttgcctga ctccccgtcg   3420
tgtagataac tacgatacgg gagggcttac catctggccc cagtgctgca atgataccgc   3480
gagacccacg ctcaccggct ccagatttat cagcaataaa ccagccagcc ggaagggccg   3540
agcgcagaag tggtcctgca actttatccg cctccatcca gtctattaat tgttgccggg   3600
aagctagagt aagtagttcg ccagttaata gtttgcgcaa cgttgttgcc attgctacag   3660
gcatcgtggt gtcacgctcg tcgtttggta tggcttcatt cagctccggt tcccaacgat   3720
caaggcgagt tacatgatcc cccatgttgt gcaaaaagc ggtagctcc ttcggtcctc   3780
cgatcgttgt cagaagtaag ttggccgcag tgttatcact catggttatg gcagcactgc   3840
ataattctct tactgtcatg ccatccgtaa gatgctttc tgtgactagt gagtactcaa   3900
ccaagtcatt ctgagaatag tgtatgcggc gaccgagttg ctcttgcccg gcgtcaatac   3960
gggataatac cgcgccacat agcagaactt taaaagtgct catcattgga aaacgttctt   4020
cggggcgaaa actctcaagg atcttaccgc tgttgagatc cagttcgatg taacccactc   4080
gtgcacccaa ctgatcttca gcatctttta ctttcaccag cgtttctggg tgagcaaaaa   4140
caggaaggca aaatgccgca aaaaagggaa taaggggac acggaaatgt tgaatactca   4200
tactcttcct ttttcaatat tattgaagca tttatcaggg ttattgtctc atgagcggat   4260
acatatttga atgtatttag aaaaataaac aaataggggg tccgcgcaca tttccccgaa   4320
aagtgccacc tgaacgaagc atctgtgctt catttttgta aacaaaaatg caacgcgaga   4380
gcgctaattt ttcaaacaaa gaatctgagc tgcatttta cagaacagaa atgcaacgcg   4440
aaagcgctat tttaccaacg aagaatctgt gcttcatttt tgtaaaacaa aaatgcaacg   4500
cgagagcgct aattttcaa acaaagaatc tgagctgcat ttttacagaa cagaaatgca   4560
acgcgagagc gctattttac caacaaagaa tctatacttc ttttttgttc tacaaaaatg   4620
catcccgaga gcgctatttt tctaacaaag catcttagat tactttttt ctcctttgtg   4680
cgctctataa tgcagtctct tgataacttt ttgcactgta ggtccgttaa ggttagaaga   4740
aggctacttt ggtgtctatt ttctcttcca taaaaaagc ctgactccac ttcccgcgtt   4800
tactgattac tagcgaagct gcgggtgcat ttttcaaga taaaggcatc cccgattata   4860
ttctataccg atgtggattg cgcatacttt gtgaacagaa agtgatagcg ttgatgattc   4920
ttcattggtc agaaaattat gaacggtttc ttctattttc tctctatata ctacgtatag   4980
gaaatgttta catttttcgta ttgttttcga ttcactctat gaatagtctc tactacaatt   5040
ttttttgtctga aagagtaata ctagagataa acataaaaaa tgtagaggtc gagtttagat   5100
gcaagttcaa ggagcgaaag gtggatgggt aggttatata gggatatagc acagagatat   5160
atagcaaaga gatactttg agcaatgttt gtggaagcgg tattcgcaat atttagtag   5220
ctcgttacag tccggtgcgt ttttggtttt ttgaaagtgc gtcttcagag cgcttttggt   5280
```

```
tttcaaaagc gctctgaagt tcctatactt tctagagaat aggaacttcg gaataggaac    5340
ttcaaagcgt ttccgaaaac gagcgcttcc gaaaatgcaa cgcgagctgc gcacatacag    5400
ctcactgttc acgtcgcacc tatatctgcg tgttgcctgt atatatatat acatgagaag    5460
aacggcatag tgcgtgttta tgcttaaatg cgtacttata tgcgtctatt tatgtaggat    5520
gaaaggtagt ctagtacctc ctgtgatatt atcccattcc atgcggggta tcgtatgctt    5580
ccttcagcac tacccttag ctgttctata tgctgccact cctcaattgg attagtctca    5640
tccttcaatg ctatcatttc ctttgatatt ggatcatggt agacaaccct taatataact    5700
tcgtataatg tatgctatac gaagttatta ggtctagaga tctgtttagc ttgcctcgtc    5760
cccgccgggt caccggcca gcgacatgga ggcccagaat accctcctg acagtcttga    5820
cgtgcgcagc tcaggggcat gatgtgactg tcgcccgtac atttagccca tacatcccca    5880
tgtataatca tttgcatcca tacattttga tggccgcacg gcgcgaagca aaaattacgg    5940
ctcctcgctg cagacctgcg agcagggaaa cgctcccctc acagacgcgt tgaattgtcc    6000
ccacgccgcg cccctgtaga gaaatataaa aggttaggat ttgccactga ggttcttcatta    6060
tcatatactt ccttttaaaa tcttgctagg atacagttct cacatcacat cgaacataa    6120
acaaccatgg gtaaggaaaa gactcacgtt tcgaggccgc gattaaattc caacatggat    6180
gctgatttat atgggtataa atgggctcgc gataatgtcg ggcaatcagg tgcgacaatc    6240
tatcgattgt atgggaagcc cgatgcgcca gagttgtttc tgaaacatgg caaaggtagc    6300
gttgccaatg atgttacaga tgagatggtc agactaaact ggctgacgga atttatgcct    6360
cttccgacca tcaagcattt tatccgtact cctgatgatg catggttact caccactgcg    6420
atccccggca aaacagcatt ccaggtatta gaagaatatc ctgattcagg tgaaaatatt    6480
gttgatgcgc tggcagtgtt cctgcgccgg ttgcattcga ttcctgtttg taattgtcct    6540
tttaacagcg atcgcgtatt tcgtctcgct caggcgcaat cacgaatgaa taacggtttg    6600
gttgatgcga gtgatttga tgacgagcgt aatggctggc ctgttgaaca agtctgaaa    6660
gaaatgcata agcttttgcc attctcaccg gattcagtcg tcactcatgg tgatttctca    6720
cttgataacc ttatttttga cgaggggaaa ttaataggtt gtattgatgt tggacgagtc    6780
ggaatcgcag accgatacca ggatcttgcc atcctatgga actgcctcgg tgagttttct    6840
ccttcattac agaaacggct ttttcaaaaa tatggtattg ataatcctga tatgaataaa    6900
ttgcagtttc atttgatgct cgatgagttt ttctaatcag tactgacaat aaaaagattc    6960
ttgttttcaa gaacttgtca tttgtatagt ttttttatat tgtagttgtt ctattttaat    7020
caaatgttag cgtgatttat attttttttc gcctcgacat catctgccca gatgcgaagt    7080
taagtgcgca gaaagtaata tcatgcgtca atcgtatgtg aatgctggtc gctatactgc    7140
tgtcgattcg atactaacgc cgccatccag tgtcgaaaac gagctctcga gaaccctaa    7200
tataacttcg tataatgtat gctatacgaa gttattaggt gatatcagat ccactag     7257

SEQ ID NO: 116        moltype = DNA   length = 8202
FEATURE               Location/Qualifiers
misc_feature          1..8202
                      note = Plasmid pCEV-G4-Km-TEF-AT-yABAB AA6T83N
source                1..8202
                      mol_type = other DNA
                      organism = synthetic construct
SEQUENCE: 116
ggagcgacct catgctatac ctgagaaagc aacctgacct acaggaaaga gttactcaag     60
aataagaatt ttcgttttaa aacctaagag tcactttaaa atttgtatac acttattttt    120
tttataactt atttaataat aaaaatcata aatcataaga aattcgctta tttagaagtg    180
tcaacaacgt atctaccaac gatttgaccc ttttccatct tttcgtaaat ttctggcaag    240
gtagacaagc cgacaacctt gattggagac ttgaccaaac ctctgcgtga gaattgttaa    300
ttaagagctc agatcttatc gtcgtcatcc ttgtaatcca tcgatactag tttttttgatt    360
aaaattaaaa aaacttttg ttttgtgtt tattctttgt tcttagaaaa gacaagttga    420
gcttgtttgt tcttgatgtt ttattatttt acaaatagctg caaatgaaga atagattcga    480
acattgtgaa gtattggcat atatcgtctc tatttatact tttttttttt cagttcgtagt    540
atattttgta ttttcctcct tttcattctt tcagttgcca ataagttaca ggggatctcg    600
aaagatggtg gggattttc cttgaaagac gacttttgc catctaatt ttccttgttg    660
cctctgaaaa ttatccagca gaagcaaatg taaagatga acctcagaag aacacgcagg    720
ggcccgaaat tgttcctacg agaagtagtg ggtcataaaa agtttattcc ctggaaaaaa    780
aattttgcgt tgcctttctg gagaattttt tcgaattagc gtgctgccac tgcatgcatt    840
tctgagaagt gtgggcattc ttccaccagt tgttcctcct aaaaaaaaaa agatttccta    900
ccccgcacaa attcctgcat accccctcatt tccacgggc cggccgcaca caccatagct    960
tcaaaatgtt tctactcctt tttttactctt ccagattttc tcggactccg cgcatcgcg    1020
taccacttca aaacacccaa gcacagcata ctaaatttcc cctctttctt cctctagggt    1080
gtcgttaatt acccgtacta aaggtttgga aaagaaaaaa gagaccgcct cgtttctttt    1140
tcttcgtcga aaaaggcaat aaaaatttt atcacgttc ttttttcttga aaattttttt    1200
ttttgatttt tttctctttc gatgacctcc cattgatatt taagttaata aacggtcttc    1260
aatttctcaa gtttcagttt cattttttct gttctattac aactttttt acttcttgct    1320
cattagaaag aaagcatagc aatcttaatct aagttttaat tacaaggatc catgagattt    1380
ccttcaattt ttactgctgt tttattcgca gcatcctccg cattagctat gcaagtacaa    1440
ttggttgaaa ccggtggtgg tttagttcaa ccaggtggta gtttgagatt atcttgtgct    1500
gcatcaggtt ttacattgga ttattcttca ataggttggt tcagacaagc tcctggtaaa    1560
gaaagagaag gtgtttcttg catatccagt tctggtgact caactaaata tgctgactcc    1620
gttaagggta gattcactac ttcaagagat aacgctaaaa atacagtcta cttgcaaatg    1680
aactcattaa agccagatga cacagcagtc tattactgtg ccgcttttag agccaccatg    1740
tgcggtgtat tcccattgtc tccttacggt aaagatgact ggggtaaagg tactttagtt    1800
actgtctcat ccggtggtgg tggttccggt ggtggtggta gtggtggtgg tggttctcaa    1860
gttcaattag tagaatccgg tggtggttta gtccaacctg gtggttta aagattatcc    1920
tgcgaagcaa gtggttttac attagattat tacggtatcg gttggtttag acaaccacct    1980
ggtaaagaaa gagaagctgt ctcttatatt tccgctagtg caagaactat attgtacgca    2040
gattctgtaa agggtagatt cacaatttca agagacaatg ccaagaacgc tgtttatttg    2100
caaatgaact ctttgaagag agaagacacc gcagtttatt actgtgccag aagagaagtt    2160
tctgcttctt cagtcaacag atggttagca gacgattatg atgtttgggg tagaggtaca    2220
```

```
caagtcgccg taagttctgg tggtggttcc ggtggtggta gtggtggtgg ttctggtggt   2280
ggttcacaat tgcaattagt agaaactggt ggtggtttgg ttcaaccagg tggttccttg   2340
agattaagtt gtgctgcatc tggttttact ttctctgatt acgttatgac atgggtcaga   2400
caagctccag gtaaaggtcc tgaatggatc gctacaatta ataccgacgg ttccacaatg   2460
agagatgaca gtaccaaggg tagattcact atttcaagag ataacgctaa gaacacattg   2520
tacttacaaa tgaactcttt gaaaccagaa gacaccgcat tatattactg tgccagaggt   2580
agagtcatat ccgccagtgc tatcagaggt gcagtaagag gtcctggtac tcaagttaca   2640
gtctcttcag gtggcggcgg tagtggcggc ggcggttctg gcggtggtgg ttcacaagtc   2700
caattggtag aatctggtgg tggtttagtt caaactggtg gttcattgag attatcctgc   2760
gcttccagtg gttccattgc aggtttcgaa actgttacat ggtcaagaca agctccaggt   2820
aaatctttgc aatgggtcgc ctcaatgacc aagactaaca acgaaatcta ttctgattca   2880
gttaagggta gattcattat ttcaagagat aatgctaaaa acaccgttta tttgcaaatg   2940
aactcattga agccagaaga tactggtgtt tacttctgca agggtcctga attaagaggt   3000
caaggtattc aagtaacagt ttcttcagtc gacatgaagt agaagttgat ttccgaagaa   3060
gacctcgagt aagcttggta ccgcggctag ctaagatccg ctctaaccga aaaggaagga   3120
gttagacaac ctgaagtcta ggtccctatt tatttttta tagttatgtt agtattaaga   3180
acgttatttta tatttcaaat ttttcttttt tttctgtaca gacgcgtgta cgcatgtaac   3240
attatactga aaaccttgct tgagaaggtt ttgggacgct cgaagatcca gctgcattaa   3300
tgaatcggcc aacgcgcggg gagaggcggt ttgcgtattg ggcgctcttc cgcttcctcg   3360
ctcactgact cgctgcgctc ggtcgttcgg ctgcggcgag cggtatcagc tcactcaaag   3420
gcggtaatac ggttatccac agaatcaggg gataacgcag gaaagaacat gtgagcaaaa   3480
ggccagcaaa aggccaggaa ccgtaaaaag gccgcgttgc tggcgttttt ccataggctc   3540
cgcccccctg acgagcatca caaaaatcga cgctcaagtc agaggtggcg aaacccgaca   3600
ggactataaa gataccaggc gtttccccct ggaagctccc tcgtgcgctc tcctgttccg   3660
accctgccgc ttaccggata cctgtccgcc tttctccctt cgggaagcgt ggcgctttct   3720
catagctcac gctgtaggta tctcagttcg gtgtaggtcg ttcgctccaa gctgggctgt   3780
gtgcacgaac cccccgttca gcccgaccgc tgcgccttat ccggtaacta tcgtcttgag   3840
tccaacccgg taagacacga cttatcgcca ctggcagcag ccactggtaa caggattagc   3900
agagcgaggt atgtaggcgg tgctacagag ttcttgaagt ggtggcctaa ctacggctac   3960
actagaagga cagtatttgg tatctgcgct ctgctgaagc cagttacctt cggaaaaaga   4020
gttggtagct cttgatccgg caaacaaacc accgctggta gcggtggttt ttttgtttgc   4080
aagcagcaga ttacgcgcag aaaaaaagga tctcaagaag atcctttgat cttttctacg   4140
gggtctgacg ctcagtggaa cgaaaactca cgttaaggga ttttggtcat gagattatca   4200
aaaaggatct tcacctagat ccttttaaat taaaaatgaa gttttaaatc aatctaaagt   4260
atatatgagt aaacttggtc tgacagttac caatgcttaa tcagtgaggc acctatctca   4320
gcgatctgtc tatttcgttc atccatagtt gcctgactcc ccgtcgtgta gataactacg   4380
atacgggagg gcttaccatc tggccccagt gctgcaatga taccgcgaga cccacgctca   4440
ccggctccag atttatcagc aataaaccag ccagccggaa gggccgagcg cagaagtggt   4500
cctgcaactt tatccgcctc catccagtct attaattgtt gccgggaagc tagagtaagt   4560
agttcgccag ttaatagttt cgcaacgtt gttgccattg ctacaggcat cgtggtgtca   4620
cgctcgtcgt ttggtatggc ttcattcagc tccggttccc aacgatcaag gcgagttaca   4680
tgatccccca tgttgtgcaa aaaagcggtt agctccttcg gtcctccgat cgttgtcaga   4740
agtaagttgg ccgcagtgtt atcactcatg gttatgccag cactgcataa ttctcttact   4800
gtcatgccat ccgtaagatg cttttctgtg actggtgagt actcaaccaa gtcattctga   4860
gaatagtgta tgcggcgacc gagttgctct tgcccggcgt caatacggga taataccgcg   4920
ccacatagca gaactttaaa agtgctcatc attggaaaac gttcttcggg gcgaaaactc   4980
tcaaggatct taccgctgtt gagatccagt tcgatgtaac ccactcgtgc acccaactga   5040
tcttcagcat cttttacttt caccagcgtt tctgggtgag caaaaacagg aaggcaaaat   5100
gccgcaaaaa agggaataag ggcgacacgg aaatgttgaa tactcatact cttcctttt   5160
caatattatt gaagcattta tcagggttat tgtctcatga gcggatacat atttgaatgt   5220
atttagaaaa ataaacaaat aggggttccg cgcacatttc cccgaaaagt gccacctgaa   5280
cgaagcatct gtgcttcatt ttgtagaaca aaaatgcaac gcgagagcgc taatttttca   5340
aacaaagaat ctgagctgca ttttacagaa cagaaatgc aacgcgaaag cgctatttta   5400
ccaacgaaga atctgtgctt cattttgta aaacaaaaat gcaacgcgag agcgctaatt   5460
tttcaaacaa agaatctgag ctgcatttt acagaacaga atgcaacgc gagagcgcta   5520
ttttaccaac aaagaatcta tacttctttt ttgttctaca aaaatgcatc ccgagagcgc   5580
tatttttcta acaagcatc ttagattact tttttttctcc tttgtgcgct ctataatgca   5640
gtctcttgat aacttttgc actgtaggtc cgttaaggtt agaagaaggc tactttggtg   5700
tctattttct cttccataaa aaaagcctga ctccacttcc cgcgtttact gattactgc   5760
gaagctgcgg gtgcattttt tcaagataaa ggcatccccg attatattct ataccgatgt   5820
ggattgcgca tactttgtga acagaaagtg atagcgttga tgattcttca ttggtcagaa   5880
aattatgaac ggtttcttct attttgtctc tatatactac gtataggaaa tgtttacatt   5940
ttcgtattgt tttcgattca ctctatgaat agttcttact acaattttt tgtctaaaga   6000
gtaatactag agataaacat aaaaaatgta gaggtcgagt ttagatgcaa gttcaaggag   6060
cgaaaggtgg atgggtaggt tatataggga tatagcacag agatatatag caaagagata   6120
cttttgagca atgtttgtgg aagcggtatt cgcaatattt tagtagctcg ttacagtccg   6180
gtgcgttttt ggttttttga aagtgcgtct tcagagcgct tttggttttc aaaagcgctc   6240
tgaagttcct atactttcta gagaatagga acttcggaat aggaacttca aagcgtttcc   6300
gaaaacgagc gcttccgaaa atgcaacgcg agctgcgcac atacagctca ctgttcacgt   6360
cgcacctata tctgcgtgtt gcctgtatat atatatacat gagaagaacg gcatagtgcg   6420
tgtttatgct taaatgcgta cttatatgcg tctatttatg taggatgaaa ggtagtctag   6480
tacctcctgt gatattatcc cattccatgc ggggtatcgt atgcttcctt cagcactacc   6540
ctttagctgt tctatatgct gccactcctc aattggatta gtctcatcct tcaatgctat   6600
catttcctt atattggat catgtagac aaccttaat ataacttcgt ataatgtatg   6660
ctatacgaag ttattaggtc tagagatctg tttagcttgc ctcgtccccg ccgggtcacc   6720
cggccagcga catggaggcc cagaatacccc tccttgacag tcttgacgtg cgcagctcag   6780
gggcatgatg tgactgtcgc ccgtacattt agcccataca tccccatgta taatcatttg   6840
catccataca ttttgatggc cgcacggcgc gaagcaaaaa ttacggctcc tcgctgcaga   6900
cctgcgagca gggaaacgct cccctcacag acgcgttgaa ttgtcccac gccgcgcccc   6960
```

-continued

```
tgtagagaaa tataaaaggt taggatttgc cactgaggtt cttctttcat atacttcctt   7020
ttaaaatctt gctaggatac agttctcaca tcacatccga acataaacaa ccatgggtaa   7080
ggaaaagact cacgtttcga ggccgcgatt aaattccaac atggatgctg atttatatgg   7140
gtataaatgg gctcgcgata atgtcgggca atcaggtgcg acaatctatc gattgtatgg   7200
gaagcccgat gcgccagagt tgtttctgaa acatggcaaa ggtagcgttg ccaatgatgt   7260
tacgatgag atggtcagac taaactggct gacggaattt atgcctcttc cgaccatcaa   7320
gcattttatc cgtactcctg atgatgcatg gttactcacc actgcgatcc ccggcaaaac   7380
agcattccag gtattagaag aatatcctga ttcaggtgaa aatattgttg atgcgctggc   7440
agtgttcctg cgccggttgc attcgattcc tgtttgtaat tgtcctttta acagcgatcg   7500
cgtatttcgt ctcgctcagg cgcaatcacg aatgaataac ggtttggttg atgcgagtga   7560
ttttgatgac gagcgtaatg gctggcctgt tgaacaagtc tggaaagaaa tgcataagct   7620
tttgccattc tcaccggatt cagtcgtcac tcatggtgat ttctcacttg ataaccttat   7680
ttttgacgag gggaaattaa taggttgtat tgatgttgga cgagtcggaa tcgcagaccg   7740
ataccaggat cttgccatcc tatggaactg cctcggtgag ttttctcctt cattacagaa   7800
acggcttttt caaaaatatg gtattgataa tcctgatatg aataaattgc agtttcattt   7860
gatgctcgat gagttttttct aatcagtact gacaataaaa agattcttgt tttcaagaac   7920
ttgtcatttg tatagttttt ttatattgta gttgttctat tttaatcaaa tgttagcgtg   7980
atttatattt tttttcgcct cgacatcatc tgcccagatg cgaagttaag tgccagaaa   8040
gtaatatcat gcgtcaatcg tatgtgaatg ctggtcgcta tactgctgtc gattcgatac   8100
taacgccgcc atccagtgtc gaaaacgagc tctcgagaac ccttaatata acttcgtata   8160
atgtatgcta tacgaagtta ttaggtgata tcagatccac ta                     8202

SEQ ID NO: 117         moltype = AA  length = 538
FEATURE                Location/Qualifiers
REGION                 1..538
                       note = AT-yABAB hAA6 T83N binding agent
source                 1..538
                       mol_type = protein
                       organism = synthetic construct
SEQUENCE: 117
MQVQLVETGG GLVQPGGSLR LSCAASGFTL DYSSIGWFRQ APGKEREGVS CISSSGDSTK    60
YADSVKGRFT TSRDNAKNTV YLQMNSLKPD DTAVYYCAAF RATMCGVFPL SPYGKDDWGK   120
GTLVTVSSGG GGSGGGGSGG GGSQVQLVES GGGLVQPGGS LRLSCEASGF TLDYYGIGWF   180
RQPPGKEREA VSYISASART ILYADSVKGR FTISRDNAKN AVYLQMNSLK REDTAVYYCA   240
RRRFSASSVN RWLADDYDVW GRGTQVAVSS GGGSGGGSGG GSGGGSQLQL VETGGGLVQP   300
GGSLRLSCAA SGFTFSDYVM TWVRQAPGKG PEWIATINTD GSTMRDDSTK GRFTISRDNA   360
KNTLYLQMNS LKPEDTALYY CARGRVISAS AIRGAVRGPG TQVTVSSGGG GSGGGGSGGG   420
GSQVQLVESG GGLVQTGGSL RLSCASSGSI AGFETVTWSR QAPGKSLQWV ASMTKTNNEI   480
YSDSVKGRFI ISRDNAKNTV YLQMNSLKPE DTGVYFCKGP ELRGQGIQVT VSSVDAAS    538
```

YEAST-BASED IMMUNOTHERAPY AGAINST *CLOSTRIDIUM DIFFICILE* INFECTION

CROSS-REFERENCE TO RELATED APPLICATIONS

This application is a divisional of U.S. Non-Provisional application Ser. No. 15/768,331, filed on Apr. 13, 2018, which is a national stage of International Patent Application No. PCT/US2016/056875, filed Oct. 13, 2016, which claims priority to U.S. Provisional Application No. 62/240,810, filed Oct. 13, 2015, the contents of each which are hereby incorporated by reference in their entirety.

STATEMENT OF FEDERALLY SPONSORED RESEARCH AND DEVELOPMENT

This invention was made with government support under Grant Numbers DK084509 and AI109776 awarded by the National Institutes of Health. The government has certain rights in the invention.

SEQUENCE LISTING

A sequence listing in electronic ST.26 XML format is filed with this application and incorporated herein by reference. The name of the XML file is "130507-0127_ST26_SL"; the file was created on Jan. 23, 2023; the size of the file is 378 KB.

BACKGROUND

The bacterium *Clostridium difficile* is the most common cause of nosocomial antibiotic-associated diarrhea as well as the etiologic agent of pseudomembranous colitis [1]. It is estimated that over 500,000 cases of *C. difficile*-associated disease (CDI) occur annually in the United States, with the annual mortality rate ranging from about 3-17%, depending on the strains. With the emergence of hypervirulent and antibiotic-resistant strains, the incidence of mortality in CDI patients is increasing rapidly [2].

CDI is mainly caused by the two *C. difficile* exotoxins TcdA and TcdB (as TcdA-TcdB-strains are avirulent) [21, 22]. The two toxins are structurally similar and exhibit a similar mode of action on host cells. Both toxins target host Rho GTPases, leading to their inactivation as well as cytoskeleton disorganization. The relative roles of the two toxins in the pathogenesis of CDI are not well understood, but it is clear that either toxin individually can cause CDI in animals [22,23].

The options for treating CDI patients are limited and the recurrence rate is high (20-35% of patients). Current standard treatment for CDI using antibiotics causes the disruption of microflora and results in a relapse rate approaching 35% [3,13]. While other interventions have been tried (e.g., probiotics, toxin-absorbing polymers, and toxoid vaccines), neither prevention nor treatment strategies have kept up with the increased incidence and severity of this infection. The risk of further episodes of CDI in recurrent patients can be more than 50% [14] and a subset of patients will have multiple recurrences. Recurrent CDI can be caused by the same strain or newly colonizing strains [15-18].

Newer immune-based therapies have been shown to be somewhat effective in clinical trials, including intravenous immunoglobulin (IVIG) against severe CDI [4-8] and human monoclonal antibodies against recurrent CDI [9]. Fidaxomicin, a narrow spectrum macrocyclic antibiotic, showed an effect similar to oral vancomycin on CDI but was significantly better at lowering the relapse rate [10]. Fecal transplantation is effective against refractory and recurrent CDI, but it is difficult to standardize and it is associated with risks [11,12].

CDI is a frustrating condition that is difficult to treat and may affect patients for months or even years, causing tremendous morbidity and mortality [19]. Accordingly, there is a need for new treatments for CDI, and means for preventing both primary and recurrent CDI in subjects at risk of developing CDI.

BRIEF SUMMARY OF INVENTION

Provided herein are antibody-based fusion protein binding agents that selectively bind *C. difficile* virulence factors TcdA and TcdB, and strains of the probiotic yeast *Saccharomyces* genetically engineered to express and secrete these *C. difficile* toxin binding agents. Both the yeast and the binding agents show utility in treating and preventing primary and recurrent CDI in a subject. Orally administered *Saccharomyces* secreting the binding agents in host intestines can relieve ongoing CDI and prevent recurrence.

The present invention is thus directed to *C. difficile* toxin binding agents, strains of *Saccharomyces* including, but not limited to, *Saccharomyces boulardii* engineered to produce the binding agents, methods of making the engineered strains of yeast, and methods of treating and preventing primary and recurrent CDI using the binding agents and the engineered strains of yeast, among other important features.

Binding Agents

The binding agents of the present invention include simple $V_HH$ peptide monomers and linked groups of $V_HH$ peptide monomers (comprising 2, 3, 4, or more monomers), as well as more complex binding agents that comprise $V_HH$ peptide monomers joined to antibody Fc domains, as well as $V_HH$ peptide monomers joined to partial or full IgG antibodies.

In a first embodiment, the present invention is directed to binding agents comprising $V_HH$ peptide monomers and linked groups of $V_HH$ peptide monomers comprising two, three, four, or more monomers, each of which binds TcdA and/or TcdB, preferably with specificity. Thus, the invention encompasses $V_HH$ peptide binding agents comprising at least one $V_HH$ peptide monomer, wherein each $V_HH$ peptide monomer has binding specificity for an epitope of *C. difficile* toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In certain aspects of this embodiment, the binding agents bind to TcdA and/or TcdB with specificity. In certain aspects of this embodiment, the binding agents exhibit TcdA and/or TcdB neutralizing activity.

In a specific aspect of this embodiment, the binding agent comprises four linked $V_HH$ peptide monomers where two of the monomers have binding specificity for epitopes of TcdA and two of the monomers have binding specificity for epitopes of TcdB. The epitopes of TcdA may be the same or different. The epitopes of TcdB may be the same or different.

In a specific aspect of this embodiment, the binding agent comprises the amino acid sequence set forth in SEQ ID NO:19 or a sequence variant thereof having at least 95% sequence identity thereto, and wherein the sequence variant retains TcdA and/or TcdB binding specificity, or the sequence variant retains toxin neutralizing activity, or both. In some instances, variant amino acids of the sequence variant are located in framework regions of the $V_HH$ peptide monomers.

In a second embodiment, the invention is directed to binding agents comprising $V_HH$ peptide monomers joined to IgG antibodies, where the binding agents bind TcdA and/or TcdB. In these IgG-based binding agents, the variable regions of the light and heavy chains of IgG antibodies are replaced by one, two, three, four or more of the $V_HH$ peptide monomers.

In certain aspects of this embodiment, these binding agents comprise two, three, four, or more linked $V_HH$ peptide monomers joined to the amino termini of IgG light and heavy chains in place of the variable regions. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In a first sub-embodiment, the invention is directed to tetra-specific, octameric binding agents comprising an IgG antibody, two sets of linked first and second $V_HH$ peptide monomers, and two sets of linked third and fourth $V_HH$ peptide monomers, wherein the IgG antibody comprises two arms, each arm comprising a heavy chain lacking a variable region and a light chain lacking a variable region, and each chain having an amino terminus, wherein for each arm of the antibody, one set of linked first and second $V_HH$ peptide monomers is joined to the amino terminus of the light chain, and one set of linked third and fourth $V_HH$ peptide monomers is joined to the amino terminus of the heavy chain, and wherein the $V_HH$ peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer).

In this sub-embodiment, the first, second, third and fourth $V_HH$ peptide monomers each has binding specificity for a different epitope.

In certain aspects of this sub-embodiment, two of the $V_HH$ peptide monomers have binding specificity for epitopes of TcdA and two of the $V_HH$ peptide monomers have binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the light (kappa) chain of the binding agent comprises the amino acid sequence set forth in SEQ ID NO:46 (AA6/E3 kappa) or a sequence variant having at least 95% sequence identity thereto, and the heavy chain of the binding agent comprises the amino acid sequence set forth in SEQ ID NO:44 (AH3/5D heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin-neutralizing activity, or both. The variant amino acids of the sequence variants may be located in framework regions of the $V_HH$ peptide monomers.

In a second sub-embodiment, the invention is directed to bi-specific or tetra-specific, tetrameric binding agents comprising an IgG antibody and first, second, third and fourth $V_HH$ peptide monomers, wherein the IgG antibody comprises two arms, each arm comprising a heavy chain lacking a variable region and a light chain lacking a variable region, and each chain having an amino terminus, wherein for a first arm of the antibody, the first $V_HH$ peptide monomer is joined to the amino terminus of the light chain, and the second $V_HH$ peptide monomer is joined to the amino terminus of the heavy chain, wherein for a second arm of the antibody, the third $V_HH$ peptide monomer is joined to the amino terminus of the light chain, and the fourth $V_HH$ peptide monomer is joined to the amino terminus of the heavy chain, and wherein the $V_HH$ peptide monomers have binding specificity for an epitope of *Clostridium difficile* toxin A (TcdA) or toxin B (TcdB). When the binding agent is "tetra-specific", it recognizes four different toxin epitopes; when "bi-specific" it recognizes two different toxin epitopes. The binding agents are "tetrameric" as they bear four $V_HH$ peptide monomers (when bi-specific, the first and third monomer have the same sequence and bind the same epitope, and the second and fourth monomers have the same sequence and bind the same epitope; when tetra-specific, each of the monomers has a different sequence and binds a different epitope).

When the binding agent is bi-specific, the first and second monomers have binding specificity for different epitopes, the first and third monomers have identical amino acid sequences, and the second and fourth monomers have identical amino acid sequences. One of the $V_HH$ peptide monomers may have binding specificity for an epitope of TcdA and one of the $V_HH$ peptide monomers may have binding specificity for an epitope of TcdB.

When the binding agent is tetra-specific, each of the $V_HH$ peptide monomers has binding specificity for a different epitope. Two of the $V_HH$ peptide monomers may have binding specificity for epitopes of TcdA and two of the $V_HH$ peptide monomers may have binding specificity for epitopes of TcdB.

In certain aspects of this sub-embodiment, each of the $V_HH$ peptide monomers has binding specificity for epitopes of TcdA.

In certain aspects of this sub-embodiment, each of the $V_HH$ peptide monomers has binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the light (kappa) chain of the binding agent comprises the amino acid sequence set forth in SEQ ID NO:40 (AA6 kappa) or a sequence variant having at least 95% sequence identity thereto, and the heavy chain of the binding agent comprises the amino acid sequence set forth in SEQ ID NO:36 (AH3 heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin neutralizing activity, or both. The variant amino acids of the sequence variant may be located in framework regions of the $V_HH$ peptide monomers.

In another specific aspect of this sub-embodiment, the light (kappa) chain of the binding agent comprises the amino acid sequence set forth in SEQ ID NO:42 (E3 kappa) or a sequence variant having at least 95% sequence identity thereto, and the heavy chain of the binding agent comprises the amino acid sequence set forth in SEQ ID NO:38 (5D heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin neutralizing activity, or both. The variant amino acids of the sequence variants may be located in framework regions of the $V_HH$ peptide monomers.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

In a third embodiment, the invention is directed to binding agents comprising $V_HH$ peptide monomers joined to antibody Fc domains, where the binding agents bind TcdA and/or TcdB. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

In certain aspects of this embodiment, these binding agents comprise two, three, four, or more linked $V_HH$ peptide monomers joined to the amino termini of the arms of the Fc domains. The $V_HH$ peptide monomers include, but are not limited to, the $V_HH$ peptide monomers 5D (SEQ ID NO:1), E3 (SEQ ID NO:3), AA6 (SEQ ID NO:5) and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In a first sub-embodiment, the invention is directed to tetra-specific, octameric binding agents comprising an antibody Fc domain and two sets of linked first, second, third and fourth $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth $V_HH$ peptide monomers is joined to the amino terminus of the arm, and where the $V_HH$ peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer).

In certain aspects of this sub-embodiment, the first, second, third and fourth $V_HH$ peptide monomers each has binding specificity for a different epitope.

In certain aspects of this sub-embodiment, two of the $V_HH$ peptide monomers have binding specificity for epitopes of TcdA and two of the $V_HH$ peptide monomers have binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the binding agent comprises the amino acid sequence set forth in SEQ ID NO:22 (ABAB-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In a second sub-embodiment, the invention is directed to bi-specific, tetrameric binding agents comprising an antibody Fc domain and two sets of linked first and second $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first and second $V_HH$ peptide monomers is joined to the amino terminus of the arm, and where the $V_HH$ peptide monomers have binding specificity for an epitope of *Clostridium difficile* toxin A (TcdA) or toxin B (TcdB). This binding agent is termed "bi-specific" as it recognizes two different toxin epitopes. It is termed "tetrameric" as it bears four $V_HH$ peptide monomers (two copies of the first monomer, and two copies of the second monomer).

In certain aspects of this sub-embodiment, the first and second $V_HH$ peptide monomers have binding specificity for the same or different epitopes.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the binding agent comprises the amino acid sequence set forth in SEQ ID NO:32 (AH3/5D-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In another specific aspect of this sub-embodiment, the binding agent comprises the amino acid sequence set forth in SEQ ID NO:34 (AA6/E3-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

The invention includes humanized variants of each the binding agents provided in the various embodiments and aspects defined herein. Likewise, the invention includes epitope binding fragments of each the binding agents provided in the various embodiments and aspects defined herein.

Polynucleotides, Expression Vectors, and Host Cells

The invention includes polynucleotides comprising nucleotide sequences encoding each the binding agents provided in the various embodiments and aspects defined herein, as well as complementary strands thereof. The invention also includes expression vectors (e.g., bacterial and yeast) comprising the polynucleotides, and host cells (e.g., bacterial, yeast, mammalian, insect) comprising the expression vectors. The invention further includes methods of producing the binding agents define herein, comprising culturing the host cells under conditions promoting expression of the binding agents encoded by the expression vectors, and recovering the binding agents from the cell cultures.

Engineered Strains of S. boulardii

In a fourth embodiment, the invention is directed to strains of Saccharomyces yeast, such as S. cerevisiae and S. boulardii, engineered to produce one or more of the binding agents defined herein. In preferred aspects, the engineered strains of Saccharomyces yeast secrete the binding agents.

The identity of the Saccharomyces yeast strain is only limited in that it can be engineered to produce, and preferably secrete, one or more of the binding agents of the invention. In preferred aspects of the invention, the strain of Saccharomyces yeast engineered to produce one or more of the binding agents is S. cerevisiae or S. boulardii. The invention thus encompasses an engineered strain of S. cerevisiae that produces one or more of the binding agents defined herein, as well as an engineered strain of S. cerevisiae that secretes one or more of the binding agents defined herein. The invention also encompasses an engineered strain of S. boulardii that produces one or more of the binding agents defined herein, as well as an engineered strain of S. boulardii that secretes one or more of the binding agents defined herein.

In an example of this embodiment, the invention is directed to engineered strains of Saccharomyces yeast that produce a binding agent comprising a $V_HH$ peptide monomer or linked groups of $V_HH$ peptide monomers comprising two, three, four, or more monomers, each of which binds TcdA and/or TcdB, preferably with specificity. Thus, the invention encompasses engineered strains of Saccharomyces yeast that produces $V_HH$ peptide binding agents comprising at least one $V_HH$ peptide monomer, wherein each $V_HH$ peptide monomer has binding specificity for an epitope of C. difficile toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In another example of this embodiment, the invention is directed to engineered strains of Saccharomyces yeast that produce binding agents comprising $V_HH$ peptide monomers joined to IgG antibodies, where the binding agents bind TcdA and/or TcdB, as defined herein. In these IgG-based binding agents, the variable regions of the light and heavy chains of IgG antibodies are replaced by one, two, three, four or more of the $V_HH$ peptide monomers.

In further example of this embodiment, the invention is directed to engineered strains of Saccharomyces yeast that produce binding agents comprising $V_HH$ peptide monomers joined to antibody Fc domains, where the binding agents bind TcdA and/or TcdB, as defined herein. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

In yet another example of this embodiment, the invention is directed to an engineered strain of Saccharomyces yeast that produces a tetra-specific, tetrameric binding agent, wherein the binding agent comprises linked first, second, third and fourth $V_HH$ peptide monomers, and wherein the $V_HH$ peptide monomers independently have binding specificity for an epitope of Clostridium difficile toxin A (TcdA) or toxin B (TcdB). In certain aspects, the first, second, third and fourth $V_HH$ peptide monomers each has binding specificity for a different epitope. In certain aspects, the two of the $V_HH$ peptide monomers have binding specificity for epitopes of TcdA and two of the $V_HH$ peptide monomers have binding specificity for epitopes of TcdB. In certain aspects, the $V_HH$ peptide monomers independently have binding specificity for an epitope in the glucosyltransferase domain, cysteine protease domain, translocation domain or receptor binding domain of TcdA or TcdB.

In a preferred example of this embodiment, the invention is directed to an engineered strain of yeast, wherein the binding agent is ABAB, wherein the first and third monomers have binding specificity for epitopes of TcdA and the first and third monomers are $V_HH$ peptide monomers AH3 (SEQ ID NO:7) and AA6 (SEQ ID NO:5), respectively, and wherein the second and forth monomers have binding specificity for epitopes of TcdB and the second and forth monomers are $V_HH$ peptide monomers 5D (SEQ ID NO:1) and E3 (SEQ ID NO:3), respectively. In certain aspects, the ABAB binding agent comprises the amino acid sequence set forth in SEQ ID NO:19, or a sequence variant having at least 95% sequence identity thereto, wherein the sequence variant retains TcdA and/or TcdB binding specificity, or the sequence variant retains toxin neutralizing activity, or both. In certain aspects, the ABAB binding agent further comprises an N-terminal secretion signal selected from the AT secretion signal (MRFPSIFTAVLFAASSALA (SEQ ID NO:99)) and the IVS secretion signal (MLLQAFLFL-LAGFAAKISA (SEQ ID NO:103)).

In certain aspects, the ABAB binding agent is expressed from a plasmid within the yeast, wherein the ABAB binding agent comprises the amino acid sequence set forth in SEQ ID NO:107, or a sequence variant having at least 95% sequence identity thereto, and wherein the sequence variant retains TcdA and/or TcdB binding specificity, or the sequence variant retains toxin neutralizing activity, or both. The plasmid may be, but is not limited to, pCEV-URA3-TEF-AT-yABAB-cMyc (SEQ ID NO:88).

In certain aspects, the ABAB binding agent coding sequence is integrated into a chromosome of the strain of yeast, wherein the ABAB binding agent comprises the amino acid sequence set forth in SEQ ID NO:109, or a sequence variant having at least 95% sequence identity thereto, and wherein the sequence variant retains TcdA and/or TcdB binding specificity, or the sequence variant retains toxin neutralizing activity, or both.

Aspects of this embodiment include engineered strains of *Saccharomyces* yeast that produce a therapeutic protein having binding specificity for a unique epitope of *Clostridium difficile* toxin A (TcdA) or toxin B (TcdB), or both. Preferably, the engineered strain of *Saccharomyces* yeast is *S. cerevisiae* or *S. boulardii*. A therapeutic protein is any protein that can bring about an improvement or cure in a medical condition in a subject, or that can inhibit or prevent a medical condition from developing in a subject. Suitable therapeutic protein include, but are not limited to, proteins that (a) replace a protein that is deficient or abnormal; (b) augment an existing pathway; (c) provide a novel function or activity; (d) interfere with a molecule or organism; and (e) deliver other compounds or proteins, such as a radionuclide, cytotoxic drug, or effector proteins. Therapeutic proteins also include antibodies and antibody-based drugs, Fc fusion proteins, anticoagulants, blood factors, bone morphogenetic proteins, engineered protein scaffolds, enzymes, growth factors, hormones, interferons, interleukins, and thrombolytics. Therapeutic proteins further include bispecific monoclonal antibodies (mAbs) and multispecific fusion proteins, mAbs conjugated with small molecule drugs, and proteins with optimized pharmacokinetics.

Methods of Making Engineered Strains of *S. boulardii*

The invention is also directed to methods of making strains of *Saccharomyces* yeast engineered to produce one or more of the binding agents defined herein.

The invention thus encompasses a method of preparing a strain of *Saccharomyces* yeast engineered to produce one or more of the binding agents defined herein comprising (a) transforming a strain of *Saccharomyces* yeast with an expression vector encoding the binding agent, and (b) screening the yeast of (a) for production of the binding agent. In a certain aspect, the expression vector is plasmid pCEV-URA3-TEF-AT-yABAB-cMyc (SEQ ID NO:88).

The invention thus encompasses a method of preparing a strain of *Saccharomyces* yeast engineered to produce one or more of the binding agents defined herein comprising (a) chromosomally integrating a polynucleotide sequence encoding the binding agent into the genome of the strain of *Saccharomyces* yeast, and (b) screening the yeast of (a) for production of the binding agent. In certain aspects, the chromosomal integration is performed via:

(a) amplifying a polynucleotide sequence encoding the ABAB binding agent from plasmid pCEV-G4-Km-TEF-AT-yABAB hAA6T83N-tagless (SEQ ID NO:90) using primers containing (i) nucleic acid sequence homologous to a selected yeast chromosomal integration site and (ii) nucleic acid sequence homologous to regions 5' and 3' of ABAB binding agent coding sequence of the plasmid, to produce an integration cassette, (b) transforming yeast with the integration cassette produced in (a) with pCRI-Sb-61 (SEQ ID NO:91) or pCRI-Sb-62 (SEQ ID NO:92) to induce a double stranded break within the corresponding yeast chromosomal delta sites under conditions promoting spontaneous integration of the integration cassette into the site of the double stranded break, (c) screening the transformed yeast of (b) for production of the ABAB binding agent.

In certain aspects of these methods, the strain of *Saccharomyces* yeast engineered to produce the binding agents is an auxotrophic strain of *Saccharomyces* yeast, such as a ura3-strain of yeast. A ura3-strain of yeast can be utilized under ura3 selection.

In certain aspects of these methods, the strain of *Saccharomyces* yeast engineered to produce the binding agents is *S. cerevisiae* or *S. boulardii*.

In certain aspects of these methods, the screening is performed using an immunoassay, such as an ELISA.

Pharmaceutical Formulations

The invention includes pharmaceutical formulations comprising one or more of the binding agents defined herein and a pharmaceutically acceptable carrier or diluent. The invention also includes pharmaceutical formulations comprising one or more of the engineered strains of *Saccharomyces* yeast defined herein and a pharmaceutically acceptable carrier or diluent. In certain aspects, the *Saccharomyces* yeast is *S. cerevisiae* or *S. boulardii*.

Methods of Treating and Preventing

In a sixth embodiment, the invention is directed to methods of treating or preventing a disease symptom induced by *C. difficile* in a subject comprising administering a therapeutically-effective amount of one or more binding agents and/or one or more engineered strains of *Saccharomyces* yeast as defined herein to a subject having *C. difficile* infection or a risk of developing *C. difficile* infection. In preferred aspects, the *Saccharomyces* yeast is *S. cerevisiae* or *S. boulardii*.

In certain aspects of this embodiment, the disease symptom induced by *C. difficile* is diarrhea.

In a seventh embodiment, the invention is directed to methods of neutralizing *C. difficile* toxin TcdA and/or TcdB in a subject infected by *C. difficile* comprising administering a therapeutically-effective amount of one or more binding agents and/or one or more engineered strains of *Saccharomyces* yeast as defined herein to a subject having *C. difficile* infection. In preferred aspects, the *Saccharomyces* yeast is *S. cerevisiae* or *S. boulardii*.

In an eighth embodiment, the invention is directed to methods of treating or preventing *C. difficile* infection in a subject comprising administering a therapeutically-effective amount of one or more of the binding agents and/or one or more engineered strains of *Saccharomyces* yeast as defined herein to a subject having *C. difficile* infection or a risk of developing *C. difficile* infection. In preferred aspects, the *Saccharomyces* yeast is *S. cerevisiae* or *S. boulardii*. In certain aspects of the eighth embodiment, the method further comprises administering a therapeutically-effective amount of an antibiotic to the subject.

In a ninth embodiment, the invention is directed to methods of maintaining normal bowel function in a subject having a *C. difficile* infection comprising administering a therapeutically-effective amount of one or more of the binding agents and/or one or more engineered strains of Saccharomyces yeast as defined herein to a subject having *C. difficile* infection or a risk of developing *C. difficile* infection. In preferred aspects, the *Saccharomyces* yeast is *S. cerevisiae* or *S. boulardii*. In certain aspects of the ninth embodiment, the method further comprises administering a therapeutically-effective amount of an antibiotic to the subject.

In certain aspects of the methods, the binding agent is in a pharmaceutical formulation comprising the binding agent and a pharmaceutically acceptable carrier or diluent.

In certain aspects of the methods, the therapeutically-effective amount of the binding agent is between 10 ug/kg and 100 mg/kg of the agent per body weight of the subject.

In certain aspects of the methods, the agent is administered to the subject orally, parenterally or rectally.

In certain aspects of the methods, the engineered strain of *Saccharomyces* yeast is in a pharmaceutical formulation comprising the engineered strain and a pharmaceutically acceptable carrier or diluent. In preferred aspects, the *Saccharomyces* yeast is *S. cerevisiae* or *S. boulardii*.

In certain aspects of the methods, the therapeutically-effective amount of the engineered strain of *Saccharomyces* yeast is between 10 ug/kg and 100 mg/kg of the engineered strain per body weight of the subject. In preferred aspects, the *Saccharomyces* yeast is *S. cerevisiae* or *S. boulardii*.

In certain aspects of the methods, the engineered strain of *Saccharomyces* yeast is administered to the subject orally, nasally or rectally. In preferred aspects, the *Saccharomyces* yeast is *S. cerevisiae* or *S. boulardii*.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of the invention.

BRIEF DESCRIPTION OF DRAWINGS

FIGS. 3A-3F. Monomeric or dimeric $V_HH$s possess potent neutralizing activity. $V_HH$s block cell rounding induced by TcdA (FIG. 3A) or TcdB (FIG. 3B) at nM concentrations. (FIG. 3C) Diagram of two heterodimers against TcdA or TcdB. His$_{(6)}$ tag on N-terminus facilitates purification; a flexible spacer (FS) separate the two $V_HH$s. (FIG. 3D) Dimer 5D/E3 increases its neutralizing activity at least 10-fold over a simple mix of the two $V_HH$s. Heterodimers fully protected mice from lethal ip challenge with TcdB (FIG. 3E) or TcdA (FIG. 3F).

FIGS. 9A-9B. Sandwich ELISA analysis of simultaneous binding of the tetraspecific antibody IgG-ABAB to both TcdA and TcdB. FIG. 9A shows serially diluted ABAB-IgG added to ELISA plates coated with TcdA (TxA), followed by TcdB (TxB). FIG. 9B shows serially diluted ABAB-IgG added to ELISA plates coated with TcdB (TxB), followed by TcdA (TxA).

(FIG. 13A) A diagram of toxins and antibodies setup in ELISA. (FIG. 13B) O.D. reading of various TcdA concentrations; 125 ng/ml of TcdA was chosen for subsequence ELISA.

(FIG. 14A) Neutralizing effect of secreted ABAB in *S. cerevisiae* culture supernatant. Sc: *S. cerevisiae* (BY4741); Sc-ABAB: *S. cerevisiae* (BY4741)-pD1214-FAKS-ABAB; r-ABAB: recombinant ABAB. ABAB in the supernatant of Sc-ABAB is able to fully protect cells from intoxication. ELISA O.D. readings of supernatants from individual Sc-ABAB clones (FIG. 14B).

(FIG. 15A) ABAB secretion measured by ELISA and normalized against cell density based on O.D. 600 in *S. cerevisiae*. Statistical significance was determined by Kruskal-Walls test followed by Dunn's Multiple comparison test. *p<0.05**p<0.01 (FIG. 15B) ABAB secretion measured by ELISA and normalized against cell density based on O.D. 600 in *S. boulardii*. Statistical significance was determined by Mann Whitney test. ****p<0.0001.

(FIG. 17A) Growth comparison in YPD containing vancomycin (1 mg/ml) versus without. (FIG. 17B) ABAB stability in *S. boulardii* culture supernatant after 2 hours of incubation determined by ELISA. (FIG. 17C) Neutralizing activity of ABAB from the culture supernatant of *S. boulardii* URA3Δ/Δ expressing ABAB. (FIG. 17D) ABAB detection in *S. boulardii* URA3Δ/Δ expressing ABAB culture supernatant by western blot. Enriched: ABAB contains c-Myc tag at the end of C-terminus and was further concentrated using α-c-Myc tag antibodies.

(FIG. 18A) Survival rate, (FIG. 18B) Weight loss, (FIG. 18C) Diarrhea incident, throughout the course of infection were recorded and presented. *significance as determined by Fisher's exact test with two tailed and 95% confidence interval; p value is 0.0108 for FIG. 18A and regular two-way ANOVA (not repeated measures) followed by Dunnett's multiple comparison test was used for FIG. 18B and FIG. 18C, *P≤0.05. "Sb:EP" is *S. boulardii* with the empty plasmid; "Sb: ABAB" is *S. boulardii* expressing ABAB.

(FIG. 19A) Survival rate, (FIG. 19B) Weight loss, (FIG. 19C) Diarrhea incident, throughout the course of infection were recorded and presented. *significance as determined by Fisher's exact test with two tailed and 95% confidence interval; p value is 0.0256 for FIG. 19A; regular two-way ANOVA (not repeated measures) followed by Dunnett's multiple comparison test for FIG. 19B and FIG. 19C. *P≤0.05P≤0.01**P≤0.0001 for FIG. 19B and FIG. 19C. "Sb:EP" is *S. boulardii* with the empty plasmid; "Sb: ABAB" is *S. boulardii* expressing ABAB.

(FIG. 20A) Survival rate, (FIG. 20B) Weight loss, (FIG. 20C) Diarrhea incident, throughout the course of infection were recorded and presented. *significance as determined by Fisher's exact test with two tailed and 95% confidence interval; p value is 0.017 for FIG. 20A; regular two-way ANOVA (not repeated measures) followed by Dunnett's multiple comparison test for FIG. 20B and FIG. 20C. *P≤0.05*P≤0.001**P≤0.0001 for FIG. 20B and FIG. 20C. "Sb:EP" is *S. boulardii* with the empty plasmid; "Sb: ABAB" is *S. boulardii* expressing ABAB.

(FIG. 22A) ABAB secretion measured by ELISA. ITG: ABAB integration cassette. Low: CRISPR plasmid to ITG ratio at 2; High: CRISPR plasmid to ITG ratio at 0.25. (FIG. 22B) ABAB secretion amount comparison. M-/-$^{Cir0}$:pKC, M-/-$^{Cir+}$:ABAB, M-/-$^{Cir0}$:ABAB are plasmid based. Ch$^{Ins}$: single site target chromosomal integration of ABAB cassette through conventional homologous recombination. C$^{RISPR}$1-2: ABAB cassette integration at site I. C$^{RISPR}$3-4: ABAB cassette integration at site II.

(FIG. 23A) Survival rate, (FIG. 23B) Weight loss, (FIG. 23C) Diarrhea incident, throughout the course of infection were recorded and presented. *significance as determined by Fisher's exact test with two tailed and 95% confidence interval; p value is 0.0325 for (FIG. 23A); regular two-way ANOVA (not repeated measures) followed by Dunnett's multiple comparison test for FIG. 23B and FIG. 23C. *P≤0.05**P≤0.01 for FIG. 23B and FIG. 23C.

DETAILED DESCRIPTION OF THE INVENTION

I. Definitions

Figure 1:
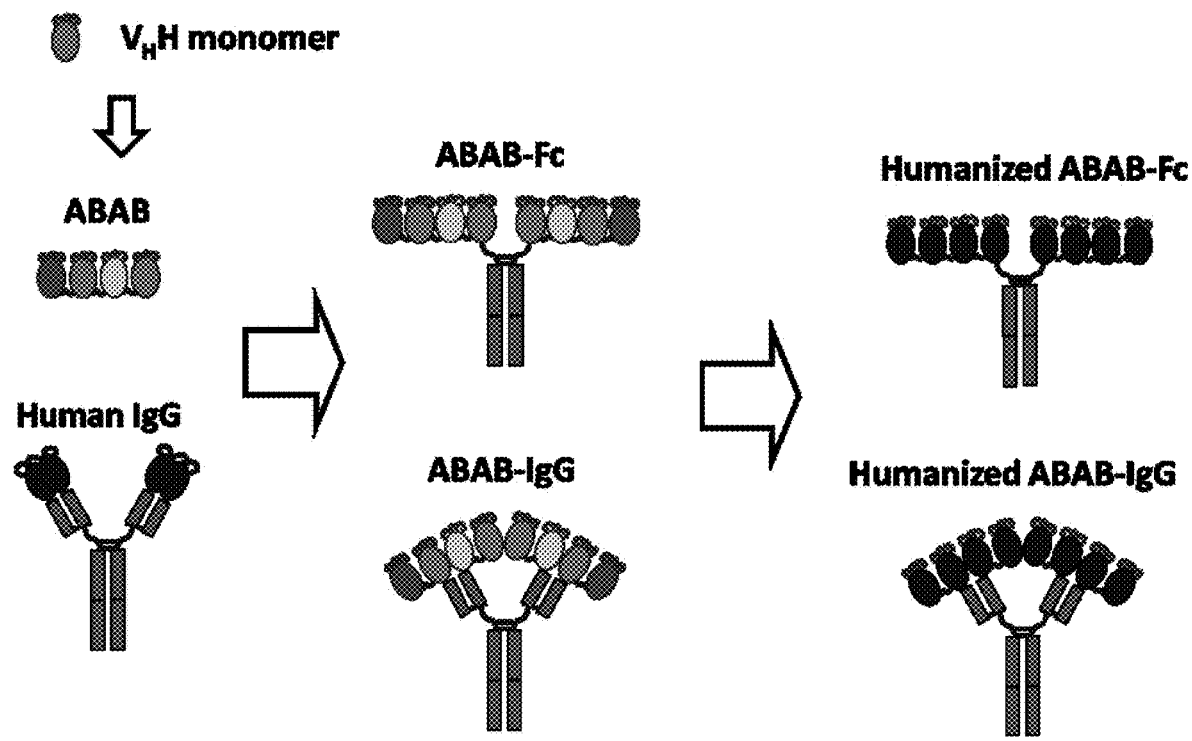
FIG. 1. Illustration of strategies for making binding agents of the invention.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

*C. difficile*-associated disease (CDI) is mainly caused by two large exotoxins, namely toxin A (TcdA) and toxin B (TcdB), produced by the bacteria. These toxins are structurally similar, large, single-chain proteins (TcdA is about 300 kD; TcdB is about 270 kD) that exhibit similar modes of action on host cells. Both toxins target host Rho GTPases, leading to enzyme inactivation, followed by cytoskeleton disorganization and apoptosis. In intestinal epithelial cells, TcdA catalyzes glucosylation of the Rho GTPases, leading to reorganization of the actin cytoskeleton with accompanying morphological changes such as complete rounding of cells and destruction of the intestinal barrier function. The toxins can individually cause CDI in animals, and TcdA⁻ TcdB⁻ strains of the bacteria are avirulent.

Numerous independent studies have demonstrated that neutralizing antibodies against the toxins confer protection against CDI [24-33]. Because TcdA and TcdB are essential virulence factors for *C. difficile*, neutralizing antibodies produced against both toxins protect against toxigenic *C. difficile* infection in animal models [30-33]. In humans, high serum levels of antitoxin antibodies are associated with reduced disease severity and incidence of relapse [9,25,29].

Therefore, a preventative rationale for systemically and orally administered antitoxin antibodies exists. However, monoclonal antibodies targeting a single epitope are typically low affinity, and use of such antibodies runs the risk of inducing mutations within the epitopes of the toxins thereby creating additional strains. Thus, neutralizing antitoxins targeting multiple, key, and conserved toxin epitopes are highly desirable.

The present invention builds on existing knowledge regarding anti-TcdA and anti-TcdB antibodies for the treatment and prevention of CDI, and the symptoms of CDI. Provided herein are antibody-based, fusion protein binding agents derived from human and camelid immunoglobulins, optionally expressed by the probiotic yeast *Saccharomyces* strain in a subject. These binding agents recognize and bind with specificity to *C. difficile* TcdA and/or TcdB. Some of these binding agents exhibit toxin-neutralizing activity. These yeast-based immunotherapeutic can be used to treat or prevent primary and recurrent CDI, as well as the symptoms of primary and recurrent CDI. In preferred aspects, the *Saccharomyces* yeast is *S. cerevisiae* or *S. boulardii*.

As discussed in detail below, camelid animals (dromedary camels, Bactrian camels, wild Bactrian camels, llamas, alpacas, vicunas, and guanacos) produce a class of functional immunoglobulins that lack light chains and are thus heavy chain-only antibodies (HCAbs) [34] with binding properties equivalent to those achieved by conventional IgG [35]. The $V_H$ domain of HCAbs, called $V_HH$, is similar to the conventional human $V_H$ domain but has unique sequence and structural characteristics [36]. DNA encoding this domain can be readily cloned and expressed in microbes to yield soluble protein monomers that retain the antigen-binding properties of the parent HCAb. These $V_HH$ peptide monomer binding agents are small (~15 kDa), easy to produce, and generally more stable than conventional antibody fragments [37-39]. $V_HH$s have being explored to treat intestinal diseases since they are relatively resistant to proteases and can be further engineered to enhance such properties [40]. They can also be produced as fusion proteins with human antibodies, such as IgG, and fragments of human antibodies, such as Fc domains.

The present invention utilizes the advantageous characteristics of HCAbs in the production of binding agents that can be used in the treatment and prevention of CDI. As disclosed herein, $V_HH$ peptide monomers were screened for TcdA and TcdB epitope recognition and binding. Those monomers that exhibited epitope binding and had toxin-neutralizing activity were linked to produce the binding agents of the invention. The binding agents include simple $V_HH$ peptide monomers and linked groups of $V_HH$ peptide monomers (comprising 2, 3, 4, or more monomers), as well as more complex binding agents that comprise $V_HH$ peptide monomers joined to antibody Fc domains, as well as $V_HH$ peptide monomers joined to IgG antibodies (see FIG. 1).

Further, *Saccharomyces boulardii*, a Generally Regarded as Safe (GRAS) organism by the FDA, is commonly available over-the-counter for use in promoting intestinal health and amelioration of gastrointestinal illness due to diarrheal diseases. This yeast strain has been studied in multiple randomized double-blinded placebo-controlled clinical trials for both safety and efficacy against intestinal diseases including CDI [42-46]. *S. boulardii* treatment significantly reduced CDI recurrence [44-46], and those recurrent patients had significantly less *S. boulardii* in stools than non-recurring patients [43]. The immune modulatory effects of *S. boulardii* that provide protection against *C. difficile* toxin-induced inflammation have been described [47-49]. In addition, *S. boulardii* may help in maintaining normal microbiota [50]; a recent clinical trial (NCT01473368) found that *S. boulardii* treatment can prevent some antibiotic-induced microbiome changes and, in parallel, can reduce antibiotic-associated diarrhea.

*S. cerevisiae* (commonly known as "brewer's yeast"), which is genetically related to *S. boulardii*, has been used successfully to express $V_HH$s with high yield [51]. *S. boulardii* is physiologically distinct from *S. cerevisiae*, although genome analysis has revealed that both genomes are remarkably similar at the nucleotide level [52,53]. Therefore, molecular genetic tools previously developed for use in *S. cerevisiae* are now being used with *S. boulardii* [54-56], making this probiotic a candidate for engineering as a therapeutic agent against CDI.

There are several additional metabolic characteristics which make *S. boulardii* ideal for use as an oral therapeutic agent. In contrast to *S. cerevisiae*, *S. boulardii* grows well at 37° C. and it is more resistant to acidic environmental conditions [57], making this strain particularly well suited for better surviving and persisting in the human intestinal tract after oral administration. In addition, an experimental murine oral colonization model with *Saccharomyces* is well characterized [58]; using this model, protection has been reported against oral challenge with enteric pathogens such as *Salmonella Typhimurium* [58,59] and *Enteritidis* [60] in conventional mice orally treated with *S. boulardii*, as well as protection against CDI challenge in pretreated gnotobiotic animals [58,61]. The probiotic *S. boulardii*, genetically engineered to secrete $V_HH$ binding agents capable of neutralizing both TcdA and TcdB of *C. difficile*, could significantly improve the therapeutic capacity of this probiotic to disrupt both ongoing and recurrent CDI.

In view of the exceptional characteristics of *S. boulardii*, strains of *S. boulardii* expressing the binding agents defined herein where produced and tested. As described in the Examples, these yeast-based immunotherapeutics can be used to treat or prevent primary and recurrent CDI, as well as the symptoms of primary and recurrent CDI.

$V_HH$ Monomers & $V_HH$ Heterodimers

Figure 2:
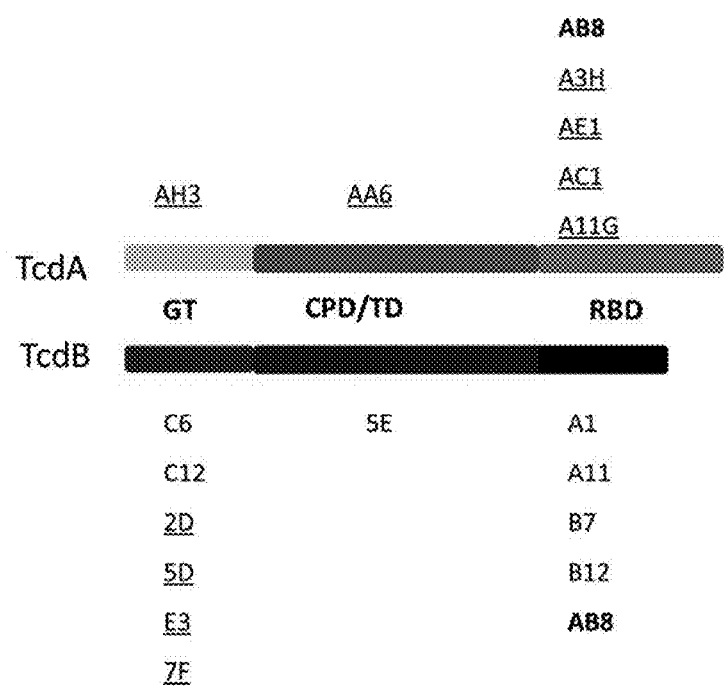
FIG. 2. A diagram of *C. difficile* toxins TcdA and TcdB, showing the glucosyltransferase domains (GT), cysteine protease domains (CPD), translocation domains (TD) and receptor binding domains (RBD) of each toxin. $V_HH$s that recognize and bind the different toxin domains are shown. Those that are underlined are those that have toxin-neutralizing activity.

As initially reported in WO 16/127104, the inventors established an efficient platform to screen $V_HH$ monomers against specific domains of both *C. difficile* toxins. Using highly immunogenic atoxic holotoxins for immunization, and bioactive chimeric toxins (with normal domain functions) for screening, panels of $V_HH$ monomers binding to different domains of TcdA or TcdB were prepared. A majority of these $V_HH$ monomers possessed potent neutralizing activity and their binding to specific domains of TcdA and TcdB was determined (FIG. 2).

Several of the $V_HH$ monomers bind to highly conserved TcdA/TcdB epitopes. For example, the E3 $V_HH$ monomer binds to the Rho GTPase binding site and blocks glucosylation; the AH3 $V_HH$ monomer binds to the GT domain of the toxin; the 7F $V_HH$ monomer binds to cysteine protease cleavage sites and blocks GT domain cleavage and release. Some $V_HH$ monomers have potent toxin neutralizing activity, capable of blocking toxin cytotoxic activity at nM concentrations (monomers underlined in FIG. 2; see also FIGS. 3A and 3B). Table 1 references amino and nucleic acid sequences in the Sequence Listing for some of these $V_HH$ peptide monomers, both wild-type and codon-optimized versions. While both the optimized and non-optimized versions can be used in the production of the various binding agents of the present invention, the codon-optimized versions are preferred for expression in mammalian cells.

The present invention includes each of the $V_HH$ peptide monomers referenced in Table 1 as well as sequence variants thereof having at least 85%, 86%, 87%, 88%, 89%, 90%, 91%, 92%, 93%, 94%, 95%, 96%, 97%, 98%, or 99% sequence identity over the entire length of the peptide sequence and retaining the toxin binding and/or neutralizing activity of the wild-type peptide. The present invention also includes polynucleotide sequences encoding each of the $V_HH$ peptide monomers of Table 1 and the sequence variants thereof, as well as complementary strands thereof.

TABLE 1

| Name | Codon Optimized? | Location of epitope | SEQ ID NO for Amino Acid Seq. | SEQ ID NO for Nucleic Acid Seq. |
| --- | --- | --- | --- | --- |
| 5D | Yes | TcdB glucosyltransferase domain | 1 | 2 |
| E3 | Yes | TcdB glucosyltransferase domain | 3 | 4 |
| AA6 | Yes | TcdA cysteine protease domain | 5 | 6 |
| AH3 | Yes | TcdA glucosyltransferase domain | 7 | 8 |
| 5D | No | TcdB glucosyltransferase domain | 48 | 49 |
| E3 | No | TcdB glucosyltransferase domain | 50 | 51 |
| AA6 | No | TcdA cysteine protease domain | 52 | 53 |
| AH3 | No | TcdA glucosyltransferase domain | 54 | 55 |

To enhance the binding activity of the peptide monomers, $V_HH$ peptide homo- and hetero-dimer binding agents were created, where two $V_HH$ peptide monomers are linked (FIG. 3C). Homodimer binding agents comprise two identical monomers that bind identical epitopes on two different toxins. Heterodimer binding agents comprise two different monomers that bind two distinct epitopes of the same toxin or distinct epitopes on two different toxins. The $V_HH$ heterodimers were found to possess substantially enhanced neutralizing activities compared with equimolar mixtures of the individual $V_HH$ peptide monomers comprising the heterodimers (FIG. 3D). Indeed, heterodimers 5D/E3 and AH3/AA6 were found to fully protect mice from lethal systemic TcdB or TcdA challenge respectively, whereas mixed 5D and E3, or AA6 alone were only partially protective (FIGS. 3E and 3F).

The $V_HH$ monomers in the homo- and hetero-dimers are linked using a short, flexible linker of between 10 and 20 amino acids. Suitable linkers include those provided in Table 2. Table 2 also includes codon-optimized versions of the three linkers. While both the optimized and non-optimized versions can be used in the production of the various binding agents of the present invention, the codon-optimized versions are preferred for expression in mammalian cells.

TABLE 2

| Name | Codon Optimized? | SEQ ID NO for Amino Acid Seq. | SEQ ID NO for Nucleic Acid Seq. |
| --- | --- | --- | --- |
| Linker-1 | Yes | 9 | 10 |
| Linker-2 | Yes | 11 | 12 |
| Linker-3 | Yes | 13 | 14 |
| Linker-1 | No | 56 | 57 |
| Linker-2 | No | 58 | 59 |
| Linker-3 | No | 60 | 61 |

It will be understood by the skilled artisan that minor changes can be made to the sequence of the flexible linker without departing from the properties of the peptide. Sequence variants of the flexible linker having at least 85%, 86%, 87%, 88%, 89%, 90%, 91%, 92%, 93%, 94%, 95%, 96%, 97%, 98%, or 99% sequence identity over the entire length of the peptide sequence and retaining properties of the linker upon which they are based may thus be used.

The present invention includes $V_HH$ peptide homodimer binding agents comprising pairs of any of the monomers listed in Table 1, linked by a flexible linker as defined above. The present invention also includes $V_HH$ peptide heterodimer binding agents comprising any combination of two of the monomers listed in Table 1, linked by a flexible linker as defined above. Exemplary heterodimers are provided in Table 3.

TABLE 3

| Name | SEQ ID NO for Amino Acid Seq. | SEQ ID NO for Nucleic Acid Seq. |
| --- | --- | --- |
| AH3-5D | 15 | 16 |
| AA6-E3 | 17 | 18 |
| 5D-E3 | 62 | 63 |
| AH3-AA6 | 64 | 65 |

The present invention also includes sequence variants of the $V_HH$ peptide homo- and hetero-dimers having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each the $V_HH$ peptide homo-heterodimers and the sequence variants thereof, as well as complementary strands thereof.

The invention also includes $V_HH$ peptide homo- and hetero-trimer binding agents where three monomers are linked using the flexible linkers defined above in Table 2. Any combination of the monomers of Table 1 may be used, including trimers comprising three copies of the same monomer, trimers comprising two copies of one monomer and a single copy of another, and trimers comprising three different monomers. Sequence variants of the $V_HH$ peptide homo- and hetero-trimers are included in the invention, having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each the $V_HH$ peptide homo- and hetero-trimers and the sequence variants thereof, as well as complementary strands thereof.

ABAB

The success of the peptide monomers and heterodimers allowed the inventors to develop binding agents comprising four linked $V_HH$ peptide monomers. This was a goal of the research as earlier work had shown that the most useful agents in the treatment and prevention of CDI would be single antibodies that can simultaneously neutralize both TcdA and TcdB as this would be necessary in order to convey full protection against most pathogenic C. difficile strains. By creating tetra-specific binding agents that recognize and bind two epitopes on each of the toxins, the binding and neutralizing activity of the proteins might be strengthened. Therefore, four domain (tetra-specific) $V_HH$ binding agents were generated.

The tetra-specific, tetrameric binding agents can be prepared from any combination of the monomers of Table 1, where the monomers are linked using the flexible linkers of Table 2. These binding agents include those having four copies of the same monomer, those having three copies of the same monomer, those having two copies of the same monomer, those having four unique monomers, and variations therein. Sequence variants of the tetramers are included in the invention, having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each tetramer and the sequence variants thereof, as well as complementary strands thereof.

ABBA is a particular binding agent of the invention that comprises four linked $V_HH$ monomers, AH3-E3-E3-AA6. ABBA thus has two identical monomers (E3) and two additional different monomers (AH3 and AA6) (See Table 1).

ABAB is another particular binding agent of the invention that comprises four linked $V_HH$ monomers, each of which has binding specificity for a different epitope of TcdA or TcdB. ABAB is thus a tetra-specific, tetrameric binding agent that consists of four distinct neutralizing $V_HH$ monomers, two against TcdA and two against TcdB. This structural feature allows ABAB to bind simultaneously to two distinct neutralizing epitopes on each toxin. As described below, affinity/avidity and neutralizing activity of ABAB is more than 3-logs higher than human monoclonal antibodies (HuMabs) currently undergoing clinical trials for treatment of CDI.

ABAB binding agent was prepared by linking $V_HH$ monomers AH3, 5D, AA6, and E3 (Table 1) using flexible linkers (Table 2). This binding agent targets conserved, non-overlapping epitopes and has excellent toxin neutralizing activity. In the design of ABAB (FIG. 4), $V_HH$ peptide monomers AH3 and AA6 were separated by placing the 5D between them because AH3 and AA6 bind to GT and TD respectively (FIG. 2), which are spatially distant to each other. This design allowed AH3 and AA6 to bind to TcdA simultaneously.

The complete amino acid sequence comprising ABAB is provided in SEQ ID NO:19; the nucleic acid sequence encoding the protein is provided in SEQ ID NO:20. The present invention thus includes the ABAB binding agent provided in SEQ ID NO: 19, as well as sequence variants of the ABAB binding agent having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The sequence variants include variants wherein the variant is humanized and/or wherein the amino acids are optimized for production and secretion by yeast.

The present invention further includes polynucleotide sequences encoding the ABAB binding agent (e.g., SEQ ID NO:20) and the sequence variants thereof, as well as complementary strands thereof.

Modified versions of the ABAB binding agent encompassed by the invention includes those having one or more of (i) a $His_{(6)}$-tag (HHHHHH; SEQ ID NO:66) at the amino terminus of the protein to aid in purification, (ii) an E-tag (GAPVPYPDPLEPR; SEQ ID NO:67) at the carboxy terminus of the protein to aid in detection; (iii) an albumin-binding peptide (ABP) (DICLPRWGCLWD; SEQ ID NO:21) at the carboxyl end of the construct to increase serum half-life of the protein as $V_HH$ monomers have a half-life of 2-3 hr and inclusion of ABP can increase the serum half-life to 10 hr (see FIG. 4); and a D7 tag (SSAPTKAKRRVVQREKT; SEQ ID NO:112) at the carboxy terminus of the protein. The invention includes versions of the ABAB binding agent having one, two, three or four of these tags and peptides. An exemplary modified ABAB binding agent that includes the His tag and the D7 tag comprises the amino acid sequence set forth in SEQ ID NO:113 (the coding sequence is set forth in SEQ ID NO:114).

When yeast strains are engineered to produce ABAB, the protein can be also modified to include a secretion signal at the amino terminus of the protein. The secretion signal may be, but is not limited to, one of the sequences shown in Table 4.

TABLE 4

Secretion sequences for protein secretion in yeast

| Secretion signal | Amino acid sequence | Abbr. |
|---|---|---|
| α-factor_full (S. cerevisiae) | MRFPSIFTAVLFAASSALAAPVNTTTEDETAQIPAEAVIGYSD LEGDFDVAVLPFSNSTNNGLLFINTTIASIAAKEEGVSLEKRE AEA (SEQ ID NO: 96) | FAKS |
| α-factor_T_kex_ste (S. cerevisiae) | MRFPSIFTAVLFAASSALAAPVNTTTEDELEGDFDVAVLPFSA SIAAKEEGVSLEKREAEA (SEQ ID NO: 97) | AKS |
| α-factor_T_kex (S. cerevisiae) | MRFPSIFTAVLFAASSALAAPVNTTTEDELEGDFDVAVLP FSASIAAKEEGVSLEKR (SEQ ID NO: 98) | AK |
| α-factor_T (S. cerevisiae) | MRFPSIFTA VLFAASSALA (SEQ ID NO: 99) | AT |
| Alpha-amylase (Aspergillus niger) | MVAWWSLFLYGLQVAAPALA (SEQ ID NO: 100) | A.A. |
| Glucoamylase (Aspergillus awamori) | MSFRSLLALSGLVCSGLA (SEQ ID NO: 101) | GA |
| Inulinase (Kluyveromyces maxianus) | MKLAYSLLLPLAGVSA (SEQ ID NO: 102) | IN |

TABLE 4-continued

Secretion sequences for protein secretion in yeast

| Secretion signal | Amino acid sequence | Abbr. |
|---|---|---|
| Invertase (*S. cerevisiae*) | MLLQAFLFLLAGFAAKISA (SEQ ID NO: 103) | IVS |
| Killer protein (*S. cerevisiae*) | MTKPTQVLVRSVSILFFITLLHLVVA (SEQ ID NO: 104) | KP |
| Lysozyme (*Gallus gallus*) | MLGKNDPMCLVLVLLGLTALLGICQG (SEQ ID NO: 105) | LZ |
| Serum albumin (*Homo sapiens*) | MKWVTFISLLFLFSSAYS (SEQ ID NO: 106) | SA |

Exemplary modified ABAB binding agents that include an amino-terminal secretion signal include AT-ABAB and IVS-ABAB.

An exemplary modified ABAB binding agent that is expressed from a plasmid in yeast or bacteria includes the ABAB binding agent set forth in SEQ ID NO: 107, which is encoded by the polynucleotide sequence set forth in SEQ ID NO: 108.

An exemplary modified ABAB binding agent that is expressed in yeast after chromosomal integration includes the ABAB binding agent set forth in SEQ ID NO:109, which is encoded by the polynucleotide sequence set forth in SEQ ID NO: 110.

Each of the binding agents of the invention binds to TcdA and/or TcdB with specificity. In certain aspects of the invention, the binding agents exhibit TcdA and/or TcdB neutralizing activity.

For the sake of clarity it can be noted that as used herein, "mono-specific", "bi-specific", "tri-specific", "tetra-specific", etc., mean the particular binding agent binds to 1, 2, 3, 4, etc., different epitopes, respectively. As used herein, "monomeric", "dimeric", "trimeric", "tetrameric", etc., mean that the particular binding agent has 1, 2, 3, 4, etc., separate $V_HH$ peptide monomers that bind to the epitopes, respectively. Thus, a mono-specific, dimeric binding agent would display two $V_HH$ peptide monomers that bind to the same epitope (e.g., a homodimer), and a bi-specific, dimeric binding agent would have two $V_HH$ peptide monomers that bind to two different epitopes (e.g., a heterodimer). A tetra-specific, octameric binding agent has eight $V_HH$ peptide monomers that recognize four different epitopes.

$V_HH$-Fc

It is well known that chimeric Fc-fusion proteins have the potential of increasing the half-life of a protein in vivo. This strategy has been applied in several FDA approved drugs, such as Etanercept. A proof-of principle study has shown that single-chain antibodies can be correctly assembled and expressed by B cells of transgenic mice carrying a mini-Ig construct encoding a dromedary $V_HH$ and the Fc domain of human IgG. Also EG2-Fc, a chimeric anti-EGFR/EGFRvIII $V_HH$, exhibited excellent tumor accumulation in vivo and has pharmacokinetic properties that could improve glioblastoma targeting.

The present invention includes binding agents comprising $V_HH$ peptide monomers joined to antibody Fc domains ($V_HH$-Fc), where the binding agents bind TcdA and/or TcdB. In these Fc domain-based binding agents, one, two, three, four or more of the $V_HH$ peptide monomers are joined to the hinge, $C_H2$ and $C_H3$ regions of the Fc domain of an antibody heavy chain. Thus, the peptide monomers replace the Fab regions of the antibody.

The $V_HH$ peptide monomers may be any of those provided in Table 1 above and include 5D (SEQ ID NO:1), E3 (SEQ ID NO:3), AA6 (SEQ ID NO:5) and AH3 (SEQ ID NO:7) $V_HH$ peptide monomers. Where two or more monomers are linked, the monomers may be linked by flexible peptide linkers, generally comprising between 10 and 20 amino acids. Suitable linkers include those linkers provided in Table 2, such as linker-1 (SEQ ID NO:9), linker-2 (SEQ ID NO:11), and linker-3 (SEQ ID NO:13).

While the $V_HH$-Fc will typically be composed of two identical chains that self-assemble intracellularly after production, the invention also includes $V_HH$-Fc binding agents comprising two different Fc chains. In such circumstances, the sequence of the $V_HH$ monomer(s) alone may differ between the two Fc chains, or the Fc chains themselves may differ in sequence, or both the $V_HH$ monomer(s) and the Fc chains may differ in sequence.

One type of $V_HH$-Fc binding agent is an octameric binding agent comprising an antibody Fc domain and first, second, third and fourth $V_HH$ peptide monomers, where the $V_HH$ peptide monomers have binding specificity for an epitope of TcdA or toxin B TcdB, where the first, second, third and fourth $V_HH$ peptide monomers are linked together and joined to amino termini of both antibody Fc domains, and where the antibody Fc domain comprises the hinge, $C_H2$ and $C_H3$ regions of an antibody heavy chain. Because this binding agent has four $V_HH$ peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes).

A specific example of a tetra-specific $V_HH$-Fc binding agent is the ABAB-Fc binding agent, a tetra-specific, octameric binding agent comprising an antibody Fc domain and two sets of linked first, second, third and fourth $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth $V_HH$ peptide monomers is joined to the amino terminus of the arm, and where the $V_HH$ peptide monomers have binding specificity for an epitope of TcdA or TcdB (see FIG. 1). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer). ABAB-Fc was found to exhibit specific binding and neutralizing activity.

The ABAB-Fc binding agent was prepared by generating an expression vector encoding the $V_H H$ peptide monomers AH3/5D/AA6/E3 (linked in the noted order) joined to a human IgG1 Fc domain. The $V_H H$ peptide monomers were separated by flexible linkers of Table 2. The nucleic acid sequence encoding each chain is provided in SEQ ID NO:23. The amino acid sequence of each chain is provided in SEQ ID NO:22. Upon self-assembly of pairs of the chains after expression, the tetra-specific, octameric binding agent resulted. The invention includes the ABAB-Fc binding agent of SEQ ID NO:22, modified versions of ABAB binding agents as defined above, and sequence variants thereof having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding these sequence variants and complementary strands thereof.

Mono-specific $V_H H$-Fc binding agents (AH3-Fc, 5D-Fc, E3-Fc, AA6-Fc) and bi-specific $V_H H$-Fc binding agents (e.g., AH3/5D-Fc and AA6/E3-Fc) were also made using this Fc-fusion system. With respect to mono-specific binding agents, single $V_H H$ peptide monomers were joined to human IgG1 Fc domains. Upon expression and assembly, pairs of the chains resulted in mono-specific, dimeric binding agents (when the chains were identical) or bi-specific, dimeric binding agents (when the chains were different). With respect to bi-specific binding agents, two linked $V_H H$ peptide monomers ($V_H H$ homo- or hetero-dimers) were joined to human IgG1 Fc domains. Upon expression and assembly, pairs of the chains resulted in bi-specific, tetrameric binding agents (when the chains were identical) or tetra-specific, tetrameric binding agents (when the chains were different). Table 5 provides the sequences for some these binding agents.

TABLE 5

| Name | SEQ ID NO for Amino Acid Seq. | SEQ ID NO for Nucleic Acid Seq. |
| --- | --- | --- |
| 5D-Fc | 24 | 25 |
| E3-Fc | 26 | 27 |
| AA6-Fc | 28 | 29 |
| AH3-Fc | 30 | 31 |
| AH3-5D-Fc | 32 | 33 |
| AA6-E3-Fc | 34 | 35 |

Specific pairings with one monomer include: 5D-Fc+5D-Fc; E3-Fc+E3-Fc; AA6-Fc+AA6-Fc; AH3-Fc+AH3-Fc; 5D-Fc+E3-Fc; 5D-Fc+AA6-Fc; 5D-Fc+AH3-Fc; E3-Fc+AA6-Fc; E3-Fc+AH3-Fc; and AA6-Fc+AH3-Fc. Specific pairings with two monomers include: AH3-5D-Fc+AH3-5D-Fc; AA6-E3-Fc+AA6-E3-Fc; and AH3-5D-Fc+AA6-E3-Fc.

Bi-specific, tetrameric $V_H H$-Fc binding agents were produced comprising an antibody Fc domain and two sets of linked first and second $V_H H$ peptide monomers, wherein the antibody Fc domain comprises two arms, each arm comprising hinge, $C_H 2$ and $C_H 3$ regions of an antibody heavy chain, and each arm having an amino terminus, wherein for each arm of the Fc domain, one set of linked first and second $V_H H$ peptide monomers is joined to the amino terminus of the arm, and where the $V_H H$ peptide monomers have binding specificity for an epitope of TcdA or TcdB. This binding agent is termed "bi-specific" as it recognizes two different toxin epitopes. It is termed "tetrameric" as it bears four $V_H H$ peptide monomers (two copies of the first monomer, and two copies of the second monomer). The first and second $V_H H$ peptide monomers may have binding specificity for the same or different epitopes. The $V_H H$ peptide monomers may independently have binding specificity for an epitope in the glucosyltransferase domain, cysteine protease domain, translocation domain or receptor binding domain of TcdA or TcdB.

A specific example of a bi-specific, tetrameric $V_H H$-Fc binding agent comprises the amino acid sequence set forth in SEQ ID NO:32 (AH3/5D-Fc). The invention also includes sequence variants thereof having at least 95% sequence identity, where the sequence variant retains toxin-neutralizing activity. The variant amino acids of the sequence variant may be located in framework regions of the $V_H H$ peptide monomers.

A specific example of a bi-specific, tetrameric $V_H H$-Fc binding agent comprises the amino acid sequence set forth in SEQ ID NO:34 (AA6/E3-Fc). The invention also includes sequence variants thereof having at least 95% sequence identity, where the sequence variant retains toxin-neutralizing activity. The variant amino acids of the sequence variant may be located in framework regions of the $V_H H$ peptide monomers.

The $V_H H$-Fc binding agents bind to TcdA and/or TcdB with specificity. In certain aspects of the invention, the binding agents exhibit TcdA and/or TcdB neutralizing activity.

$V_H H$-IgG

The present invention also includes binding agents comprising $V_H H$ peptide monomers joined to more of an antibody that the Fc domain alone. $V_H H$-IgG binding agents comprise one, two, three, four or more of the $V_H H$ peptide monomers are joined to the light (kappa or lambda) and heavy chains of an IgG antibody lacking the variable regions of the antibody. Thus, the peptide monomers replace the variable regions of the antibody.

The $V_H H$ peptide monomers may be any of those provided in Table 1 above and include 5D (SEQ ID NO:1), E3 (SEQ ID NO:3), AA6 (SEQ ID NO:5) and AH3 (SEQ ID NO:7) $V_H H$ peptide monomers. Where two or more monomers are linked, the monomers may be linked by flexible peptide linkers, generally comprising between 10 and 20 amino acids. Suitable linkers include those linkers provided in Table 2, such as linker-1 (SEQ ID NO:9), linker-2 (SEQ ID NO:11), and linker-3 (SEQ ID NO:13).

$V_H H$-IgG binding agents include octameric binding agents comprising an IgG antibody and first, second, third and fourth $V_H H$ peptide monomers, wherein the $V_H H$ peptide monomers have binding specificity for an epitope of TcdA or TcdB, wherein first and second $V_H H$ peptide monomers are linked together and joined to amino termini of both light chains of the antibody, wherein the light chains lack the antibody variable regions, and wherein third and fourth $V_H H$ peptide monomers are linked together and joined to amino termini of both heavy chains of the antibody, wherein the heavy chains lack the antibody variable regions. Because this binding agent has four $V_H H$ peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes).

A specific example of a tetra-specific $V_HH$-IgG binding agent is the ABAB-IgG binding agent, a tetra-specific, octameric binding agent comprising an IgG antibody, two sets of linked first and second $V_HH$ peptide monomers, and two sets of linked third and fourth $V_HH$ peptide monomers, wherein the IgG antibody comprises two arms, each arm comprising a heavy chain lacking a variable region and a light chain lacking a variable region, and each chain having an amino terminus, wherein for each arm of the antibody, one set of linked first and second $V_HH$ peptide monomers is joined to the amino terminus of the light chain, and one set of linked third and fourth $V_HH$ peptide monomers is joined to the amino terminus of the heavy chain, and wherein the $V_HH$ peptide monomers have binding specificity for an epitope of TcdA or TcdB (see FIG. 1). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer). In certain aspects, the first, second, third and fourth $V_HH$ peptide monomers may each have binding specificity for a different epitope. In certain aspects, two of the $V_HH$ peptide monomers may have binding specificity for epitopes of TcdA and two of the $V_HH$ peptide monomers may have binding specificity for epitopes of TcdB. In certain aspects, the $V_HH$ peptide monomers independently have binding specificity for an epitope in the glucosyltransferase domain, cysteine protease domain, translocation domain or receptor binding domain of TcdA or TcdB.

A specific example of a tetra-specific, octameric ABAB-IgG binding agent comprises a light (kappa) chain having the amino acid sequence set forth in SEQ ID NO:46 (AA6/E3 kappa) or a sequence variant having at least 95% sequence identity thereto, and a heavy chain having the amino acid sequence set forth in SEQ ID NO:44 (AH3/5D heavy) or a sequence variant having at least 95% sequence identity thereto. In this aspect, the sequence variants retain toxin-neutralizing activity. The variant amino acids of the sequence variant may be located in framework regions of the $V_HH$ peptide monomers. This binding agent was produced by preparing two separate expression vectors, the first encoding the $V_HH$ peptide monomers AH3/5D (linked in the noted order) joined to the human IgG1 antibody heavy chain lacking the variable region and the second encoding the $V_HH$ peptide monomers AA6/E3 (linked in the noted order) joined to the human IgG1 antibody light (kappa) chain lacking the variable region. The nucleotide sequence encoding the AA6/E3-IgG1 light (kappa) chain is provided in SEQ ID NO:47. The nucleotide sequence encoding the AH3/5D-IgG1 heavy chain is provided in SEQ ID NO:45. The invention includes sequence variants of ABAB-IgG having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding these sequence variants and complementary strands thereof.

Bi-specific or tetra-specific, tetrameric IgG binding agents are included in the invention. Such binding agents comprise an IgG antibody and first, second, third and fourth $V_HH$ peptide monomers, wherein the IgG antibody comprises two arms, each arm comprising a heavy chain lacking a variable region and a light chain lacking a variable region, and each chain having an amino terminus, wherein for a first arm of the antibody, the first $V_HH$ peptide monomer is joined to the amino terminus of the light chain, and the second $V_HH$ peptide monomer is joined to the amino terminus of the heavy chain, wherein for a second arm of the antibody, the third $V_HH$ peptide monomer is joined to the amino terminus of the light chain, and the fourth $V_HH$ peptide monomer is joined to the amino terminus of the heavy chain, and where the $V_HH$ peptide monomers have binding specificity for an epitope of TcdA or TcdB. When the binding agent is "tetra-specific", it recognizes four different toxin epitopes; when "bi-specific" it recognizes two different toxin epitopes. The binding agents "tetrameric" as they bear four $V_HH$ peptide monomers (when bi-specific, the first and second monomer have the same sequence and bind the same epitope, and the third and fourth monomers have the same sequence and bind the same epitope; when tetra-specific, each of the monomers has a different sequence and binds a different epitope).

When the binding agent is bi-specific, the first and third monomers have binding specificity for different epitopes, the first and second monomers have identical amino acid sequences, and the third and fourth monomers have identical amino acid sequences. In certain aspects, one of the $V_HH$ peptide monomers has binding specificity for an epitope of TcdA and one of the $V_HH$ peptide monomers has binding specificity for an epitope of TcdB.

When the binding agent is tetra-specific, each of the $V_HH$ peptide monomers has binding specificity for a different epitope. In certain aspects, two of the $V_HH$ peptide monomers have binding specificity for epitopes of TcdA and two of the $V_HH$ peptide monomers have binding specificity for epitopes of TcdB.

In certain aspects, each of the $V_HH$ peptide monomers has binding specificity for epitopes of TcdA. In other aspects, each of the $V_HH$ peptide monomers has binding specificity for epitopes of TcdB.

In certain aspects, the $V_HH$ peptide monomers independently have binding specificity for an epitope in the glucosyltransferase domain, cysteine protease domain, translocation domain or receptor binding domain of TcdA or TcdB.

A specific example of a bi-specific, tetrameric IgG binding agent comprises a light (kappa) chain having the amino acid sequence set forth in SEQ ID NO:40 (AA6 kappa) and a heavy chain having the amino acid sequence set forth in SEQ ID NO:36 (AH3 heavy). The invention also includes sequence variants thereof having at least 95% sequence identity, where the sequence variant retains toxin neutralizing activity. The variant amino acids of the sequence variant may be located in framework regions of the $V_HH$ peptide monomers.

Another specific example of a bi-specific, tetrameric IgG binding agent comprises a light (kappa) chain having the amino acid sequence set forth in SEQ ID NO:42 (E3 kappa) and a heavy chain having the amino acid sequence set forth in SEQ ID NO:38 (5D heavy). The invention also includes sequence variants thereof having at least 95% sequence identity, where the sequence variant retains toxin neutralizing activity. The variant amino acids of the sequence variant may be located in framework regions of the $V_HH$ peptide monomers.

Table 6 provides the sequences used to generate bi- and tetra-specific $V_HH$-IgG binding agents. Other suitable pairings include (i) 5D-IgG1-heavy chain+AA6-light (kappa or lambda) chain, and (ii) AH3-IgG1-heavy chain+E3-light (kappa or lambda) chain.

TABLE 6

| Name | SEQ ID NO for Amino Acid Seq. | SEQ ID NO for Nucleic Acid Seq. |
| --- | --- | --- |
| AH3-IgG1 heavy chain | 36 | 37 |
| 5D-IgG1 heavy chain | 38 | 39 |
| AA6-IgG1 light (kappa) chain | 40 | 41 |
| E3-IgG1 light (kappa) chain | 42 | 43 |
| AH3/5D-IgG1 heavy chain | 44 | 45 |
| AA6/E3-IgG light (kappa) chain | 46 | 47 |

However, the present invention includes IgG1 heavy chains joined to any of AH3, 5D, AA6 and E3, and IgG1 light (kappa or lambda) chains joined to any of AH3, 5D, AA6 and E3. Further, all possible combinations of the heavy and light (kappa or lambda) chains are encompassed herein.

Humanized Binding Agents

Due to their small size and the high degree of identity of their framework to the human $V_H$ framework of family III, $V_H H$ peptide monomers are expected to exhibit low immunogenicity when administered to humans. While the systemic application of small monovalent $V_H H$ monomers seems to induce little, if any, neutralizing antibody responses, protein immunogenicity generally increases with size and complexity. Two major hurdles for repeated and/or long-term in vivo use of $V_H H$ monomers are their likely short half-life and potential immunogenicity. To increase the valence and circulating half-life, $V_H H$ monomers can be fused with human IgG and Fc domains as discussed herein. To address possible immunogenicity, the $V_H H$ monomers can be humanized as needed without compromising their expression level, affinity, solubility, and stability. These strategies should result in good expression, stability, and solubility of humanized $V_H H$ monomers (h$V_H H$ monomers), while retaining the antigen specificity and affinity of the loop donor $V_H H$.

h$V_H H$ monomers that gain highest identity to human $V_H$ gene(s) and possess the highest binding/neutralizing activity are selected, after which they are transferred into the $V_H H$-multimers (e.g., ABAB), $V_H H$-Fc and $V_H H$-IgG constructs to generate fully humanized binding agents, such as fully humanized ABAB, ABAB-IgG and ABAB-Fc binding agents. The protein sequences of these humanized binding agents can be essentially identical to that of a human antibody variant, despite the non-human origin of some of its CDR segments that are responsible for the ability of the antibody to bind to its target antigen. Therefore, this strategy decreases the chance for potential immunogenicity in vivo and thus increase their safety and half-life in vivo.

The binding agents of the present invention thus encompasses humanized versions of each of the binding agents defined herein, comprising h$V_H H$ peptide monomers.

Epitope Binding Fragments

The binding agents of the invention include epitope binding fragments of each of the $V_H H$-Fc and $V_H H$-IgG binding agents defined herein. Because the $V_H H$-Fc and $V_H H$-IgG binding agents are comparable in structure to human IgG antibodies, where the variable regions are replace by the $V_H H$ monomers, terms for human antibody fragments are also applicable to the such binding agents. The fragments include, but are not limited to, Fab fragments, F(ab')$_2$ fragments, single chain Fv (scFv) antibodies, and fragments produced by an Fab expression library, as well as bi-specific antibody and triple-specific antibodies.

The $V_H H$-Fc and $V_H H$-IgG binding agents of the invention include fully human, humanized, and chimeric binding agents. The binding agents may be monoclonal or polyclonal. Further, the binding agents may be recombinant binding agents.

The binding agents may be produced in any species of animal, though preferably from a mammal such as a human, simian, mouse, rat, rabbit, guinea pig, horse, cow, sheep, goat, pig, dog or cat. For example, the binding agents can be human or humanized, or any binding agent preparation suitable for administration to a human.

Polynucleotide, Expression Vectors, Host Cells and Method of Making

The invention includes polynucleotides comprising nucleotide sequences encoding each the binding agents provided herein, as well as complementary strands thereof.

The invention also includes expression vectors comprising the polynucleotides, and host cells comprising the expression vectors. Suitable expression vectors include, e.g., pcDNA3.1 and pSec-His, as well as plasmids used to transform yeast cells into producers and secretors of the binding agents of the invention. Suitable host cells include, e.g., Chinese hamster ovary cells (CHO cells), human embryonic kidney cells 293 (HEK 293 cells), yeast cells, and insect cells.

The invention further includes methods of producing the binding agents defined herein, comprising culturing the host cells under conditions promoting expression of the binding agents encoded by the expression vectors, and recovering the binding agents from the cell cultures.

Engineered Strains of Yeast

Each of the binding agents of the invention may also be produced by engineered strains of *Saccharomyces* yeast. Accordingly, the invention is also directed to strains of *Saccharomyces* yeast, such as *S. cerevisiae* and *S. boulardii*, engineered to produce one or more of the binding agents defined herein including, but not limited to, $V_H H$ monomer binding agents (see Table 1), $V_H H$ homodimer binding agents, $V_H H$ heterodimer binding agents (see Table 3), ABAB binding agents, $V_H H$-Fc binding agents (see Table 5), $V_H H$-IgG binding agents (see Table 6), and epitope biding fragments thereof. In preferred aspects, the engineered strains of *Saccharomyces* yeast secrete the binding agents.

The identity of the *Saccharomyces* yeast strain is only limited in that it can be engineered to produce, and preferably secrete, one or more of the binding agents of the invention. In preferred aspects of the invention, the strain of *Saccharomyces* yeast engineered to produce one or more of the binding agents is *S. cerevisiae* or *S. boulardii*. The invention thus encompasses an engineered strain of *S. cerevisiae* that produces one or more of the binding agents defined herein, as well as an engineered strain of *S. cerevisiae* that secretes one or more of the binding agents defined herein. The invention also encompasses an engineered strain of *S. boulardii* that produces one or more of the binding agents defined herein, as well as an engineered strain of *S. boulardii* that secretes one or more of the binding agents defined herein. Suitable stains of yeast also include *Schizosaccharomyces pombe, Saccharomyces paradoxus*, and *Saccharomyces unisporus*.

*S. boulardii* is an FDA-designated Generally Regarded as Safe (GRAS) organism and it is commonly available over-the-counter for use in promoting intestinal health and amelioration of gastrointestinal illness due to diarrheal diseases. This species of yeast has been studied in multiple randomized double-blinded placebo-controlled clinical trials for both safety and efficacy against intestinal diseases including CDI [42-46]. A suitable strain of *S. boulardii* is the *S. boulardii* strain MYA796 (ATCC, Manassas, VA).

A particular example of the engineered strains of *Saccharomyces* yeast of the invention is an engineered strain of *Saccharomyces* yeast that produces a binding agent comprising a $V_HH$ peptide monomer or linked groups of $V_HH$ peptide monomers comprising two, three, four, or more monomers, each of which binds TcdA and/or TcdB, preferably with specificity. Thus, the invention encompasses engineered strains of *Saccharomyces* yeast that produces $V_HH$ peptide binding agents comprising at least one $V_HH$ peptide monomer, wherein each $V_HH$ peptide monomer has binding specificity for an epitope of *C. difficile* toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

Another particular example of the engineered strains of *Saccharomyces* yeast of the invention is an engineered strain of *Saccharomyces* yeast that produces binding agents comprising $V_HH$ peptide monomers joined to IgG antibodies, where the binding agents bind TcdA and/or TcdB, as defined herein. In these IgG-based binding agents, the variable regions of the light and heavy chains of IgG antibodies are replaced by one, two, three, four or more of the $V_HH$ peptide monomers.

A further particular example of the engineered strains of *Saccharomyces* yeast of the invention is an engineered strain of *Saccharomyces* yeast that produces binding agents comprising $V_HH$ peptide monomers joined to antibody Fc domains, where the binding agents bind TcdA and/or TcdB, as defined herein. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

An additional particular example of the engineered strains of *Saccharomyces* yeast of the invention is an engineered strain of *Saccharomyces* yeast that produces a tetra-specific, tetrameric binding agent, wherein the binding agent comprises linked first, second, third and fourth $V_HH$ peptide monomers, and wherein the $V_HH$ peptide monomers independently have binding specificity for an epitope of *Clostridium difficile* toxin A (TcdA) or toxin B (TcdB). In certain aspects, the first, second, third and fourth $V_HH$ peptide monomers each has binding specificity for a different epitope. In certain aspects, the two of the $V_HH$ peptide monomers have binding specificity for epitopes of TcdA and two of the $V_HH$ peptide monomers have binding specificity for epitopes of TcdB. In certain aspects, the $V_HH$ peptide monomers independently have binding specificity for an epitope in the glucosyltransferase domain, cysteine protease domain, translocation domain or receptor binding domain of TcdA or TcdB. Suitable $V_HH$ peptide monomers include the AH3 monomer (SEQ ID NO:7), the AA6 monomer (SEQ ID NO:5), the 5D monomer (SEQ ID NO:1), and the E3 monomer (SEQ ID NO:3). Other monomers include, but are not limited to, those provided in Table 1.

In a preferred example, the invention is directed to an engineered strain of yeast, wherein the binding agent is ABAB, wherein the first and third monomers have binding specificity for epitopes of TcdA and the first and third monomers are $V_HH$ peptide monomers AH3 (SEQ ID NO:7) and AA6 (SEQ ID NO:5), respectively, and wherein the second and forth monomers have binding specificity for epitopes of TcdB and the second and forth monomers are $V_HH$ peptide monomers 5D (SEQ ID NO:1) and E3 (SEQ ID NO:3), respectively.

The ABAB binding agent may comprise the amino acid sequence set forth in SEQ ID NO:19, or a sequence variant having at least 95% sequence identity thereto, wherein the sequence variant retains TcdA and/or TcdB binding specificity, or the sequence variant retains toxin neutralizing activity, or both.

The ABAB binding agent may also comprises an N-terminal secretion signal selected from the secretion signals provided in Table 4. In preferred aspects, the N-terminal secretion signal is the AT secretion signal (MRFPSIFTAVL-FAASSALA (SEQ ID NO:99)) or the IVS secretion signal (MLLQAFLFLLAGFAAKISA (SEQ ID NO:103)).

The ABAB binding agent may be expressed from a plasmid within the yeast. The plasmid may be, but is not limited to, pCEV-URA3-TEF-AT-yABAB-cMyc (SEQ ID NO:88). The ABAB binding agent encoded by the plasmid may comprises the amino acid sequence set forth in SEQ ID NO:107, or a sequence variant having at least 95% sequence identity thereto, and wherein the sequence variant retains TcdA and/or TcdB binding specificity, or the sequence variant retains toxin neutralizing activity, or both.

The ABAB binding agent may also be expressed from coding sequence integrated into a chromosome of yeast. The ABAB binding agent expressed from coding sequence integrated into a yeast chromosome may comprises the amino acid sequence set forth in SEQ ID NO:109, or a sequence variant having at least 95% sequence identity thereto, and wherein the sequence variant retains TcdA and/or TcdB binding specificity, or the sequence variant retains toxin neutralizing activity, or both.

The invention is also directed to engineered strains of *Saccharomyces* yeast that produce a therapeutic protein having binding specificity for a unique epitope of *Clostridium difficile* toxin A (TcdA) or toxin B (TcdB), or both. Preferably, the engineered strain of *Saccharomyces* yeast is *S. cerevisiae* or *S. boulardii*. A therapeutic protein is any protein that can bring about an improvement or cure in a medical condition in a subject, or that can inhibit or prevent a medical condition from developing in a subject. Suitable therapeutic protein include, but are not limited to, proteins that (a) replace a protein that is deficient or abnormal; (b) augment an existing pathway; (c) provide a novel function or activity; (d) interfere with a molecule or organism; and (e) deliver other compounds or proteins, such as a radionuclide, cytotoxic drug, or effector proteins. Therapeutic proteins also include antibodies and antibody-based drugs, Fc fusion proteins, anticoagulants, blood factors, bone morphogenetic proteins, engineered protein scaffolds, enzymes, growth factors, hormones, interferons, interleukins, and thrombolytics. Therapeutic proteins further include bispecific monoclonal antibodies (mAbs) and multispecific fusion proteins, mAbs conjugated with small molecule drugs, and proteins with optimized pharmacokinetics.

Methods of Making Engineered Yeast Strains

The invention is also directed to methods of engineering strains of *Saccharomyces* yeast to produce one or more of the binding agents defined herein. The means used to produce the engineered strains of yeast are not particularly limited and there are a number of well-established techniques available for engineering yeast to produce homologous and heterologous proteins that will be known to the skilled artisan. In certain aspects of these methods, *S. cerevisiae* or *S. boulardii* is engineered to produce the binding agents.

As an example, *Saccharomyces* yeast may be engineered to produce one or more of the binding agents defined herein by (a) transforming a strain of *Saccharomyces* yeast with an expression vector encoding the binding agent, and (b) screening the resulting yeast for production of the binding agent. In a certain aspect, the expression vector is plasmid pCEV-URA3-TEF-AT-yABAB-cMyc (SEQ ID NO:88). While this plasmid encodes a particular ABAB binding agent, the coding region for this binding agent can be replaced by the coding region of any of the binding agents defined herein.

As a further example, *Saccharomyces* yeast may be engineered to produce one or more of the binding agents defined herein by (a) chromosomally integrating a polynucleotide sequence encoding the binding agent into the genome of the strain of *Saccharomyces* yeast, and (b) screening the yeast of (a) for production of the binding agent. In certain aspects, the chromosomal integration is performed using a CRISPR technique [85-88]. As an example, such a method may include the steps of: (a) amplifying a polynucleotide sequence encoding the ABAB binding agent from plasmid pCEV-G4-Km-TEF-AT-yA-BAB hAA6T83N-tagless (SEQ ID NO:90) using primers containing (i) nucleic acid sequence homologous to a selected yeast chromosomal integration site and (ii) nucleic acid sequence homologous to regions 5' and 3' of ABAB binding agent coding sequence of the plasmid, to produce an integration cassette, (b) transforming yeast with the integration cassette produced in (a) with pCRI-Sb-δ1 (SEQ ID NO:91) or pCRI-Sb-δ2 (SEQ ID NO:92) to induce a double stranded break within the corresponding yeast chromosomal delta sites under conditions promoting spontaneous integration of the integration cassette into the site of the double stranded break, (c) screening the transformed yeast of (b) for production of the ABAB binding agent.

While the plasmid pCEV-G4-Km-TEF-AT-yABAB hAA6T83N-tagless encodes a particular ABAB binding agent, the coding region for this binding agent can be replaced by the coding region of any of the binding agents defined herein.

Suitable means used to screen the yeast for production of the binding agents will be readily apparent to the skilled artisan and include, but are not limited to immunoassays, such as an ELISA or a western blot.

Methods of Treatment and Prevention

The binding agents and engineered strains of *Saccharomyces* yeast of the invention can be used in methods of treating or preventing a disease symptom induced by *C. difficile* in a subject. These methods generally comprise administering a therapeutically-effective amount of one or more binding agents and/or one or more engineered strains of *Saccharomyces* yeast as defined herein to a subject having *C. difficile* infection or a risk of developing *C. difficile* infection. In certain aspects of this embodiment, the disease symptom induced by *C. difficile* is diarrhea The binding agents and engineered strains of *Saccharomyces* yeast of the invention can also be used in of neutralizing *C. difficile* toxin TcdA and/or TcdB in a subject infected by *C. difficile*. These methods generally comprise administering a therapeutically-effective amount of one or more binding agents and/or one or more engineered strains of *Saccharomyces* yeast as defined herein to a subject having *C. difficile* infection.

The binding agents and engineered strains of *Saccharomyces* yeast of the invention can further be used in methods of treating *C. difficile* infection in a subject. These methods generally comprise administering a therapeutically-effective amount of one or more of the binding agents and/or one or more engineered strains of *Saccharomyces* yeast as defined herein to a subject having *C. difficile* infection. These same methods can be used to treat CDI, as defined herein.

The binding agents and engineered strains of *Saccharomyces* yeast of the invention can also be used in methods of maintaining normal bowel function in a subject having a *C. difficile* infection. These methods generally comprise administering a therapeutically-effective amount of one or more of the binding agents and/or one or more engineered strains of *Saccharomyces* yeast as defined herein to a subject having *C. difficile* infection or a risk of developing *C. difficile* infection.

The binding agents and engineered strains of *Saccharomyces* yeast can also be used in immunoprophylaxis in order to prevent immediate CDI threats. In addition, passive immunoprophylaxis can be used to prevent both immediate and longer-term CDI threats. Each approach has its own particular advantages and is suitable to target a particular high-risk population. These methods generally comprises administering a therapeutically-effective amount of one or more of the binding agent and/or one or more engineered strains of *Saccharomyces* yeast as defined herein to a subject a risk of developing *C. difficile* infection.

In preferred aspects of the methods of the invention, the *Saccharomyces* yeast is *S. cerevisiae* or *S. boulardii*.

Each of the methods of the invention may include administration of the one or more binding agents and/or the one or more engineered strains of *Saccharomyces* yeast in one or more pharmaceutical formulations comprising the binding agents and/or the engineered strains of *Saccharomyces* yeast and a pharmaceutically acceptable carrier or diluent. In preferred aspects, the *Saccharomyces* yeast is *S. cerevisiae* or *S. boulardii*.

As used herein, the terms "treat", "treating", and "treatment" have their ordinary and customary meanings, and include one or more of: blocking, ameliorating, or decreasing in severity and/or frequency a symptom of a *C. difficile* infection or a *C. difficile*-related disease (CDI) in a subject; and/or partly or fully inhibiting the biological activity and/or promoting the immunologic clearance of *C. difficile* TcdA and/or TcdB in a subject infected with *C. difficile*; and/or growth, division, spread, or proliferation of *C. difficile* cells or a *C. difficile* infection in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%1, 0%, 5% or 1% versus a subject in which the methods of the present invention have not been practiced.

As used herein, the terms "prevent", "preventing" and "prevention" have their ordinary and customary meanings, and include one or more of, stopping, averting, avoiding, alleviating or blocking *C. difficile* from colonizing, developing or progressing in a subject; and/or partly or fully inhibiting the biological activity and/or toxic effects of TcdA and/or TcdB in a subject infected with *C. difficile*; and/or stopping, averting, avoiding, alleviating or blocking the growth, division, spread, or proliferation of bacterial cells or bacterial infection in a subject. Prevention means stopping by at least about 95% versus a subject to which the prevention has not been administered. Preferably, the stopping is about 100%, about 99%, about 98%, about 97%, about 96% or about 95%. The results of the prevention may continue for a period of days (such as 1, 2, 3, 4, 5, 6 or 7 days), weeks (such as 1, 2, 3 or 4 weeks) or months (such as 1, 2, 3, 4, 5, 6 or more months).

The method of treating and preventing provided herein can be supplemented by also administering a therapeutically-effective amount of an antibiotic to the subject. Preferably, the antibiotic will have antibacterial activity against *C. difficile*.

Pharmaceutical Formulations

While the binding agents and engineered strains of *Saccharomyces* yeast may be administered directly to a subject, the methods of the present invention are preferably based on the administration of a pharmaceutical formulation comprising one or more binding agents and/or one or more engineered strains of *Saccharomyces* yeast, and a pharmaceutically acceptable carrier or diluent. Thus, the invention includes pharmaceutical formulations comprising one or more of the binding agents and/or one or more engineered strains of *Saccharomyces* yeast defined herein and a pharmaceutically acceptable carrier or diluent.

Pharmaceutically acceptable carriers and diluents are commonly known and will vary depending on the particular binding agent or engineered strains of *Saccharomyces* yeast being administered and the mode of administration. Examples of generally used carriers and diluents include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising binding agents and/or engineered strains of *Saccharomyces* yeast will typically have been prepared and cultured in the absence of any non-human components, such as animal serum (e.g., bovine serum albumin).

Pharmaceutical formulations comprising one or more binding agents and/or one or more engineered strains of *Saccharomyces* yeast may be administered to a subject using modes and techniques known to the skilled artisan. Characteristic of CDI disease may make it more amenable to treatment and prevention using colonic delivery of therapeutic agents, i.e., targeted delivery of binding agents to the lower GI tract, e.g., the large intestine or colon. Other modes of delivery include, but are not limited to, oral, nasal, anal, and via intravenous injection or aerosol administration. Other modes include, without limitation, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

Depending on the means of administration, the dosage may be administered all at once, such as with an oral formulation in a capsule or liquid, or slowly over a period of time, such as with an intramuscular or intravenous administration.

The amount of binding agents, alone or in a pharmaceutical formulation, administered to a subject is an amount effective for the treatment or prevention of infection. Thus, therapeutically effective amounts are administered to subjects when the methods of the present invention are practiced. In general, between about 1 ug/kg and about 1000 mg/kg of the binding agent per body weight of the subject is administered. Suitable ranges also include between about 50 ug/kg and about 500 mg/kg, and between about 10 ug/kg and about 100 mg/kg. However, the amount of binding agent administered to a subject will vary between wide limits, depending upon the location, source, extent and severity of the infection, the age and condition of the subject to be treated, the means of administration, etc. A physician will ultimately determine appropriate dosages to be used.

The amount of the engineered strains of *Saccharomyces* yeast, alone or in a pharmaceutical formulation, administered to a subject is an amount effective for the treatment or prevention of infection. Thus, therapeutically effective amounts are administered to subjects when the methods of the present invention are practiced. In general, between about 1 ug/kg and about 1000 mg/kg of the engineered strains of *Saccharomyces* yeast per body weight of the subject is administered. Suitable ranges also include between about 50 ug/kg and about 500 mg/kg, and between about 10 ug/kg and about 100 mg/kg. However, the amount of the engineered strains of *Saccharomyces* yeast administered to a subject will vary between wide limits, depending upon the location, source, extent and severity of the infection, the age and condition of the subject to be treated, the means of administration, etc. A physician will ultimately determine appropriate dosages to be used.

Administration frequencies of the binding agents, the engineered strains of *Saccharomyces* yeast, and pharmaceutical formulations comprising the binding agents and/or engineered strains of *Saccharomyces* yeast will vary depending on factors that include the location of the bacterial infection, the particulars of the infection to be treated or prevented, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment or prevention will be based on location and severity of the infection being treated or the relative risk of contracting the infection, and will be best determined by the attending physician. However, continuation of treatment is contemplated to last for a number of days, weeks, or months.

In each embodiment and aspect of the invention, the subject is a human, a non-human primate, bird, horse, cow, goat, sheep, a companion animal, such as a dog, cat or rodent, or other mammal. The subjects to which the methods of the present invention can be applied include subjects having an underlying disease or condition that makes them more susceptible to *C. difficile* infections.

The invention also provides a kit comprising one or more containers filled with one or more of the binding agents, one or more of the engineered strains of *Saccharomyces* yeast, or one or more pharmaceutical formulations comprising binding agents and/or the engineered strains of *Saccharomyces* yeast. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

III. Examples $V_H H$ Monomer and Heterodimer Binding Agents

An efficient platform to screen single domain (monomeric), mono-specific $V_H H$ peptide monomers against specific domains of toxins TcdA and TcdB was established. Using highly immunogenic atoxic holotoxins for immunization, and bioactive chimeric toxins (with normal domain functions) for screening, panels of $V_H H$ monomers binding to different domains of TcdA or TcdB were prepared. A majority of these $V_H H$ monomers possessed potent neutralizing activity and their binding to specific domains was determined (FIG. 2). The atoxic holotoxins have point mutations at their enzymatic glucosyltransferase domains as described previously [33]. The bioactive chimeric toxins were created by switching the functional domains between TcdA and TcdB, which was also described previously [33].

Several of the $V_H H$ monomers bind to highly conserved TcdA/TcdB epitopes. For example, $V_H H$ E3 binds to the Rho GTPase binding site and blocks glucosylation; $V_H H$ AH3 binds to the GT domain of the toxin; $V_H H$ 7F binds to cysteine protease cleavage sites and blocks GT domain cleavage and release. Some $V_H H$ monomers have potent neutralizing activity capable of blocking toxin cytotoxic activity at nM concentrations (See Table 1; FIGS. 3A and 3B).

To enhance the binding activity, two domain (dimeric), bi-specific $V_H H$ heterodimers were created (Table 3; FIG. 3C), allowing a single protein to target two distinctive epitopes of the toxins. These bi-specific $V_H H$ heterodimers possessed substantially enhanced neutralizing activities compared with equimolar mixtures of the same two $V_H H$ monomers (FIG. 3D). Heterodimers 5D/E3 and AH3/AA6 were found to fully protect mice from lethal systemic TcdB or TcdA challenge respectively, whereas mixed 5D and E3, or AA6 alone were only partially protective (FIGS. 3E and 3F).

A tetra-valent, tri-specific $V_H H$ binding agent (ABA) was generated by genetically fusing $V_H H$s with the highest neutralizing activities targeting conserved, non-overlapping epitopes (AH3/E3/E3/AA6) [41]. This rationally designed toxin binder achieved a substantially enhancing binding affinity and neutralizing activity over the individual monomers and potent therapeutic efficacy against fulminant CDI. ABA was able to broadly neutralize toxins from 11 different TcdA$^+$TcdB$^+$ C. difficile clinical isolates but failed to neutralize TcdB derived from two TcdA$^-$TcdB$^+$ strains. The amino acid sequence of ABA is set forth in SEQ ID NO:111.

The $V_H H$ monomers comprising the heterodimers were linked using a flexible linker selected from SEQ ID NOs: 9-13 (Table 2).

ABAB Binding Agent

Four domain (tetrameric), tetra-specific $V_H H$ binding agents were generated by linking $V_H H$ monomers AH3, 5D, E3, and AA6, namely ABBA (AH3/5D/E3/AA6) and ABAB (AH3/5D/AA6/E3). These tetra-specific, tetrameric binding agent targets conserved, non-overlapping epitopes and had excellent toxin neutralizing activity. In the design of ABAB (FIG. 4), $V_H H$ peptide monomers AH3 and AA6 were separated by placing the 5D monomers between them because AH3 and AA6 bind to GT and TD respectively (FIG. 2), which are spatially distant to each other. This design allowed AH3 and AA6 to bind to TcdA simultaneously.

Figure 4:
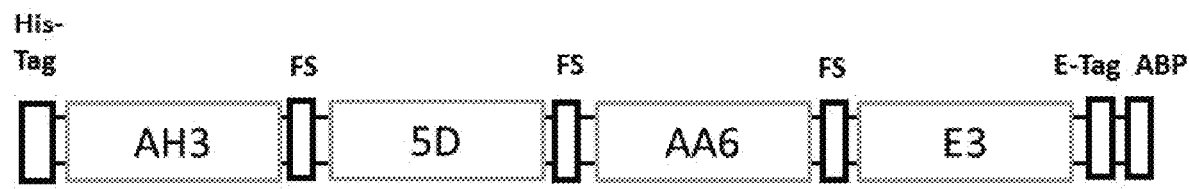
FIG. 4. Diagram of ABAB. His-tag and E-tag are epitope tags for purification and detection, respectively. FS: flexible linker; ABP: albumin binding peptide.

In the construction of the ABAB binding agent, flexible linkers were placed between the $V_H H$ monomers (see FIG. 4). The complete nucleic acid sequence encoding ABAB is provided in SEQ ID NO:20; the amino acid sequence of the protein is provided in SEQ ID NO:19.

In certain variants, a His$_{(6)}$-tag was provided at the amino terminus of the protein to aid in purification, an E-tag was provided at the carboxy terminus of the protein to aid in detection, and/or an albumin-binding peptide (ABP, DICL-PRWGCLWD; SEQ ID NO:21) was placed at the carboxyl end of the construct to increase serum half-life of the protein (See FIG. 4).

ABAB was found to exhibit substantial enhanced binding affinity (Table 7) and neutralizing activity (Table 8) over the individual monomers and ABA. In Table 8, Vero cells were exposed to 5 ng/ml of TcdA in the presence of serially diluted AA6, AH3, ABAB or Merck anti-TcdA HuMab [9]. The minimal doses of antibodies protecting cells from TcdA-induced cell rounding are shown.

TABLE 7

| | $V_H H_S$ | $K_{on}$ (Ms$^{-1}$) | $K_{off}$ (s$^{-1}$) | $K_D$ (nM) |
|---|---|---|---|---|
| TcdA | AH3 | $2.20 \times 10^4$ | $7.10 \times 10^{-4}$ | 32.0 |
| | AA6 | $3.52 \times 10^4$ | $6.92 \times 10^{-4}$ | 19.7 |
| | ABAB | $6.96 \times 10^5$ | $1.21 \times 10^{-6}$ | 0.002 |
| TcdB | 5D | $1.52 \times 10^6$ | $9.94 \times 10^{-4}$ | 0.65 |
| | E3 | $2.95 \times 10^6$ | $9.4 \times 10^{-5}$ | 0.03 |
| | ABAB | $1.79 \times 10^6$ | $3.57 \times 10^{-6}$ | 0.002 |

TABLE 8

| AA6 | AH3 | ABAB | Merck Anti-TcdA HuMab |
|---|---|---|---|
| 8 nM | 8 nM | 0.25 nM | >10 nM |

ABAB was also found to compete with all four individual $V_H H$ peptide monomers in a competition ELISA and can simultaneously bind to both TcdA and TcdB as determined by sandwich ELISA. Furthermore, ABAB is broadly reactive, capable of neutralizing toxins from the 13 different C. difficile strains that represent most of the current epidemic strains (Table 9).

TABLE 9

| Strains | Ribo-type | REA type | PFGE type | Toxins | Place/date of isolation | ABAB neutralization |
|---|---|---|---|---|---|---|
| R20291 | 27 | BI | NAP1 | TcdA/TcdB | London/2006 | Yes |
| CD196 | 27 | BI | NAP1 | TcdA/TcdB | France/1985 | Yes |
| 630 | 12 | R | | TcdA/TcdB | Zurich/1982 | Yes |
| M120 | 78 | BK | NAP7, 8, 9 | TcdA/TcdB | UK/2007 | Yes |
| BI-9 | 1 | J | NAP2 | TcdA/TcdB | Gerding Collection | Yes |
| Liv024 | 1 | J | NAP2 | TcdA/TcdB | Liverpool/2009 | Yes |
| Liv022 | 106 | DH | NAP11 | TcdA/TcdB | Liverpool/2009 | Yes |
| TL178 | 2 | G | NAP6 | TcdA/TcdB | Belfast/2009 | Yes |
| TL176 | 14 | Y | NAP4 | TcdA/TcdB | Cambridge, UK/2009 | Yes |
| TL174 | 15 | | | TcdA/TcdB | Cambridge, UK/2009 | Yes |
| CD305 | 23 | | | TcdA/TcdB | London/2008 | Yes |
| CFS | 17 | | | TcdB | Belgium/1995/ human | Yes |
| M68 | 17 | | | TcdB | Dublin/2006/ human | Yes |

Figure 5A:
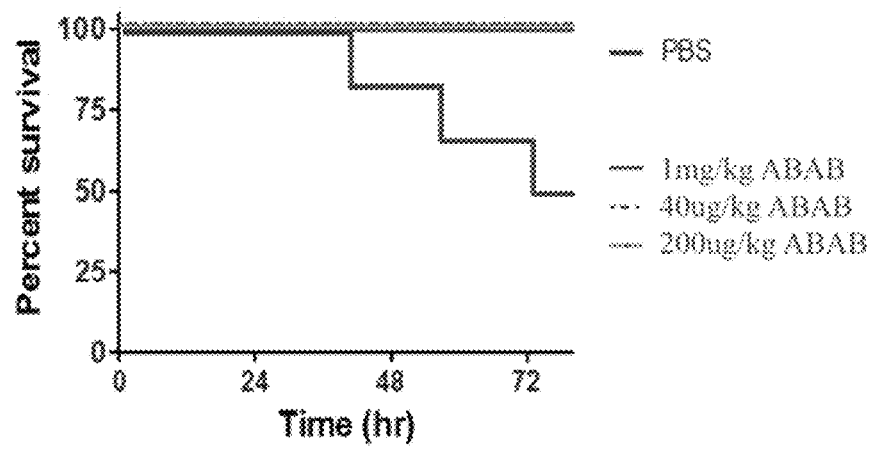
FIGS. 5A-5B. ABAB is highly potent in protecting mice from *C. difficile* spore (FIG. 5A) and toxin (FIG. 5B) challenge. MK HuMabs: a mixture of Merck anti-TcdA (actoxumab) and anti-TcdB (bezlotoxumab) human monoclonal antibodies that are undergoing clinical trials.
Figure 5B:
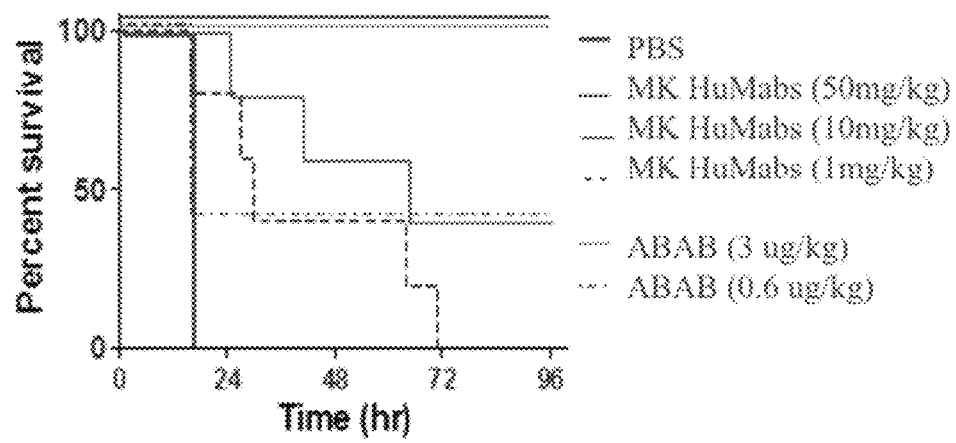

Since ABAB shows high potency in binding to and neutralizing both toxins, its efficacy in treating fulminant CDI was evaluated. A single injection with as low as 40 µg/kg of ABAB one-day post *C. difficile* spore challenge reversed fulminant CDI in mice. None of the ABAB-treated mice died whereas 50% of control mice became moribund by 3 days post-infection (FIG. 5A). ABAB is 4-log more potent in preventing mortality after systemic challenge with TcdA and TcdB than the Merck HuMabs (FIG. 5B) [9]. Thus, ABAB possesses extraordinary in vivo efficacy against *C. difficile* toxins and spore challenge.

Figure 6A:
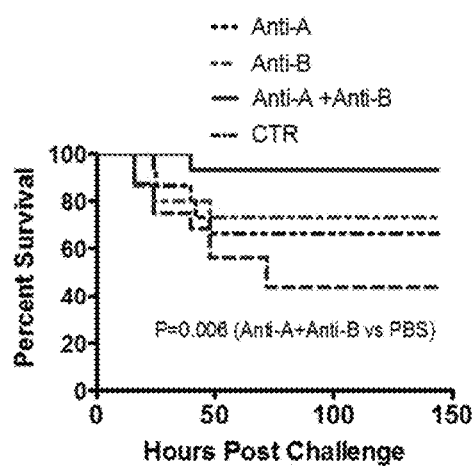
FIGS. 6A-6B. Anti-toxin sera against both toxins protect mice from CDI. Mice were i.p. injected with 50 ul alpaca anti-sera against TcdA ("Anti-A"), TcdB ("Anti-B"), TcdA+TcdB ("Anti-A+Anti-B") or with 100 ul presera or PBS ("CTR") for 4 hours before *C. difficile* spore (UK1 strain, $10^6$ spores/mouse) inoculation. Mouse survival (FIG. 6A; Anti-A+Anti-B vs. PBS, p=0.006) and weight loss (FIG. 6B) are illustrated (*, p<0.05 between Anti-A+Anti-B vs. control).
Figure 6B:
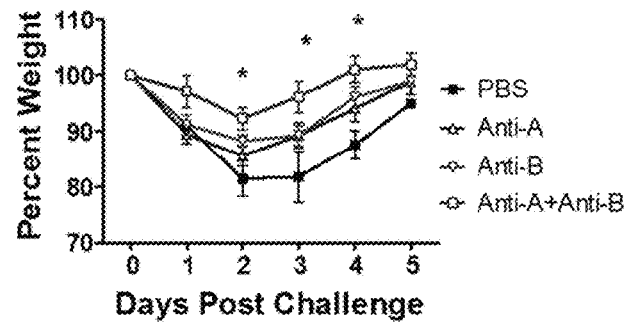

Animal and human studies demonstrated that passively administered antitoxin antibodies provide protection against CDI. The initial studies here also showed that antitoxin polysera protected mice from primary CDI (FIGS. 6A and 6B) and recurrent/relapse CDI. These findings and results from FIGS. 5A and 5B supported the hypothesis and provided the rationale for development of a parenteral ABAB immunization strategy for preventing CDI. To achieve the goal of optimizing ABAB for systemic delivery, chimeric and humanized ABAB were generated as illustrated in FIG. 1, i.e., $V_HH$-Fc and $V_HH$-IgG binding agents as well as the humanized proteins h$V_HH$-Fc and h$V_HH$-IgG, after which leading proteins were evaluated for in vivo neutralizing activity and protection in animal models. Details regarding the preparation and testing of the additional binding agents are provided in the following paragraphs.

ABAB-Fc

ABAB-Fc binding agent was prepared by generating an expression vector encoding the $V_HH$ peptide monomers AH3/5D/AA6/E3 (linked in the noted order) joined to a human IgG1 Fc domain. The $V_HH$ peptide monomers were separated by flexible linkers of Table 2. The nucleic acid sequence encoding the protein is provided in SEQ ID NO:23. ABAB-Fc was expressed and purified from stable transfected HEK293 cell line culture supernatant using protein A beads under conditions permitting disulfide bond formation and bi-valent molecule production. The expression levels were about 20 mg/L of culture supernatant. ABAB-Fc is fully functional in binding and neutralizing both TcdA and TcdB (data not shown). The amino acid sequence of ABAB-Fc is provided in SEQ ID NO:22.

Mono-specific $V_HH$-Fc binding agents (AH3-Fc, 5D-Fc, E3-Fc, AA6-Fc) and bi-specific $V_HH$-Fc binding agents (AH3/5D-Fc) and AA6/E3-Fc) were also made using this Fc-fusion system. Table 5 above provides the sequences for these additional binding agents.

ABAB-IgG

As illustrated in FIG. 1, bi-specific $V_HH$-IgG (AH3/5D-IgG and E3/AA6-IgG) can be generated by fusing monomers with human IgG heavy and light (kappa or lambda) chains separately. Tetra-specific $V_HH$-IgG (ABAB-IgG) binding agents can be generated by fusing dimers with human IgG heavy and light chains separately. Co-transfecting the heavy and light chain constructs generates the AH3/5D-IgG, E3/AA6-IgG and ABAB-IgG chimeric proteins. The separation of two $V_HH$s into heavy and light chains likely improves the yield and stability of bi-specific and tetra-specific $V_HH$ chimeric proteins. This allows determination of whether $V_HH$-human IgG chimeric antibody helps the stability and efficacy of ABAB in vivo. Similarly, further improvement of in vivo half-life of ABAB-IgG can also be tested in ABAB-IgG variants with enhanced binding affinity to FcRn receptor.

Bi-specific (AH3/5D-IgG1 and E3/AA6-IgG1) and tetra-specific (ABAB-IgG1) IgG1 binding agents were prepared by co-transfecting expression vectors encoding the heavy and light (kappa) chain of each binding agent. The $V_HH$ peptide monomers were separated by flexible linkers of Table 2.

Bi-specific, tetrameric $V_HH$-IgG1 binding agents were produced by preparing two separate expression vectors, the first encoding a $V_HH$ peptide monomer joined to the human IgG1 antibody heavy chain ($C_H1$-Hinge-$C_H2$-$C_H3$) lacking the heavy chain variable region and the second encoding a $V_HH$ peptide monomer joined to the human IgG1 antibody light (kappa) chain (CK) lacking the light chain variable region. These binding agents are bi-specific and tetrameric in that each light chain of the resulting binding agent is linked to a first $V_HH$ monomer and each heavy chain of the resulting binding agent is linked to a second $V_HH$ monomer. Table 6 above provides the sequences for these additional binding agents. Suitable pairings include (i) AH3-IgG1-heavy chain+AA6-light (kappa or lambda) chain, (ii) 5D-IgG1-heavy chain+E3-light (kappa or lambda) chain, (iii) 5D-IgG1-heavy chain+AA6-light (kappa or lambda) chain, and (iv) AH3-IgG1-heavy chain+E3-light (kappa or lambda) chain.

Tetra-specific, octameric ABAB-IgG binding agents were prepared. These binding agents are tetra-specific and octameric in that each light (kappa or lambda) chain of the resulting binding agent is joined to two (a first and second) linked $V_HH$ monomers and each heavy chain of the resulting binding agent is joined to a two (a third and fourth) linked $V_HH$ monomer, where the first, second, third and fourth monomers binds to a different epitope.

Figure 7:
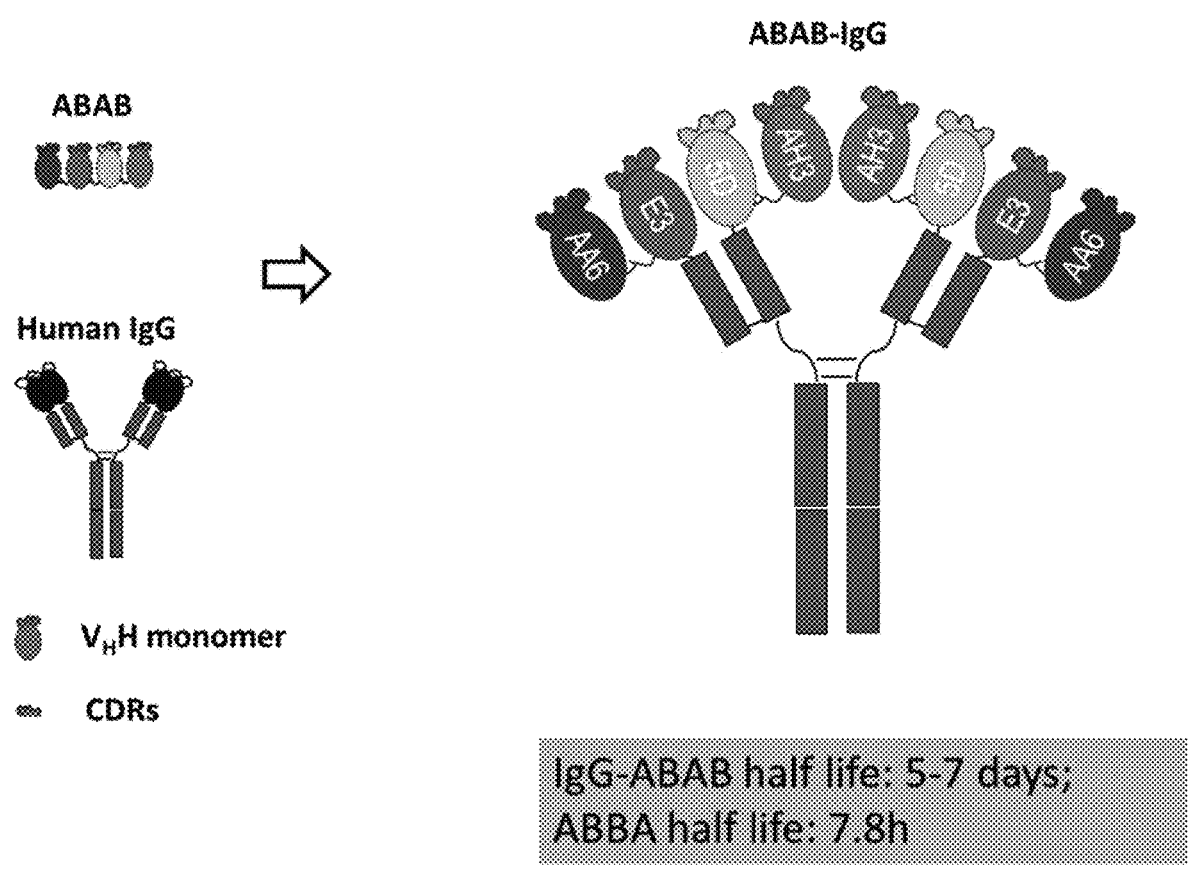
FIG. 7. The diagram of the ABAB and ABAB-IgG molecules.

A particular tetra-specific, octameric ABAB-IgG (FIG. 7) binding agent was produced by preparing two separate expression vectors, the first encoding the $V_HH$ peptide monomers AH3/5D (linked in the noted order) joined to the human IgG1 antibody heavy chain ($C_H1$-Hinge-$C_H2$-$C_H3$) lacking the heavy chain variable region and the second encoding the $V_HH$ peptide monomers AA6/E3 (linked in the noted order) joined to the human IgG1 antibody light (kappa) chain (CK) lacking the light chain variable region. The nucleotide sequence encoding the AH3/5D-IgG1 heavy chain is provided in SEQ ID NO:45; the amino acid sequence is provided in SEQ ID NO:44. The nucleotide sequence encoding the AA6/E3-IgG1 kappa chain is provided in SEQ ID NO:47; the amino acid sequence is provided in SEQ ID NO:46.

The bi-specific (AH3/5D-IgG1 and E3/AA6-IgG1) and tetra-specific (ABAB-IgG1) IgG1 binding agents were expressed and purified from stable transfected HEK293 cell line culture supernatant using protein A beads under conditions permitting disulfide bond formation and bi-valent molecule production. SDS-PAGE shows more than 90% purity of the purified ABAB-IgG1 with total molecular weight (light and heavy chains together) around 218 KDa on non-reduced gel (data not shown). The molecular weight of heavy chain is 68 KDa and light chain is 41 KDa showed on reduced gel.

Figure 8A:
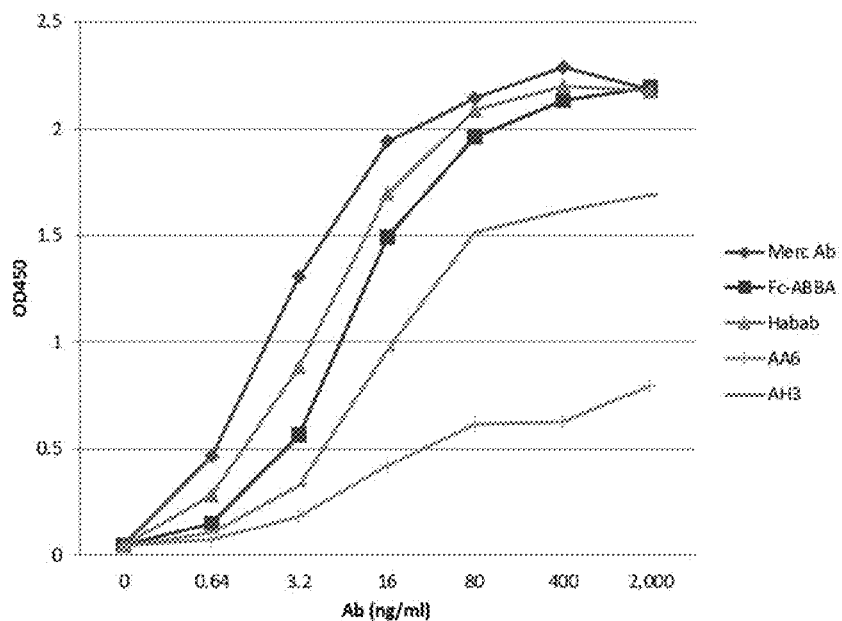
FIGS. 8A-8B. ELISA analysis of binding of ABAB-IgG to TcdA (FIG. 8A) and TcdB (FIG. 8B) as compared with the binding of the individual VHHs to the respective toxins.
Figure 8B:
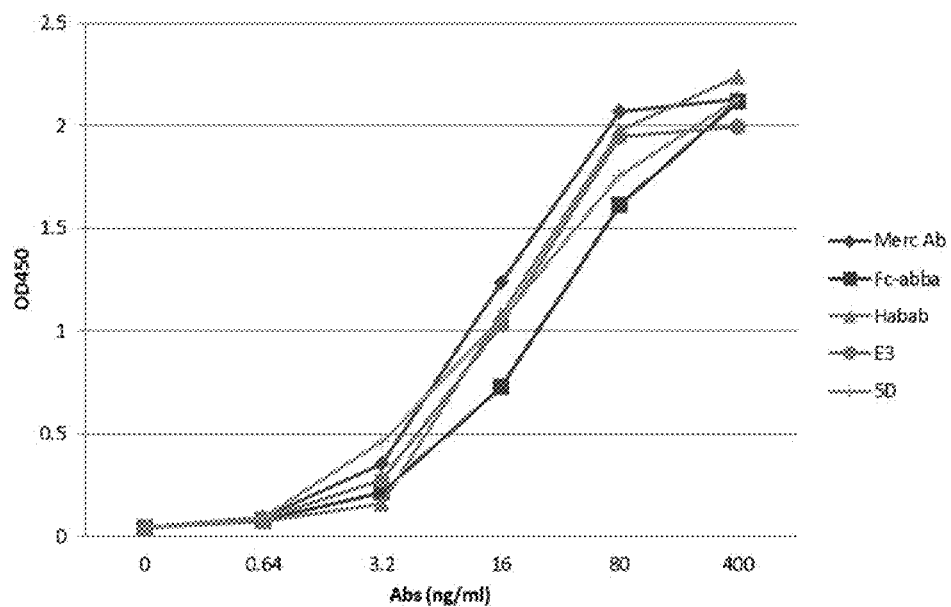

The binding of ABAB-IgG1 to TcdA and TcdB was determined. FIGS. 8A-8B illustrate the comparison of binding ABAB-IgG1 to both toxins with the individual components (AH3, AA6, E3, and 5D). FIG. 8A shows the results of experiments where plates were coated with 1 ug/ml TcdA (TxA). Serially diluted ABAB-IgG was added in concentrations of 0, 0.64, 3.2, 16, 80, 400 and 2,000 ng/ml. The plates were washed and Merck Ab (anti-TcdA), Fc-ABBA (ABAB-Fc), Habab (ABAB-IgG), and $V_HH$ anti-TcdB monomers AA6 and AH3 were added in the indicated amounts (ng/ml). Appropriate labeled antibodies were used for detection. FIG. 8B shows the results of experiments where plates were coated with 1 ug/ml TcdB (TxB). Serially diluted ABAB-IgG was added in concentrations of 0, 0.64, 3.2, 16, 80 and 400 ng/ml. The plates were washed and Merck Ab (Anti-TcdB), Fc-abba (ABAB-Fc), Habab (ABAB-IgG), and $V_HH$ anti-TcdB monomers E3 and 5D were added in the indicated amounts (ng/ml). Appropriate labeled antibodies were used for detection.

As expected, the tetra-specific antibody can bind to TcdA and TcdB simultaneously as determined by sandwich ELISA (FIGS. 9A-9B). In a first set of experiments, plates were coated with 1 ug/ml TcdA (TxA). Serially diluted ABAB-IgG (Habab) was added in concentrations of 0, 1.6, 8, 40, 200 and 1000 ng/ml. The plates were washed and the following amounts of TcdB were added: 1.6, 8, 40, 200, and 1000 ng/ml. Mouse anti-TxB antibodies (500×) and goat anti-mouse-IgG-HRP (3000×) antibodies were used for detection. The results provided in FIG. 9A show that TxB is detected by coating TxA, suggesting IgG-ABAB binds to TxA/B simultaneously. In a second set of experiments, plates were coated with 1 ug/ml TcdB (TxB). Serially diluted ABAB-IgG (Habab) was added in concentrations of 0, 1.6, 8, 40, 200 and 1000 ng/ml. The plates were washed and the following amounts of TcdA were added: 1.6, 8, 40, 200, and 1000 ng/ml. Mouse anti-TxA antibodies (500×) and goat anti-mouse-IgG-RP (3000×) antibodies were used for detection. The results provided in FIG. 9B show that TxA is detected by coating TxB, again suggesting IgG-ABAB binds to TxA/B simultaneously.

Figure 10A:
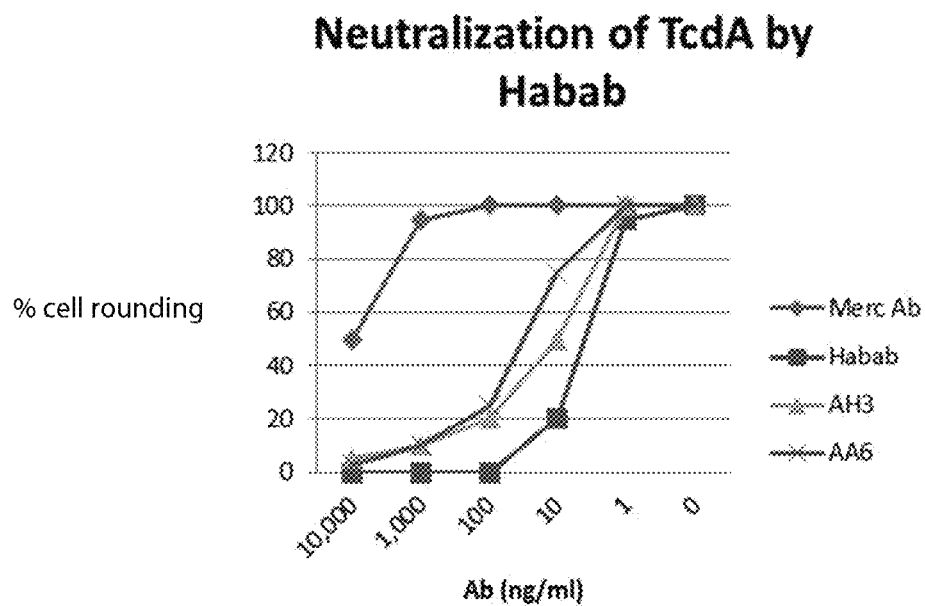
FIGS. 10A-10B. ABAB-IgG neutralizing activities against TcdA (FIG. 10A) and TcdB (FIG. 10B).
Figure 10B:
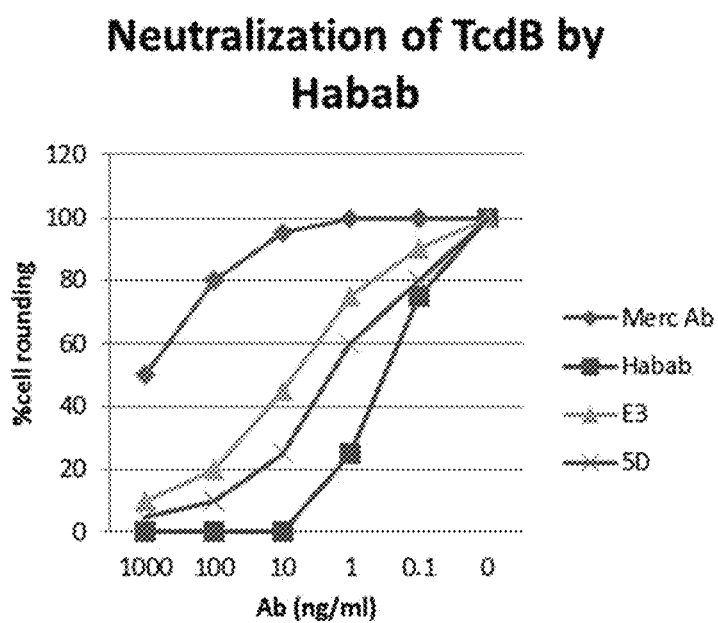

The neutralizing activities of ABAB-IgG1 against cytopathic effects of the toxins on cultured cells were also examined. TcdA (100 ng/ml, FIG. 10A) was mixed with serially diluted Merck anti-TcdA human monoclonal antibody, ABAB-IgG1 (Hababa), and $V_HH$ anti-TcdA monomers AA6 and AH3 before adding to Vero cell monolayers in 100 ul culture medium and incubated at 37° C. for 24 hours. The results provided in FIG. 10A show that ABAB-IgG1 is at least 1000-fold more potent than Merck antibodies in neutralizing TcdA. In similar experiments, TcdB (10 pg/ml, FIG. 10B) was mixed with serially diluted Merck anti-TcdB human monoclonal antibody, ABAB-IgG1 (Hababa), and $V_HH$ anti-TcdB monomers E3 and 5D before adding to Vero cell monolayers in 100 ul culture medium and incubated at 37° C. for 24 hours. The results provided in FIG. 10B show that ABAB-IgG1 is at least 1000-fold more potent than Merck antibodies in neutralizing TcdB.

Figure 11:
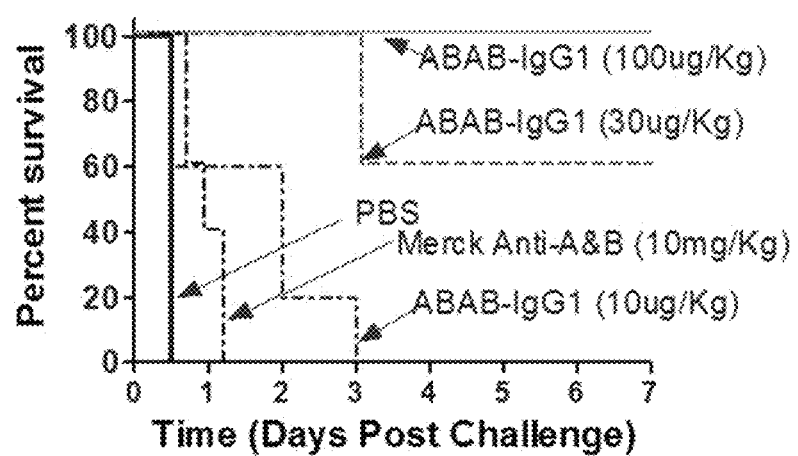
FIG. 11. Graph showing in vivo neutralizing activity of ABAB-IgG against *C. difficile* infection in mice versus Merck antibodies against TcdA and TcdB (actoxumab and bezlotoxumab).

The in vivo neutralizing activities of ABAB-IgG1 were studied in a mouse model of CDI, the results of which are shown in FIG. 11. Mice were challenged with lethal dose of a mixed TcdA and TcdB (25 ng each toxin per mouse) and 4 hour later, ABAB-IgG (10, 30 or 100 ug/kg), a mixture of Merck anti-toxin A and anti-toxin B antibodies (10 mg/kg) or PBS was administered to the mice. The results demonstrate that the neutralizing activity of ABAB-IgG was much greater than the Merck antibody, and at lower concentrations.

Animal Testing of ABAB-IgG

Figure 12:
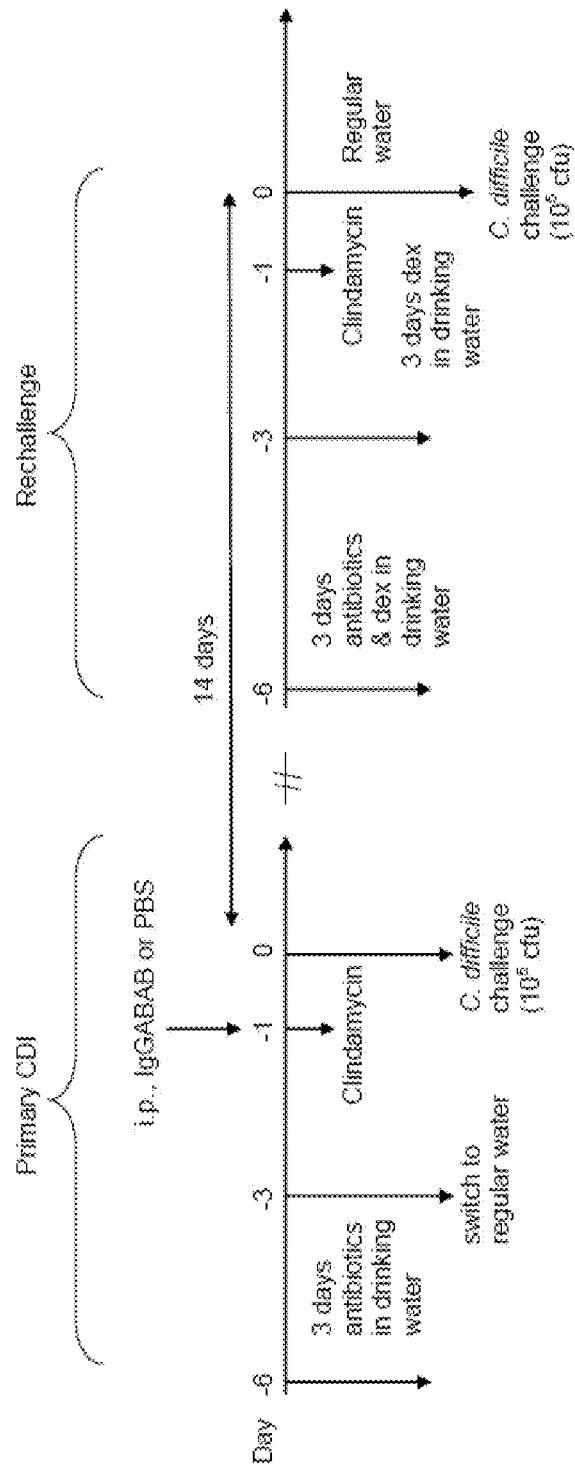
FIG. 12. Design of studies on the effects of prophylactic ABAB-IgG against *C. difficile* infection.

The ABAB-IgG binding agent was tested in both prophylactic treatment and re-challenge survival assays. FIG. 12 provides the experimental design of both studies. 6-8 week old female C57 mice were used, and the conditions included PBS: 10 ml/kg, i.p., n=14; ABAB-IgG: 200 ug/kg, i.p., n=10; ABAB-IgG: 1 mg/kg, i.p., n=10; ABAB-IgG: 5 mg/kg, i.p., n=10.

Table 10 provides a summary of the results seen with prophylactic treatment of mice against *C. difficile* spores (UK1, a 027/BI/NAP1 epidemic strain). ABAB-IgG or PBS was administered one day prior to administrating of *C. difficile* spores. As can be seen, ABAB-IgG showed dose-related prophylactic protection against CDI, where 5 mg/kg showed complete protection on all the parameters examined and 200 ug/kg was found to be more potent than 200 ug/kg of bi-specific $V_HH$ fusion antibody ABA [41].

TABLE 10

| | Diarrhea | | | Weight Change | | | Sur- |
|---|---|---|---|---|---|---|---|
| | Day 1 Occurrence | Day 2 score | score | Overall | Day 2 | Day 3 | Day 4 | vival |
| 200 µg/kg | — | — | — | √ | — | √ | √ |
| 1 mg/kg | √ | — | √ | — | √ | √ | — | √ |
| 5 mg/kg | √ | √ | √ | √ | √ | √ | √ | √ |

Table 11 provides a summary of the results seen with re-challenge of mice against *C. difficile* spores. ABAB-IgG or PBS was administered 15 days prior to administrating of *C. difficile* spores. As can be seen, one dose of ABAB-IgG showed some protection against the CDI caused by re-challenge of spores, but the protection was much less efficient compared to that during the primary challenge. This may be due to the drop of the antibody level with time and the generation of antibody in the PBS group following primary challenge.

TABLE 11

| | Diarrhea | | | Weight Change | | | Sur- |
|---|---|---|---|---|---|---|---|
| | Day 1 Occurrence | Day 2 score | score | Overall | Day 2 | Day 3 | Day 4 | vival |
| 200 µg/kg | √ | √ | — | — | — | — | — | — |
| 1 mg/kg | √ | — | — | — | — | — | √ | — |
| 5 mg/kg | — | — | — | √ | — | — | — | — |

Intestinal delivery of IgG-ABAB was also tested for protection of mice from fulminant CDI. After a single IgG-ABAB injection into mouse ceca after a laparotomy, mice were completely protected against fulminant CDI of death outcomes whereas 50% of control mice succumbed (data not shown). Disease progress and severity were assessed daily using a clinical scoring system modified from a previous publication [62], which included four criteria (activity level, posture, coat, and diarrhea) each graded on a scale from 0 to 4 and added together to generate a score with a maximum value of 16. A normal mouse would score 0 and a mouse found dead was scored as 16. Mice with scores equal to or higher than 11 should be euthanized. Only one mouse in the IgG-ABAB treatment group developed transient diarrhea whereas mice injected with PBS developed severe CDI disease symptoms (data not shown). Thus, Ig-ABAB manually delivered by injection into mouse intestines showed potent therapeutic efficacy.

Expression, Purification and Evaluation of Binding Agents

A variety of selection criteria is used to select the binding agents generated in the experiments described in the approaches herein. First, each of the constructs defined herein can be used in transient transfections of 293T cells for making small-scale recombinant proteins by Protein A affinity chromatography. The production yield of each construct can be determined by quantitative ELISA. Second, binding activity of recombinant proteins can be screened using ELISA and surface plasmon resonance (SPR) to select constructs that preserve their original binding activities against the toxins. Third, the proteins are evaluated for neutralizing activity in in vitro assays (FIG. 3).

Accumulating observations indicate that polyreactivity and/or autoreactivity of in vivo recombinant binding agents are potential issues related to their in vivo safety and half-life. The application of the selected ABAB binding agents as a systemic binding agent for preventing primary acute CDI likely requires that the chimeric and humanized ABAB proteins are limited in polyreactivity and/or autoreactivity. Progress in protein proteomics has made it possible to screen for polyreactivity and autoreactivity of recombinant antibodies in vitro, which is a great tool for surrogate therapeutic antibodies. Therefore, selected humanized binding agents with good yield, high binding affinity, and potent neutralizing activity can be further tested for potential polyreactivity and autoreactivity using the auto-antigen microarray test and ProtoArray protein microarrays (Invitrogen).

From the above in vitro assays, candidate ABAB-Fc and ABAB-IgG binding agents can be evaluated for their in vivo toxicity, serum half-life, and immunogenicity.

Generation of S. cerevisiae Secreting ABAB (Sc-ABAB)

Means for in vivo production and delivery of the binding agents to the gut of subjects having CDI or at risk of developing CDI were developed. Because S. cerevisiae is genetically similar to S. boulardii [52,53] and genetic tools are readily available for S. cerevisiae, S. cerevisiae was first used for ABAB secretion validation.

Figure 13A:
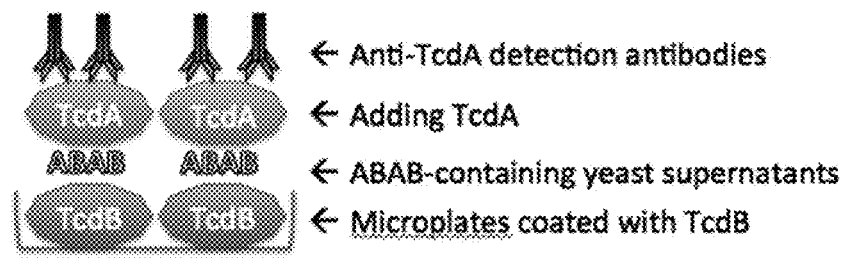
FIGS. 13A-13B. Bi-specific sandwich ELISA.
Figure 13B:
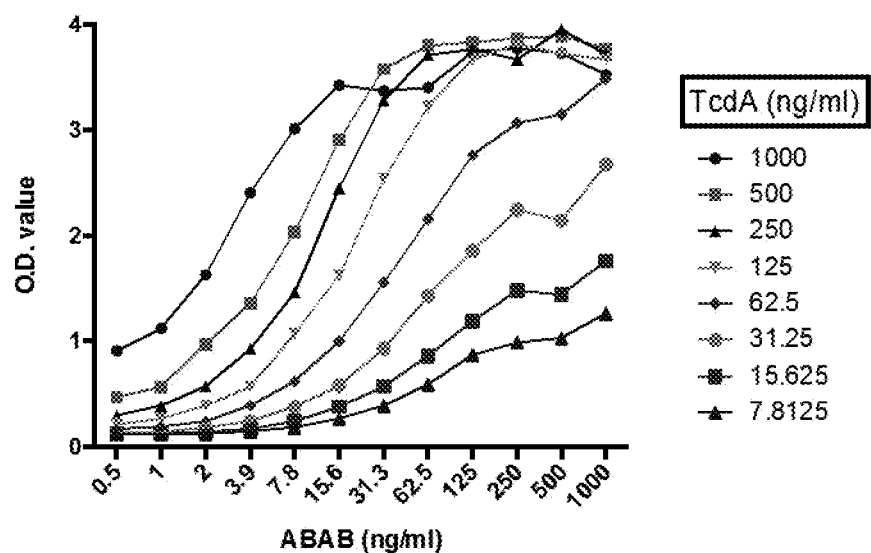

A novel bi-specific sandwich ELISA method was first developed to evaluate ABAB secretion. The setting utilizes purified TcdA and TcdB as binding antigens for ABAB bispecificity and α-TcdA antibodies for detection (FIG. 13A). For standardization, plates were coated with TcdB (1 ug/ml) into which was added serially diluted ABBA ((AH3-E3-E3-AA6)) standard. Serial diluted rTcdA (1 ug/ml to 7.8 ng/ml) was then added. The capture of TcdA was then measured by adding monoclonal antibody against TcdA followed by HRP conjugated secondary antibody. The results for the standard curves are shown in FIG. 13B. Based on these results, a standard curve derived using 125 ng/ml of rTcdA was chosen for determining secretion levels of ABAB in yeast culture supernatants and used for all subsequent ELISA.

A shuttle plasmid (pD1214-FAKS) containing origins of replication from both E. coli (pUC) and yeast (2 micron circle), as well as a yeast auxotrophic selection marker URA3 (conferring the ability to synthesize uracil), was obtained from DNA 2.0 (Newark, CA). The sequence encoding ABAB (SEQ ID NO:20), and His tag (SEQ ID NO:66) and D7 tag (SEQ ID NO:112) at the N-terminus and C-terminus of ABAB respectively, was inserted into this plasmid backbone in which transcription was controlled by the strong constitutive yeast translational elongation factor promoter ($P_{TEF}$) and extracellular secretion provided by fusion to the alpha mating factor secretion signal leader sequence (FAKS). The sequence of the resulting plasmid (pD1214-FAKS-His-hABAB-D7) is provided in SEQ ID NO:68.

Plasmid pD1214-FAKS-His-hABAB-D7 was transformed into the S. cerevisiae strain BY4741 (MATa his3 Δ1 leu2 Δ0 Met15 Δ0 ura3 Δ0), an URA3 knockout S288C-derivative laboratory strain. Yeast transformants were then cultured in YNB medium containing dropout mix without uracil (6.8 g YNB, 20 g glucose, 2 g dropout mix in 1 L of sterile ddH$_2$O) at 250 rpm at 30° C. overnight to reach O.D. 1 in a shaker. The cells were then centrifuged down and lysed by sonication in 1×SDS loading buffer. After sonication, total cell lysates were treated at 98° C. for 5 minutes before loading on a SDS gel. Same amount of yeast control cell lysates were loaded in each well except the control cells were not viable in YNB medium without uracil and therefore were cultured in YNB complimented with uracil.

Figure 14A:
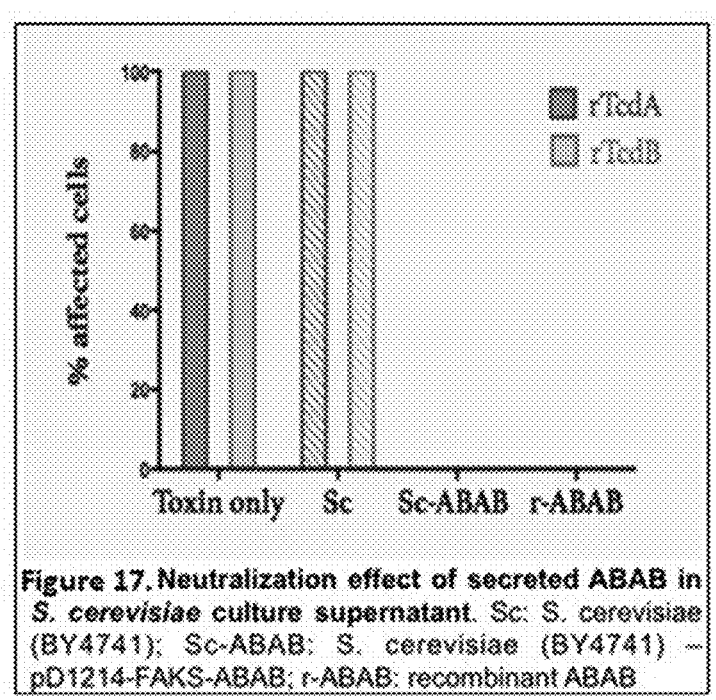
FIGS. 14A-14B. Activity of ABAB secreted by Sc-ABAB.
Figure 14B:
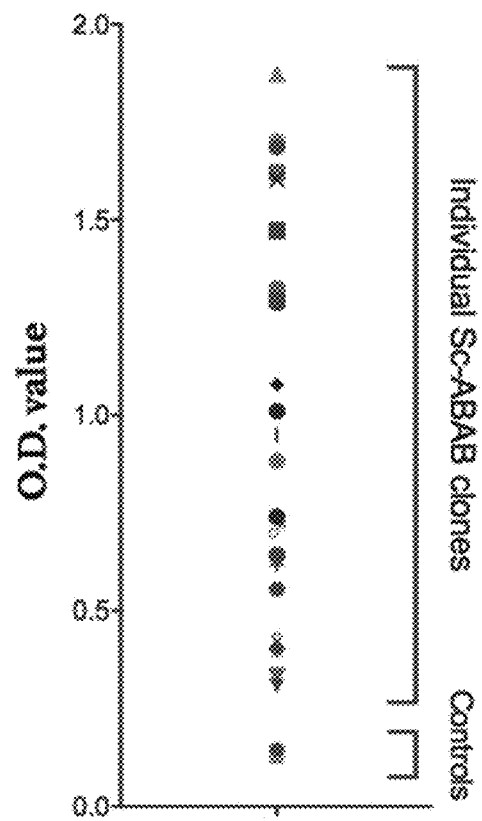

Culture supernatants from 25 yeast transformants as well as 3 yeast control colonies were centrifuged to spin down cells, and the cell-free supernatants were then diluted with 2.5% milk in PBS containing 0.05% of tween 20 at 1:3 ratio and screened by the ELISA as described above after 24 hrs of incubation in a shaker at 250 rpm and 30° C. FIG. 14B shows that all the yeast transformants secreted ABAB in culture supernatant compared to the culture supernatant from the yeast control colonies.

A cell-based neutralizing assay was used to assess the biological activity of secreted ABAB in culture supernatant. In this assay, sufficient amount of toxin A or toxin B to cause 100% cell rounding in 4 hours were added with PBS, cell-free culture supernatant from BY4741 control colony or BY4741-ABAB colony. Recombinant ABAB was used a positive control. The biological activity of secreted ABAB in culture supernatant was determined by the level of neutralizing activity to prevent cell rounding. Full length ABAB secreted from S. cerevisiae indeed retains its neutralizing activity when compared with purified recombinant ABAB (FIG. 14A). These combined results imply the plausibility of ABAB secretion by S. boulardii.

In further experiments, it was demonstrated that oral gavage of mice with Sc-ABAB at doses of $10^{10}$ CFU had no adverse effects on mice, and mice shed live Sc-ABAB as determined by plating feces on Sabouraud CAF-Agar (data not shown). Isolates recovered from mice retained their ability to produce functional ABAB using the assay described above.

ABAB Secretion Optimization

ABAB secretion level is imperatively linked to in vivo therapeutic efficacy. Therefore, the possibility of further optimizing ABAB secretion by replacing the existing FAKS secretion signal with a number of commercially available secretion signals was explored. Secretion sequences facilitate co-translational or post-translational translocation of heterogeneous proteins into the endoplasmic reticulum and Golgi compartments prior to extracellular export. Although α-mating factor is a commonly used signal sequence for heterologous protein secretion that typically generates good yields of the secreted proteins in S. cerevisiae [69,70], studies have shown that other secretion sequences from other proteins such as inulinase or invertase could be more suitable for secreting certain heterologous proteins [71,72].

11 different commercially available secretion signals (Table 4; DNA 2.0, Newark, CA) were genetically fused with ABAB individually under the control of TEF promoter in the same pD1214 plasmid backbone. Plasmids encoding ABAB with alternative secretion signals include the following plasmids where the FAKS secretion signal is replaced by the noted new secretion signals from Table 4 and where both the his-tag and D7-tag are removed:

Plasmid pD1214-AKS-hABAB (SEQ ID NO:70)
Plasmid pD1214-AK-hABAB (SEQ ID NO:71)
Plasmid pD1214-AT-hABAB (SEQ ID NO:72)
Plasmid pD1214-AA-hABAB (SEQ ID NO:73)
Plasmid pD1214-GA-hABAB (SEQ ID NO:74)
Plasmid pD1214-IN-hABAB (SEQ ID NO:75)
Plasmid pD1214-IVS-hABAB (SEQ ID NO:76)
Plasmid pD1214-KP-hABAB (SEQ ID NO:77)

Plasmid pD1214-LZ-hABAB (SEQ ID NO:78)
Plasmid pD1214-SA-hABAB (SEQ ID NO:79)

Figure 15A:
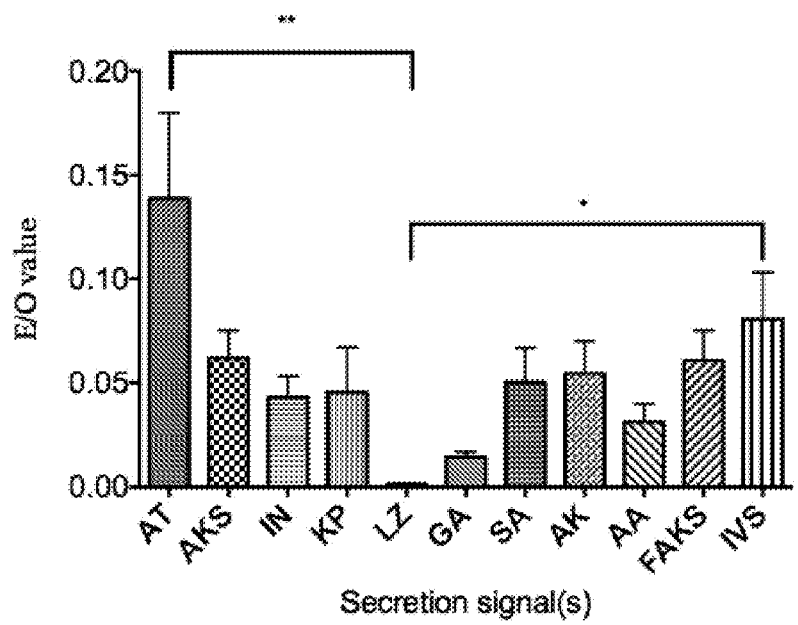
FIGS. 15A-15B. ABAB secretion level with various secretion signals.

In addition, both the his-tag and D7-tag in the original ABAB construct (pD1214-FAKS-His-hABAB-D7) were removed to produce plasmid pD1214-FAKS-hABAB (SEQ ID NO:69) and culture incubation temperature was raised to 37° C. to better accommodate in vivo and clinical testing relevant scenarios. All 11 plasmids were then transformed in BY4741 and 5 independent colonies from each selective plate were selected to generate culture supernatants. The amount of secreted ABAB was determined by the same ELISA as described above. In addition, E/O value was used to provide a fair comparison across all groups. E/O value is defined by ELISA O.D. value normalizes against culture O.D. value. Two of the best secretion signals for ABAB were found to be AT and IVS (Table 4; FIG. 15A).

Figure 15B:
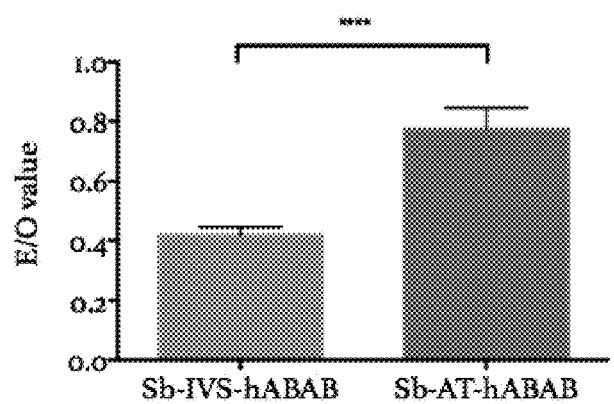

Due to the unavailability of an auxotrophic mutant strain for *S. boulardii*, another 2 um-based plasmid carrying the aphA1 gene encoding resistance to G418 (pCEV-G4-Km; SEQ ID NO:80; a gift from Lars Nielsen & Claudia Vickers (Addgene plasmid #46819)) was used instead of pD1214 plasmids to confirm ABAB secretion in *S. boulardii*. The best two secretion signals for *S. cerevisiae* (AT and IVS) were fused with ABAB genetically and inserted in the pCEV-G4-Km plasmid backbone to generate plasmids pCEV-G4-Km-TEF-AT-hABAB*(SEQ ID NO:81) and pCEV-G4-Km-TEF-IVS-hABAB*(SEQ ID NO:82). Both plasmids were used to transform *S. boulardii* (strain MYA796) and ABAB secretion with AT and IVS in *S. boulardii* was comparable with *S. cerevisiae* as determined by ELISA (FIG. 15B). A further construct, pCEV-G4-Km-TEF-AT-hABAB (SEQ ID NO:83), was prepared which differs from pCEV-G4-Km-TEF-AT-hABAB* in that it contains a molecular cloning site between the AT and hABAB sequence.

ABAB secretion was then further optimized by yeast codon optimization (yABAB) at the nucleotide level in the construct having the AT secretion signal, producing plasmid pCEV-G4-Km-TEF-AT-yABAB (SEQ ID NO:84). A sequence containing 40 nucleotides between $P_{TEF}$ and ABAB coding sequence was also found to be dispensable for ABAB secretion and removed resulting in plasmid pCEV-G4-Km-TEF-X40-AT-yABAB (SEQ ID NO:85). A further sequence containing two restriction cloning sites between AT and ABAB sequence was found to negatively impact ABAB secretion and therefore this sequence was also omitted (plasmid pCEV-G4-Km-TEF-AT-$^{RS}$yABAB; SEQ ID NO:115) for subsequent study to maximize ABAB secretion.

Next, the amount of secretion of the individual monomers was measured and AA6 was found to be secreted the least. To improve AA6 secretion, and thus further optimize ABAB secretion, a panel of key amino acid residues was utilized. A T83N mutation was found to improve AA6 secretion. In addition, *S. boulardii* carrying the hAA6 sequence was found to secrete more AA6 than the one carrying the yeast optimized yAA6 sequence. Therefore, a comparison was undertaken between ABAB carrying the T83N mutation within AA6 (AT-yABAB T83N; plasmid pCEV-G4-Km-TEF-AT-yABAB AA6T83N; SEQ ID NO:116) and ABAB where the yAA6 sequence was replaced by the hAA6 T83N sequence (AT-yABAB hAA6 T83N; plasmid pCEV-G4-Km-TEF-AT-yABAB hAA6T83N, which has the sequence of SEQ ID NO:90 but lacks the coding sequence for c-Myc)) to determined which sequence exhibited better secretion. It was found that there was no significance difference between these constructs and AT-yABAB hAA6 T83N was concluded as the final sequence moving forward. The nucleotide sequence encoding AT-yABAB hAA6 T83N is provided in plasmid pCEV-G4-Km-TEF-AT-yABAB hAA6T83N-tagless (SEQ ID NO:90). The amino acid sequence of AT-yABAB hAA6 T83N is provided in SEQ ID NO: 117.

Generation of an Auxotrophic *S. boulardii* Strain

The expression plasmid encoding ABAB can be cloned into the *S. boulardii* strain. The *S. boulardii* strain can tolerate normal body temperature and acidic conditions better than *S. cerevisiae*, which can improve efficacy as a novel oral yeast-based therapeutic strategy. Two modifications to a wild-type *S. boulardii* strain can be made to preserve the in vivo stability of the expression plasmid conferred by the yeast URA3 metabolic selection marker: 1) a diploid auxotrophic mutant carrying a deletion in both chromosomal alleles of URA3 can be constructed, and 2) the endogenous 2 micron circle can be cured from *S. boulardii* to prevent unintended recombination from interfering with ABAB expression.

The most straightforward and efficient method for constructing auxotrophic mutants in wild-type *Saccharomyces* strains involves targeted deletion of chromosomally encoded genes by homologous recombination, which occurs at very high frequencies in *Saccharomyces*. Complete deletion of the targeted gene is preferred over selection of spontaneous mutations which can revert back to the wild type. Thus a gene deletion is preferred for the haploid state in *S. cerevisiae* which is typically induced from wild-type diploid via sporulation using a nutritionally poor growth medium and incubating at low temperature (30° C.). However, *S. boulardii* is sporulation deficient and recalcitrant to formation of haploid cells under normal sporulation conditions [64,65]. A two-step process for deletion of both chromosomal gene alleles (e.g. URA3) was used in which each deletion step can be selected for. The process is outlined schematically in FIG. 16.

All chromosomal deletions were carried out by lithium acetate-facilitated genetic transformation [73] of linear DNA deletion cassettes. Lithium acetate-based transformation originated from a *S. cerevisiae* protocol and was found to be compatible with *S. boulardii* although *S. boulardii* was found to be much harder to transform [55,56]. The difference is around 100 fold. Transformation efficiency in *S. cerevisiae* can be improved by adjusting glucose concentration and heat shock time [74]. Therefore various glucose concentrations and heat shock times were incorporated in *S. boulardii* transformation for optimization. The best condition tested for *S. boulardii* was 2% glucose in preculture and 20 minutes of heat shock time at 42° C. and these conditions were used for all transformation procedures in all studies.

Figure 16:
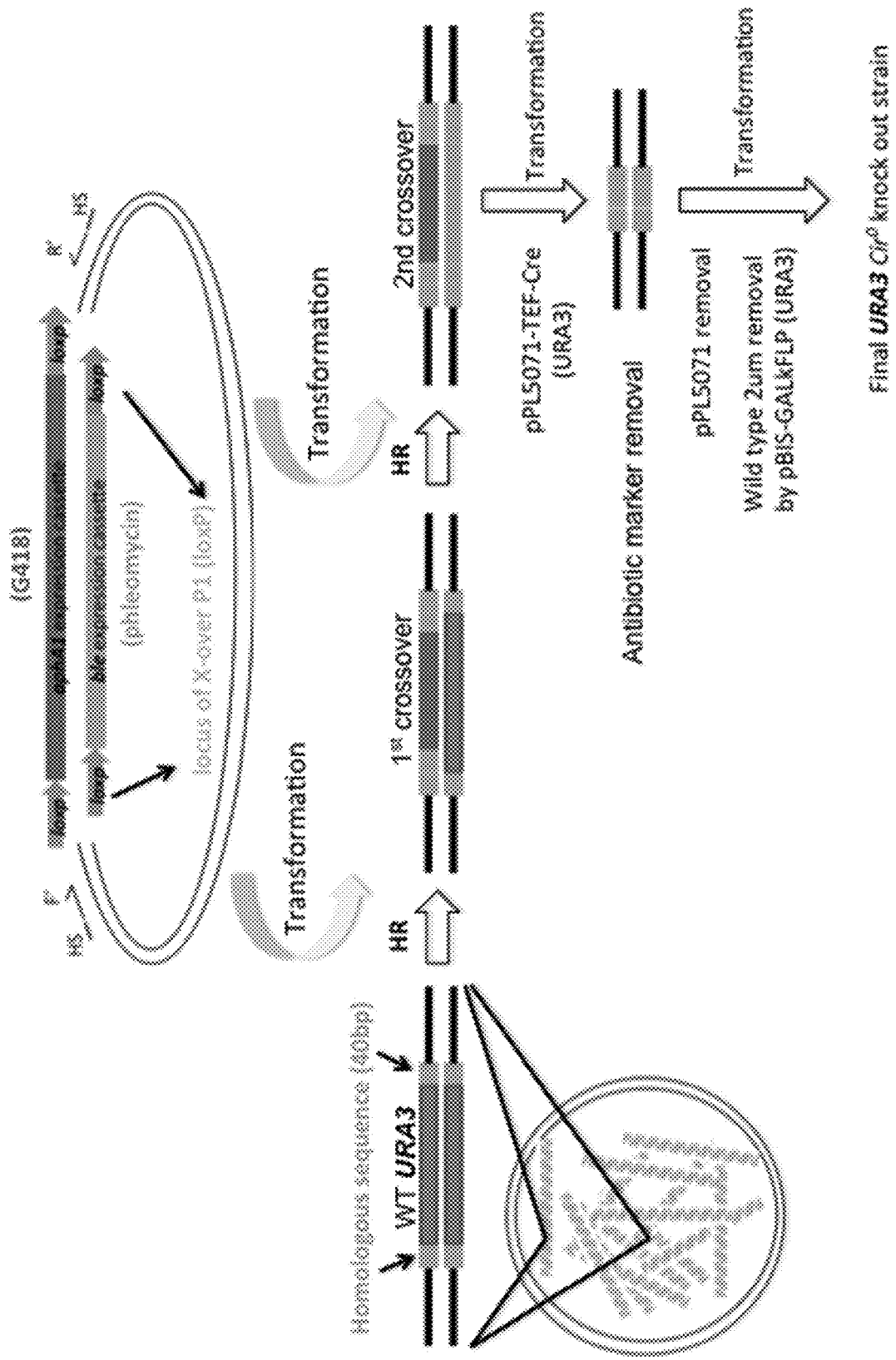
FIG. 16. A diagram of targeted deletion of chromosomally encoded genes by homologous recombination in *S. boulardii*.

Two deletion cassettes containing the genes aphA1 and ble, which confer resistance to G418 and phleomycin in yeast respectively, were generated by PCR using pCEV-G4-Km (SEQ ID NO:80) and pCEV-G4-Ph (SEQ ID NO:86) (a gift from Lars Nielsen & Claudia Vickers (Addgene plasmid #46820)) as templates. Both deletion cassettes are flanked by two locus of X-over P1 (loxP) in the same direction, allowing for antibiotic resistance genes spin out using Cre-recombinase. 40 base pairs of homologous sequences upstream of URA3 promoter ($P_{URA3}$) and downstream of the stop codon of URA3 were incorporated in PCR primers to generate two final deletion cassettes for site-specific gene deletion in *S. boulardii* (see FIG. 16). The exact sequence and location of URA3 gene on chromosome V on *S. boulardii* was mapped using URA3 gene annotation from online-published sequence from *Saccharomyces* genome database (SGD). Selection for crossover 1 replacing the first URA3 allele with aphA1 deletion cassette is selected for using resistance to G418 [66]; the second crossover replacing the second URA3 allele with ble deletion cassette is selected for using resistance to phleomycin [75] (FIG. 16). The replacement of both URA3 alleles with aphA1 and ble deletion cassettes was evidenced by resistance to both antibiotics (data not shown) as well as lack of growth on minimal synthetic medium plates lacking uracil (data not shown). Yeast phenotype was also confirmed by growth on Sabouraud plate with chloramphenicol (100 ug/ml) (data not shown). In addition, three sets of unique primers targeting the URA3, aphA1 or ble genes in the URA3 chromosomal region was designed and performed PCR using wild type (WT), URA3Δ::aphA1/URA3 ($1^{st}$ crossover) and URA3Δ::aphA1/Δ::ble ($2^{nd}$ crossover) genomic DNA as templates. Expected PCR product sizes targeting the URA3, aphA1 or ble genes in the URA3 chromosomal region are 766 bp, 1183 bp, and 662 bp respectively. DNA electrophoresis of PCR products from WT, $1^{st}$ crossover and $2^{nd}$ crossover clones using these three sets of unique primers confirmed the absence of URA3 alleles and integration of the aphA1 and ble deletion cassettes of the $2^{nd}$ crossover strain.

The $2^{nd}$ crossover strain was then transformed with pPL5071_TEF1-Cre_URA3 (pPL5071; SEQ ID NO:95) [76] to remove the aphA1 and ble deletion cassettes. Strain carries pPL5071 expresses Cre recombinase constitutively under $P_{TEF}$. Cre recombinase then targets loxp sequences flanking the aphA1 and ble deletion cassettes; this causes the excision of the aphA1 and ble deletion cassettes, leaving only one loxp site in the URA3 chromosomal region. Strains that underwent successful excision of the aphA1 and ble deletion cassettes cannot grow in the presence of either G418 or phleomycin; yet retain the loss of both URA3 alleles, therefore can only grow on minimal synthetic medium plate in the presence of uracil and showed no growth on minimal synthetic medium plate without uracil supplement.

Removal of pPL5071 was achieved by growth in YPD and selecting for colonies later grown on minimal synthetic medium containing uracil and the pyrimidine analog 5-fluoro-orotic acid (5-FOA) [77]. Strains possessing pPL5071 carry the URA3 gene that can synthesize the toxic intermediate 5-fluorodeoxyuridine a potent inhibitor of thymidylate synthetase, which interrupts DNA synthesis and leads to cell death and allows selection of strains that have lost pPL5071. The absence of pPL5071 also was confirmed by pPL5071 specific primers by PCR and DNA electrophoresis of the PCR product.

The 2 um plasmid is a very stable 6.1 kb plasmid that is ubiquitous in *Saccharomyces* strains. This plasmid confers no selective advantage to the yeast host organism, and it is remarkably stable due to the presence of an efficient REP1-REP2-STB plasmid partitioning system [68]. *S. boulardii* strains used also contain this plasmid as confirmed via PCR. To remove the 2 um plasmid, pBIS-GALkFLP-URA3 (SEQ ID NO:87) [67] was used to cure 2 um plasmid, followed by removal with uracil and 5-FOA. Loss of the 2 um plasmid was confirmed by PCR using primers specific for the origin of replication.

The auxotrophic strain of *S. boulardii* that results from these manipulations is termed *S. boulardii* URA3 Δ/Δ.

Auxotrophic *S. boulardii* Strain for In Situ Delivery of ABAB

For constructing the auxotrophic *S. boulardii* strain for in situ delivery of ABAB, the aphA1 cassette of the plasmid pCEV-G4-Km-TEF-X40-AT-yABAB (SEQ ID NO:85) was replaced by the URA3 cassette from pD plasmid to generate the plasmid pCEV-URA3-TEF-AT-yABAB-cMyc (SEQ ID NO:88). This plasmid was then used to transform *S. boulardii* URA3 Δ/Δ. The resulting strain secretes fully functional ABAB when compared with purified ABAB in a cell toxicity assay (FIG. 17C). Western blotting showed the corresponding ABAB band from *S. boulardii* culture supernatant using α-Llama antibodies conjugated with HRP (FIG. 17D). C-terminus end of ABAB contains c-Myc tag and can be further pulled down by α-c-Myc antibodies (FIG. 17D).

Figure 17A:
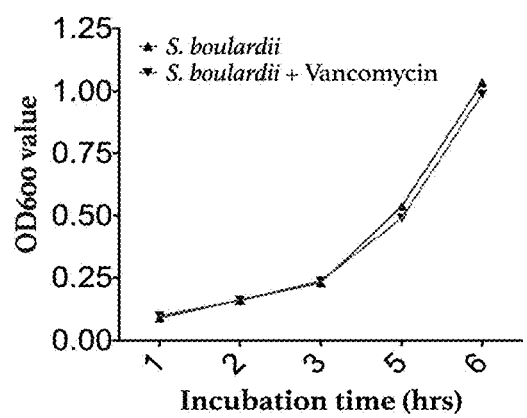
FIGS. 17A-17D. *S. boulardii* URA3Δ/Δ expressing ABAB.
Figure 17B:
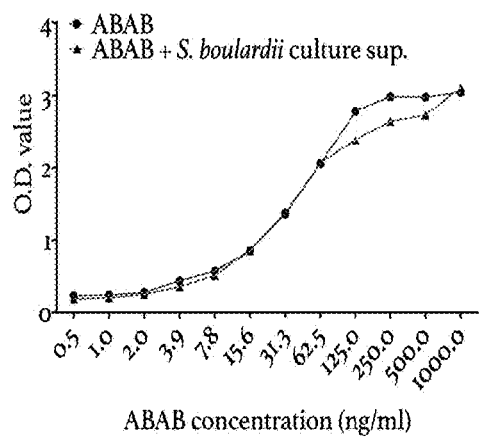
Figure 17C:
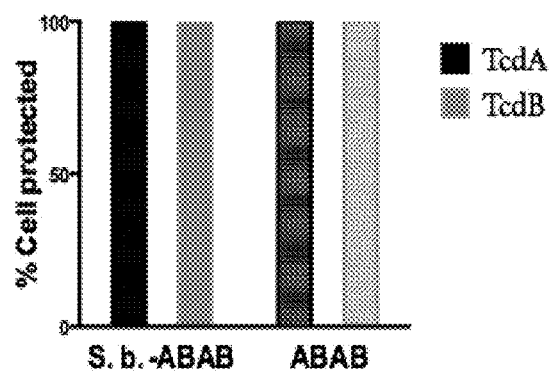
Figure 17D:
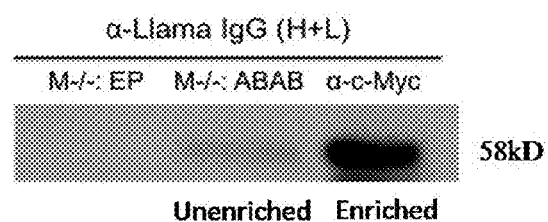

For empty plasmid (EP) control, AT-yABAB sequence was later removed from pCEV-URA3-TEF-AT-yABAB-cMyc (SEQ ID NO:88) to generate pCEV-URA3-TEF-cMyc (SEQ ID NO:89). *S. boulardii* URA3 Δ/Δ strain transformed with this plasmid results a strain complemented with URA3 but does not secrete ABAB. *S. boulardii* URA3 Δ/Δ strain secreting ABAB also showed no growth inhibition when cultured in YPD containing vancomycin (1 mg/ml) (FIG. 17A). This suggests *S. boulardii* can be co-administered with vancomycin typically used to treat CDI patients and secretes ABAB to treat ongoing CDI. In addition, purified ABAB is stable in culture supernatant collected from *S. boulardii* at O.D. 10 over 2 hours period of time suggests secreted ABAB is likely to diffuse out from *S. boulardii* without being degraded.

Safety Assessment of *S. boulardii* Delivered Orally to Antibiotic-Treated Mice

Prior to evaluating whether *S. boulardii* URA3 Δ/Δ expressing ABAB can protect mice in CDI models [20,33, 62,78], a safety assessment was performed to determine safe doses of *S. boulardii* in antibiotic-treated mice. In this safety assessment mice were first supplied with an antibiotic cocktail in their daily drinking water for three days and then switched to regular water. One day before oral delivery of *S. boulardii*, mice were injected with clindamycin intraperitoneally. This completes the antibiotic treatment for the mice and *S. boulardii* was then orally delivered to the mice for safety assessment, which includes monitoring of daily weight change and persistence of *S. boulardii* in their stool samples of these antibiotic-treated mice. Mice exhibited no signs of illness and steadily weight increase during 6 days of monitoring when $10^{10}$ cells of *S. boulardii* were delivered orally consistent with the idea of *S. boulardii* as a GRAS organism. For the subsequent CDI mouse studies, however, only $10^9$ cells of *S. boulardii* were given due to the ease of pellet resuspension and less variability of the dosing amount to the mice, which can occur with high viscosity present in resuspension. *S. boulardii* also shows limited colonization in these antibiotic-treated mice GI tracts; three days after the final gavage, no detectable *S. boulardii* were recovered from Sabouroud plate (data not shown).

Protection of *S. boulardii* Expressing ABAB Against Primary CDI in Mice

Figure 18A:
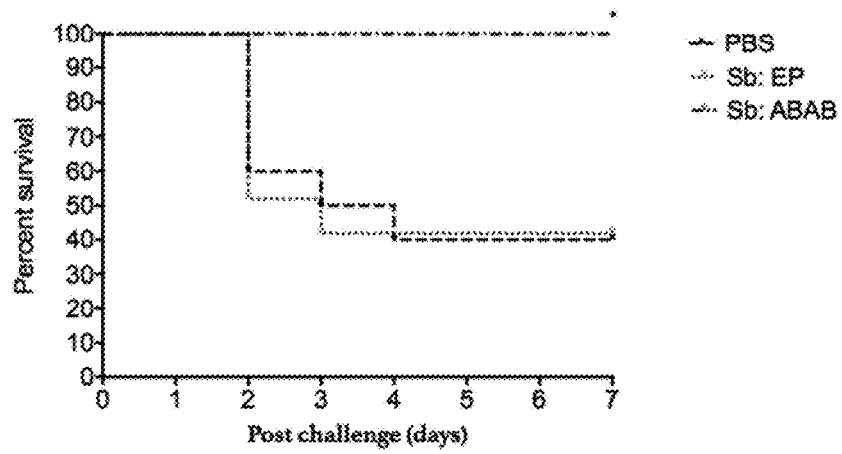
FIGS. 18A-18C. Protection of *S. boulardii* expressing ABAB in CDI prevention in mice.
Figure 18B:
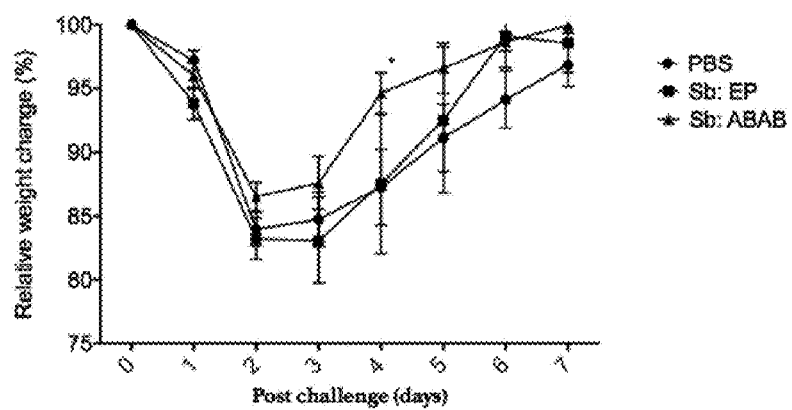
Figure 18C:
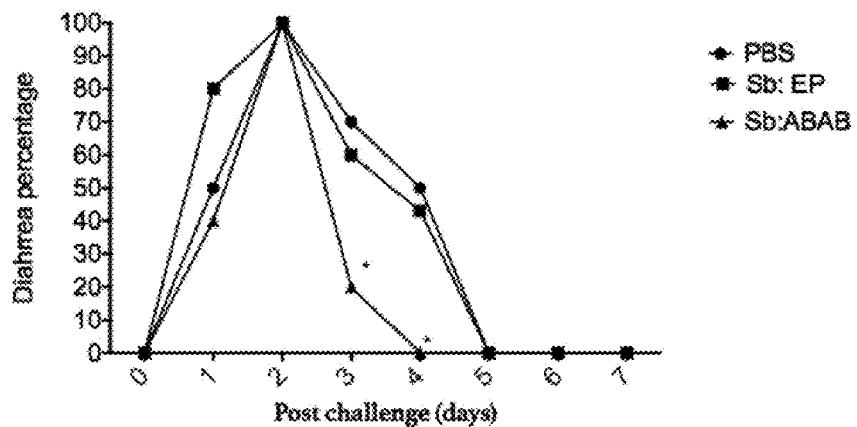
Figure 19A:
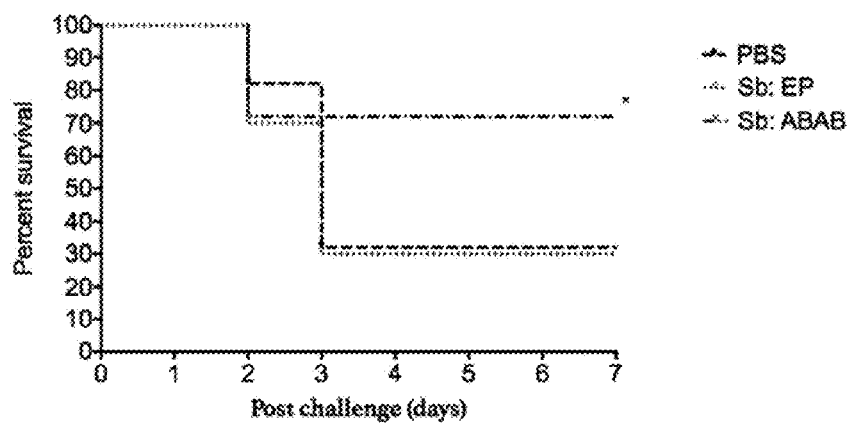
FIGS. 19A-19C. Protection of *S. boulardii* expressing ABAB in treating CDI mice.
Figure 19B:
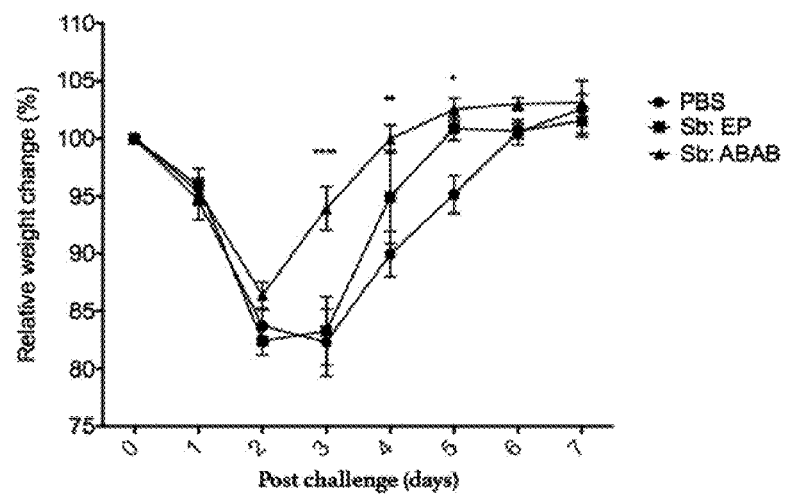
Figure 19C:
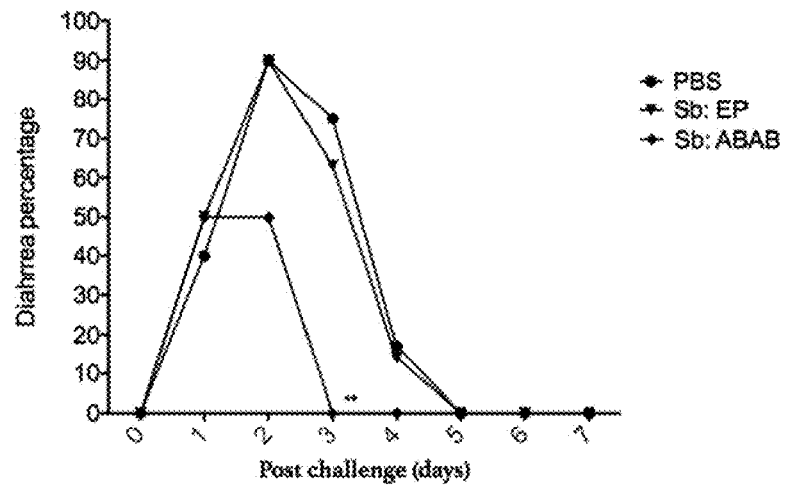

Protection of *S. boulardii* expressing ABAB was evaluated using established primary mouse CDI models. *S. boulardii* expressing ABAB was delivered either as preventative or treatment against primary CDI in mice. In brief, primary CDI was established in mice by supplementing a mixture of antibiotic into their drinking water for three days, and then intraperitoneal injection of clindamycin 24 hours prior to *C. difficile* spore challenge. $10^5$ *C. difficile* spores (UK1, a 027/BI/NAP1 epidemic strain) were gavaged in the mice to induce CDI. For preventative evaluation, mice started receiving an oral dose of *S. boulardii* the day after switching to regular drinking water, which continued every day for 7 days. For therapeutic evaluation, mice received an oral dose of *S. boulardii* at 6, 24, 48, and 72 hours after spore challenge. Controls included PBS and *S. boulardii* transformed with an empty plasmid. In both methods, mice receiving S. boulardii expressing ABAB were significantly protected against CDI-induced deaths (FIGS. 18A and 19A; PBS: negative control; Sb:EP: S. boulardii transformed with an empty plasmid; Sb:BAB: S. boulardii secreting ABAB). CDI mice typically suffered weight loss with most weight drops around day 2 to day 3 due to diarrhea and gradually recovered. Weights of mice receiving S. boulardii expressing ABAB recovered significantly sooner (FIGS. 18B and 19B) and had significant reduced percentage of diarrhea incidents after day 2 post challenge (FIGS. 18C and 19C).

Protection of S. boulardii Expressing ABAB Against Recurrence CDI in Mice

Figure 20A:
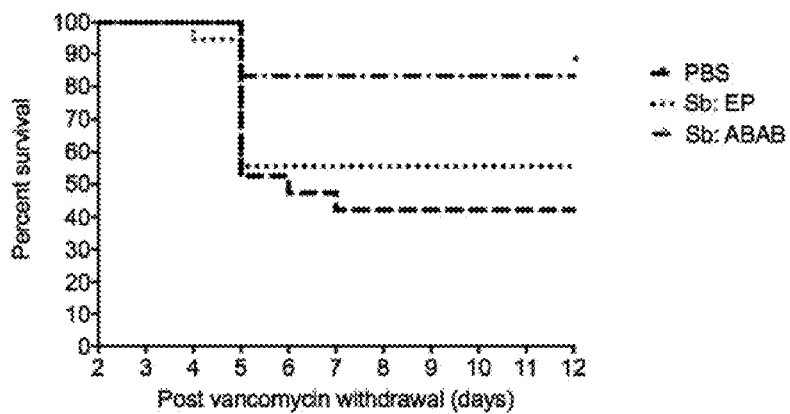
FIGS. 20A-20C. Protection of *S. boulardii* expressing ABAB in CDI recurrent mice.
Figure 20B:
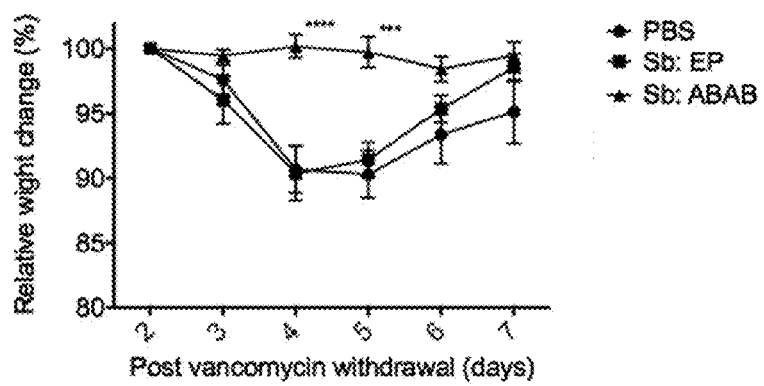
Figure 20C:
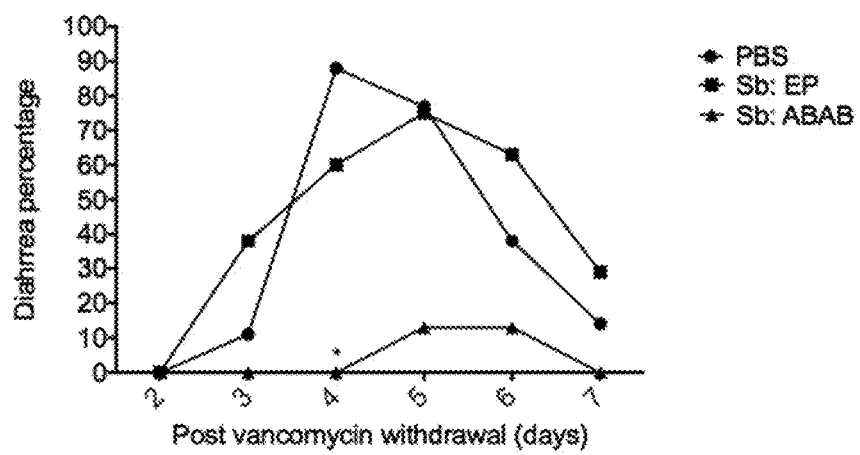

Protection of S. boulardii expressing ABAB was evaluated against recurrence CDI in mice. To induce recurrent CDI, mice were given three days of antibiotic cocktail in their daily drinking water. After three days of antibiotic water, mice were then switched back to drinking regular water. One day before oral delivery of $10^5$ C. difficile spores (UK1, a 027/BI/NAP1 epidemic strain), mice were injected with clindamycin intraperitoneally. Six hours after spore challenge, regular water was changed to water containing 0.5 mg/ml of vancomycin for six days and regular water was switched back again for the rest of study. Mice typically develop signs of CDI after 4 days of vancomycin withdrawal without another C. difficile spore challenge. During the course of recurrence model, S. boulardii was orally delivered along with vancomycin water once every day for 12 days. This model is used to evaluate protection efficacy of S. boulardii expressing ABAB for preventing CDI recurrence in mice. Survival rate, weight loss and diarrhea incident of these mice were monitored on a daily basis. Controls included PBS and S. boulardii transformed with an empty plasmid. Mice receiving S. boulardii expressing ABAB were significantly protected against recurrence-induced CDI deaths (FIG. 20A; PBS: negative control; Sb:EP: S. boulardii transformed with an empty plasmid; Sb:BAB: S. boulardii secreting ABAB). Similar to primary CDI mice, recurrent CDI mice also typically suffered weight loss with most weight drops around day 4 to day 5 after vancomycin water withdrawal. Mice receiving S. boulardii expressing ABAB were significantly protected from weight loss (FIG. 20B) and had significant reduced percentage of diarrhea recurrence incidents (FIG. 20C).

Stability Optimization of ABAB Cassette Through Chromosomal Integration

Genome editing using a CRISPR-Cas9 based system has been recently demonstrated both in S. cerevisiae and S. boulardii [79-81]. In addition, large fragment deletion can be achieved by targeting two guide sequences simultaneously [82]. Foreign genes are typically more steadily maintained when integrated into chromosomes versus introduced via plasmids when there is no selection pressure. However, chromosomal integration often requires multiple rounds of integration to achieve high copies. A protocol reported in a recent publication overcame this hurdle through targeting multiple copies of common sequences such as δ sites in S. cerevisiae genome through CRISPR-induced double stain breaks and achieved concurrent integration of large fragments in these sites [83]. DNA double strain break can be repaired either by non-homologous end joining or homologous recombination; however, when endogenous homologous sequences are present, host preferentially uses homologous sequences to repair DNA double strain break by homologous recombination [83].

δ sites are long terminal repeats (LTRs) belong to the Ty element I and II and are the most abundant LTRs in S. cerevisiae. There are five types of Ty elements (1-5) represented by the class II transposon (retrotransposon) that is more commonly found in S. cerevisiae. It is estimated that there are about 51 retrotransposons (Ty1-5) and 251 δ sites across S. cerevisiae genomes [84]. Such δ sites are appealing target sequences for ABAB expression cassette integration into S. boulardii chromosomes. However, much less is known about δ sites in S. boulardii. Therefore, Ty1-H3 (Genbank accession no. M18706) [84] was first used as a probe to survey Ty1-2 elements in S. boulardii strain MYA796 (ATCC, Manassas, VA) (draft genome obtained from NCBI) to identify possible Ty1-2 elements and their δ sites in the S. boulardii genome. Surprisingly, no full Ty1-2 elements were found in MYA796. A total of 57 δ sites were found; this includes 44 full δ sites and 12 partial sites as well as a partial Ty element containing 1 full δ site identified across all 16 chromosomes (Table 12).

TABLE 12

Number of δ sites and their distribution on MYA796 chromosomes

|  | Full δ site | Full Ty1, 2 elements | Partial δ site 60 < X < 200 bp | Partial Ty1, 2 element with full δ site |
|---|---|---|---|---|
| Ch I | 0 | 0 | 1 | 0 |
| Ch II | 0 | 0 | 0 | 0 |
| Ch III | 1 | 0 | 0 | 0 |
| Ch IV | 5 | 0 | 1 | 1 |
| Ch V | 2 | 0 | 1 | 0 |
| Ch VI | 2 | 0 | 0 | 0 |
| Ch VII | 8 | 0 | 1 | 0 |
| Ch VIII | 2 | 0 | 0 | 0 |
| Ch IX | 3 | 0 | 0 | 0 |
| Ch X | 3 | 0 | 1 | 0 |
| Ch XI | 0 | 0 | 0 | 0 |
| Ch XII | 8 | 0 | 1 | 0 |
| Ch XIII | 2 | 0 | 1 | 0 |
| Ch XIV | 1 | 0 | 0 | 0 |
| Ch XV | 2 | 0 | 4 | 0 |
| Ch XVI | 5 | 0 | 1 | 0 |
| Total | 44 | 0 | 12 | 1 |

Figure 21:
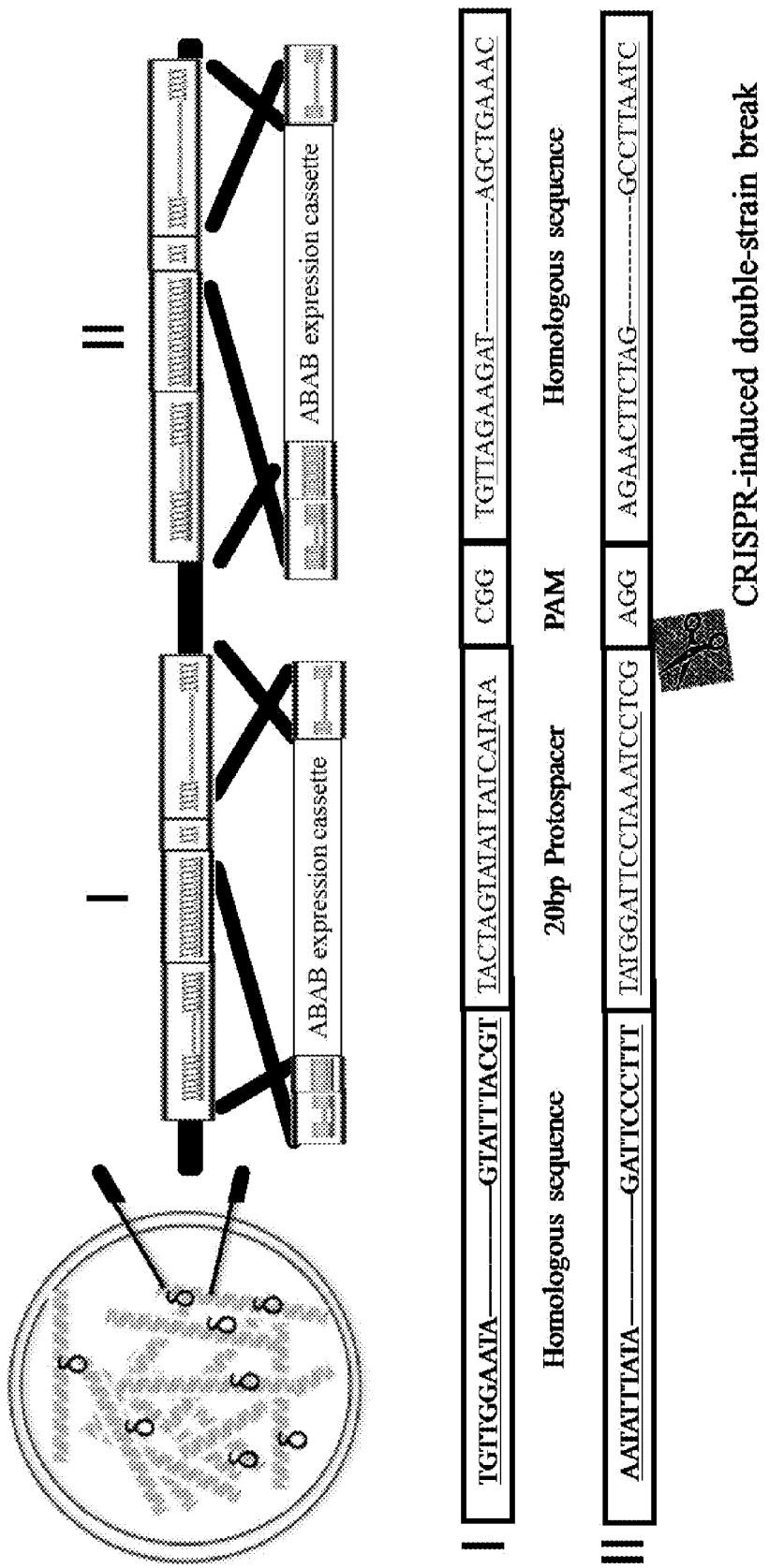
FIG. 21. A diagram of δ site-targeted chromosomal integration using CRISPR. Ty1-H3 (Genbank accession no. M18706) was used to blast against draft genome of MYA796 to obtain δ site sequences. Compiled sequences were used to identify common protospacer adjacent motif (PAM) sites and protospacers. Two PAM site sequences were chosen based on best coverage for multiple sites and common homologous sequences located upstream and downstream of the protospacer and PAM sites for simple integration of ABAB expression cassette. PAM site "I" is provided in SEQ ID NO:93; PAM site "II" is provided in SEQ ID NO:94. Homologous recombination sequences used in primers to generate ABAB expression cassette by PCR are underlined.

Due to S. boulardii diploid state; there are about 114 δ sites across the S. boulardii genome. To allow simple multiple δ site targeting by CRISPR, all 57 δ site sequences were compiled for multiple sequence alignment using MUSCLE to identify protospacer adjacent motif (PAM) sites that present in high numbers among the 57 δ sequences. Two PAM sites were chosen based on the highest number of δ sequences having uniformity in protospacers as the upstream and downstream sequences. The sequences of these PAM sites are illustrated in FIG. 21 and the specific sequences are as follows:

PAM Site I
(SEQ ID NO: 93)
TGTTGGAATAAAAATCAACTATCATCTACTAACTAGTATTTACGTTACTA

GTATATTATCATATACGGTGTTAGAAGATGACGCAAATGATGAGAAATAG

TCATCTAAATTAGTGGAAGCTGAAAC

PAM Site II
(SEQ ID NO: 94)
AATATTTATAGAATTGTGTAGAATTGCAGATTCCCTTTTATGGATTCCTA

AATCCTCGAGGAGAACTTCTAGTATATCTACATACCTAATATTATAGCCT

TAATC.

In both Pam Site I and Pam Site II, the sequences underscored by a dashed line correspond to the upstream homologous sequences; the sequences underscored by a single line correspond to the 20 bp protospacers; the sequences underscored by a double line correspond to the PAM sequences; the sequences underscored by a wavy line correspond to the downstream homologous sequences.

These two PAM sites, accompanied by their common upstream and downstream homologous sequences within the δ sites, allow simple chromosomal integration of ABAB expression cassettes into *S. boulardii* genomes. ABAB integration cassettes containing homologous recombination sequences were generated by PCR using primers containing the upstream homologous sequences with the last three nucleotides removed at the 3' end and the downstream homologous sequences with the first two nucleotides removed at the 5' end and the corresponding annealing sequences needed for PCR using plasmid pCEV-G4-Km-TEF-AT-yABAB hAA6T83N-tagless as template (SEQ ID NO:90).

Figure 22A:
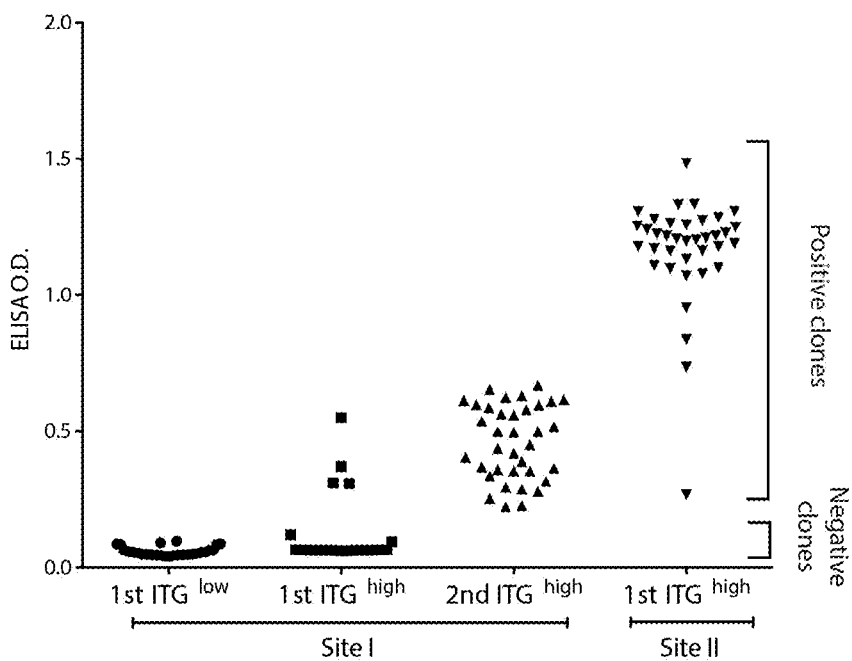
FIGS. 22A-22B. ABAB secretion of *S. boulardii* using CRISPR-based targeting δ site chromosomal integration.
Figure 22B:
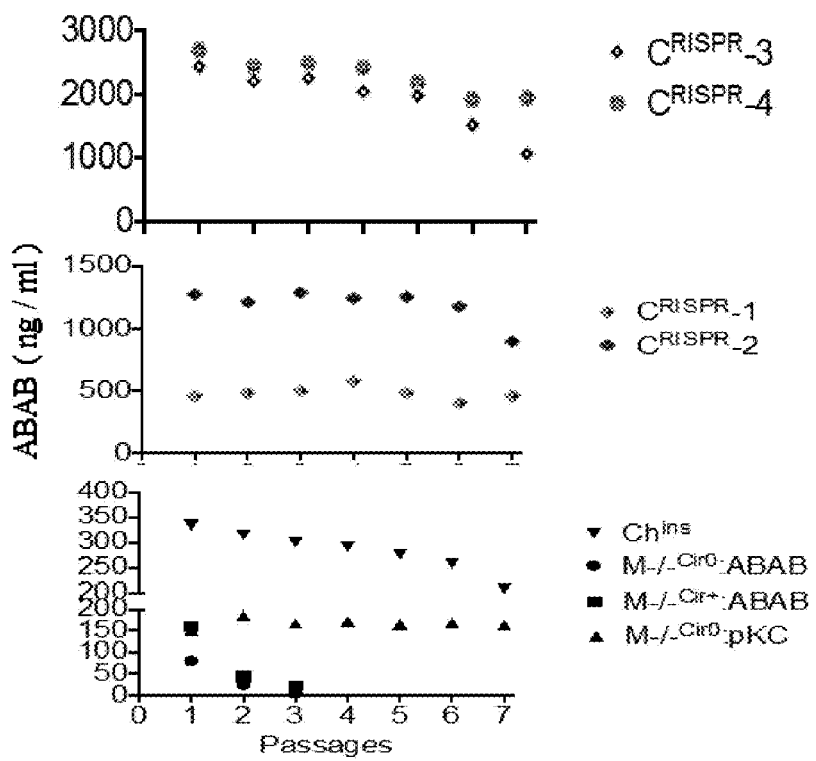
Figure 23A:
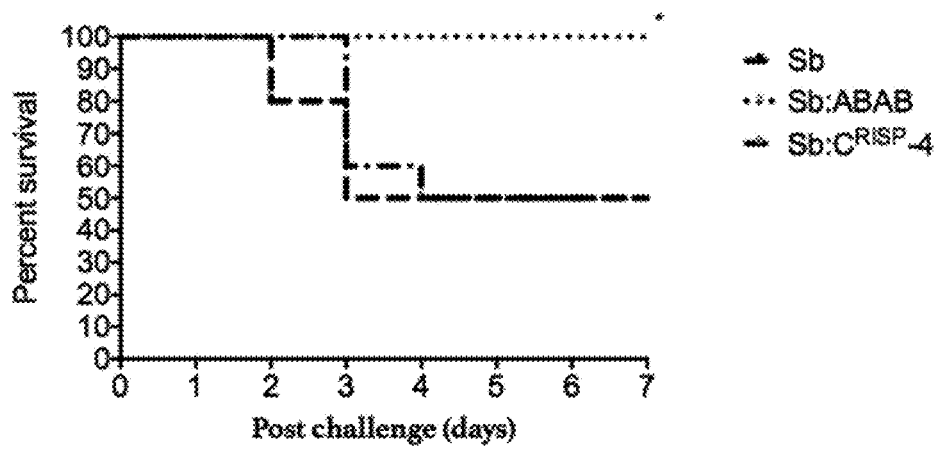
FIGS. 23A-23C. Protection of *S. boulardii* expressing ABAB in treating CDI mice.
Figure 23B:
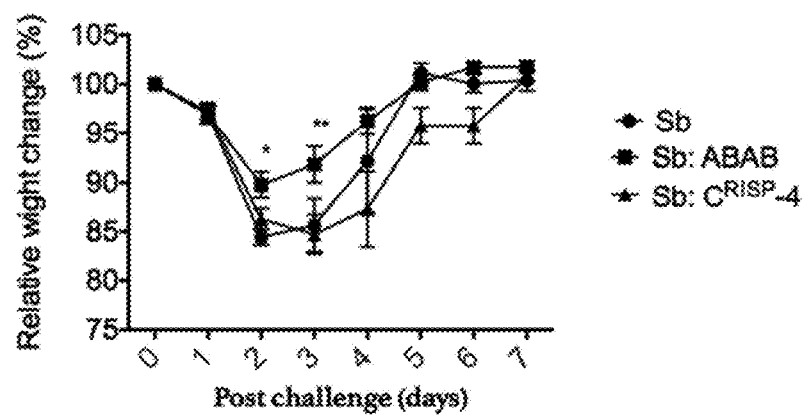
Figure 23C:
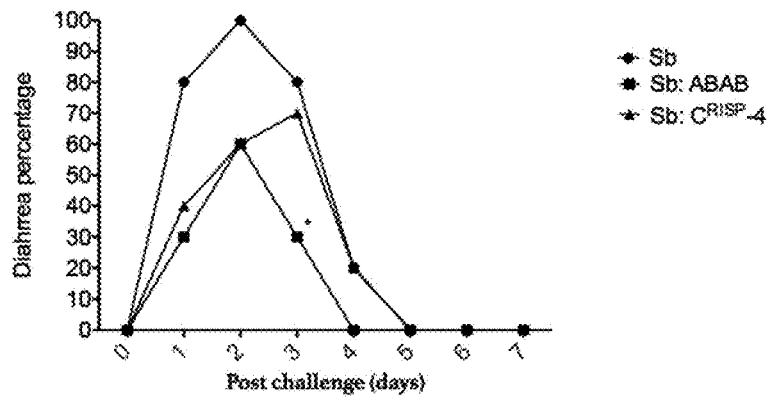

PCR products of the ABAB integration cassette with CRISPR plasmids contain the corresponding guide sequence (pCRI-Sb-δ1 (SEQ ID NO:91) and pCRI-Sb-δ2 (SEQ ID NO:92)) were then cotransformed with *S. bouladii* for ABAB integrations into chromosomes independently and sequentially to target PAM site I and PAM site II. The ratio of PCR product to CRISPR plasmid was found to be important for generating successful integration clones (FIG. 22A; ITG$^{low}$ versus ITG$^{high}$). In addition, a repeat transformation of the highest ABAB secretion clone from ITG$^{high}$ group with the same integration cassette and CRISPR plasmid did not further improve the overall ABAB secretion of independent clones (FIG. 22A; $2^{nd}$ ITG$^{high}$). ABAB secretion of the highest ABAB secretion clone (C$^{RISPR}$-2) from ITG$^{high}$ group was then further improved by cotransforming the second set of ABAB integration cassette containing the homologous recombination sequences and its corresponding guide sequence in CRISPR plasmid targeting site II (FIG. 22A). Two highest ABAB secretion clones, C$^{RISP}$-3 and C$^{RISPR}$-4 were selected. ABAB secretion amount and stability over time of these four representative clones are shown in FIG. 22B. A preliminary mouse CDI study was performed. However, C$^{RISPR}$-4 was found to be not better than previously M-/-:ABAB clone that showed protection in a number of mouse CDI models (FIG. 23).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:
1. Cloud, J. & Kelly, C. P. Update on *Clostridium difficile* associated disease. *Curr Opin Gastroenterol* 23, 4-9 (2007).
2. Kelly, C. P. & LaMont, J. T. *Clostridium difficile*—more difficult than ever. *N Engl J Med* 359, 1932-1940 (2008).
3. Barbut, F., et al. Epidemiology of recurrences or reinfections of *Clostridium difficile*-associated diarrhea. *J Clin Microbiol* 38, 2386-2388 (2000).
4. Hassoun, A. & Ibrahim, F. Use of intravenous immunoglobulin for the treatment of severe *Clostridium difficile* colitis. *Am J Geriatr Pharmacother* 5, 48-51 (2007).
5. Shahani, L. & Koirala, J. Intravenous immunoglobulin in treatment of *Clostridium difficile* colitis. *BMJ Case Rep* 2012(2012).
6. Saito, T., et al. Evidence of intravenous immunoglobulin as a critical supportive therapy against *Clostridium difficile* toxin-mediated lethality in mice. *J Antimicrob Chemother* 66, 1096-1099 (2011).
7. Abougergi, M. S. & Kwon, J. H. Intravenous immunoglobulin for the treatment of *Clostridium difficile* infection: a review. *Dig Dis Sci* 56, 19-26 (2011).
8. Sokol, H., Maury, E., Seksik, P., Cosnes, J. & Beaugerie, L. Single immunoglobulin infusion can reverse hemodynamic failure associated with severe *Clostridium difficile* colitis. *Am J Gastroenterol* 104, 2649-2650 (2009).
9. Lowy, I., et al. Treatment with monoclonal antibodies against *Clostridium difficile* toxins. *N Engl J Med* 362, 197-205 (2010).
10. Louie, T. J., et al. Fidaxomicin versus vancomycin for *Clostridium difficile* infection. *The New England journal of medicine* 364, 422-431 (2011).
11. Rao, K. & Young, V. B. Fecal Microbiota Transplantation for the Management of *Clostridium difficile* Infection. *Infectious disease clinics of North America* 29, 109-122 (2015).
12. Vyas, D., Aekka, A. & Vyas, A. Fecal transplant policy and legislation. *World journal of gastroenterology: WJG* 21, 6-11 (2015).
13. Tonna, I. & Welsby, P. D. Pathogenesis and treatment of *Clostridium difficile* infection. *Postgrad Med J* 81, 367-369 (2005).
14. McFarland, L. V., Elmer, G. W. & Surawicz, C. M. Breaking the cycle: treatment strategies for 163 cases of recurrent *Clostridium difficile* disease. *The American journal of gastroenterology* 97, 1769-1775 (2002).
15. O'Neill, G. L., Beaman, M. H. & Riley, T. V. Relapse versus reinfection with *Clostridium difficile*. *Epidemiol Infect* 107, 627-635 (1991).
16. Wilcox, M. H., Fawley, W. N., Settle, C. D. & Davidson, A. Recurrence of symptoms in *Clostridium difficile* infection—relapse or reinfection? *J Hosp Infect* 38, 93-100 (1998).
17. Johnson, S., Adelmann, A., Clabots, C. R., Peterson, L. R. & Gerding, D. N. Recurrences of *Clostridium difficile* diarrhea not caused by the original infecting organism. *J Infect Dis* 159, 340-343 (1989).
18. Tang-Feldman, Y., Mayo, S., Silva Jr, J., Jr. & Cohen, S. H. Molecular analysis of *Clostridium difficile* strains isolated from 18 cases of recurrent *Clostridium difficile*-associated diarrhea. *J Clin Microbiol* 41, 3413-3414 (2003).
19. Johnson, S. Recurrent *Clostridium difficile* infection: causality and therapeutic approaches. *Int J Antimicrob Agents* 33 Suppl 1, S33-36 (2009).
20. Sun, X., et al. Mouse relapse model of *Clostridium difficile* infection. *Infection and immunity* 79, 2856-2864 (2011).
21. Seal, D., et al. Treatment of relapsing *Clostridium difficile* diarrhoea by administration of a non-toxigenic strain. *Eur J Clin Microbiol* 6, 51-53 (1987).
22. Kuehne, S. A., et al. The role of toxin A and toxin B in *Clostridium difficile* infection. *Nature* (2010).

23. Lyras, D., et al. Toxin B is essential for virulence of *Clostridium difficile*. *Nature* 458, 1176-1179 (2009).
24. Libby, J. M. & Wilkins, T. D. Production of antitoxins to two toxins of *Clostridium difficile* and immunological comparison of the toxins by cross-neutralization studies. *Infection and immunity* 35, 374-376 (1982).
25. Katchar, K., et al. Association between IgG2 and IgG3 subclass responses to toxin A and recurrent *Clostridium difficile*-associated disease. *Clinical gastroenterology and hepatology: the official clinical practice journal of the American Gastroenterological Association* 5, 707-713 (2007).
26. Ghose, C., et al. Transcutaneous immunization with *Clostridium difficile* toxoid A induces systemic and mucosal immune responses and toxin A-neutralizing antibodies in mice. *Infection and immunity* 75, 2826-2832 (2007).
27. Sougioultzis, S., et al. *Clostridium difficile* toxoid vaccine in recurrent *C. difficile*-associated diarrhea. *Gastroenterology* 128, 764-770 (2005).
28. Kyne, L., Warny, M., Qamar, A. & Kelly, C. P. Association between antibody response to toxin A and protection against recurrent *Clostridium difficile* diarrhoea. *Lancet* 357, 189-193 (2001).
29. Leav, B. A., et al. Serum anti-toxin B antibody correlates with protection from recurrent *Clostridium difficile* infection (CDI). *Vaccine* 28, 965-969 (2010).
30. Fernie, D. S., Thomson, R. O., Batty, I. & Walker, P. D. Active and passive immunization to protect against antibiotic associated caecitis in hamsters. *Dev Biol Stand* 53, 325-332 (1983).
31. Kim, P. H., Iaconis, J. P. & Rolfe, R. D. Immunization of adult hamsters against *Clostridium difficile*-associated ileocecitis and transfer of protection to infant hamsters. *Infection and immunity* 55, 2984-2992 (1987).
32. Lyerly, D. M., Bostwick, E. F., Binion, S. B. & Wilkins, T. D. Passive immunization of hamsters against disease caused by *Clostridium difficile* by use of bovine immunoglobulin G concentrate. *Infection and immunity* 59, 2215-2218 (1991).
33. Wang, H., et al. A chimeric toxin vaccine protects against primary and recurrent *Clostridium difficile* infection. *Infection and immunity* 80, 2678-2688 (2012).
34. Hamers-Casterman, C., et al. Naturally occurring antibodies devoid of light chains. *Nature* 363, 446-448 (1993).
35. van der Linden, R., et al. Induction of immune responses and molecular cloning of the heavy chain antibody repertoire of *Lama glama*. *J Immunol Methods* 240, 185-195 (2000).
36. Harmsen, M. M. & De Haard, H. J. Properties, production, and applications of camelid single-domain antibody fragments. *Appl Microbiol Biotechnol* 77, 13-22 (2007).
37. Arbabi Ghahroudi, M., Desmyter, A., Wyns, L., Hamers, R. & Muyldermans, S. Selection and identification of single domain antibody fragments from camel heavy-chain antibodies. *FEBS Lett* 414, 521-526 (1997).
38. van der Linden, R. H., et al. Comparison of physical chemical properties of llama $V_HH$ antibody fragments and mouse monoclonal antibodies. *Biochim Biophys Acta* 1431, 37-46 (1999).
39. Dumoulin, M., et al. Single-domain antibody fragments with high conformational stability. *Protein Sci* 11, 500-515 (2002).
40. Hussack, G., Hirama, T., Ding, W., Mackenzie, R. & Tanha, J. Engineered single-domain antibodies with high protease resistance and thermal stability. *PloS one* 6, e28218 (2011).
41. Yang, Z., et al. A novel multivalent, single-domain antibody targeting TcdA and TcdB prevents fulminant *Clostridium difficile* infection in mice. *The Journal of infectious diseases* 210, 964-972 (2014).
42. McFarland, L. V. Systematic review and meta-analysis of *Saccharomyces boulardii* in adult patients. *World J. Gastroenterol.* 16, 2202-2222 (2010).
43. Elmer, G. W., McFarland, L. V., Surawicz, C. M., Danko, L. & Greenberg, R. N. Behaviour of *Saccharomyces boulardii* in recurrent *Clostridium difficile* disease patients. *Aliment. Pharmacol. Ther.* 13, 1663-1668 (1999).
44. Surawicz, C. M., et al. The search for a better treatment for recurrent *Clostridium difficile* disease: use of high-dose vancomycin combined with *Saccharomyces boulardii*. *Clin. Infect. Dis.* 31, 1012-1017 (2000).
45. McFarland, L. V., et al. A randomized placebo-controlled trial of *Saccharomyces boulardii* in combination with standard antibiotics for *Clostridium difficile* disease. *Jama* 271, 1913-1918 (1994).
46. Czerucka, D., Piche, T. & Rampal, P. Review article: yeast as probiotics—*Saccharomyces boulardii*. *Alimentary pharmacology & therapeutics* 26, 767-778 (2007).
47. Sougioultzis, S., et al. *Saccharomyces boulardii* produces a soluble anti-inflammatory factor that inhibits NF-kappaB-mediated IL-8 gene expression. *Biochemical and biophysical research communications* 343, 69-76 (2006).
48. Qamar, A., et al. *Saccharomyces boulardii* stimulates intestinal immunoglobulin A immune response to *Clostridium difficile* toxin A in mice. *Infection and immunity* 69, 2762-2765 (2001).
49. Chen, X., et al. *Saccharomyces boulardii* inhibits ERK1/2 mitogen-activated protein kinase activation both in vitro and in vivo and protects against *Clostridium difficile* toxin A-induced enteritis. *The Journal of biological chemistry* 281, 24449-24454 (2006).
50. Barc, M. C., et al. Molecular analysis of the digestive microbiota in a gnotobiotic mouse model during antibiotic treatment: Influence of *Saccharomyces boulardii*. *Anaerobe* 14, 229-233 (2008).
51. Gorlani, A., de Haard, H. & Verrips, T. Expression of VHHs in *Saccharomyces cerevisiae*. *Methods in molecular biology* 911, 277-286 (2012).
52. Khatri, I., et al. Gleaning evolutionary insights from the genome sequence of a probiotic yeast *Saccharomyces boulardii*. *Gut Pathog.* 5, 30 (2013).
53. Batista, T. M., Marques, E. T., Jr., Franco, G. R. & Douradinha, B. Draft Genome Sequence of the Probiotic Yeast *Saccharomyces cerevisiae* var. *boulardii* Strain ATCC MYA-796. *Genome announcements* 2, 578-579 (2014).
54. Hamedi, H., et al. Generation of a uracil auxotroph strain of the probiotic yeast *Saccharomyces boulardii* as a host for the recombinant protein production. *Avicenna journal of medical biotechnology* 5, 29-34 (2013).
55. Hudson, L. E., et al. Functional heterologous protein expression by genetically engineered probiotic yeast *Saccharomyces boulardii*. *PLoS One* 9, e1 12660 (2014).
56. Douradinha, B., et al. Novel insights in genetic transformation of the probiotic yeast *Saccharomyces boulardii*. *Bioengineered* 5, 21-29 (2014).

57. Fietto, J. L., et al. Molecular and physiological comparisons between *Saccharomyces cerevisiae* and *Saccharomyces boulardii*. *Canadian journal of microbiology* 50, 615-621 (2004).
58. Martins, F. S., et al. Screening of yeasts as probiotic based on capacities to colonize the gastrointestinal tract and to protect against enteropathogen challenge in mice. *The Journal of general and applied microbiology* 51, 83-92 (2005).
59. Martins, F. S., Veloso, L. C., Arantes, R. M. & Nicoli, J. R. Effects of yeast probiotic formulation on viability, revival and protection against infection with *Salmonella enterica* ssp. *enterica* serovar *Typhimurium* in mice. *Lett. Appl. Microbiol.* 49, 738-744 (2009).
60. Wu, D., Teng, D., Wang, X., Dai, C. & Wang, J. *Saccharomyces boulardii* prevention of the hepatic injury induced by *Salmonella Enteritidis* infection. *Can. J. Microbiol.* 60, 681-686 (2014).
61. Elmer, G. W. & Corthier, G. Modulation of *Clostridium difficile* induced mortality as a function of the dose and the viability of the *Saccharomyces boulardii* used as a preventative agent in gnotobiotic mice. *Can. J. Microbiol.* 37, 315-317 (1991).
62. Chen, X., et al. A mouse model of *Clostridium difficile*-associated disease. *Gastroenterology* 135, 1984-1992 (2008).
63. Pawlowski, S. W., et al. Murine model of *Clostridium difficile* infection with aged gnotobiotic C57BL/6 mice and a BI/NAP1 strain. *The Journal of infectious diseases* 202, 1708-1712 (2010).
64. McFarland, L. V. *Saccharomyces boulardii* is not *Saccharomyces cerevisiae*. *Clin. Infect. Dis.* 22, 200-201 (1996).
65. Edwards-Ingram, L., et al. Genotypic and physiological characterization of *Saccharomyces boulardii*, the probiotic strain of *Saccharomyces cerevisiae*. *Appl. Environ. Microbiol.* 73, 2458-2467 (2007).
66. Panchal, C. J., Whitney, G. K. & Stewart, G. G. Susceptibility of *Saccharomyces* spp. and *Schwanniomyces* spp. to the aminoglycoside antibiotic G418. *Appl. Environ. Microbiol.* 47, 1164-1166 (1984).
67. Tsalik, E. L. & Gartenberg, M. R. Curing *Saccharomyces cerevisiae* of the 2 micron plasmid by targeted DNA damage. *Yeast* 14, 847-852 (1998).
68. Chan, K. M., Liu, Y. T., Ma, C. H., Jayaram, M. & Sau, S. The 2 micron plasmid of *Saccharomyces cerevisiae*: a miniaturized selfish genome with optimized functional competence. *Plasmid* 70, 2-17 (2013).
69. Brake, A. J., et al. Alpha-factor-directed synthesis and secretion of mature foreign proteins in *Saccharomyces cerevisiae*. *Proceedings of the National Academy of Sciences of the United States of America* 81, 4642-4646 (1984).
70. Porro, D., Sauer, M., Branduardi, P. & Mattanovich, D. Recombinant protein production in yeasts. *Molecular biotechnology* 31, 245-259 (2005).
71. Chung, B. H., Nam, S. W., Kim, B. M. & Park, Y. H. Highly efficient secretion of heterologous proteins from *Saccharomyces cerevisiae* using inulinase signal peptides. *Biotechnology and bioengineering* 49, 473-479 (1996).
72. Hahm, M. S. & Chung, B. H. Secretory expression of human growth hormone in *Saccharomyces cerevisiae* using three different leader sequences. *Biotechnology and Bioprocess Engineering* 6, 306-309 (2001).
73. Gietz, R. D. & Schiestl, R. H. High-efficiency yeast transformation using the LiAc/SS carrier DNA/PEG method. *Nat. Protoc.* 2, 31-4 (2007).
74. Konishi, T. & Harata, M. Improvement of the transformation efficiency of *Saccharomyces cerevisiae* by altering carbon sources in pre-culture. *Biosci. Biotechnol. Biochem.* 78, 1090-1093 (2014).
75. Gatignol, A., Baron, M. & Tiraby, G. Phleomycin resistance encoded by the ble gene from transposon Tn 5 as a dominant selectable marker in *Saccharomyces cerevisiae*. *MGG Mol. Gen. Genet.* 207, 342-348 (1987).
76. Macdonald, C. & Piper, R. C. Puromycin- and methotrexate-resistance cassettes and optimized Cre-recombinase expression plasmids for use in yeast. *Yeast* 32, 423-438 (2015).
77. Boeke, J. D., LaCroute, F. & Fink, G. R. A positive selection for mutants lacking orotidine-5'-phosphate decarboxylase activity in yeast: 5-fluoro-orotic acid resistance. *Mol Gen Genet* 197, 345-346 (1984).
78. Yang, Z. et al. Intravenous adenovirus expressing a multi-specific, single-domain antibody neutralizing TcdA and TcdB protects mice from *Clostridium difficile* infection. *Pathog. Dis.* 74, ftw078 (2016).
79. DiCarlo, J. E. et al. Genome engineering in *Saccharomyces cerevisiae* using CRISPR-Cas systems. *Nucleic Acids Res.* 41, 4336-43 (2013).
80. Bao, Z. et al. Homology-Integrated CRISPR-Cas (HI-CRISPR) System for One-Step Multigene Disruption in *Saccharomyces cerevisiae*. *ACS Synth. Biol.* 4, 585-594 (2015).
81. Liu, J.-J. et al. Metabolic engineering of a probiotic *Saccharomyces boulardii*. *Appl. Environ. Microbiol.* AEM.00057-16 (2016). doi:10.1128/AEM.00057-16
82. Hao, H. et al. Large fragment deletion using a CRISPR/Cas9 system in *Saccharomyces cerevisiae*. (2016). doi: 10.1016/j.ab.2016.07.008.This
83. Shi, S., Liang, Y., Zhang, M. M., Ang, E. L. & Zhao, H. A highly efficient single-step, markerless strategy for multi-copy chromosomal integration of large biochemical pathways in *Saccharomyces cerevisiae*. *Metab. Eng.* 33, 19-27 (2016).
84. Kim, J. M. et al. Transposable Elements and Genome Organization: A Comprehensive Survey of Retrotransposons Revealed by the Complete *Saccharomyces cerevisiae*. *Genome Research*. 8(5): 464-478 (1998).
85. Bao Z, Xiao H, Liang J, Zhang L, Xiong X, Sun N, Si T, Zhao H. Homology-Integrated CRISPR-Cas (HI-CRISPR) System for One-Step Multigene Disruption in *Saccharomyces cerevisiae*. *ACS Synth Biol.* 4(5):585-94 (2015).
86. DiCarlo J E, Norville J E, Mali P, Rios X, Aach J, Church G M. Genome engineering in *Saccharomyces cerevisiae* using CRISPR-Cas systems. *Nucleic Acids Res* 41:4336-43 (2013).
87. Liu J-J, Kong I I, Zhang G-C, Jayakody L N, Kim H, Xia P-F, Kwak S, Sung B H, Sohn J-H, Walukiewicz H E, Rao C V., Jin Y-S. Metabolic engineering of a probiotic *Saccharomyces boulardii*. *Appl Environ Microbiol.* 82(8): 2280-7 (2016).
88. Shi S, Liang Y, Zhang M M, Ang E L, Zhao H. A highly efficient single-step, markerless strategy for multi-copy chromosomal integration of large biochemical pathways in *Saccharomyces cerevisiae*. *Metab Eng* 33:19-27 (2016).

The invention claimed is:

1. A method of treating a *Clostridum difficile* (*C. difficile*) infection in a subject, comprising administering an effective amount of an engineered strain of *Saccharomyces boulardii* yeast to the subject, wherein the engineered strain of *Saccharomyces boulardii* yeast produces a tetra-specific, tetra-meric ABAB binding agent comprising: (i) a first, a second, a third, and a fourth linked $V_HH$ peptide monomer each independently having binding specificity for an epitope of *C. difficile* toxin A (TcdA) or *C. difficile* toxin B (TcdB), and (ii) an amino acid sequence of SEQ ID NO: 109 or an amino acid sequence that is at least 95% identical to SEQ ID NO: 109.

2. The method of claim 1, wherein two of the monomers have binding specificity for epitopes of TcdA and two of the monomers have binding specificity for epitopes of TcdB.

3. The method of claim 1, wherein the monomers independently have binding specificity for an epitope in the glucosyltransferase domain, cysteine protease domain, translocation domain, or receptor binding domain of TcdA or TcdB.

4. The method of claim 1, wherein the first $V_HH$ peptide monomer comprises an amino acid sequence of SEQ ID NO: 7, the second $V_HH$ peptide monomer comprises an amino acid sequence of SEQ ID NO: 1, the third $V_HH$ peptide monomer comprises an amino acid sequence of SEQ ID NO: 5, and the fourth $V_HH$ peptide monomer comprises an amino acid sequence of SEQ ID NO: 3.

5. The method of claim 1, wherein the ABAB binding agent comprises an amino acid sequence of SEQ ID NO 19.

6. The method of claim 1, wherein the ABAB binding agent further comprises an N-terminal secretion signal selected from SEQ ID NO:99 and SEQ ID NO: 103.

7. The method of claim 1, wherein the ABAB binding agent comprises an amino acid sequence of SEQ ID NO: 107.

8. The method of claim 1, wherein the ABAB binding agent comprises the amino acid sequence of SEQ ID NO: 109.

9. The method of claim 1, wherein the engineered strain of *Saccharomyces boulardii* yeast is administered in an amount between 10 µg/kg and 100 mg/kg per body weight of the subject.

10. The method of claim 1, wherein the engineered strain of *Saccharomyces boulardii* yeast is administered to the subject orally, nasally or rectally.

11. The method of claim 1, wherein the engineered strain of *Saccharomyces boulardii* yeast is in a pharmaceutical formulation comprising a pharmaceutically acceptable carrier or diluent.

12. The method of claim 1 further comprising administering an antibiotic to the subject.

* * * * *